(12) United States Patent  
Alpert et al.

(10) Patent No.: US 9,089,591 B2  
(45) Date of Patent: Jul. 28, 2015

(54) COMPOSITIONS AND METHODS FOR TREATMENT OF EAR DISORDERS

(71) Applicants: Evgenia Alpert, Jerusalem (IL); Igor Spivak, Jaifa (IL); Amir Bar-Ilan, Haifa (IL)

(72) Inventors: Evgenia Alpert, Jerusalem (IL); Igor Spivak, Jaifa (IL); Amir Bar-Ilan, Haifa (IL)

(73) Assignee: QUARK PHARMACEUTICALS, INC., Fremont, CA (US)

( * ) Notice: Subject to any disclaimer, the term of this patent is extended or adjusted under 35 U.S.C. 154(b) by 0 days.

(21) Appl. No.: 13/867,837

(22) Filed: Apr. 22, 2013

(65) Prior Publication Data

US 2014/0066493 A1 Mar. 6, 2014

Related U.S. Application Data

(62) Division of application No. 12/994,725, filed as application No. PCT/IL2009/000570 on Jun. 7, 2009, now Pat. No. 8,431,692.

(60) Provisional application No. 61/131,162, filed on Jun. 6, 2008.

(51) Int. Cl.
| | |
|---|---|
| A61K 48/00 | (2006.01) |
| C07H 21/02 | (2006.01) |
| C07H 21/04 | (2006.01) |
| A61K 31/713 | (2006.01) |
| A61K 9/00 | (2006.01) |
| C12N 15/113 | (2010.01) |

(52) U.S. Cl.
CPC ............. *A61K 31/713* (2013.01); *A61K 9/0046* (2013.01); *C12N 15/113* (2013.01); *C12N 2310/14* (2013.01)

(58) Field of Classification Search
CPC ..... A61K 48/00; C12N 15/111; C12N 15/113
See application file for complete search history.

(56) References Cited

U.S. PATENT DOCUMENTS

| 5,898,031 A | 4/1999 | Crooke |
|---|---|---|
| 5,929,042 A | 7/1999 | Troy et al. |
| 6,107,094 A | 8/2000 | Crooke |
| 6,153,737 A | 11/2000 | Manoharan et al. |
| 6,235,886 B1 | 5/2001 | Manoharan et al. |
| 6,395,713 B1 | 5/2002 | Beigelman et al. |
| 6,602,858 B2 | 8/2003 | Beigelman |
| 7,056,704 B2 | 6/2006 | Tuschl et al. |
| 7,078,196 B2 | 7/2006 | Tuschl et al. |
| 7,087,581 B1 | 8/2006 | Loewenheim |
| 7,452,987 B2 | 11/2008 | Giese et al. |
| 7,825,099 B2 | 11/2010 | Feinstein |
| 7,893,245 B2 | 2/2011 | Giese et al. |
| 7,910,566 B2 | 3/2011 | Feinstein |
| 8,097,710 B2 | 1/2012 | Baulcombe et al. |
| 2003/0027783 A1 | 2/2003 | Zernicka-Goetz et al. |
| 2003/0108923 A1 | 6/2003 | Tuschl et al. |
| 2004/0001811 A1 | 1/2004 | Kreutzer et al. |
| 2004/0038921 A1 | 2/2004 | Kreutzer et al. |
| 2004/0053875 A1 | 3/2004 | Kreutzer et al. |
| 2004/0192626 A1 | 9/2004 | McSwiggen et al. |
| 2004/0203145 A1 | 10/2004 | Zamore et al. |
| 2004/0229266 A1 | 11/2004 | Tuschl et al. |
| 2004/0259247 A1 | 12/2004 | Tuschl et al. |
| 2004/0265839 A1 | 12/2004 | Mello et al. |
| 2005/0020525 A1 | 1/2005 | McSwiggen et al. |
| 2005/0037988 A1 | 2/2005 | Zamore et al. |
| 2005/0042647 A1 | 2/2005 | Baker et al. |
| 2005/0119202 A1 | 6/2005 | Kreutzer et al. |
| 2005/0181382 A1 | 8/2005 | Zamore et al. |
| 2005/0233342 A1 | 10/2005 | Manoharan et al. |
| 2005/0255487 A1 | 11/2005 | Khvorova et al. |
| 2005/0260620 A1 | 11/2005 | Christiano et al. |
| 2006/0069056 A1 | 3/2006 | Feinstein et al. |
| 2006/0217329 A1 | 9/2006 | Feinstein et al. |
| 2007/0031844 A1 | 2/2007 | Khvorova et al. |
| 2007/0032441 A1 | 2/2007 | McSwiggen et al. |
| 2007/0042982 A1 | 2/2007 | Bentwich |
| 2007/0243242 A1* | 10/2007 | Smith ........................... 424/450 |
| 2008/0020007 A1 | 1/2008 | Zang |

(Continued)

FOREIGN PATENT DOCUMENTS

| WO | WO 00/44914 | 8/2000 |
|---|---|---|
| WO | WO 01/68836 | 9/2001 |

(Continued)

OTHER PUBLICATIONS

Chiu and Rana, (2002) "RNAi in Human Cells: basic Structural and Function Features of Small Interfering RNA". Molecular Cell, 19:549-561.

Maeda et al., (2009) "Therapeutic regulation of gene expression in the inner ear using RNA interference" Adv Otorhinolaryngol, 66:13-36.

Seidman et al., (2003) "Pharmacologic manipulation of the labyrinth with novel and traditional agents delivered to the inner ear" ENT-Ear Nose Throat J., April pp. 276-300.

Swan et al., (2008) "Inner Ear Drug Delivery for Auditory Applications" Adv Drug Deliv Rev., 60(15):1583-1599.

Final Office Action issued Mar. 14, 2011 in respect of U.S. Appl. No. 11/978,089 (US 2009/0162365).

(Continued)

*Primary Examiner* — Amy Bowman
(74) *Attorney, Agent, or Firm* — John P. White; Cooper & Dunham LLP

(57) ABSTRACT

The present invention relates to pharmaceutical compositions useful for topical, non-invasive delivery of an oligonucleotide to the ear and to methods for the treatment of an ear disorder, including hearing loss arising from chemical-induced ototoxicity, acoustic trauma and presbycusis; and microbial infections. The method comprises topically administering to the ear of a subject in need thereof a pharmaceutical composition comprising an inhibitory oligonucleotide, a permeability enhancer and a pharmaceutically acceptable carrier, wherein the oligonucleotide reduces or inhibits expression of a gene associated with the ear disorder in the subject.

15 Claims, 49 Drawing Sheets

(56) References Cited

U.S. PATENT DOCUMENTS

| | | | |
|---|---|---|---|
| 2008/0064650 | A1 | 3/2008 | Feinstein et al. |
| 2008/0108583 | A1 | 5/2008 | Feinstein |
| 2008/0311051 | A1 | 12/2008 | Chauvier et al. |
| 2009/0105173 | A1 | 4/2009 | Feinstein |
| 2009/0124568 | A1* | 5/2009 | Heller et al. .................. 514/44 |
| 2009/0162365 | A1 | 6/2009 | Feinstein et al. |
| 2009/0192104 | A1 | 7/2009 | McSwiggen et al. |
| 2009/0263323 | A1 | 10/2009 | Krause et al. |
| 2010/0029746 | A1 | 2/2010 | Feinstein |
| 2010/0272722 | A1 | 10/2010 | Feinstein et al. |
| 2010/0292301 | A1 | 11/2010 | Feinstein et al. |
| 2011/0112168 | A1 | 5/2011 | Feinstein et al. |
| 2011/0142917 | A1 | 6/2011 | Albert et al. |
| 2011/0229557 | A1 | 9/2011 | Feinstein et al. |
| 2011/0251260 | A1* | 10/2011 | Feinstein et al. ............ 514/44 A |

FOREIGN PATENT DOCUMENTS

| | | |
|---|---|---|
| WO | WO 02/24720 | 3/2002 |
| WO | WO 02/055693 | 7/2002 |
| WO | WO 03/064621 | 8/2003 |
| WO | WO 03/070918 | 8/2003 |
| WO | WO 03/074654 | 9/2003 |
| WO | WO 2004/103389 | 12/2004 |
| WO | WO 2005/055921 | 6/2005 |
| WO | WO 2005/119251 | 12/2005 |
| WO | WO 2007/014075 | 2/2007 |
| WO | WO 2007/084684 | 7/2007 |
| WO | WO 2007/087451 | 8/2007 |
| WO | WO 2008/050329 | 5/2008 |
| WO | WO 2008/104978 | 9/2008 |
| WO | WO 2009/044392 | 4/2009 |

OTHER PUBLICATIONS

Amendment filed Jan. 19, 2012 in response to Final Office Action issued Mar. 14, 2012 in respect of U.S. Appl. No. 11/978,089 (US 2009/0162365).
Extended European Search Report and Opinion issued Jan. 9, 2011 in respect of EP 11170912.7 (Divisional application of EPO National Phase application of PCT/IL2007/001278).
Supplementary European Search Report and Opinion issued Dec. 6, 2011 in respect of EP 08808012.2 (EPO National Phase application of PCT/IL2008/001197).
Wang et al., (2005) "Endotoxemic Acute Renal Failure is Attenuated in Caspase-1-Deficient Mice" Am J Physiol Renal Physiology, 288:F997-F1004.
Written Opinion of the International Searching Authority (ISA/US) issued on Nov. 25, 2009 in connection with PCT International Application No. PCT/IL2009/000570.
International Preliminary Report on Patentability issued by the International Searching Authority (ISA/US) on Dec. 16, 2010 in connection with PCT International Application No. PCT/IL2009/000570.
Amarzguioui et al., Tolerance for mutations and chemical modifications in a siRNA, Nucleic Acids Research, (2003), 31(2):589-595.
Barik, Silence of the transcripts: RNA interference in medicine. J. Mol. Med (2005) 83: 764-773.
Bass, Double-Stranded RNA as a Template for Gene Silencing, Cell, (2000), 101:235-238.
Bernstein, et al., The rest is silence. RNA. (2001), 7(11):1509-21.
Bralasch RNA interference in mammalian cells by chemically-modified RNA (2003). Biochem., 42(26):7967-75.
Breuskin et al., Strategies to regenerate hair cells:Identification of progenitors and critical genes. Hearing Research 2008 236:1-10.
Caplen et al., Specific inhibition of gene expression by small double-stranded RNAs in invertebrate and vertebrate systems. PNAS (2001), 98:9742-974.
Chakraborty, Potentiality of small interfering RNAs (siRNA) as recent therapeutic targets for gene-silencing. Current Drug Targets (2007) 8(3):469-82).
Chalk et al., Improved and automated prediction of effective siRNA. BBRC. (2004). 319(1): 264-274.
Chiu et al., siRNA function in RNAi: a chemical modification analysis. RNA, (2003) 9(9):1034-1048.
Czauderna, et al., Structural variations and stabilising modifications of synthetic siRNAS in mammalian cells, Nucleic Acids Res., (2003), 31(11):2705-2716.
Dykxhoorn et al., The silent treatment: siRNAs as small molecule drugs Gene Ther. (2006). 13:541-552.
Elbashir et al., Duplexes of 21-nucleotide RNAs mediate RNA interference in cultured mammalian cells. Nature (2001), 411:494-498.
Elbashir, et al., Functional anatomy of siRNAs for mediating efficient RNAi in *Drosophila melanogaster* embryo lysate, EMBO J., (2001), 20:6877-6888.
Elbashir, et al., RNA interference is mediated by 21- and 22-nucleotide RNAs, Genes Dev., (2001), 15:188-200.
Fire, et al., Potent and specific genetic interference by double-stranded RNA in *Caenorhabditis elegans*, Nature, (1998), 391:806-811.
Levenkova et al., Gene specific siRNA selector, Bioinform. (2004), 20(3):430-432.
Mahato et al., "Modulation of Gene Expression by Antisense and Antigene Oligodeoxynucleotides and Small Interfering RNA." Expert Opinion on Drug Delivery (2005), 2(1):3-28.
McManus, et al., Gene silencing using micro-RNA designed hairpins, RNA, (2002), 8:842-850.
McManus and Sharp, Gene silencing in mammals by small interfering RNAs. Nature Rev Genet, (2002), 3:737-747.
Paddison et al., siRNAs and shRNAs: skeleton keys to the human genome. Curr Opin Mol. Ther. (2003), 5(3): 217-224.
Prakash et al., Positional Effect of Chemical Modifications on Short Interference RNA Activity in Mammalian Cells, J. Med. Chem., (2005), 48:4247-4253.
Sharp, RNAi and double-strand RNA, Genes & Dev., (1999), 13:139-141.
Scherer et al., Therapeutic Applications of RNA Interference: Recent Advances in siRNA Design. Advances in Genetics, (2004), vol. 52, 1-21.
Ui-Tei et al., Guidelines for the selection of highly effective siRNA sequences for mammalian and chick RNA interference. NAR (2004), 32(3):936-948.
Ui-Tei et al., Essential notes regarding the design of functional siRNAs for efficient mammalian RNAi. J Biomed Biotechnol (2006), 2006:65052.
Wang et al., A peptide inhibitor of c-Jun N-terminal lipase protects against both aminoglycoside and acoustic trauma-induced auditory hair cell death and hearing loss. J. Neuroscience (2003), 23(24):8596-8607.
Zamore, et al., RNAi: Double-Stranded RNA Directs the ATP-Dependent Cleavage of mRNA at 21 to 23 Nucleotide Intervals, Cell, (2000), 101:25-33.
Zhang et al., Pifithrin-alpha suppresses p53 and protects cochlear and vestibular hair cells from cisplatin-induced apoptosis. Neuroscience (2003), 120:191-205.
International Search Report issued by the International Searching Authority (ISA/US) on Nov. 25, 2009 in connection with International Application No. PCT/IL2009/000570.
Written Opinion of the International Searching Authority issued by the International Searching Authority (ISA/US) on Nov. 25, 2009 in connection with International Application No. PCT/IL2009/000570.

* cited by examiner 3 days termination 3 days after inoculation

FIGURE 4

Table A1: HES1 - hairy and enhancer of split 1

| No. | SEQ ID NO. | Sense siRNA | SEQ ID NO. | AntiSense siRNA | Other Sp | Human-8400709 ORF:237-1079 |
|---|---|---|---|---|---|---|
| 1 | 37 | GCGCCUUUGUAUUAUAAAA | 449 | UUUUAUAAUACAAAGGCGC | Rat,Ms | [1301-1319] 3'UTR |
| 2 | 38 | CAAGUAAAAGAGACACAAA | 450 | UUUGUGUCUCUUUUACUUG | | [147-165] 5'UTR |
| 3 | 39 | CUCUAAACAGGAACUUGAA | 451 | UUCAAGUUCCUGUUUAGAG | | [1137-1155] 3'UTR |
| 4 | 40 | GGUGCUGAUAACAGCGGAA | 452 | UUCCGCUGUUAUCAGCACC | Ms | [21-39] 5'UTR |
| 5 | 41 | UGCCAAGAUGUUUGAAAA | 453 | UUUUCAAACAUCUUUGGCA | Rat,Ms | [1367-1385] 3'UTR |
| 6 | 42 | CUUGAAUACUGGGAGAGAA | 454 | UUCUCUCCCAGUAUUCAAG | | [1150-1168] 3'UTR |
| 7 | 43 | GUAAAAGAGACACAAACAA | 455 | UUGUUUGUGUCUCUUUUAC | | [150-168] 5'UTR |
| 8 | 44 | CGUGAAGAACUCCAAAAAU | 456 | AUUUUUGGAGUUCUUCACG | | [181-199] 5'UTR |
| 9 | 45 | GAACUUGAAUACUGGGAGA | 457 | UCUCCCAGUAUUCAAGUUC | | [1147-1165] 3'UTR |
| 10 | 46 | GGACAUUCUGGAAAUGACA | 458 | UGUCAUUUCCAGAAUGUCC | | [470-488] ORF |
| 11 | 47 | GGAGAAAAGACGAAGAGCA | 459 | UGCUCUUCGUCUUUUCUCC | GP | [362-380] ORF |
| 12 | 48 | CAGCAUCUGAGCACAGAAA | 460 | UUUCUGUGCUCAGAUGCUG | | [325-343] ORF |
| 13 | 49 | AGAAAGUCAUCAAAGCCUA | 461 | UAGGCUUUGAUGACUUUCU | Rat,Ms,GP,Chn | [339-357] ORF |
| 14 | 50 | AGCACAGAAAGUCAUCAAA | 462 | UUUGAUGACUUUCUGUGCU | Rat,Ms,Chn | [334-352] ORF |
| 15 | 51 | CUUCCCUCCGGACUCUAAA | 463 | UUUAGAGUCCGGAGGGAAG | | [1125-1143] 3'UTR |
| 16 | 52 | GAGAGAAGAGGACUUUUUU | 464 | AAAAAAGUCCUCUUCUCUC | | [1162-1180] 3'UTR |
| 17 | 53 | UCACCAAGUAGCCACAAAA | 465 | UUUUGUGGCUACUUGGUGA | | [84-102] 5'UTR |
| 18 | 54 | GCCUAUUAUGGAGAAAUAG | 466 | UCUUUUCUCCAUAAUAGGC | | [353-371] ORF |
| 19 | 55 | GGCAUUCCAAGCUGGAGAA | 467 | UUCUCCAGCUUGGAAUGCC | Rat,GP,Chn | [448-466] ORF |
| 20 | 56 | UGAAAACACUGAUUUUGGA | 468 | UCCAAAAUCAGUGUUUUCA | Rat,Ms,GP,Chn | [406-424] ORF |
| 21 | 57 | UCGUGAAGAACUCCAAAAA | 469 | UUUUUGGAGUUCUUCACGA | | [180-198] 5'UTR |
| 22 | 58 | CUUUUUUAUGUGAUGCCAA | 470 | UUGGCAUCACAUAAAAAAG | | [1354-1372] 3'UTR |
| 23 | 59 | GUUACUUUUUGUAGAGAGA | 471 | UCUCUCUACAAAAAGUAAC | | [1220-1238] 3'UTR |
| 24 | 60 | AGUCUGAGCCAGCUGAAAA | 472 | UUUUCAGCUGGCUCAGACU | | [393-411] ORF |
| 25 | 61 | CCAGCUGAUAUAAUGGAGA | 473 | UCUCCAUUAUAUCAGCUGG | Rat,Ms,Chn | [240-258] ORF |
| 26 | 62 | GGGAGAGAAGAGGACUUUU | 474 | AAAAGUCCUCUUCUCUCCC | | [1160-1178] 3'UTR |
| 27 | 63 | ACUGCAUGACCCAGAUCAA | 475 | UUGAUCUGGGUCAUGCAGU | Rat,Ms,GP,Chn | [670-688] ORF |
| 28 | 64 | GCUGAUAUAAUGGAGAAAA | 476 | UUUUCUCCAUUAUAUCAGC | Rat,Ms,Chn | [243-261] ORF |
| 29 | 65 | UUGCUUUCCUCAUUCCCAA | 477 | UUGGGAAUGAGGAAAGCAA | | [922-940] ORF |
| 30 | 66 | UGAUUUUGGAUGCUCUGAA | 478 | UUCAGAGCAUCCAAAAUCA | | [415-433] ORF |
| 31 | 67 | UCAAGUAAAAGAGACACAA | 479 | UUGUGUCUCUUUUACUUGA | | [146-164] 5'UTR |
| 32 | 68 | GGAUGCUCUGAAGAAAGAU | 480 | AUCUUUCUUCAGAGCAUCC | | [422-440] ORF |
| 33 | 69 | CUGGAACAGCGCUACUGAU | 481 | AUCAGUAGCGCUGUUCCAG | | [66-84] 5'UTR |
| 34 | 70 | GGAUAAACCAAAGACAGCA | 482 | UGCUGUCUUUGGUUUAUCC | | [311-329] ORF |
| 35 | 71 | GGAGCUGGUGCUGAUAACA | 483 | UGUUAUCAGCACCAGCUCC | | [15-33] 5'UTR |
| 36 | 72 | UGCUCAGUAGUUUUGUGAA | 484 | UUCACAAAACUACUGAGCA | | [123-141] 5'UTR |
| 37 | 73 | AGAAGAGGACUUUUUUGAU | 485 | AUCAAAAAAGUCCUCUUCU | | [1165-1183] 3'UTR |
| 38 | 74 | GGAGAGAAGAGGACUUUUU | 486 | AAAAAGUCCUCUUCUCUCC | | [1161-1179] 3'UTR |
| 39 | 75 | UUUGGAUGCUCUGAAGAAA | 487 | UUUCUUCAGAGCAUCCAAA | | [419-437] ORF |
| 40 | 76 | AGUAAAAGAGACACAAACA | 488 | UGUUUGUGUCUCUUUUACU | | [149-167] 5'UTR |
| 41 | 77 | UGCGCCUUUGUAUUAUAAA | 489 | UUUAUAAUACAAAGGCGCA | Rat,Ms | [1300-1318] 3'UTR |
| 42 | 78 | GCCAGUUUGCUUUCCUCAU | 490 | AUGAGGAAAGCAAACUGGC | | [916-934] ORF |
| 43 | 79 | UUCUGGAAAUGACAGUGAA | 491 | UUCACUGUCAUUUCCAGAA | Rat | [475-493] ORF |
| 44 | 80 | CACUGAUUUUGGAUGCUCU | 492 | AGAGCAUCCAAAAUCAGUG | | [412-430] ORF |
| 45 | 81 | GUAUUAAGUGACUGACCAU | 493 | AUGGUCAGUCACUUAAUAC | Rat,Ms,GP | [1242-1260] 3'UTR |
| 46 | 82 | GAUUUUGGAUGCUCUGAAG | 494 | CUUCAGAGCAUCCAAAAUC | | [416-434] ORF |
| 47 | 83 | GCAUCUGAGCACAGAAAGU | 495 | ACUUUCUGUGCUCAGAUGC | | [327-345] ORF |
| 48 | 84 | ACAGCAUCUGAGCACAGAA | 496 | UUCUGUGCUCAGAUGCUGU | | [324-342] ORF |
| 49 | 85 | AGCUGAUAUAAUGGAGAAA | 497 | UUUCUCCAUUAUAUCAGCU | Rat,Ms,Chn | [242-260] ORF |
| 50 | 86 | GUGAAGAACUCCAAAAAUA | 498 | UAUUUUUGGAGUUCUUCAC | | [182-200] 5'UTR |
| 51 | 87 | UUUCGUGAAGAACUCCAAA | 499 | UUUGGAGUUCUUCACGAAA | | [178-196] 5'UTR |
| 52 | 88 | AGAUCAAUGCCAUGACCUA | 500 | UAGGUCAUGGCAUUGAUCU | | [682-700] ORF |
| 53 | 89 | AUAGCUCGCGGCAUUCCAA | 501 | UUGGAAUGCCGCGAGCUAU | | [439-457] ORF |
| 54 | 90 | CGCUACUGAUCACCAAGUA | 502 | UACUUGGUGAUCAGUAGCG | | [75-93] 5'UTR |
| 55 | 91 | GAAAGUCUGAGCCAGCUGA | 503 | UCAGCUGGCUCAGACUUUC | | [390-408] ORF |
| 56 | 92 | ACCAAGUAGCCACAAAAUA | 504 | UAUUUUGUGGCUACUUGGU | | [86-104] 5'UTR |
| 57 | 93 | UGGAAAUGACAGUGAAGCA | 505 | UGCUUCACUGUCAUUUCCA | Rat | [478-496] ORF |
| 58 | 94 | AAAGUCUGAGCCAGCUGAA | 506 | UUCAGCUGGCUCAGACUUU | | [391-409] ORF |
| 59 | 95 | AAAAGACGAAGAGCAAGAA | 507 | UUCUUGCUCUUCGUCUUUU | | [366-384] ORF |
| 60 | 96 | GAGAAGAGGACUUUUUUGA | 508 | UCAAAAAAGUCCUCUUCUC | | [1164-1182] 3'UTR |

FIGURE 4 Continued

| | | | | | | |
|---|---|---|---|---|---|---|
| 61 | 97 | UGGUGCUGAUAACAGCGGA | 509 | UCCGCUGUUAUCAGCACCA | Ms | [20-38] 5'UTR |
| 62 | 98 | CCAUGCACUAUAUUUGUAU | 510 | AUACAAAUAUAGUGCAUGG | | [1257-1275] 3'UTR |
| 63 | 99 | AGCUGAAAACACUGAUUUU | 511 | AAAAUCAGUGUUUUCAGCU | GP,Chn | [403-421] ORF |
| 64 | 100 | UGAUGCCAAAGAUGUUUGA | 512 | UCAAACAUCUUUGGCAUCA | Rat,Ms | [1364-1382] 3'UTR |
| 65 | 101 | UUUUGUAGAGAGAGCUGUA | 513 | UACAGCUCUCUCUACAAAA | | [1226-1244] 3'UTR |
| 66 | 102 | GAAAGAUAGCUCGCGGCAU | 514 | AUGCCGCGAGCUAUCUUUC | | [434-452] ORF |
| 67 | 103 | AGCUGUAUUAAGUGACUGA | 515 | UCAGUCACUUAAUACAGCU | Rat,Ms,GP | [1238-1256] 3'UTR |
| 68 | 104 | CGGACAUUCUGGAAAUGAC | 516 | GUCAUUUCCAGAAUGUCCG | | [469-487] ORF |
| 69 | 105 | AAGUCAUCAAAGCCUAUUA | 517 | UAAUAGGCUUUGAUGACUU | | [342-360] ORF |
| 70 | 106 | AGUUUUGUGAAAGUCUCAA | 518 | UUGAGACUUUCACAAAACU | | [131-149] 5'UTR |
| 71 | 107 | AUGCCAAAGAUGUUUGAAA | 519 | UUUCAAACAUCUUUGGCAU | Rat,Ms | [1366-1384] 3'UTR |
| 72 | 108 | UGUAUUAAGUGACUGACCA | 520 | UGGUCAGUCACUUAAUACA | Rat,Ms,GP | [1241-1259] 3'UTR |
| 73 | 109 | GAAGAGGACUUUUUUGAUU | 521 | AAUCAAAAAAGUCCUCUUC | | [1166-1184] 3'UTR |
| 74 | 110 | UCCGGACUCUAAACAGGAA | 522 | UUCCUGUUUAGAGUCCGGA | | [1131-1149] 3'UTR |
| 75 | 111 | CACCAAGUAGCCACAAAAU | 523 | AUUUUGUGGCUACUUGGUG | | [85-103] 5'UTR |
| 76 | 112 | CUGCAUGACCCAGAUCAAU | 524 | AUUGAUCUGGGUCAUGCAG | | [671-689] ORF |
| 77 | 113 | UAUGGAGAAAAGACGAAGA | 525 | UCUUCGUCUUUUCUCCAUA | | [359-377] ORF |
| 78 | 114 | UAUUAUGGAGAAAAGACGA | 526 | UCGUCUUUUCUCCAUAAUA | | [356-374] ORF |
| 79 | 115 | AUUGGAUUGCGCCUUUGUA | 527 | UACAAAGGCGCAAUCCAAU | Rat,Ms | [1293-1311] 3'UTR |
| 80 | 116 | GGACUUUUUUGAUUAAGUG | 528 | CACUUAAUCAAAAAAGUCC | | [1171-1189] 3'UTR |
| 81 | 117 | UCUUCCCUCCGGACUCUAA | 529 | UUAGAGUCCGGAGGGAAGA | | [1124-1142] 3'UTR |
| 82 | 118 | AGCCUAUUAUGGAGAAAAG | 530 | CUUUUCUCCAUAAUAGGCU | | [352-370] ORF |
| 83 | 119 | AGAGCUGUAUUAAGUGACU | 531 | AGUCACUUAAUACAGCUCU | Rat,Ms,GP | [1236-1254] 3'UTR |
| 84 | 120 | UUUUGGAUGCUCUGAAGAA | 532 | UUCUUCAGAGCAUCCAAAA | | [418-436] ORF |
| 85 | 121 | AAGUCUGAGCCAGCUGAAA | 533 | UUUCAGCUGGCUCAGACUU | | [392-410] ORF |
| 86 | 122 | ACGACACCGGAUAAACCAA | 534 | UUGGUUUAUCCGGUGUCGU | Chn | [303-321] ORF |
| 87 | 123 | AAAAUGCCAGCUGAUAUAAU | 535 | AUUAUAUCAGCUGGCAUUU | Rat,Ms,Chn | [235-253] 5'UTR+ORF |
| 88 | 124 | AUUGCGCCUUUGUAUUAUA | 536 | UAUAAUACAAAGGCGCAAU | Rat,Ms | [1298-1316] 3'UTR |
| 89 | 125 | UGAAUACUGGGAGAAGAA | 537 | UCUUCUCUCCCAGUAUUCA | | [1152-1170] 3'UTR |
| 90 | 126 | ACUUGAAUACUGGGAGAA | 538 | UCUCUCCCAGUAUUCAAGU | | [1149-1167] 3'UTR |
| 91 | 127 | AAAGCCUAUUAUGGAGAAA | 539 | UUUCUCCAUAAUAGGCUUU | | [350-368] ORF |
| 92 | 128 | UAGGUUUGUGAAAGUCUCA | 540 | UGAGACUUUCACAAACUA | | [130-148] 5'UTR |
| 93 | 129 | GAUGUUUGAAAAUGCUCUU | 541 | AAGAGCAUUUUCAAACAUC | Ms | [1374-1392] 3'UTR |
| 94 | 130 | GUGGUUACUUUGUGUUUUU | 542 | AAAAACACAAAGUAACCAC | | [1187-1205] 3'UTR |
| 95 | 131 | CUGGGAGAGAAGAGGACUU | 543 | AAGUCCUCUUCUCUCCCAG | | [1158-1176] 3'UTR |
| 96 | 132 | ACGUGCGAGGGCGUUAAUA | 544 | UAUUAACGCCCUCGCACGU | | [615-633] ORF |
| 97 | 133 | AGUCAUCAAAGCCUAUUAU | 545 | AUAAUAGGCUUUGAUGACU | | [343-361] ORF |
| 98 | 134 | AAGGCGGACAUUCUGGAAA | 546 | UUUCCAGAAUGUCCGCCUU | | [465-483] ORF |
| 99 | 135 | AAGCCUAUUAUGGAGAAAA | 547 | UUUUCUCCAUAAUAGGCUU | | [351-369] ORF |
| 100 | 136 | CUCAGAUGACAUUUCGUUU | 548 | AAACGAAAUGUCAUCUGAG | | [1321-1339] 3'UTR |
| 101 | 137 | GCCAAAGAUGUUUGAAAAU | 549 | AUUUUCAAACAUCUUUGGC | Ms | [1368-1386] 3'UTR |
| 102 | 138 | CCUCAGCACUUGCUCAGUA | 550 | UACUGAGCAAGUGCUGAGG | | [113-131] 5'UTR |
| 103 | 139 | UAGAGAGACUGCUAUUAAG | 551 | CUUAAUACAGCUCUCUCUA | | [1231-1249] 3'UTR |
| 104 | 140 | UCUAAACAGGAACUUGAAU | 552 | AUUCAAGUUCCUGUUUAGA | | [1138-1156] 3'UTR |
| 105 | 141 | CGGACUCUAAACAGGAACU | 553 | AGUUCCUGUUUAGAGUCCG | | [1133-1151] 3'UTR |
| 106 | 142 | UCUCCUUGGUCCUGGAACA | 554 | UGUUCCAGGACCAAGGAGA | | [55-73] 5'UTR |
| 107 | 143 | CAAAGAUGUUUGAAAAUGC | 555 | GCAUUUUCAAACAUCUUUG | Ms | [1370-1388] 3'UTR |
| 108 | 144 | UUUCGUUUUUACACGAGA | 556 | UCUCGUGUAAAAACGAAA | Rat,Ms | [1332-1350] 3'UTR |
| 109 | 145 | AGUGACUGACCAUGCACUA | 557 | UAGUGCAUGGUCAGUCACU | GP | [1248-1266] 3'UTR |
| 110 | 146 | GGAACUUGAAUACUGGGAG | 558 | CUCCCAGUAUUCAAGUUCC | | [1146-1164] 3'UTR |
| 111 | 147 | GCUUCAGCGGAGUGCAUGAA | 559 | UUCAUGCACUCGCUGAAGC | Rat,Ms,GP,Chn | [574-592] ORF |
| 112 | 148 | GCGGACAUUCUGGAAAUGA | 560 | UCAUUUCCAGAAUGUCCGC | | [468-486] ORF |
| 113 | 149 | GAAAACACUGAUUUUGGAU | 561 | AUCCAAAAUCAGUGUUUUC | Rat,Ms,GP,Chn | [407-425] ORF |
| 114 | 150 | AAAGACGAAGAGCAAGAAU | 562 | AUUCUUGCUCUUCGUCUUU | | [367-385] ORF |
| 115 | 151 | CAGAUGACAUUUCGUUUUU | 563 | AAAAACGAAAUGUCAUCUG | | [1323-1341] 3'UTR |
| 116 | 152 | AGCUCAGAUGACAUUUCGU | 564 | ACGAAAUGUCAUCUGAGCU | | [1319-1337] 3'UTR |
| 117 | 153 | GAAUACUGGGAGAGAAGAG | 565 | CUCUUCUCUCCCAGUAUUC | | [1153-1171] 3'UTR |
| 118 | 154 | ACAGGAACUUGAAUACUGG | 566 | CCAGUAUUCAAGUUCCUGU | | [1143-1161] 3'UTR |
| 119 | 155 | GGCCAGUUUGCUUUCCUCA | 567 | UGAGGAAAGCAAACUGGCC | | [915-933] ORF |
| 120 | 156 | UGAUCACCAAGUAGCCACA | 568 | UGUGGCUACUUGGUGAUCA | | [81-99] 5'UTR |
| 121 | 157 | AAGCAGCAUCUGAGCACA | 569 | UGUGCUCAGAUGCUGUCUU | | [321-339] ORF |
| 122 | 158 | ACCGGAUAAACCAAAGACA | 570 | UGUCUUUGGUUUAUCCGGU | Chn | [308-326] ORF |
| 123 | 159 | GCCAGCUGAUAUAAUGGAG | 571 | CUCCAUUAUAUCAGCUGGC | Rat,Ms,Chn | [239-257] ORF |
| 124 | 160 | AAAAUGCCAGCUGAUAUAA | 572 | UUAUAUCAGCUGGCAUUUU | Rat,Ms,Chn | [234-252] 5'UTR+ORF |
| 125 | 161 | AAGUCUCAAGUAAAAGAGA | 573 | UCUCUUUUACUUGAGACUU | | [141-159] 5'UTR |
| 126 | 162 | AACGCAGUGUCACCUUCCA | 574 | UGGAAGGUGACACUGCGUU | Ms | [1011-1029] ORF |
| 127 | 163 | GACCCAGAUCAAUGCCAUG | 575 | CAUGGCAUUGAUCUGGGUC | | [677-695] ORF |
| 128 | 164 | GAGUGCAUGAACGAGGUGA | 576 | UCACCUCGUUCAUGCACUC | Rat,Ms,GP,Chn | [582-600] ORF |

FIGURE 4 Continued

| | | | | | | | |
|---|---|---|---|---|---|---|---|
| 129 | 165 | AGAAGGCGGACAUUCUGGA | 577 | UCCAGAAUGUCCGCCUUCU | | [463-481] ORF |
| 130 | 166 | AGAAAGAUAGCUCGCGGCA | 578 | UGCCGCGAGCUAUCUUUCU | | [433-451] ORF |
| 131 | 167 | GACAGCAUCUGAGCACAGA | 579 | UCUGUGCUCAGAUGCUGUC | | [323-341] ORF |
| 132 | 168 | CCGGAUAAACCAAAGACAG | 580 | CUGUCUUUGGUUUAUCCGG | Chn | [309-327] ORF |
| 133 | 169 | CACGACACCGGAUAAACCA | 581 | UGGUUUAUCCGGUGUCGUG | Chn | [302-320] ORF |
| 134 | 170 | GCACUUGCUCAGUAGUUUU | 582 | AAAACUACUGAGCAAGUGC | | [118-136] 5'UTR |
| 135 | 171 | AGAUGUUUGAAAAUGCUCU | 583 | AGAGCAUUUUCAAACAUCU | Ms | [1373-1391] 3'UTR |
| 136 | 172 | AUAAAAGCUCAGAUGACAU | 584 | AUGUCAUCUGAGCUUUUAU | | [1314-1332] 3'UTR |
| 137 | 173 | GAAGUUACUUUUUGUAGAG | 585 | CUCUACAAAAAGUAACUUC | | [1217-1235] 3'UTR |
| 138 | 174 | CUCCGGACUCUAAACAGGA | 586 | UCCUGUUUAGAGUCCGGAG | | [1130-1148] 3'UTR |
| 139 | 175 | GCGCUACUGAUCACCAAGU | 587 | ACUUGGUGAUCAGUAGCGC | | [74-92] 5'UTR |
| 140 | 176 | CCAGCUGAAAACACUGAUU | 588 | AAUCAGUGUUUUCAGCUGG | GP,Chn | [401-419] ORF |
| 141 | 177 | AUUAUGGAGAAAAGACGAA | 589 | UUCGUCUUUUCUCCAUAAU | | [357-375] ORF |
| 142 | 178 | CAAAGACAGCAUCUGAGCA | 590 | UGCUCAGAUGCUGUCUUUG | | [319-337] ORF |
| 143 | 179 | GUCUCAAGUAAAAGAGACA | 591 | UGUCUCUUUUACUUGAGAC | | [143-161] 5'UTR |
| 144 | 180 | UCAGUAGUUUUGUGAAAGU | 592 | ACUUUCACAAAACUACUGA | | [126-144] 5'UTR |
| 145 | 181 | GUGACUGACCAUGCACUAU | 593 | AUAGUGCAUGGUCAGUCAC | GP | [1249-1267] 3'UTR |
| 146 | 182 | UGACCCAGAUCAAUGCCAU | 594 | AUGGCAUUGAUCUGGGUCA | | [676-694] ORF |
| 147 | 183 | GAAGAAAGAUAGCUCGCGG | 595 | CCGCGAGCUAUCUUUCUUC | | [431-449] ORF |
| 148 | 184 | ACACCGGAUAAACCAAAGA | 596 | UCUUUGGUUUAUCCGGUGU | Chn | [306-324] ORF |
| 149 | 185 | UUUUCGUGAAGAACUCCAA | 597 | UUGGAGUUCUUCACGAAAA | | [177-195] 5'UTR |
| 150 | 186 | AAGUAAAAGAGACACAAAC | 598 | GUUUGUGUCUCUUUUACUU | | [148-166] 5'UTR |
| 151 | 187 | CGCCUUUGUAUUAUAAAAG | 599 | CUUUUAUAAUACAAAGGCG | Rat,Ms | [1302-1320] 3'UTR |
| 152 | 188 | AUAUAAUAAACCCUCAGCA | 600 | UGCUGAGGGUUUAUUAUAU | | [102-120] 5'UTR |
| 153 | 189 | AUACUGGGAGAGAAGAGGA | 601 | UCCUCUUCUCUCCCAGUAU | | [1155-1173] 3'UTR |
| 154 | 190 | GGCGGACAUUCUGGAAAUG | 602 | CAUUUCCAGAAUGUCCGCC | | [467-485] ORF |
| 155 | 191 | UGGAGAAGGCGGACAUUCU | 603 | AGAAUGUCCGCCUUCUCCA | | [460-478] ORF |
| 156 | 192 | AGUAGUUUUGUGAAAGUCU | 604 | AGACUUUCACAAAACUACU | | [128-146] 5'UTR |
| 157 | 193 | GAUGCCAAAGAUGUUUGAA | 605 | UUCAAACAUCUUUGGCAUC | Rat,Ms | [1365-1383] 3'UTR |
| 158 | 194 | AUGUGAUGCCAAAGAUGUU | 606 | AACAUCUUUGGCAUCACAU | Rat,Ms | [1361-1379] 3'UTR |
| 159 | 195 | UUGGAUUGCGCCUUUGUAU | 607 | AUACAAAGGCGCAAUCCAA | Rat,Ms | [1294-1312] 3'UTR |
| 160 | 196 | UCAGCGAGUGCAUGAACGA | 608 | UCGUUCAUGCACUCGCUGA | Rat,Ms,GP,Chn | [577-595] ORF |
| 161 | 197 | CCUAUUAUGGAGAAAAGAC | 609 | GUCUUUUCUCCAUAAUAGG | | [354-372] ORF |
| 162 | 198 | AGCCAGUGUCAACACGACA | 610 | UGUCGUGUUGACACUGGCU | Rat,Ms | [290-308] ORF |
| 163 | 199 | GUAGUUUUGUGAAAGUCUC | 611 | GAGACUUUCACAAAACUAC | | [129-147] 5'UTR |
| 164 | 200 | CUAAGGUGUUUGGAGGCUU | 612 | AAGCCUCCAAACACCUUAG | | [874-892] ORF |
| 165 | 201 | AGUGCAUGAACGAGGUGAC | 613 | GUCACCUCGUUCAUGCACU | Rat,Ms,GP,Chn | [583-601] ORF |
| 166 | 202 | AAAUGACAGUGAAGCACCU | 614 | AGGUGCUUCACUGUCAUUU | Rat | [481-499] ORF |
| 167 | 203 | AGAAAAGACGAAGAGCAAG | 615 | CUUGCUCUUCGUCUUUUCU | GP | [364-382] ORF |
| 168 | 204 | UUCGUGAAGAACUCCAAAA | 616 | UUUUGGAGUUCUUCACGAA | | [179-197] 5'UTR |
| 169 | 205 | UCUUUUUUAUGUGAUGCCA | 617 | UGGCAUCACAUAAAAAAGA | | [1353-1371] 3'UTR |
| 170 | 206 | CUGACCAUGCACUAUAUUU | 618 | AAAUAUAGUGCAUGGUCAG | GP | [1253-1271] 3'UTR |
| 171 | 207 | AGUUGUUACUUUGUGUUUU | 619 | AAAACACAAAGUAACUAC | | [1186-1204] 3'UTR |
| 172 | 208 | AGAGAAGAGGACUUUUUUG | 620 | CAAAAAAGUCCUCUUCUCU | | [1163-1181] 3'UTR |
| 173 | 209 | AGGUGUUUGGAGGCUUCCA | 621 | UGGAAGCCUCCAAACACCU | | [877-895] ORF |
| 174 | 210 | UGAGCCAGCUGAAAACACU | 622 | AGUGUUUUCAGCUGGCUCA | Chn | [397-415] ORF |
| 175 | 211 | CAGAAAGUCAUCAAAGCCU | 623 | AGGCUUUGAUGACUUUCUG | Rat,Ms,GP,Chn | [338-356] ORF |
| 176 | 212 | GCUCUUAAAAUAUCUUCCU | 624 | AGGAAGAUAUUUUAAGAGC | Rat,Ms | [1387-1405] 3'UTR |
| 177 | 213 | GUUAAUACCGAGGUGCGCA | 625 | UGCGCACCUCGGUAUUAAC | | [627-645] ORF |
| 178 | 214 | CUGAUUUGGAUGCUCUGA | 626 | UCAGAGCAUCCAAAAUCAG | | [414-432] ORF |
| 179 | 215 | GUCUGAGCCAGCUGAAAAC | 627 | GUUUUCAGCUGGCUCAGAC | | [394-412] ORF |
| 180 | 216 | UGCCAGCUGAUAUAAUGGA | 628 | UCCAUUAUAUCAGCUGGCA | Rat,Ms,Chn | [238-256] ORF |
| 181 | 217 | AAGUGGUUACUUUGUGUUU | 629 | AAACACAAAGUAACCACUU | | [1185-1203] 3'UTR |
| 182 | 218 | CAGGAACUUGAAUACUGGG | 630 | CCCAGUAUUCAAGUUCCUG | | [1144-1162] 3'UTR |
| 183 | 219 | GGACUCUAAACAGGAACUU | 631 | AAGUUCCUGUUUAGAGUCC | | [1134-1152] 3'UTR |
| 184 | 220 | AUCACCAAGUAGCCACAAA | 632 | UUUGUGGCUACUUGGUGAU | | [83-101] 5'UTR |
| 185 | 221 | GAUCACCAAGUAGCCACAA | 633 | UUGUGGCUACUUGGUGAUC | | [82-100] 5'UTR |
| 186 | 222 | AAAUGAAAGUCUGAGCCAG | 634 | CUGGCUCAGACUUUCAUUU | | [386-404] ORF |
| 187 | 223 | GAAUAAAAUGAAAGUCUGAG | 635 | CUCAGACUUUCAUUUUAUUC | | [382-400] ORF |
| 188 | 224 | CUAUUAUGGAGAAAAGACG | 636 | CGUCUUUUCUCCAUAAUAG | | [355-373] ORF |
| 189 | 225 | AUCUGAGCACAGAAAGUCA | 637 | UGACUUUCUGUGCUCAGAU | | [329-347] ORF |
| 190 | 226 | GUUUUGUGAAAGUCUCAAG | 638 | CUUGAGACUUUCACAAAAC | | [132-150] 5'UTR |
| 191 | 227 | CAUUUCGUUUUUUACACGA | 639 | UCGUGUAAAAAACGAAAUG | Rat,Ms | [1330-1348] 3'UTR |
| 192 | 228 | AGGAACUUGAAUACUGGGA | 640 | UCCCAGUAUUCAAGUUCCU | | [1145-1163] 3'UTR |
| 193 | 229 | CCGGACUCUAAACAGGAAC | 641 | GUUCCUGUUUAGAGUCCGG | | [1132-1150] 3'UTR |
| 194 | 230 | UUUGCUUUCCUCAUUCCCA | 642 | UGGGAAUGAGGAAAGCAAA | | [921-939] ORF |
| 195 | 231 | GGAAAUGACAGUGAAGCAC | 643 | GUGCUUCACUGUCAUUUCC | Rat | [479-497] ORF |
| 196 | 232 | GACAUUUCGUUUUUUACAC | 644 | GUGUAAAAAACGAAAUGUC | Rat,Ms | [1328-1346] 3'UTR |

FIGURE 4 Continued

| | | | | | | | |
|---|---|---|---|---|---|---|---|
| 197 | 233 | AUUUUGGAUGCUCUGAAGA | 645 | UCUUCAGAGCAUCCAAAAU | | [417-435] ORF |
| 198 | 234 | UAAAUGAAAGUCUGAGCCA | 646 | UGGCUCAGACUUUCAUUUA | | [385-403] ORF |
| 199 | 235 | UGUCAACACGACACCGGAU | 647 | AUCCGGUGUCGUGUUGACA | Chn | [296-314] ORF |
| 200 | 236 | CUUGCUCAGUAGUUUUGUG | 648 | CACAAAACUACUGAGCAAG | | [121-139] 5'UTR |
| 201 | 237 | UUUUAUGUGAUGCCAAAGA | 649 | UCUUUGGCAUCACAUAAAA | Rat,Ms | [1357-1375] 3'UTR |
| 202 | 238 | CGUUUUUUACACGAGAUUU | 650 | AAAUCUCGUGUAAAAAACG | Rat,Ms | [1335-1353] 3'UTR |
| 203 | 239 | UGUUCAUAUUGGAUUGCGC | 651 | GCGCAAUCCAAUAUGAACA | Rat,Ms | [1286-1304] 3'UTR |
| 204 | 240 | ACUGACCAUGCACUAUAUU | 652 | AAUAUAGUGCAUGGUCAGU | GP | [1252-1270] 3'UTR |
| 205 | 241 | UUGAAUACUGGGAGAGAAG | 653 | CUUCUCUCCCAGUAUUCAA | | [1151-1169] 3'UTR |
| 206 | 242 | CUCAAGUAAAAGAGACACA | 654 | UGUGUCUCUUUUACUUGAG | | [145-163] 5'UTR |
| 207 | 243 | UUGUAGAGAGAGCUGUAUU | 655 | AAUACAGCUCUCUCUACAA | | [1228-1246] 3'UTR |
| 208 | 244 | AGUUACUUUUUGUAGAGAG | 656 | CUCUCUACAAAAAGUAACU | Rat,Ms | [1219-1237] 3'UTR |
| 209 | 245 | UGAUUAAGUGGUUACUUUG | 657 | CAAAGUAACCACUUAAUCA | GP | [1180-1198] 3'UTR |
| 210 | 246 | GAGGACUUUUUUGAUUAAG | 658 | CUUAAUCAAAAAAGUCCUC | | [1169-1187] 3'UTR |
| 211 | 247 | GCCAGCUGAAAACACUGAU | 659 | AUCAGUGUUUUCAGCUGGC | GP,Chn | [400-418] ORF |
| 212 | 248 | UCAGCACUUGCUCAGUAGU | 660 | ACUACUGAGCAAGUGCUGA | | [115-133] 5'UTR |
| 213 | 249 | GAUUAAGUGGUUACUUUGU | 661 | ACAAAGUAACCACUUAAUC | GP | [1181-1199] 3'UTR |
| 214 | 250 | UAAGGUGUUUGGAGGCUUC | 662 | GAAGCCUCCAAACACCUUA | | [875-893] ORF |
| 215 | 251 | GCUACUGAUCACCAAGUAG | 663 | CUACUUGGUGAUCAGUAGC | | [76-94] 5'UTR |
| 216 | 252 | ACUGAUUUUGGAUGCUCUG | 664 | CAGAGCAUCCAAAAUCAGU | | [413-431] ORF |
| 217 | 253 | CUGAAAACACUGAUUUUGG | 665 | CCAAAAUCAGUGUUUUCAG | Rat,Ms,GP,Chn | [405-423] ORF |
| 218 | 254 | GUGCUGAUAACAGCGGAAU | 666 | AUUCCGCUGUUAUCAGCAC | Ms | [22-40] 5'UTR |
| 219 | 255 | UUAUGUGAUGCCAAAGAUG | 667 | CAUCUUUGGCAUCACAUAA | Rat,Ms | [1359-1377] 3'UTR |
| 220 | 256 | UGGAUUGCGCCUUUGUAUU | 668 | AAUACAAAGGCGCAAUCCA | Rat,Ms | [1295-1313] 3'UTR |
| 221 | 257 | GCUGUAUUAAGUGACUGAC | 669 | GUCAGUCACUUAAUACAGC | Rat,Ms,GP | [1239-1257] 3'UTR |
| 222 | 258 | ACUGGGAGAGAAGAGGACU | 670 | AGUCCUCUUCUCUCCCAGU | | [1157-1175] 3'UTR |
| 223 | 259 | AGCUGGUGCUGAUAACAGC | 671 | GCUGUUAUCAGCACCAGCU | | [17-35] 5'UTR |
| 224 | 260 | UCAAAGCCUAUUAUGGAGA | 672 | UCUCCAUAAUAGGCUUUGA | | [348-366] ORF |
| 225 | 261 | CGGAUAAACCAAAGACAGC | 673 | GCUGUCUUUGGUUUAUCCG | Chn | [310-328] ORF |
| 226 | 262 | UCUUUUCGUGAAGAACUC | 674 | GAGUUCUUCACGAAAAGA | | [174-192] 5'UTR |
| 227 | 263 | UGAAAGUCUCAAGUAAAAG | 675 | CUUUUACUUGAGACUUUCA | | [138-156] 5'UTR |
| 228 | 264 | UUUUGUGAAAGUCUCAAGU | 676 | ACUUGAGACUUUCACAAAA | | [133-151] 5'UTR |
| 229 | 265 | CUCAGUAGUUUUGUGAAAG | 677 | CUUUCACAAAACUACUGAG | | [125-143] 5'UTR |
| 230 | 266 | GACUCUAAACAGGAACUUG | 678 | CAAGUUCCUGUUUAGAGUC | | [1135-1153] 3'UTR |
| 231 | 267 | UUGGAUGCUCUGAAGAAAG | 679 | CUUUCUUCAGAGCAUCCAA | | [420-438] ORF |
| 232 | 268 | UAUUGGAUUGCGCCUUUGU | 680 | ACAAAGGCGCAAUCCAAUA | Rat,Ms | [1292-1310] 3'UTR |
| 233 | 269 | GAGAGCUGUAUUAAGUGAC | 681 | GUCACUUAAUACAGCUCUC | Rat,Ms,GP | [1235-1253] 3'UTR |
| 234 | 270 | UCUGGAAAUGACAGUGAAG | 682 | CUUCACUGUCAUUUCCAGA | Rat | [476-494] ORF |
| 235 | 271 | AGCAUGCGACACGAAAAG | 683 | CUUUCUGUGUCGCAUGCU | | [326-344] ORF |
| 236 | 272 | CCAAAGAUGUUUGAAAAUG | 684 | CAUUUUCAAACAUCUUUGG | Ms | [1369-1387] 3'UTR |
| 237 | 273 | UCAGAUGACAUUUCGUUUU | 685 | AAAACGAAAUGUCAUCUGA | | [1322-1340] 3'UTR |
| 238 | 274 | ACAGCGCUACUGAUCACCA | 686 | UGGUGAUCAGUAGCGCUGU | | [71-89] 5'UTR |
| 239 | 275 | UCUGAGCACAGAAAGUCAU | 687 | AUGACUUUCUGUGCUCAGA | Rat,Ms | [330-348] ORF |
| 240 | 276 | AGCACUUGCUCAGUAGUUU | 688 | AAACUACUGAGCAAGUGCU | | [117-135] 5'UTR |
| 241 | 277 | CAGCACUUGCUCAGUAGUU | 689 | AACUACUGAGCAAGUGCUG | | [116-134] 5'UTR |
| 242 | 278 | AUAAUAAACCCUCAGCACU | 690 | AGUGCUGAGGGUUUAUUAU | | [104-122] 5'UTR |
| 243 | 279 | UGUUUGGAGGCUUCCAGGU | 691 | ACCUGGAAGCCUCCAAACA | | [880-898] ORF |
| 244 | 280 | CAGCUGAAAACACUGAUUU | 692 | AAAUCAGUGUUUUCAGCUG | GP,Chn | [402-420] ORF |
| 245 | 281 | UCAUCAAAGCCUAUUAUGG | 693 | CCAUAAUAGGCUUUGAUGA | | [345-363] ORF |
| 246 | 282 | ACUUGCUCAGUAGUUUUGU | 694 | ACAAAACUACUGAGCAAGU | | [120-138] 5'UTR |
| 247 | 283 | CUGUAUUAAGUGACUGACC | 695 | GGUCAGUCACUUAAUACAG | Rat,Ms,GP | [1240-1258] 3'UTR |
| 248 | 284 | UUUGUAGAGAGAGCUGUAU | 696 | AUACAGCUCUCUCUACAAA | | [1227-1245] 3'UTR |
| 249 | 285 | CUUUUGUAGAGAGAGCUG | 697 | CAGCUCUCUCUACAAAAG | | [1224-1242] 3'UTR |
| 250 | 286 | UACUGGGAGAGAAGAGGAC | 698 | GUCCUCUUCUCUCCCAGUA | | [1156-1174] 3'UTR |
| 251 | 287 | CCAGAUCAAUGCCAUGACC | 699 | GGUCAUGGCAUUGAUCUGG | | [680-698] ORF |
| 252 | 288 | GCAUGACCCAGAUCAAUGC | 700 | GCAUUGAUCUGGGUCAUGC | | [673-691] ORF |
| 253 | 289 | CUCUGAAGAAAGAUAGCUC | 701 | GAGCUAUCUUUCUUCAGAG | | [427-445] ORF |
| 254 | 290 | GCUGAAAACACUGAUUUUG | 702 | CAAAAUCAGUGUUUUCAGC | GP,Chn | [404-422] ORF |
| 255 | 291 | CACCGGAUAAACCAAAGAC | 703 | GUCUUUGGUUUAUCCGGUG | Chn | [307-325] ORF |
| 256 | 292 | CAGUAGUUUUGUGAAAGUC | 704 | GACUUUCACAAAACUACUG | | [127-145] 5'UTR |
| 257 | 293 | GUUUUUUACACGAGAUUUC | 705 | GAAAUCUCGUGUAAAAAAC | Rat,Ms | [1336-1354] 3'UTR |
| 258 | 294 | AACCCUCAGCACUUGCUCA | 706 | UGAGCAAGUGCUGAGGGUU | | [110-128] 5'UTR |
| 259 | 295 | AAAAGCUCAGAUGACAUUU | 707 | AAAUGUCAUCUGAGCUUUU | | [1316-1334] 3'UTR |
| 260 | 296 | UUAUAAAAGCUCAGAUGAC | 708 | GUCAUCUGAGCUUUUAUAA | | [1312-1330] 3'UTR |
| 261 | 297 | UGCUUUCCUCAUUCCCAAC | 709 | GUUGGGAAUGAGGAAAGCA | | [923-941] ORF |
| 262 | 298 | CGAUGGCCAGUUUGCCUUUC | 710 | GAAAGCAAACUGGCCAUCG | | [911-929] ORF |
| 263 | 299 | CCCAGAUCAAUGCCAUGAC | 711 | GUCAUGGCAUUGAUCUGGG | | [679-697] ORF |
| 264 | 300 | GCUCUGAAGAAAGAUAGCU | 712 | AGCUAUCUUUCUUCAGAGC | | [426-444] ORF |

FIGURE 4 Continued

| | | | | | | | |
|---|---|---|---|---|---|---|---|
| 265 | 301 | AGCGCUACUGAUCACCAAG | 713 | CUUGGUGAUCAGUAGCGCU | | | [73-91] 5'UTR |
| 266 | 302 | AUGAAAGUCUGAGCCAGCU | 714 | AGCUGGCUCAGACUUUCAU | | | [388-406] ORF |
| 267 | 303 | AUCAAAGCCUAUUAUGGAG | 715 | CUCCAUAAUAGGCUUUGAU | | | [347-365] ORF |
| 268 | 304 | UGAGCACAGAAAGUCAUCA | 716 | UGAUGACUUUCUGUGCUCA | Rat,Ms | | [332-350] ORF |
| 269 | 305 | CUCAGCACUUGCUCAGUAG | 717 | CUACUGAGCAAGUGCUGAG | | | [114-132] 5'UTR |
| 270 | 306 | UAUAAUAAACCCUCAGCAC | 718 | GUGCUGAGGGUUUAUUAUA | | | [103-121] 5'UTR |
| 271 | 307 | GACUUUUUUGAUUAAGUGG | 719 | CCACUUAAUCAAAAAGUC | | | [1172-1190] 3'UTR |
| 272 | 308 | GCUAAGGUGUUUGGAGGCU | 720 | AGCCUCCAAACACCUUAGC | | | [873-891] ORF |
| 273 | 309 | AGGGCGUUAAUACCGAGGU | 721 | ACCUCGGUAUUAACGCCCU | | | [622-640] ORF |
| 274 | 310 | UGAGCACAGACCCAAGUGU | 722 | ACACUUGGGUCUGUGCUCA | | | [535-553] ORF |
| 275 | 311 | GUCAUCAAAGCCUAUUAUG | 723 | CAUAAUAGGCUUUGAUGAC | | | [344-362] ORF |
| 276 | 312 | UAAACCAAAGACAGCAUCU | 724 | AGAUGCUGUCUUUGGUUUA | | | [314-332] ORF |
| 277 | 313 | GGAGAAAAAUUCCUCGUCC | 725 | GGACGAGGAAUUUUUCUCC | Rat,Chn | | [254-272] ORF |
| 278 | 314 | UUGCUCAGUAGUUUUGUGA | 726 | UCACAAAACUACUGAGCAA | | | [122-140] 5'UTR |
| 279 | 315 | GAGCUGUAUUAAGUGACUG | 727 | CAGUCACUUAAUACAGCUC | Rat,Ms,GP | | [1237-1255] 3'UTR |
| 280 | 316 | GCAUUCCAAGCUGGAGAAG | 728 | CUUCUCCAGCUUGGAAUGC | Rat,GP,Chn | | [449-467] ORF |
| 281 | 317 | UCUGAGCCAGCUGAAAACA | 729 | UGUUUUCAGCUGGCUCAGA | | | [395-413] ORF |
| 282 | 318 | GCCUUUGUAUUAUAAAAGC | 730 | GCUUUUAUAAUACAAAGGC | | | [1303-1321] 3'UTR |
| 283 | 319 | AAGUGACUGACCAUGCACU | 731 | AGUGCAUGGUCAGUCACUU | Rat,Ms,GP | | [1247-1265] 3'UTR |
| 284 | 320 | GAGCCAGCUGAAAACACUG | 732 | CAGUGUUUUCAGCUGGCUC | Chn | | [398-416] ORF |
| 285 | 321 | AAUGAAAGUCUGAGCCAGC | 733 | GCUGGCUCAGACUUUCAUU | | | [387-405] ORF |
| 286 | 322 | UGGAGAAAAGACGAAGAGC | 734 | GCUCUUCGUCUUUUCUCCA | GP | | [361-379] ORF |
| 287 | 323 | AUGGAGAAAAGACGAAGAG | 735 | CUCUUCGUCUUUUCUCCAU | GP | | [360-378] ORF |
| 288 | 324 | CCAAAGACAGCAUCUGAGC | 736 | GCUCAGAUGCUGUCUUUGG | | | [318-336] ORF |
| 289 | 325 | UCUCUCCUUGGUCCUGGAA | 737 | UUCCAGGACCAAGGAGAGA | Rat,Ms | | [53-71] 5'UTR |
| 290 | 326 | UCGUUUUUUACACGAGAUU | 738 | AAUCUCGUGUAAAAAACGA | Rat,Ms | | [1334-1352] 3'UTR |
| 291 | 327 | ACUUUUUGUAGAGAGAGCU | 739 | AGCUCUCUCUACAAAAAGU | | | [1223-1241] 3'UTR |
| 292 | 328 | UUAAGUGGUUACUUUGUGU | 740 | ACACAAAGUAACCACUUAA | | | [1183-1201] 3'UTR |
| 293 | 329 | AAACAGGAACUUGAAUACU | 741 | AGUAUUCAAGUUCCUGUUU | | | [1141-1159] 3'UTR |
| 294 | 330 | GAUCAAUGCCAUGACCUAC | 742 | GUAGGUCAUGGCAUUGAUC | | | [683-701] ORF |
| 295 | 331 | UUAUGGAGAAAAGACGAAG | 743 | CUUCGUCUUUUCUCCAUAA | | | [358-376] ORF |
| 296 | 332 | AACACGACACCGGAUAAAC | 744 | GUUUAUCCGGUGUCGUGUU | Chn | | [300-318] ORF |
| 297 | 333 | UGGCCAGUUUGCUUUCCUC | 745 | GAGGAAAGCAAACUGGCCA | | | [914-932] ORF |
| 298 | 334 | AACUGCAUGACCCAGAUCA | 746 | UGAUCUGGGUCAUGCAGUU | Rat,Ms,GP,Chn | | [669-687] ORF |
| 299 | 335 | UCUGAAGAAAGAUAGCUCG | 747 | CGAGCUAUCUUUCUUCAGA | | | [428-446] ORF |
| 300 | 336 | AUGCUCUGAAGAAAGAUAG | 748 | CUAUCUUUCUUCAGAGCAU | | | [424-442] ORF |
| 301 | 337 | CUGAGCCAGCUGAAAACAC | 749 | GUGUUUUCAGCUGGCUCAG | Chn | | [396-414] ORF |
| 302 | 338 | ACCAAAGACAGCAUCUGAG | 750 | CUCAGAUGCUGUCUUUGGU | | | [317-335] ORF |
| 303 | 339 | UGCUGAUAACAGCGGAAUC | 751 | GAUUCCGCUGUUAUCAGCA | Ms | | [23-41] 5'UTR |
| 304 | 340 | UGUGAUGCCAAAGAUGUUU | 752 | AAACAUCUUUGGCAUCACA | Rat,Ms | | [1362-1380] 3'UTR |
| 305 | 341 | GACAUUCUGGAAAUGACAG | 753 | CUGUCAUUUCCAGAAUGUC | Rat | | [471-489] ORF |
| 306 | 342 | AGACAGCAUCUGAGCACAG | 754 | CUGUGCUCAGAUGCUGUCU | | | [322-340] ORF |
| 307 | 343 | GAGAAAAAUUCCUCGUCCC | 755 | GGGACGAGGAAUUUUUCUC | Rat,Chn | | [255-273] ORF |
| 308 | 344 | UUCGUUUUUUACACGAGAU | 756 | AUCUCGUGUAAAAAACGAA | Rat,Ms | | [1333-1351] 3'UTR |
| 309 | 345 | CAGAUCAAUGCCAUGACCU | 757 | AGGUCAUGGCAUUGAUCUG | | | [681-699] ORF |
| 310 | 346 | UGCAUGACCCAGAUCAAUG | 758 | CAUUGAUCUGGGUCAUGCA | | | [672-690] ORF |
| 311 | 347 | ACUGAUCACCAAGUAGCCA | 759 | UGGCUACUUGGUGAUCAGU | | | [79-97] 5'UTR |
| 312 | 348 | ACACGACACCGGAUAAACC | 760 | GGUUUAUCCGGUGUCGUGU | Chn | | [301-319] ORF |
| 313 | 349 | UACUUUUGUAGAGAGAGC | 761 | GCUCUCUCUACAAAAAGUA | | | [1222-1240] 3'UTR |
| 314 | 350 | CUGAAGAAAGAUAGCUCGC | 762 | GCGAGCUAUCUUUCUUCAG | | | [429-447] ORF |
| 315 | 351 | AGCCAGCUGAAAACACUGA | 763 | UCAGUGUUUUCAGCUGGCU | GP,Chn | | [399-417] ORF |
| 316 | 352 | AAAGUCAUCAAAGCCUAUU | 764 | AAUAGGCUUUGAUGACUUU | | | [341-359] ORF |
| 317 | 353 | CUGAGCACAGAAAGUCAUC | 765 | GAUGACUUUCUGUGCUCAG | Rat,Ms | | [331-349] ORF |
| 318 | 354 | AGUCUGAAGAAAGAGAGAC | 766 | GUCUCUUUUACUUGAGACU | | | [142-160] 5'UTR |
| 319 | 355 | UGCUCUGAAGAAAGAUAGC | 767 | GCUAUCUUUCUUCAGAGCA | | | [425-443] ORF |
| 320 | 356 | UAAAAUAUCUUCCUUUGGG | 768 | CCCAAAGGAAGAUAUUUUA | Rat,Ms | | [1392-1410] 3'UTR |
| 321 | 357 | GUGAUGCCAAAGAUGUUUG | 769 | CAAACAUCUUUGGCAUCAC | Rat,Ms | | [1363-1381] 3'UTR |
| 322 | 358 | AAUACUGGGAGAGAAGAGG | 770 | CCUCUUCUCUCCCAGUAUU | | | [1154-1172] 3'UTR |
| 323 | 359 | AAUAAAUGAAAGUCUGAGC | 771 | GCUCAGACUUUCAUUUAUU | | | [383-401] ORF |
| 324 | 360 | AAACCAAAGACAGCAUCUG | 772 | CAGAUGCUGUCUUUGGUUU | | | [315-333] ORF |
| 325 | 361 | AGUUUGCUUUCCUCAUUCC | 773 | GGAAUGAGGAAAGCAAACU | | | [919-937] ORF |
| 326 | 362 | CUGGAAAUGACAGUGAAGC | 774 | GCUUCACUGUCAUUUCCAG | Rat | | [477-495] ORF |
| 327 | 363 | CAUUCCAAGCUGGAGAAGG | 775 | CCUUCUCCAGCUUGGAAUG | Rat,GP,Chn | | [450-468] ORF |
| 328 | 364 | AACACUGAUUUUGGAUGCU | 776 | AGCAUCCAAAAUCAGUGUU | | | [410-428] ORF |
| 329 | 365 | UUUUUAUGUGAUGCCAAAG | 777 | CUUUGGCAUCACAUAAAAA | Rat,Ms | | [1356-1374] 3'UTR |
| 330 | 366 | AAAGCUCAGAUGACAUUUC | 778 | GAAAUGUCAUCUGAGCUUU | | | [1317-1335] 3'UTR |
| 331 | 367 | AUUCUGGAAAUGACAGUGA | 779 | UCACUGUCAUUUCCAGAAU | Rat | | [474-492] ORF |
| 332 | 368 | ACAGAAAGUCAUCAAAGCC | 780 | GGCUUUGAUGACUUUCUGU | Rat,Ms,GP,Chn | | [337-355] ORF |

FIGURE 4 Continued

| | | | | | | |
|---|---|---|---|---|---|---|
| 333 | 369 | AUGCCAGCUGAUAUAAUGG | 781 | CCAUUAUAUCAGCUGGCAU | Rat,Ms,Chn | [237-255] ORF |
| 334 | 370 | UCAUAUUGGAUUGCGCCUU | 782 | AAGGCGCAAUCCAAUAUGA | Rat,Ms | [1289-1307] 3'UTR |
| 335 | 371 | GUUUGCUUUCCUCAUUCCC | 783 | GGGAAUGAGGAAAGCAAAC | | [920-938] ORF |
| 336 | 372 | AAGAAAGAUAGCUCGCGGC | 784 | GCCCGCGAGCUAUCUUUCUU | | [432-450] ORF |
| 337 | 373 | AUGGAGAAAAAUUCCUCGU | 785 | ACGAGGAAUUUUUCUCCAU | Rat,Chn | [252-270] ORF |
| 338 | 374 | GUCUACCUCUCUCCUUGGU | 786 | ACCAAGGAGAGAGGUAGAC | Rat,Ms | [46-64] 5'UTR |
| 339 | 375 | AAGAUGUUUGAAAAUGCUC | 787 | GAGCAUUUUCAAACAUCUU | Ms | [1372-1390] 3'UTR |
| 340 | 376 | UUUUUGUAGAGAGCUGU | 788 | ACAGCUCUCUCUACAAAAA | | [1225-1243] 3'UTR |
| 341 | 377 | GAAAUGACAGUGAAGCACC | 789 | GGUGCUUCACUGUCAUUUC | Rat | [480-498] ORF |
| 342 | 378 | UGCUCUUAAAAUAUCUUCC | 790 | GGAAGAUAUUUUAAGAGCA | Rat,Ms | [1386-1404] 3'UTR |
| 343 | 379 | UAUUAAGUGACUGACCAUG | 791 | CAUGGUCAGUCACUUAAUA | Rat,Ms,GP | [1243-1261] 3'UTR |
| 344 | 380 | AAAACACUGAUUUGGAUG | 792 | CAUCCAAAAUCAGUGUUUU | Rat,Ms,GP,Chn | [408-426] ORF |
| 345 | 381 | UCAAUGCCAUGACCUACCC | 793 | GGGUAGGUCAUGGCAUUGA | | [685-703] ORF |
| 346 | 382 | ACAUUCUGGAAAUGACAGU | 794 | ACUGUCAUUUCCAGAAUGU | Rat | [472-490] ORF |
| 347 | 383 | UGAAGAAAGAUAGCUCGCG | 795 | CGCGAGCUAUCUUUCUUCA | | [430-448] ORF |
| 348 | 384 | UGGAGAAAAAUUCCUCGUC | 796 | GACGAGGAAUUUUUCUCCA | Rat,Chn | [253-271] ORF |
| 349 | 385 | UUUUUCGUGAAGAACUCCA | 797 | UGGAGUUCUUCACGAAAAA | | [176-194] 5'UTR |
| 350 | 386 | UACUGAUCACCAAGUAGCC | 798 | GGCUACUUGGUGAUCAGUA | | [78-96] 5'UTR |
| 351 | 387 | AUUCCAAGCUGGAGAAGGC | 799 | GCCUUCUCCAGCUUGGAAU | Rat,GP,Chn | [451-469] ORF |
| 352 | 388 | CAUCUGAGCACAGAAAGUC | 800 | GACUUUCUGUGCUCAGAUG | | [328-346] ORF |
| 353 | 389 | AAAGUCUCAAGUAAAAGAG | 801 | CUCUUUUACUUGAGACUUU | | [140-158] 5'UTR |
| 354 | 390 | AUAUUGGAUUGCGCCUUUG | 802 | CAAAGGCGCAAUCCAAUAU | Rat,Ms | [1291-1309] 3'UTR |
| 355 | 391 | UCCCUCCGGACUCUAAACA | 803 | UGUUUAGAGUCCGGAGGGA | | [1127-1145] 3'UTR |
| 356 | 392 | CAACUGCAUGACCCAGAUC | 804 | GAUCUGGGUCAUGCAGUUG | Rat,Ms,GP,Chn | [668-686] ORF |
| 357 | 393 | AAACACUGAUUUUGGAUGC | 805 | GCAUCCAAAAUCAGUGUUU | Rat,Ms,GP,Chn | [409-427] ORF |
| 358 | 394 | AAAGACAGCAUCUGAGCAC | 806 | GUGCUCAGAUGCUGUCUUU | | [320-338] ORF |
| 359 | 395 | AAUGGAGAAAAAUUCCUCG | 807 | CGAGGAAUUUUUCUCCAUU | Rat,Chn | [251-269] ORF |
| 360 | 396 | UUCUUUUUCGUGAAGAACU | 808 | AGUUCUUCACGAAAAAGAA | | [173-191] 5'UTR |
| 361 | 397 | UUACUUUUUGUAGAGAGAG | 809 | CUCUCUCUACAAAAAGUAA | | [1221-1239] 3'UTR |
| 362 | 398 | ACCCAGAUCAAUGCCAUGA | 810 | UCAUGGCAUUGAUCUGGGU | | [678-696] ORF |
| 363 | 399 | AUGACCCAGAUCAAUGCCA | 811 | UGGCAUUGAUCUGGGUCAU | | [675-693] ORF |
| 364 | 400 | CUUCAGCAGUGCAUGAAC | 812 | GUUCAGCACUCGCUGAAG | Rat,Ms,GP,Chn | [575-593] ORF |
| 365 | 401 | CAUUCUGGAAAUGACAGUG | 813 | CACUGUCAUUUCCAGAAUG | Rat | [473-491] ORF |
| 366 | 402 | CACUUGCUCAGUAGUUUUG | 814 | CAAAACUACUGAGCAAGUG | | [119-137] 5'UTR |
| 367 | 403 | AUGGCCAGUUUGCUUUCCU | 815 | AGGAAAGCAAACUGGCCAU | | [913-931] ORF |
| 368 | 404 | UGAAAGUCUGAGCCAGCUG | 816 | CAGCUGGCUCAGACUUUCA | | [389-407] ORF |
| 369 | 405 | AUUUCGUUUUUACACGAG | 817 | CUCGUGUAAAAAACGAAAU | Rat,Ms | [1331-1349] 3'UTR |
| 370 | 406 | UAAGUGGUUACUUUGUGUU | 818 | AACACAAAGUAACCACUUA | | [1184-1202] 3'UTR |
| 371 | 407 | AAUAUAAUAAACCCUCAGC | 819 | GCUGAGGGUUUAUUAUAUU | | [101-119] 5'UTR |
| 372 | 408 | CUUUCCUCAUUCCCAACGG | 820 | CCGUUGGGAAUGAGGAAAG | | [925-943] ORF |
| 373 | 409 | CUACUGAUCACCAAGUAGC | 821 | GCUACUUGGUGAUCAGUAG | | [77-95] 5'UTR |
| 374 | 410 | ACAUUUCGUUUUUUACACG | 822 | CGUGUAAAAAACGAAAUGU | Rat,Ms | [1329-1347] 3'UTR |
| 375 | 411 | GUUCAUAUUGGAUUGCGCC | 823 | GGCGCAAUCCAAUAUGAAC | Rat,Ms | [1287-1305] 3'UTR |
| 376 | 412 | UAAGUGACUGACCAUGCAC | 824 | GUGCAUGGUCAGUCACUUA | Rat,Ms,GP | [1246-1264] 3'UTR |
| 377 | 413 | AUUAAGUGACUGACCAUGC | 825 | GCAUGGUCAGUCACUUAAU | Rat,Ms,GP | [1244-1262] 3'UTR |
| 378 | 414 | CUGAUCACCAAGUAGCCAC | 826 | GUGGCUACUUGGUGAUCAG | | [80-98] 5'UTR |
| 379 | 415 | UAAUGGAGAAAAAUUCCUC | 827 | GAGGAAUUUUUCUCCAUUA | Rat,Ms,Chn | [250-268] ORF |
| 380 | 416 | UUCCCUCCGGACUCUAAAC | 828 | GUUUAGAGUCCGGAGGGAA | | [1126-1144] 3'UTR |
| 381 | 417 | GCUUUCCUCAUUCCCAACG | 829 | CGUUGGGAAUGAGGAAAGC | | [924-942] ORF |
| 382 | 418 | CAUGACCCAGAUCAAUGCC | 830 | GGCAUUGAUCUGGGUCAUG | | [674-692] ORF |
| 383 | 419 | ACACUGAUUUUGGAUGCUC | 831 | GAGCAUCCAAAAUCAGUGU | | [411-429] ORF |
| 384 | 420 | AUAAACCAAAGACAGCAUC | 832 | GAUGCUGUCUUUGGUUUAU | | [313-331] ORF |
| 385 | 421 | GCUGAUAACAGCGGAAUCC | 833 | GGAUUCCGCUGUUAUCAGC | Ms | [24-42] 5'UTR |
| 386 | 422 | UUAAUACCGAGGUGCGCAC | 834 | GUGCGCACCUCGGUAUUAA | | [628-646] ORF |
| 387 | 423 | CUGAUAACAGCGGAAUCCC | 835 | GGGAUUCCGCUGUUAUCAG | Ms | [25-43] 5'UTR |
| 388 | 424 | UAAACCCUCAGCACUUGCU | 836 | AGCAAGUGCUGAGGGUUUA | | [108-126] 5'UTR |
| 389 | 425 | AUUAUGUGGUUACUUUGUG | 837 | CACAAAGUAACCACUUAAU | | [1182-1200] 3'UTR |
| 390 | 426 | AACUUGAAAUACUGGGAGAG | 838 | CUCUCCCAGUAUUUCAAGUU | | [1148-1166] 3'UTR |
| 391 | 427 | AAACCCUCAGCACUUGCUC | 839 | GAGCAAGUGCUGAGGGUUU | | [109-127] 5'UTR |
| 392 | 428 | UAAUACCGAGGUGCGCACU | 840 | AGUGCGCACCUCGGUAUUA | | [629-647] ORF |
| 393 | 429 | AAGAUAGCUCGCGGCAUUC | 841 | GAAUGCCGCGAGCUAUCUU | | [436-454] ORF |
| 394 | 430 | UCUCAAGUAAAAGAGACAC | 842 | GUGUCUCUUUUACUUGAGA | | [144-162] 5'UTR |
| 395 | 431 | UUCAGCGAGUGCAUGAACG | 843 | CGUUCAUGCACUCGCUGAA | Rat,Ms,GP,Chn | [576-594] ORF |
| 396 | 432 | AUUCUUUUUCGUGAAGAAC | 844 | GUUCUUCACGAAAAAGAAU | | [172-190] 5'UTR |
| 397 | 433 | UUCAUAUUGGAUUGCGCCU | 845 | AGGCGCAAUCCAAUAUGAA | Rat,Ms | [1288-1306] 3'UTR |
| 398 | 434 | UUUCCUCAUUCCCAACGGG | 846 | CCCGUUGGGAAUGAGGAAA | | [926-944] ORF |
| 399 | 435 | UACCUCUCUCCUUGGUCCU | 847 | AGGACCAAGGAGAGAGGUA | Rat,Ms | [49-67] 5'UTR |
| 400 | 436 | AUAAAUGAAAGUCUGAGCC | 848 | GGCUCAGACUUUCAUUUAU | | [384-402] ORF |

FIGURE 4 Continued

| | | | | | | | |
|---|---|---|---|---|---|---|---|
| 401 | 437 | CUUUUUCGUGAAGAACUCC | 849 | GGAGUUCUUCACGAAAAAG | | | [175-193] 5'UTR |
| 402 | 438 | AUGUUCAUAUUGGAUUGCG | 850 | CGCAAUCCAAUAUGAACAU | Rat,Ms | | [1285-1303] 3'UTR |
| 403 | 439 | GAUGGCCAGUUUGCUUUCC | 851 | GGAAAGCAAACUGGCCAUC | | | [912-930] ORF |
| 404 | 440 | AAGGUGUUUGGAGGCUUCC | 852 | GGAAGCCUCCAAACACCUU | | | [876-894] ORF |
| 405 | 441 | AUGACAGUGAAGCACCUCC | 853 | GGAGGUGCUUCACUGUCAU | Rat,GP,Chn | | [483-501] ORF |
| 406 | 442 | UUCUUUUUUAUGUGAUGCC | 854 | GGCAUCACAUAAAAAAGAA | | | [1352-1370] 3'UTR |
| 407 | 443 | AUCAAUGCCAUGACCUACC | 855 | GGUAGGUCAUGGCAUUGAU | | | [684-702] ORF |
| 408 | 444 | UCUACCUCUCUCCUUGGUC | 856 | GACCAAGGAGAGAGGUAGA | Rat,Ms | | [47-65] 5'UTR |
| 409 | 445 | AUAAACCCUCAGCACUUGC | 857 | GCAAGUGCUGAGGGUUUAU | | | [107-125] 5'UTR |
| 410 | 446 | AAUGACAGUGAAGCACCUC | 858 | GAGGUGCUUCACUGUCAUU | Rat | | [482-500] ORF |
| 411 | 447 | UAUGUUCAUAUUGGAUUGC | 859 | GCAAUCCAAUAUGAACAUA | Rat,Ms | | [1284-1302] 3'UTR |
| 412 | 448 | AACAGCGCUACUGAUCACC | 860 | GGUGAUCAGUAGCGCUGUU | | | [70-88] 5'UTR |

| | | | | | | | |
|---|---|---|---|---|---|---|---|
| 262 | 861 | CAUUCUGGAAAUGACAGUGAAGC | 1244 | GCUUCACUGUCAUUUCCAGAAUG | Rat | | [473-495] ORF |
| 263 | 862 | ACAUUCUGGAAAUGACAGUGAAG | 1245 | CUUCACUGUCAUUUCCAGAAUGU | Rat | | [472-494] ORF |
| 264 | 863 | GACAUUCUGGAAAUGACAGUGAA | 1246 | UUCACUGUCAUUUCCAGAAUGUC | Rat | | [471-493] ORF |
| 265 | 864 | AACACUGAUUUUGGAUGCUCUGA | 1247 | UCAGAGCAUCCAAAAUCAGUGUU | | | [410-432] ORF |
| 266 | 865 | AAACACUGAUUUUGGAUGCUCUG | 1248 | CAGAGCAUCCAAAAUCAGUGUUU | | | [409-431] ORF |
| 267 | 866 | AAAACACUGAUUUUGGAUGCUCU | 1249 | AGAGCAUCCAAAAUCAGUGUUUU | | | [408-430] ORF |
| 268 | 867 | GUAUUAAGUGACUGACCAUGCAC | 1250 | GUGCAUGGUCAGUCACUUAAUAC | Rat,Ms,GP | | [1242-1264] 3'UTR |
| 269 | 868 | UGUAUUAAGUGACUGACCAUGCA | 1251 | UGCAUGGUCAGUCACUUAAUACA | Rat,Ms,GP | | [1241-1263] 3'UTR |
| 270 | 869 | CUGUAUUAAGUGACUGACCAUGC | 1252 | GCAUGGUCAGUCACUUAAUACAG | Rat,Ms,GP | | [1240-1262] 3'UTR |
| 271 | 870 | GCUGUAUUAAGUGACUGACCAUG | 1253 | CAUGGUCAGUCACUUAAUACAGC | Rat,Ms,GP | | [1239-1261] 3'UTR |
| 272 | 871 | AGCUGUAUUAAGUGACUGACCAU | 1254 | AUGGUCAGUCACUUAAUACAGCU | Rat,Ms,GP | | [1238-1260] 3'UTR |
| 273 | 872 | GCAUCUGAGCACAGAAAGUCAUC | 1255 | GAUGACUUUCUGUGCUCAGAUGC | | | [327-349] ORF |
| 274 | 873 | AGCAUCUGAGCACAGAAAGUCAU | 1256 | AUGACUUUCUGUGCUCAGAUGCU | | | [326-348] ORF |
| 275 | 874 | AAAGACAGCAUCUGAGCACAGAA | 1257 | UUCUGUGCUCAGAUGCUGUCUUU | | | [320-342] ORF |
| 276 | 875 | GUGAAGAACUCCAAAAAUAAAAU | 1258 | AUUUUAUUUUUGGAGUUCUUCAC | | | [182-204] 5'UTR |
| 277 | 876 | CUUUUUCGUGAAGAACUCCAAAA | 1259 | UUUUGGAGUUCUUCACGAAAAAG | | | [175-197] 5'UTR |
| 278 | 877 | UCUUUUUCGUGAAGAACUCCAAA | 1260 | UUUGGAGUUCUUCACGAAAAAGA | | | [174-196] 5'UTR |
| 279 | 878 | AGAUCAAUGCCAUGACCUACCCC | 1261 | GGGGUAGGUCAUGGCAUUGAUCU | | | [682-704] ORF |
| 280 | 879 | CAGAUCAAUGCCAUGACCUACCC | 1262 | GGGUAGGUCAUGGCAUUGAUCUG | | | [681-703] ORF |
| 281 | 880 | CCAGAUCAAUGCCAUGACCUACC | 1263 | GGUAGGUCAUGGCAUUGAUCUGG | | | [680-702] ORF |
| 282 | 881 | CCCAGAUCAAUGCCAUGACCUAC | 1264 | GUAGGUCAUGGCAUUGAUCUGGG | | | [679-701] ORF |
| 283 | 882 | ACCCAGAUCAAUGCCAUGACCUA | 1265 | UAGGUCAUGGCAUUGAUCUGGGU | | | [678-700] ORF |
| 284 | 883 | AUAGCUCGCGGCAUUCCAAGCUG | 1266 | CAGCUUGGAAUGCCGCGAGCUAU | | | [439-461] ORF |
| 285 | 884 | GAUAGCUCGCGGCAUUCCAAGCU | 1267 | AGCUUGGAAUGCCGCGAGCUAUC | | | [438-460] ORF |
| 286 | 885 | AGAUAGCUCGCGGCAUUCCAAGC | 1268 | GCUUGGAAUGCCGCGAGCUAUCU | | | [437-459] ORF |
| 287 | 886 | AAGAUAGCUCGCGGCAUUCCAAG | 1269 | CUUGGAAUGCCGCGAGCUAUCUU | | | [436-458] ORF |
| 288 | 887 | AAAGAUAGCUCGCGGCAUUCCAA | 1270 | UUGGAAUGCCGCGAGCUAUCUUU | | | [435-457] ORF |
| 289 | 888 | CGCUACUGAUCACCAAGUAGCCA | 1271 | UGGCUACUUGGUGAUCAGUAGCG | | | [75-97] 5'UTR |
| 290 | 889 | GCGCUACUGAUCACCAAGUAGCC | 1272 | GGCUACUUGGUGAUCAGUAGCGC | | | [74-96] 5'UTR |
| 291 | 890 | AGCGCUACUGAUCACCAAGUAGC | 1273 | GCUACUUGGUGAUCAGUAGCGCU | | | [73-95] 5'UTR |
| 292 | 891 | AUGAAAGUCUGAGCCAGCUGAAA | 1274 | UUUCAGCUGGCUCAGACUUUCAU | | | [388-410] ORF |
| 293 | 892 | AAUGAAAGUCUGAGCCAGCUGAA | 1275 | UUCAGCUGGCUCAGACUUUCAUU | | | [387-409] ORF |
| 294 | 893 | AAAUGAAAGUCUGAGCCAGCUGA | 1276 | UCAGCUGGCUCAGACUUUCAUUU | | | [386-408] ORF |
| 295 | 894 | UGGAAAUGACAGUGAAGCACCUC | 1277 | GAGGUGCUUCACUGUCAUUUCCA | Rat | | [478-500] ORF |
| 296 | 895 | CUGGAAAUGACAGUGAAGCACCU | 1278 | AGGUGCUUCACUGUCAUUUCCAG | Rat | | [477-499] ORF |
| 297 | 896 | UCUGGAAAUGACAGUGAAGCACC | 1279 | GGUGCUUCACUGUCAUUUCCAGA | Rat | | [476-498] ORF |
| 298 | 897 | CCGGACUCUAAACAGGAACUUGA | 1280 | UCAAGUUCCUGUUUAGAGUCCGG | | | [1132-1154] 3'UTR |
| 299 | 898 | CCAGUUUGCUUUCCUCAUUCCCA | 1281 | UGGGAAUGAGGAAAGCAAACUGG | | | [917-939] ORF |
| 300 | 899 | GAGCUGGUGCUGAUAACAGCGGA | 1282 | UCCGCUGUUAUCAGCACCAGCUC | Ms | | [16-38] 5'UTR |
| 301 | 900 | AACAGCGCUACUGAUCACCA | 1283 | UGGGUGAUCAGUAGCGCUGUUCCA | | | [67-89] 5'UTR |
| 302 | 901 | CCAUGCACUAUAUUUGUAUAUAU | 1284 | AUAUAUACAAAUAUAGUGCAUGG | | | [1257-1279] 3'UTR |
| 303 | 902 | ACCAUGCACUAUAUUUGUAUAUA | 1285 | UAUAUACAAAUAUAGUGCAUGGU | | | [1256-1278] 3'UTR |
| 304 | 903 | GACCAUGCACUAUAUUUGUAUAU | 1286 | AUAUACAAAUAUAGUGCAUGGUC | | | [1255-1277] 3'UTR |
| 305 | 904 | UGACCAUGCACUAUAUUUGUAUA | 1287 | UAUACAAAUAUAGUGCAUGGUCA | | | [1254-1276] 3'UTR |
| 306 | 905 | CUGACCAUGCACUAUAUUUGUAU | 1288 | AUACAAAUAUAGUGCAUGGUCAG | | | [1253-1275] 3'UTR |
| 307 | 906 | CCAGCUGAAAACACUGAUUUUGG | 1289 | CCAAAAUCAGUGUUUUCAGCUGG | GP,Chn | | [401-423] ORF |
| 308 | 907 | GCCAGCUGAAAACACUGAUUUUG | 1290 | CAAAAUCAGUGUUUUCAGCUGGC | GP,Chn | | [400-422] ORF |
| 309 | 908 | AGCCAGCUGAAAACACUGAUUUU | 1291 | AAAAUCAGUGUUUUCAGCUGGCU | GP,Chn | | [399-421] ORF |
| 310 | 909 | UGCCAAAGAUGUUUGAAA | 1292 | UUUCAAACAUCUUUGGCAUCACA | Rat,Ms | | [1362-1384] 3'UTR |
| 311 | 910 | AUGUGAUGCCAAAGAUGUUUGAA | 1293 | UUCAAACAUCUUUGGCAUCACAU | Rat,Ms | | [1361-1383] 3'UTR |
| 312 | 911 | UAUGUGAUGCCAAAGAUGUUUGA | 1294 | UCAAACAUCUUUGGCAUCACAUA | Rat,Ms | | [1360-1382] 3'UTR |
| 313 | 912 | CUUUUUGUAGAGAGAGCUGUAUU | 1295 | AAUACAGCUCUCUCUACAAAAAG | | | [1224-1246] 3'UTR |
| 314 | 913 | ACUUUUUGUAGAGAGAGCUGUAU | 1296 | AUACAGCUCUCUCUACAAAAAGU | | | [1223-1245] 3'UTR |
| 315 | 914 | UACUUUUUGUAGAGAGAGCUGUA | 1297 | UACAGCUCUCUCUACAAAAAGUA | | | [1222-1244] 3'UTR |

FIGURE 4 Continued

| | | | | | | | |
|---|---|---|---|---|---|---|---|
| 316 | 915 | GAAAGAUAGCUCGCGGCAUUCCA | 1298 | UGGAAUGCCGCGAGCUAUCUUUC | | [434-456] ORF |
| 317 | 916 | AGAAAGAUAGCUCGCGGCAUUCC | 1299 | GGAAUGCCGCGAGCUAUCUUUCU | | [433-455] ORF |
| 318 | 917 | AAGAAAGAUAGCUCGCGGCAUUC | 1300 | GAAUGCCGCGAGCUAUCUUUCUU | | [432-454] ORF |
| 319 | 918 | GAAGAAAGAUAGCUCGCGGCAUU | 1301 | AAUGCCGCGAGCUAUCUUUCUUC | | [431-453] ORF |
| 320 | 919 | UGAAGAAAGAUAGCUCGCGGCAU | 1302 | AUGCCGCGAGCUAUCUUUCUUCA | | [430-452] ORF |
| 321 | 920 | GAGCUGUAUUAAGUGACUGACCA | 1303 | UGGUCAGUCACUUAAUACAGCUC | Rat,Ms,GP | [1237-1259] 3'UTR |
| 322 | 921 | AGAGCUGUAUUAAGUGACUGACC | 1304 | GGUCAGUCACUUAAUACAGCUCU | Rat,Ms,GP | [1236-1258] 3'UTR |
| 323 | 922 | GAGAGCUGUAUUAAGUGACUGAC | 1305 | GUCAGUCACUUAAUACAGCUCUC | Rat,Ms,GP | [1235-1257] 3'UTR |
| 324 | 923 | AGAGAGCUGUAUUAAGUGACUGA | 1306 | UCAGUCACUUAAUACAGCUCUCU | Rat,Ms,GP | [1234-1256] 3'UTR |
| 325 | 924 | AGAGAGAGCUGUAUUAAGUGACU | 1307 | AGUCACUUAAUACAGCUCUCUCU | | [1232-1254] 3'UTR |
| 326 | 925 | UAGAGAGAGCUGUAUUAAGUGAC | 1308 | GUCACUUAAUACAGCUCUCUCUA | | [1231-1253] 3'UTR |
| 327 | 926 | AAAGUCAUCAAAGCCUAUUAUGG | 1309 | CCAUAAUAGGCUUUGAUGACUUU | | [341-363] ORF |
| 328 | 927 | GAAAGUCUCAAGUAAAAGAGACA | 1310 | UGUCUCUUUUACUUGAGACUUUC | | [139-161] 5'UTR |
| 329 | 928 | UGAAAGUCUCAAGUAAAAAGAGAC | 1311 | GUCUCUUUUACUUGAGACUUUCA | | [138-160] 5'UTR |
| 330 | 929 | UAGUUUUGUGAAAGUCUCAAGUA | 1312 | UACUUGAGACUUUCACAAAACUA | | [130-152] 5'UTR |
| 331 | 930 | GUAGUUUUGUGAAAGUCUCAAGU | 1313 | ACUUGAGACUUUCACAAAACUAC | | [129-151] 5'UTR |
| 332 | 931 | AGUAGUUUUGUGAAAGUCUCAAG | 1314 | CUUGAGACUUUCACAAAACUACU | | [128-150] 5'UTR |
| 333 | 932 | CAGUAGUUUUGUGAAAGUCUCAA | 1315 | UUGAGACUUUCACAAAACUACUG | | [127-149] 5'UTR |
| 334 | 933 | GAGAGAGCUGUAUUAAGUGACUG | 1316 | CAGUCACUUAAUACAGCUCUCUC | Rat,Ms,GP | [1233-1255] 3'UTR |
| 335 | 934 | GAAGAGGACUUUUUUGAUUAAGU | 1317 | ACUUAAUCAAAAAAGUCCUCUUC | | [1166-1188] 3'UTR |
| 336 | 935 | UCCGGACUCUAAACAGGAACUUG | 1318 | CAAGUUCCUGUUUAGAGUCCGGA | | [1131-1153] 3'UTR |
| 337 | 936 | CUCCGGACUCUAAACAGGAACUU | 1319 | AAGUUCCUGUUUAGAGUCCGGAG | | [1130-1152] 3'UTR |
| 338 | 937 | CCUCCGGACUCUAAACAGGAACU | 1320 | AGUUCCUGUUUAGAGUCCGGAGG | | [1129-1151] 3'UTR |
| 339 | 938 | CCCUCCGGACUCUAAACAGGAAC | 1321 | GUUCCUGUUUAGAGUCCGGAGGG | | [1128-1150] 3'UTR |
| 340 | 939 | UCCCUCCGGACUCUAAACAGGAA | 1322 | UUCCUGUUUAGAGUCCGGAGGGA | | [1127-1149] 3'UTR |
| 341 | 940 | CUGCAUGACCCAGAUCAAUGCCA | 1323 | UGGCAUUGAUCUGGGUCAUGCAG | | [671-693] ORF |
| 342 | 941 | AUUAUGGAGAAAAGACGAAGAGC | 1324 | GCUCUUCGUCUUUUCUCCAUAAU | | [357-379] ORF |
| 343 | 942 | UAUUAUGGAGAAAAGACGAAGAG | 1325 | CUCUUCGUCUUUUCUCCAUAAUA | | [356-378] ORF |
| 344 | 943 | CUAUUAUGGAGAAAAGACGAAGA | 1326 | UCUUCGUCUUUUCUCCAUAAUAG | | [355-377] ORF |
| 345 | 944 | CCUAUUAUGGAGAAAAGACGAAG | 1327 | CUUCGUCUUUUCUCCAUAAUAGG | | [354-376] ORF |
| 346 | 945 | AUAUUGGAUUGCGCCUUUGUAUU | 1328 | AAUACAAAGGCGCAAUCCAAUAU | Rat,Ms | [1291-1313] 3'UTR |
| 347 | 946 | CAUAUUGGAUUGCGCCUUUGUAU | 1329 | AUACAAAGGCGCAAUCCAAUAUG | Rat,Ms | [1290-1312] 3'UTR |
| 348 | 947 | UCAUAUUGGAUUGCGCCUUUGUA | 1330 | UACAAAGGCGCAAUCCAAUAUGA | Rat,Ms | [1289-1311] 3'UTR |
| 349 | 948 | UAAGUGACUGACCAUGCACUAUA | 1331 | UAUAGUGCAUGGUCAGUCACUUA | GP | [1246-1268] 3'UTR |
| 350 | 949 | UUAAGUGACUGACCAUGCACUAU | 1332 | AUAGUGCAUGGUCAGUCACUUAA | Rat,Ms,GP | [1245-1267] 3'UTR |
| 351 | 950 | AUUAAGUGACUGACCAUGCACUA | 1333 | UAGUGCAUGGUCAGUCACUUAAU | Rat,Ms,GP | [1244-1266] 3'UTR |
| 352 | 951 | UAUUAAGUGACUGACCAUGCACU | 1334 | AGUGCAUGGUCAGUCACUUAAUA | Rat,Ms,GP | [1243-1265] 3'UTR |
| 353 | 952 | AGGACUUUUUUGAUUAAGUGGUU | 1335 | AACCACUUAAUCAAAAAAGUCCU | | [1170-1192] 3'UTR |
| 354 | 953 | GAGGACUUUUUUGAUUAAGUGGU | 1336 | ACCACUUAAUCAAAAAAGUCCUC | | [1169-1191] 3'UTR |
| 355 | 954 | AGAGGACUUUUUUGAUUAAGUGG | 1337 | CCACUUAAUCAAAAAAGUCCUCU | | [1168-1190] 3'UTR |
| 356 | 955 | AAGAGGACUUUUUUGAUUAAGUG | 1338 | CACUUAAUCAAAAAAGUCCUCUU | | [1167-1189] 3'UTR |
| 357 | 956 | CCUCUCUUCCCUCCGGACUCUAA | 1339 | UUAGAGUCCGGAGGGAAGAGAGG | | [1120-1142] 3'UTR |
| 358 | 957 | AACCAAAGACAGCAUCUGACAC | 1340 | GUGUCAGAUGCUGUCUUUGGUU | | [316-338] ORF |
| 359 | 958 | AAACCAAAGACAGCAUCUGAGCA | 1341 | UGCUCAGAUGCUGUCUUUGGUUU | | [315-337] ORF |
| 360 | 959 | UAAACCAAAGACAGCAUCUGAGC | 1342 | GCUCAGAUGCUGUCUUUGGUUUA | | [314-336] ORF |
| 361 | 960 | AUAAACCAAAGACAGCAUCUGAG | 1343 | CUCAGAUGCUGUCUUUGGUUUAU | | [313-335] ORF |
| 362 | 961 | GAUAAACCAAAGACAGCAUCUGA | 1344 | UCAGAUGCUGUCUUUGGUUUAUC | | [312-334] ORF |
| 363 | 962 | ACUGACCAUGCACUAUAUUUGUA | 1345 | UACAAAUAUAGUGCAUGGUCAGU | GP | [1252-1274] 3'UTR |
| 364 | 963 | AAAUGCCAGCUGAUAUAAUGGAG | 1346 | CUCCAUUAUAUCAGCUGGCAUUU | Rat,Ms,Chn | [235-257] 5'UTR+ORF |
| 365 | 964 | AAAAUGCCAGCUGAUAUAAUGGA | 1347 | UCCAUUAUAUCAGCUGGCAUUUU | Rat,Ms,Chn | [234-256] 5'UTR+ORF |
| 366 | 965 | UGAAUACGGGAGAGAAGAGGAC | 1348 | GUCCUCUUCUCUCCCAGUAUUCA | | [1152-1174] 3'UTR |
| 367 | 966 | UUGAAUACGGGAGAGAAGAGGA | 1349 | UCCUCUUCUCUCCCAGUAUUCAA | | [1151-1173] 3'UTR |
| 368 | 967 | CUAAACAGGAACUUGAAUACGG | 1350 | CCAGUAUUCAAGUUCCUGUUUAG | | [1139-1161] 3'UTR |
| 369 | 968 | UCUAAACAGGAACUUGAAUACUG | 1351 | CAGUAUUCAAGUUCCUGUUUAGA | | [1138-1160] 3'UTR |
| 370 | 969 | UCAGUAGUUUUGUGAAAGUCUCA | 1352 | UGAGACUUUCACAAAACUACUGA | | [126-148] 5'UTR |
| 371 | 970 | GAUGUUUGAAAAUGCUCUUAAAA | 1353 | UUUUAAGAGCAUUUUCAAACAUC | Ms | [1374-1396] 3'UTR |
| 372 | 971 | AGAUGUUUGAAAAUGCUCUUAAA | 1354 | UUUAAGAGCAUUUUCAAACAUCU | Ms | [1373-1395] 3'UTR |
| 373 | 972 | AAGAUGUUUGAAAAUGCUCUUAA | 1355 | UUAAGAGCAUUUUCAAACAUCUU | Ms | [1372-1394] 3'UTR |
| 374 | 973 | AAAGAUGUUUGAAAAUGCUCUUA | 1356 | UAAGAGCAUUUUCAAACAUCUUU | Ms | [1371-1393] 3'UTR |
| 375 | 974 | CAAAGAUGUUUGAAAAUGCUCUU | 1357 | AAGAGCAUUUUCAAACAUCUUUG | Ms | [1370-1392] 3'UTR |
| 376 | 975 | GUGGUUACUUUGUGUUUUUUUAA | 1358 | UUAAAAAAACACAAAGUAACCAC | | [1187-1209] 3'UTR |
| 377 | 976 | AGUGGUUACUUUGUGUUUUUUUA | 1359 | UAAAAAAACACAAAGUAACCACU | | [1186-1208] 3'UTR |
| 378 | 977 | AAGUGGUUACUUUGUGUUUUUUU | 1360 | AAAAAAACACAAAGUAACCACUU | | [1185-1207] 3'UTR |
| 379 | 978 | UAAGUGGUUACUUUGUGUUUUUU | 1361 | AAAAAACACAAAGUAACCACUUA | | [1184-1206] 3'UTR |
| 380 | 979 | UUAAGUGGUUACUUUGUGUUUUU | 1362 | AAAAACACAAAGUAACCACUUAA | | [1183-1205] 3'UTR |
| 381 | 980 | AUACGGGAGAGAAGAGGACUUU | 1363 | AAAGUCCUCUUCUCUCCCAGUAU | | [1155-1177] 3'UTR |
| 382 | 981 | AAUACGGGAGAGAAGAGGACUU | 1364 | AAGUCCUCUUCUCUCCCAGUAUU | | [1154-1176] 3'UTR |
| 383 | 982 | ACGUGCGAGGGCGUUAAUACCGA | 1365 | UCGGUAUUAACGCCCUCGCACGU | | [615-637] ORF |

FIGURE 4 Continued

| | | | | | | |
|---|---|---|---|---|---|---|
| 384 | 983 | CACGUGCGAGGGCGUUAAUACCG | 1366 | CGGUAUUAACGCCCUCGCACGUG | | [614-636] ORF |
| 385 | 984 | CCACGUGCGAGGGCGUUAAUACC | 1367 | GGUAUUAACGCCCUCGCACGUGG | | [613-635] ORF |
| 386 | 985 | UCCACGUGCGAGGGCGUUAAUAC | 1368 | GUAUUAACGCCCUCGCACGUGGA | | [612-634] ORF |
| 387 | 986 | GUCCACGUGCGAGGGCGUUAAUA | 1369 | UAUUAACGCCCUCGCACGUGGAC | | [611-633] ORF |
| 388 | 987 | UAUAAAAGCUCAGAUGACAUUUC | 1370 | GAAAUGUCAUCUGAGCUUUUAUA | | [1313-1335] 3'UTR |
| 389 | 988 | UUAUAAAAGCUCAGAUGACAUUU | 1371 | AAAUGUCAUCUGAGCUUUUAUAA | | [1312-1334] 3'UTR |
| 390 | 989 | AUUAUAAAAGCUCAGAUGACAUU | 1372 | AAUGUCAUCUGAGCUUUUAUAAU | | [1311-1333] 3'UTR |
| 391 | 990 | UAUUAUAAAAGCUCAGAUGACAU | 1373 | AUGUCAUCUGAGCUUUUAUAAUA | | [1310-1332] 3'UTR |
| 392 | 991 | GUAUUAUAAAAGCUCAGAUGACA | 1374 | UGUCAUCUGAGCUUUUAUAAUAC | | [1309-1331] 3'UTR |
| 393 | 992 | CUCAGAUGACAUUUCGUUUUUUA | 1375 | UAAAAAACGAAAUGUCAUCUGAG | | [1321-1343] 3'UTR |
| 394 | 993 | GCUCAGAUGACAUUUCGUUUUUU | 1376 | AAAAAACGAAAUGUCAUCUGAGC | | [1320-1342] 3'UTR |
| 395 | 994 | AGCUCAGAUGACAUUUCGUUUUU | 1377 | AAAAACGAAAUGUCAUCUGAGCU | | [1319-1341] 3'UTR |
| 396 | 995 | AAGCUCAGAUGACAUUUCGUUUU | 1378 | AAAACGAAAUGUCAUCUGAGCUU | | [1318-1340] 3'UTR |
| 397 | 996 | AAAGCUCAGAUGACAUUUCGUUU | 1379 | AAACGAAAUGUCAUCUGAGCUUU | | [1317-1339] 3'UTR |
| 398 | 997 | GCCAAAGAUGUUUGAAAAUGCUC | 1380 | GAGCAUUUUCAAACAUCUUUGGC | Ms | [1368-1390] 3'UTR |
| 399 | 998 | CCUCAGCACUUGCUCAGUAGUUU | 1381 | AAACUACUGAGCAAGUGCUGAGG | | [113-135] 5'UTR |
| 400 | 999 | CCCUCAGCACUUGCUCAGUAGUU | 1382 | AACUACUGAGCAAGUGCUGAGGG | | [112-134] 5'UTR |
| 401 | 1000 | ACCCUCAGCACUUGCUCAGUAGU | 1383 | ACUACUGAGCAAGUGCUGAGGGU | | [111-133] 5'UTR |
| 402 | 1001 | AACCCUCAGCACUUGCUCAGUAG | 1384 | CUACUGAGCAAGUGCUGAGGGUU | | [110-132] 5'UTR |
| 403 | 1002 | AAACCCUCAGCACUUGCUCAGUA | 1385 | UACUGAGCAAGUGCUGAGGGUUU | | [109-131] 5'UTR |
| 404 | 1003 | UUCAUAUUGGAUUGCGCCUUUGU | 1386 | ACAAAGGCGCAAUCCAAUAUGAA | Rat,Ms | [1288-1310] 3'UTR |
| 405 | 1004 | GUUCAUAUUGGAUUGCGCCUUUG | 1387 | CAAAGGCGCAAUCCAAUAUGAAC | Rat,Ms | [1287-1309] 3'UTR |
| 406 | 1005 | UGUUCAUAUUGGAUUGCGCCUUU | 1388 | AAAGGCGCAAUCCAAUAUGAACA | Rat,Ms | [1286-1308] 3'UTR |
| 407 | 1006 | UCUCCUUGGUCCUGGAACAGCGC | 1389 | GCGCUGUUCCAGGACCAAGGAGA | | [55-77] 5'UTR |
| 408 | 1007 | CUCUCCUUGGUCCUGGAACAGCG | 1390 | CGCUGUUCCAGGACCAAGGAGAG | | [54-76] 5'UTR |
| 409 | 1008 | UCUCUCCUUGGUCCUGGAACAGC | 1391 | GCUGUUCCAGGACCAAGGAGAGA | | [53-75] 5'UTR |
| 410 | 1009 | CUCUCUCCUUGGUCCUGGAACAG | 1392 | CUGUUCCAGGACCAAGGAGAGAG | | [52-74] 5'UTR |
| 411 | 1010 | CCUCUCUCCUUGGUCCUGGAACA | 1393 | UGUUCCAGGACCAAGGAGAGAGG | | [51-73] 5'UTR |
| 412 | 1011 | CCAAAGAUGUUUGAAAAUGCUCU | 1394 | AGAGCAUUUUCAAACAUCUUUGG | Ms | [1369-1391] 3'UTR |
| 413 | 1012 | UUUCGUUUUUUACACGAGAUUUC | 1395 | GAAAUCUCGUGUAAAAAACGAAA | Rat,Ms | [1332-1354] 3'UTR |
| 414 | 1013 | AUUUCGUUUUUUACACGAGAUUU | 1396 | AAAUCUCGUGUAAAAAACGAAAU | Rat,Ms | [1331-1353] 3'UTR |
| 415 | 1014 | CAUUUCGUUUUUUACACGAGAUU | 1397 | AAUCUCGUGUAAAAAACGAAAUG | Rat,Ms | [1330-1352] 3'UTR |
| 416 | 1015 | ACAUUUCGUUUUUUACACGAGAU | 1398 | AUCUCGUGUAAAAAACGAAAUGU | Rat,Ms | [1329-1351] 3'UTR |
| 417 | 1016 | GACAUUUCGUUUUUUACACGAGA | 1399 | UCUCGUGUAAAAAACGAAAUGUC | Rat,Ms | [1328-1350] 3'UTR |
| 418 | 1017 | AACAGGAACUUGAAUACUGGGAG | 1400 | CUCCCAGUAUUCAAGUUCCUGUU | | [1142-1164] 3'UTR |
| 419 | 1018 | GCUUCAGCGAGUGCAUGAACGAG | 1401 | CUCGUUCAUGCACUCGCUGAAGC | Rat,Ms,GP,Chn | [574-596] ORF |
| 420 | 1019 | GGCUUCAGCGAGUGCAUGAACGA | 1402 | UCGUUCAUGCACUCGCUGAAGCC | Rat,Ms,GP,Chn | [573-595] ORF |
| 421 | 1020 | CGGCUUCAGCGAGUGCAUGAACG | 1403 | CGUUCAUGCACUCGCUGAAGCCG | Rat,Ms,GP,Chn | [572-594] ORF |
| 422 | 1021 | CCGGCUUCAGCGAGUGCAUGAAC | 1404 | GUUCAUGCACUCGCUGAAGCCGG | Rat,Ms,GP,Chn | [571-593] ORF |
| 423 | 1022 | GCCGGCUUCAGCGAGUGCAUGAA | 1405 | UUCAUGCACUCGCUGAAGCCGGC | Rat,Ms,GP,Chn | [570-592] ORF |
| 424 | 1023 | GAAAACACUGAUUUUGGAUGCUC | 1406 | GAGCAUCCAAAAUCAGUGUUUUC | Rat,Ms,GP,Chn | [407-429] ORF |
| 425 | 1024 | CAGAUGACAUUUCGUUUUUUACA | 1407 | UGUAAAAAACGAAAUGUCAUCUG | | [1323-1345] 3'UTR |
| 426 | 1025 | UCAGAUGACAUUUCGUUUUUUAC | 1408 | GUAAAAAACGAAAUGUCAUCUGA | | [1322-1344] 3'UTR |
| 427 | 1026 | AAAAGCUCAGAUGACAUUUCGUU | 1409 | AACGAAAUGUCAUCUGAGCUUUU | | [1316-1338] 3'UTR |
| 428 | 1027 | UAAAAGCUCAGAUGACAUUUCGU | 1410 | ACGAAAUGUCAUCUGAGCUUUUA | | [1315-1337] 3'UTR |
| 429 | 1028 | GAAUACUGGGAGAGAAGAGGACU | 1411 | AGUCCUCUUCUCUCCCAGUAUUC | | [1153-1175] 3'UTR |
| 430 | 1029 | AAACAGGAACUUGAAUACUGGGA | 1412 | UCCCAGUAUUCAAGUUCCUGUUU | | [1141-1163] 3'UTR |
| 431 | 1030 | UAAACAGGAACUUGAAUACUGGG | 1413 | CCCAGUAUUCAAGUUCCUGUUUA | | [1140-1162] 3'UTR |
| 432 | 1031 | CGAUGGCCAGUUUGCUUUCCUCA | 1414 | UGAGGAAAGCAAACUGGCCAUCG | | [911-933] ORF |
| 433 | 1032 | ACUGACACCAAGUAGCCACAAA | 1415 | UUUGUGGCUACUUGGUGAUCAGU | | [79-101] 5'UTR |
| 434 | 1033 | UACUGAUCACCAAGUAGCCACAA | 1416 | UUGUGGCUACUUGGUGAUCAGUA | | [78-100] 5'UTR |
| 435 | 1034 | CUACUGAUCACCAAGUAGCCACA | 1417 | UGUGGCUACUUGGUGAUCAGUAG | | [77-99] 5'UTR |
| 436 | 1035 | CAAAGACAGCAUCUGAGCACAGA | 1418 | UCUGUGCUCAGAUGCUGUCUUUG | | [319-341] ORF |
| 437 | 1036 | CCAAAGACAGCAUCUGAGCACAG | 1419 | CUGUGCUCAGAUGCUGUCUUUGG | | [318-340] ORF |
| 438 | 1037 | ACCAAAGACAGCAUCUGAGCACA | 1420 | UGUGCUCAGAUGCUGUCUUUGGU | | [317-339] ORF |
| 439 | 1038 | ACACCGGAUAAACCAAAGACAGC | 1421 | GCUGUCUUUGGUUUAUCCGGUGU | Chn | [306-328] ORF |
| 440 | 1039 | GACACCGGAUAAACCAAAGACAG | 1422 | CUGUCUUUGGUUUAUCCGGUGUC | Chn | [305-327] ORF |
| 441 | 1040 | AAGUCUCAAGUAAAGAGACACA | 1423 | UGUGUCUCUUUACUUGAGACUU | | [141-163] 5'UTR |
| 442 | 1041 | AAAGUCUCAAGUAAAGAGACAC | 1424 | GUGUCUCUUUACUUGAGACUUU | | [140-162] 5'UTR |
| 443 | 1042 | AACGCAGUGUCACCUUCCAGCGG | 1425 | CCGCUGGAAGGUGACACUGCGUU | Ms | [1011-1033] ORF |
| 444 | 1043 | CAACGCAGUGUCACCUUCCAGCG | 1426 | CGCUGGAAGGUGACACUGCGUUG | Ms | [1010-1032] ORF |
| 445 | 1044 | CCAACGCAGUGUCACCUUCCAGC | 1427 | GCUGGAAGGUGACACUGCGUUGG | Ms | [1009-1031] ORF |
| 446 | 1045 | CCCAACGCAGUGUCACCUUCCAG | 1428 | CUGGAAGGUGACACUGCGUUGGG | Ms | [1008-1030] ORF |
| 447 | 1046 | CCCCAACGCAGUGUCACCUUCCA | 1429 | UGGAAGGUGACACUGCGUUGGGG | Ms | [1007-1029] ORF |
| 448 | 1047 | GACCCAGAUCAAUGCCAUGACCU | 1430 | AGGUCAUGGCAUUGAUCUGGGUC | | [677-699] ORF |
| 449 | 1048 | UGACCCAGAUCAAUGCCAUGACC | 1431 | GGUCAUGGCAUUGAUCUGGGUCA | | [676-698] ORF |
| 450 | 1049 | AUGACCCAGAUCAAUGCCAUGAC | 1432 | GUCAUGGCAUUGAUCUGGGUCAU | | [675-697] ORF |
| 451 | 1050 | CAUGACCCAGAUCAAUGCCAUGA | 1433 | UCAUGGCAUUGAUCUGGGUCAUG | | [674-696] ORF |

FIGURE 4 Continued

| | | | | | | |
|---|---|---|---|---|---|---|
| 452 | 1051 | GCAUGACCCAGAUCAAUGCCAUG | 1434 | CAUGGCAUUGAUCUGGGUCAUGC | | [673-695] ORF |
| 453 | 1052 | GAGUGCAUGAACGAGGUGACCCG | 1435 | CGGGUCACCUCGUUCAUGCACUC | Rat,Ms,GP,Chn | [582-604] ORF |
| 454 | 1053 | CGAGUGCAUGAACGAGGUGACCC | 1436 | GGGUCACCUCGUUCAUGCACUCG | Rat,Ms,GP,Chn | [581-603] ORF |
| 455 | 1054 | GCGAGUGCAUGAACGAGGUGACC | 1437 | GGUCACCUCGUUCAUGCACUCGC | Rat,Ms,GP,Chn | [580-602] ORF |
| 456 | 1055 | AGCGAGUGCAUGAACGAGGUGAC | 1438 | GUCACCUCGUUCAUGCACUCGCU | Rat,Ms,GP,Chn | [579-601] ORF |
| 457 | 1056 | CAGCGAGUGCAUGAACGAGGUGA | 1439 | UCACCUCGUUCAUGCACUCGCUG | Rat,Ms,GP,Chn | [578-600] ORF |
| 458 | 1057 | CUGGAGAAGGCGGACAUUCUGGA | 1440 | UCCAGAAUGUCCGCCUUCUCCAG | | [459-481] ORF |
| 459 | 1058 | CUGAAGAAAGAUAGCUCGCGGCA | 1441 | UGCCGCGAGCUAUCUUUCUUCAG | | [429-451] ORF |
| 460 | 1059 | GCACUUGCUCAGUAGUUUUGUGA | 1442 | UCACAAAACUACUGAGCAAGUGC | | [118-140] 5'UTR |
| 461 | 1060 | AGCACUUGCUCAGUAGUUUUGUG | 1443 | CACAAAACUACUGAGCAAGUGCU | | [117-139] 5'UTR |
| 462 | 1061 | CAGCACUUGCUCAGUAGUUUUGU | 1444 | ACAAAACUACUGAGCAAGUGCUG | | [116-138] 5'UTR |
| 463 | 1062 | UCAGCACUUGCUCAGUAGUUUUG | 1445 | CAAAACUACUGAGCAAGUGCUGA | | [115-137] 5'UTR |
| 464 | 1063 | CUCAGCACUUGCUCAGUAGUUUU | 1446 | AAAACUACUGAGCAAGUGCUGAG | | [114-136] 5'UTR |
| 465 | 1064 | AUAAAAGCUCAGAUGACAUUUCG | 1447 | CGAAAUGUCAUCUGAGCUUUUAU | | [1314-1336] 3'UTR |
| 466 | 1065 | AAGAAGUUACUUUUUGUAGAGAG | 1448 | CUCUCUACAAAAAGUAACUUCUU | | [1215-1237] 3'UTR |
| 467 | 1066 | UAAGAAGUUACUUUUUGUAGAGA | 1449 | UCUCUACAAAAAGUAACUUCUUA | | [1214-1236] 3'UTR |
| 468 | 1067 | CUAAGAAGUUACUUUUUGUAGAG | 1450 | CUCUACAAAAAGUAACUUCUUAG | | [1213-1235] 3'UTR |
| 469 | 1068 | UUCCCUCCGGACUCUAAACAGGA | 1451 | UCCUGUUUAGAGUCCGGAGGGAA | | [1126-1148] 3'UTR |
| 470 | 1069 | GAGCCAGCUGAAAACACUGAUUU | 1452 | AAAUCAGUGUUUUCAGCUGGCUC | GP,Chn | [398-420] ORF |
| 471 | 1070 | UGAGCCAGCUGAAAACACUGAUU | 1453 | AAUCAGUGUUUUCAGCUGGCUCA | GP,Chn | [397-419] ORF |
| 472 | 1071 | CUCAGUAGUUUUGUGAAAGUCUC | 1454 | GAGACUUUCACAAAACUACUGAG | | [125-147] 5'UTR |
| 473 | 1072 | UGCAUGACCCAGAUCAAUGCCAU | 1455 | AUGGCAUUGAUCUGGGUCAUGCA | | [672-694] ORF |
| 474 | 1073 | UCUGAAGAAAGAUAGCUCGCGGC | 1456 | GCCGCGAGCUAUCUUUCUUCAGA | | [428-450] ORF |
| 475 | 1074 | CUCUGAAGAAAGAUAGCUCGCGG | 1457 | CCGCGAGCUAUCUUUCUUCAGAG | | [427-449] ORF |
| 476 | 1075 | UUCUUUUUCGUGAAGAACUCCAA | 1458 | UUGGAGUUCUUCACGAAAAAGAA | | [173-195] 5'UTR |
| 477 | 1076 | UUUAUGUGAUGCCAAAGAUGUUU | 1459 | AAACAUCUUUGGCAUCACAUAAA | Rat,Ms | [1358-1380] 3'UTR |
| 478 | 1077 | UUUUAUGUGAUGCCAAAGAUGUU | 1460 | AACAUCUUUGGCAUCACAUAAAA | Rat,Ms | [1357-1379] 3'UTR |
| 479 | 1078 | UUUUUAUGUGAUGCCAAAGAUGU | 1461 | ACAUCUUUGGCAUCACAUAAAAA | Rat,Ms | [1356-1378] 3'UTR |
| 480 | 1079 | UUUUUUAUGUGAUGCCAAAGAUG | 1462 | CAUCUUUGGCAUCACAUAAAAAA | Rat,Ms | [1355-1377] 3'UTR |
| 481 | 1080 | CGCCUUUGUAUUAUAAAAGCUCA | 1463 | UGAGCUUUUAUAAUACAAAGGCG | Rat,Ms | [1302-1324] 3'UTR |
| 482 | 1081 | UAAUAAACCCUCAGCACUUGCUC | 1464 | GAGCAAGUGCUGAGGGUUUAUUA | | [105-127] 5'UTR |
| 483 | 1082 | AUAAUAAACCCUCAGCACUUGCU | 1465 | AGCAAGUGCUGAGGGUUUAUUAU | | [104-126] 5'UTR |
| 484 | 1083 | UAUAAUAAACCCUCAGCACUUGC | 1466 | GCAAGUGCUGAGGGUUUAUUAUA | | [103-125] 5'UTR |
| 485 | 1084 | AUAUAAUAAACCCUCAGCACUUG | 1467 | CAAGUGCUGAGGGUUUAUUAUAU | | [102-124] 5'UTR |
| 486 | 1085 | AAUAUAAUAAACCCUCAGCACUU | 1468 | AAGUGCUGAGGGUUUAUUAUAUU | | [101-123] 5'UTR |
| 487 | 1086 | AAAUAUAAUAAACCCUCAGCACU | 1469 | AGUGCUGAGGGUUUAUUAUAUUU | | [100-122] 5'UTR |
| 488 | 1087 | AAAAUAUAAUAAACCCUCAGCAC | 1470 | GUGCUGAGGGUUUAUUAUAUUUU | | [99-121] 5'UTR |
| 489 | 1088 | CAAAAUAUAAUAAACCCUCAGCA | 1471 | UGCUGAGGGUUUAUUAUAUUUUG | | [98-120] 5'UTR |
| 490 | 1089 | AGAGGCGGCUAAGGUGUUUGGAG | 1472 | CUCCAAACACCUUAGCCGCCUCU | | [866-888] ORF |
| 491 | 1090 | GAGAGGCGGCUAAGGUGUUUGGA | 1473 | UCCAAACACCUUAGCCGCCUCUC | | [865-887] ORF |
| 492 | 1091 | GGAGAGGCGGCUAAGGUGUUUGG | 1474 | CCAAACACCUUAGCCGCCUCUCC | | [864-886] ORF |
| 493 | 1092 | UGGAGAGGCGGCUAAGGUGUUUG | 1475 | CAAACACCUUAGCCGCCUCUCCA | | [863-885] ORF |
| 494 | 1093 | CUGGAGAGGCGGCUAAGGUGUUU | 1476 | AAACACCUUAGCCGCCUCUCCAG | | [862-884] ORF |
| 495 | 1094 | GCUGGAGAAGGCGGACAUUCUGG | 1477 | CCAGAAUGUCCGCCUUCUCCAGC | | [458-480] ORF |
| 496 | 1095 | AGCUGGAGAAGGCGGACAUUCUG | 1478 | CAGAAUGUCCGCCUUCUCCAGCU | | [457-479] ORF |
| 497 | 1096 | AAGCUGGAGAAGGCGGACAUUCU | 1479 | AGAAUGUCCGCCUUCUCCAGCUU | | [456-478] ORF |
| 498 | 1097 | UUAUGUGAUGCCAAAGAUGUUUG | 1480 | CAAACAUCUUUGGCAUCACAUAA | Rat,Ms | [1359-1381] 3'UTR |
| 499 | 1098 | UCAGCGAGUGCAUGAACGAGGUG | 1481 | CACCUCGUUCAUGCACUCGCUGA | Rat,Ms,GP,Chn | [577-599] ORF |
| 500 | 1099 | UUCAGCGAGUGCAUGAACGAGGU | 1482 | ACCUCGUUCAUGCACUCGCUGAA | Rat,Ms,GP,Chn | [576-598] ORF |
| 501 | 1100 | CUUCAGCGAGUGCAUGAACGAGG | 1483 | CCUCGUUCAUGCACUCGCUGAAG | Rat,Ms,GP,Chn | [575-597] ORF |
| 502 | 1101 | AGCCAGUGUCAACACGACACCGG | 1484 | CCGGUGUCGUGUUGACACUGGCU | Rat,Ms | [290-312] ORF |
| 503 | 1102 | CAGCCAGUGUCAACACGACACCG | 1485 | CGGUGUCGUGUUGACACUGGCUG | Rat,Ms | [289-311] ORF |
| 504 | 1103 | CCAGCCAGUGUCAACACGACACC | 1486 | GGUGUCGUGUUGACACUGGCUGG | Rat,Ms | [288-310] ORF |
| 505 | 1104 | CCCAGCCAGUGUCAACACGACAC | 1487 | GUGUCGUGUUGACACUGGCUGGG | Rat,Ms | [287-309] ORF |
| 506 | 1105 | CCCCAGCCAGUGUCAACACGACA | 1488 | UGUCGUGUUGACACUGGCUGGGG | Rat,Ms | [286-308] ORF |
| 507 | 1106 | CUAAGGUGUUUGGAGGCUUCCAG | 1489 | CUGGAAGCCUCCAAACACCUUAG | | [874-896] ORF |
| 508 | 1107 | GCUAAGGUGUUUGGAGGCUUCCA | 1490 | UGGAAGCCUCCAAACACCUUAGC | | [873-895] ORF |
| 509 | 1108 | GGCUAAGGUGUUUGGAGGCUUCC | 1491 | GGAAGCCUCCAAACACCUUAGCC | | [872-894] ORF |
| 510 | 1109 | CGGCUAAGGUGUUUGGAGGCUUC | 1492 | GAAGCCUCCAAACACCUUAGCCG | | [871-893] ORF |
| 511 | 1110 | GCGGCUAAGGUGUUUGGAGGCUU | 1493 | AAGCCUCCAAACACCUUAGCCGC | | [870-892] ORF |
| 512 | 1111 | AGUGCAUGAACGAGGUGACCCGC | 1494 | GCGGGUCACCUCGUUCAUGCACU | Rat,Ms,GP,Chn | [583-605] ORF |
| 513 | 1112 | AAAUGACAGUGAAGCACCUCCGG | 1495 | CCGGAGGUGCUUCACUGUCAUUU | Rat | [481-503] ORF |
| 514 | 1113 | GAAAUGACAGUGAAGCACCUCCG | 1496 | CGGAGGUGCUUCACUGUCAUUUC | Rat | [480-502] ORF |
| 515 | 1114 | GGAAAUGACAGUGAAGCACCUCC | 1497 | GGAGGUGCUUCACUGUCAUUUCC | Rat | [479-501] ORF |
| 516 | 1115 | GAUUUCUUUUUAUGUGAUGCCAA | 1498 | UGGCAUCACAUAAAAAGAAAUC | | [1349-1371] 3'UTR |
| 517 | 1116 | AUUUAGUGGUUACUUUGUGUUUU | 1499 | AAAACACAAAGUAACCACUUAAU | | [1182-1204] 3'UTR |
| 518 | 1117 | AGGUGUUUGGAGGCUUCCAGGUG | 1500 | CACCUGGAAGCCUCCAAACACCU | | [877-899] ORF |
| 519 | 1118 | AAGGUGUUUGGAGGCUUCCAGGU | 1501 | ACCUGGAAGCCUCCAAACACCUU | | [876-898] ORF |

FIGURE 4 Continued

| | | | | | | | |
|---|---|---|---|---|---|---|---|
| 520 | 1119 | UAAGGUGUUUGGAGGCUUCCAGG | 1502 | CCUGGAAGCCUCCAAACACCUUA | | | [875-897] ORF |
| 521 | 1120 | CUGAGCCAGCUGAAAACACUGAU | 1503 | AUCAGUGUUUUCAGCUGGCUCAG | Chn | | [396-418] ORF |
| 522 | 1121 | UCUGAGCCAGCUGAAAACACUGA | 1504 | UCAGUGUUUUCAGCUGGCUCAGA | Chn | | [395-417] ORF |
| 523 | 1122 | GUCUGAGCCAGCUGAAAACACUG | 1505 | CAGUGUUUUCAGCUGGCUCAGAC | Chn | | [394-416] ORF |
| 524 | 1123 | GCUCUUAAAAUAUCUUCCUUUGG | 1506 | CCAAAGGAAGAUAUUUUAAGAGC | Rat,Ms | | [1387-1409] 3'UTR |
| 525 | 1124 | UGCUCUUAAAAUAUCUUCCUUUG | 1507 | CAAAGGAAGAUAUUUUAAGAGCA | Rat,Ms | | [1386-1408] 3'UTR |
| 526 | 1125 | AUGCUCUUAAAAUAUCUUCCUUU | 1508 | AAAGGAAGAUAUUUUAAGAGCAU | Rat,Ms | | [1385-1407] 3'UTR |
| 527 | 1126 | AAUGCUCUUAAAAUAUCUUCCUU | 1509 | AAGGAAGAUAUUUUAAGAGCAUU | Rat,Ms | | [1384-1406] 3'UTR |
| 528 | 1127 | AAAUGCUCUUAAAAUAUCUUCCU | 1510 | AGGAAGAUAUUUUAAGAGCAUUU | Rat,Ms | | [1383-1405] 3'UTR |
| 529 | 1128 | CCGAUGGCCAGUUUGCUUUCCUC | 1511 | GAGGAAAGCAAACUGGCCAUCGG | | | [910-932] ORF |
| 530 | 1129 | CCCGAUGGCCAGUUUGCUUUCCU | 1512 | AGGAAAGCAAACUGGCCAUCGGG | | | [909-931] ORF |
| 531 | 1130 | UCCCGAUGGCCAGUUUGCUUUCC | 1513 | GGAAAGCAAACUGGCCAUCGGGA | | | [908-930] ORF |
| 532 | 1131 | CUCCCGAUGGCCAGUUUGCUUUC | 1514 | GAAAGCAAACUGGCCAUCGGGAG | | | [907-929] ORF |
| 533 | 1132 | GCUCCCGAUGGCCAGUUUGCUUU | 1515 | AAAGCAAACUGGCCAUCGGGAGC | | | [906-928] ORF |
| 534 | 1133 | GUUAAUACCGAGGUGCGCACUCG | 1516 | CGAGUGCGCACCUCGGUAUUAAC | | | [627-649] ORF |
| 535 | 1134 | CGUUAAUACCGAGGUGCGCACUC | 1517 | GAGUGCGCACCUCGGUAUUAACG | | | [626-648] ORF |
| 536 | 1135 | GCGUUAAUACCGAGGUGCGCACU | 1518 | AGUGCGCACCUCGGUAUUAACGC | | | [625-647] ORF |
| 537 | 1136 | GGCGUUAAUACCGAGGUGCGCAC | 1519 | GUGCGCACCUCGGUAUUAACGCC | | | [624-646] ORF |
| 538 | 1137 | GGGCGUUAAUACCGAGGUGCGCA | 1520 | UGCGCACCUCGGUAUUAACGCCC | | | [623-645] ORF |
| 539 | 1138 | GAUUAAGUGGUUACUUUGUGUUU | 1521 | AAACACAAAGUAACCACUUAAUC | | | [1181-1203] 3'UTR |
| 540 | 1139 | UAAAUGAAAGUCUGAGCCAGCUG | 1522 | CAGCUGGCUCAGACUUUCAUUUA | | | [385-407] ORF |
| 541 | 1140 | AUAAAUGAAAGUCUGAGCCAGCU | 1523 | AGCUGGCUCAGACUUUCAUUUAU | | | [384-406] ORF |
| 542 | 1141 | AAUAAAUGAAAGUCUGAGCCAGC | 1524 | GCUGGCUCAGACUUUCAUUUAUU | | | [383-405] ORF |
| 543 | 1142 | GAAUAAAUGAAAGUCUGAGCCAG | 1525 | CUGGCUCAGACUUUCAUUUAUUC | | | [382-404] ORF |
| 544 | 1143 | AGAAUAAAUGAAAGUCUGAGCCA | 1526 | UGGCUCAGACUUUCAUUUAUUCU | | | [381-403] ORF |
| 545 | 1144 | AAGAAUAAAUGAAAGUCUGAGCC | 1527 | GGCUCAGACUUUCAUUUAUUCUU | | | [380-402] ORF |
| 546 | 1145 | CAAGAAUAAAUGAAAGUCUGAGC | 1528 | GCUCAGACUUUCAUUUAUUCUUG | | | [379-401] ORF |
| 547 | 1146 | GCAAGAAUAAAUGAAAGUCUGAG | 1529 | CUCAGACUUUCAUUUAUUCUUGC | | | [378-400] ORF |
| 548 | 1147 | CAUCUGAGCACAGAAAGUCAUCA | 1530 | UGAUGACUUUCUGUGCUCAGAUG | | | [328-350] ORF |
| 549 | 1148 | UGACAUUUCGUUUUUACACGAG | 1531 | CUCGUGUAAAAAACGAAAUGUCA | Rat,Ms | | [1327-1349] 3'UTR |
| 550 | 1149 | AUGACAUUUCGUUUUUUACACGA | 1532 | UCGUGUAAAAAACGAAAUGUCAU | Rat,Ms | | [1326-1348] 3'UTR |
| 551 | 1150 | GAUGACAUUUCGUUUUUUACACG | 1533 | CGUGUAAAAAACGAAAUGUCAUC | Rat,Ms | | [1325-1347] 3'UTR |
| 552 | 1151 | AGAUGACAUUUCGUUUUUUACAC | 1534 | GUGUAAAAAACGAAAUGUCAUCU | Rat,Ms | | [1324-1346] 3'UTR |
| 553 | 1152 | CAGUGUCAACACGACACCGGAUA | 1535 | UAUCCGGUGUCGUGUUGACACUG | Chn | | [293-315] ORF |
| 554 | 1153 | CCAGUGUCAACACGACACCGGAU | 1536 | AUCCGGUGUCGUGUUGACACUGG | Chn | | [292-314] ORF |
| 555 | 1154 | CGUUUUUUACACGAGAUUUCUUU | 1537 | AAAGAAAUCUCGUGUAAAAAACG | Rat,Ms | | [1335-1357] 3'UTR |
| 556 | 1155 | UCGUUUUUUACACGAGAUUUCUU | 1538 | AAGAAAUCUCGUGUAAAAAACGA | Rat,Ms | | [1334-1356] 3'UTR |
| 557 | 1156 | UUCGUUUUUACACGAGAUUUCU | 1539 | AGAAAUCUCGUGUAAAAAACGAA | Rat,Ms | | [1333-1355] 3'UTR |
| 558 | 1157 | AUGUUCAUAUUGGAUUGCGCCUU | 1540 | AAGGCGCAAUCCAAUAUGAACAU | Rat,Ms | | [1285-1307] 3'UTR |
| 559 | 1158 | UAUGUUCAUAUUGGAUUGCGCCU | 1541 | AGGCGCAAUCCAAUAUGAACAUA | Rat,Ms | | [1284-1306] 3'UTR |
| 560 | 1159 | AUAUGUUCAUAUUGGAUUGCGCC | 1542 | GGCGCAAUCCAAUAUGAACAUAU | Rat,Ms | | [1283-1305] 3'UTR |
| 561 | 1160 | UAUAUGUUCAUAUUGGAUUGCGC | 1543 | GCGCAAUCCAAUAUGAACAUAUA | Rat,Ms | | [1282-1304] 3'UTR |
| 562 | 1161 | UGAUUAAGUGGUUACUUUGUGUU | 1544 | AACACAAAGUAACCACUUAAUCA | GP | | [1180-1202] 3'UTR |
| 563 | 1162 | UUGAUUAAGUGGUUACUUUGUGU | 1545 | ACACAAAGUAACCACUUAAUCAA | GP | | [1179-1201] 3'UTR |
| 564 | 1163 | UUUGAUUAAGUGGUUACUUUGUG | 1546 | CACAAAGUAACCACUUAAUCAAA | GP | | [1178-1200] 3'UTR |
| 565 | 1164 | UUUUGAUUAAGUGGUUACUUUGU | 1547 | ACAAAGUAACCACUUAAUCAAAA | GP | | [1177-1199] 3'UTR |
| 566 | 1165 | UUUUUGAUUAAGUGGUUACUUUG | 1548 | CAAAGUAACCACUUAAUCAAAAA | GP | | [1176-1198] 3'UTR |
| 567 | 1166 | GCUACUGAUCACCAAGUAGCCAC | 1549 | GUGGCUACUUGGUGAUCAGUAGC | | | [76-98] 5'UTR |
| 568 | 1167 | GUGCUGAUAACAGCGGAAUCCCC | 1550 | GGGGAUUCCGCUGUUAUCAGCAC | Ms | | [22-44] 5'UTR |
| 569 | 1168 | AUUCUUUUUCGUGAAGAACUCCA | 1551 | UGGAGUUCUUCACGAAAAAGAAU | | | [172-194] 5'UTR |
| 570 | 1169 | AAUUCUUUUUCGUGAAGAACUCC | 1552 | GGAGUUCUUCACGAAAAAGAAUU | | | [171-193] 5'UTR |
| 571 | 1170 | AAAUUCUUUUUCGUGAAGAACUC | 1553 | GAGUUCUUCACGAAAAAGAAUUU | | | [170-192] 5'UTR |
| 572 | 1171 | UGUUUGGAGGCUUCCAGGUGGUA | 1554 | UACCACCUGGAAGCCUCCAAACA | | | [880-902] ORF |
| 573 | 1172 | GUGUUUGGAGGCUUCCAGGUGGU | 1555 | ACCACCUGGAAGCCUCCAAACAC | | | [879-901] ORF |
| 574 | 1173 | GGUGUUUGGAGGCUUCCAGGUGG | 1556 | CCACCUGGAAGCCUCCAAACACC | | | [878-900] ORF |
| 575 | 1174 | UUACUUUUUGUAGAGAGCUGU | 1557 | ACAGCUCUCUACAAAAAGUAA | | | [1221-1243] 3'UTR |
| 576 | 1175 | GCUCUGAAGAAAGAUAGCUCGCG | 1558 | CGCGAGCUAUCUUUCUUCAGAGC | | | [426-448] ORF |
| 577 | 1176 | UGCUCUGAAGAAAGAUAGCUCGC | 1559 | GCGAGCUAUCUUUCUUCAGAGCA | | | [425-447] ORF |
| 578 | 1177 | AUGCUCUGAAGAAAGAUAGCUCG | 1560 | CGAGCUAUCUUUCUUCAGAGCAU | | | [424-446] ORF |
| 579 | 1178 | GUUUUUUACACGAGAUUUCUUUU | 1561 | AAAAGAAAUCUCGUGUAAAAAAC | Rat,Ms | | [1336-1358] 3'UTR |
| 580 | 1179 | UAAACCCUCAGCACUUGCUCAGU | 1562 | ACUGAGCAAGUGCUGAGGGUUUA | | | [108-130] 5'UTR |
| 581 | 1180 | AAUAAACCCUCAGCACUUGCUCA | 1563 | UGAGCAAGUGCUGAGGGUUUAUU | | | [106-128] 5'UTR |
| 582 | 1181 | UGUAUUAUAAAAGCUCAGAUGAC | 1564 | GUCAUCUGAGCUUUUAUAAUACA | | | [1308-1330] 3'UTR |
| 583 | 1182 | UGCUUUCCUCAUUCCCAACGGGG | 1565 | CCCCGUUGGGAAUGAGGAAAGCA | | | [923-945] ORF |
| 584 | 1183 | GACUUUUUUGAUUAAGUGGUUAC | 1566 | GUAACCACUUAAUCAAAAAAGUC | | | [1172-1194] 3'UTR |
| 585 | 1184 | GGCGGCUAAGGUGUUUGGAGGCU | 1567 | AGCCUCCAAACACCUUAGCCGCC | | | [869-891] ORF |
| 586 | 1185 | AGGGCGUUAAUACCGAGGUGCGC | 1568 | GCGCACCUCGGUAUUAACGCCCU | | | [622-644] ORF |
| 587 | 1186 | GAGGGCGUUAAUACCGAGGUGCG | 1569 | CGCACCUCGGUAUUAACGCCCUC | | | [621-643] ORF |

FIGURE 4 Continued

| | | | | | | |
|---|---|---|---|---|---|---|
| 588 | 1187 | CGAGGGCGUUAAUACCGAGGUGC | 1570 | GCACCUCGGUAUUAACGCCCUCG | | [620-642] ORF |
| 589 | 1188 | GCGAGGGCGUUAAUACCGAGGUG | 1571 | CACCUCGGUAUUAACGCCCUCGC | | [619-641] ORF |
| 590 | 1189 | UGCGAGGGCGUUAAUACCGAGGU | 1572 | ACCUCGGUAUUAACGCCCUCGCA | | [618-640] ORF |
| 591 | 1190 | UGAGCACAGACCCAAGUGUGCUG | 1573 | CAGCACACUUGGGUCUGUGCUCA | | [535-557] ORF |
| 592 | 1191 | CUGAGCACAGACCCAAGUGUGCU | 1574 | AGCACACUUGGGUCUGUGCUCAG | | [534-556] ORF |
| 593 | 1192 | GCUGAGCACAGACCCAAGUGUGC | 1575 | GCACACUUGGGUCUGUGCUCAGC | | [533-555] ORF |
| 594 | 1193 | CGCUGAGCACAGACCCAAGUGUG | 1576 | CACACUUGGGUCUGUGCUCAGCG | | [532-554] ORF |
| 595 | 1194 | GCGCUGAGCACAGACCCAAGUGU | 1577 | ACACUUGGGUCUGUGCUCAGCGC | | [531-553] ORF |
| 596 | 1195 | GGAGAAAAAUUCCUCGUCCCCGG | 1578 | CCGGGGACGAGGAAUUUUUCUCC | Rat,Chn | [254-276] ORF |
| 597 | 1196 | UGGAGAAAAAUUCCUCGUCCCCG | 1579 | CGGGGACGAGGAAUUUUUCUCCA | Rat,Chn | [253-275] ORF |
| 598 | 1197 | AUGGAGAAAAAUUCCUCGUCCCC | 1580 | GGGGACGAGGAAUUUUUCUCCAU | Rat,Chn | [252-274] ORF |
| 599 | 1198 | AAUGGAGAAAAAUUCCUCGUCCC | 1581 | GGGACGAGGAAUUUUUCUCCAUU | Rat,Chn | [251-273] ORF |
| 600 | 1199 | UAAUGGAGAAAAAUUCCUCGUCC | 1582 | GGACGAGGAAUUUUUCUCCAUUA | Rat,Chn | [250-272] ORF |
| 601 | 1200 | GCAUUCCAAGCUGGAGAAGGCGG | 1583 | CCGCCUUCUCCAGCUUGGAAUGC | Rat,GP,Chn | [449-471] ORF |
| 602 | 1201 | GCCUUUGUAUUAUAAAAGCUCAG | 1584 | CUGAGCUUUUAUAAUACAAAGGC | | [1303-1325] 3'UTR |
| 603 | 1202 | ACCUCUCUCCUUGGUCCUGGAAC | 1585 | GUUCCAGGACCAAGGAGAGAGGU | Rat,Ms | [50-72] 5'UTR |
| 604 | 1203 | UACCUCUCUCCUUGGUCCUGGAA | 1586 | UUCCAGGACCAAGGAGAGAGGUA | Rat,Ms | [49-71] 5'UTR |
| 605 | 1204 | GAUCAAUGCCAUGACCUACCCCG | 1587 | CGGGGUAGGUCAUGGCAUUGAUC | | [683-705] ORF |
| 606 | 1205 | AGCAAGAAUAAAUGAAAGUCUGA | 1588 | UCAGACUUUCAUUUAUUCUUGCU | Ms | [377-399] ORF |
| 607 | 1206 | UGCUGAUAACAGCGGAAUCCCCC | 1589 | GGGGGAUUCCGCUGUUAUCAGCA | Ms | [23-45] 5'UTR |
| 608 | 1207 | GAGAAAAAUUCCUCGUCCCCGGU | 1590 | ACCGGGGACGAGGAAUUUUUCUC | Rat,Chn | [255-277] ORF |
| 609 | 1208 | UAAAAUAUCUUCCUUUGGGGAAG | 1591 | CUUCCCCAAAGGAAGAUAUUUUA | Rat,Ms | [1392-1414] 3'UTR |
| 610 | 1209 | UUAAAAUAUCUUCCUUUGGGGAA | 1592 | UUCCCCAAAGGAAGAUAUUUUAA | Rat,Ms | [1391-1413] 3'UTR |
| 611 | 1210 | CUUAAAAUAUCUUCCUUUGGGGA | 1593 | UCCCCAAAGGAAGAUAUUUUAAG | Rat,Ms | [1390-1412] 3'UTR |
| 612 | 1211 | UCUUAAAAUAUCUUCCUUUGGGG | 1594 | CCCCAAAGGAAGAUAUUUUAAGA | Rat,Ms | [1389-1411] 3'UTR |
| 613 | 1212 | CUCUUAAAAUAUCUUCCUUUGGG | 1595 | CCCAAAGGAAGAUAUUUUAAGAG | Rat,Ms | [1388-1410] 3'UTR |
| 614 | 1213 | CAUUCCAAGCUGGAGAAGGCGGA | 1596 | UCCGCCUUCUCCAGCUUGGAAUG | Rat,GP,Chn | [450-472] ORF |
| 615 | 1214 | AUAAUGGAGAAAAAUUCCUCGUC | 1597 | GACGAGGAAUUUUUCUCCAUUAU | Rat,Chn | [249-271] ORF |
| 616 | 1215 | UAUAAUGGAGAAAAAUUCCUCGU | 1598 | ACGAGGAAUUUUUCUCCAUUAUA | Rat,Chn | [248-270] ORF |
| 617 | 1216 | GUCUACCUCUCUCCUUGGUCCUG | 1599 | CAGGACCAAGGAGAGAGGUAGAC | Rat,Ms | [46-68] 5'UTR |
| 618 | 1217 | CGUCUACCUCUCUCCUUGGUCCU | 1600 | AGGACCAAGGAGAGAGGUAGACG | Rat,Ms | [45-67] 5'UTR |
| 619 | 1218 | CCGUCUACCUCUCUCCUUGGUCC | 1601 | GGACCAAGGAGAGAGGUAGACGG | Rat,Ms | [44-66] 5'UTR |
| 620 | 1219 | CCCGUCUACCUCUCUCCUUGGUC | 1602 | GACCAAGGAGAGAGGUAGACGGG | Rat,Ms | [43-65] 5'UTR |
| 621 | 1220 | CCCCGUCUACCUCUCUCCUUGGU | 1603 | ACCAAGGAGAGAGGUAGACGGGG | Rat,Ms | [42-64] 5'UTR |
| 622 | 1221 | AAAAUGCUCUUAAAAUAUCUUCC | 1604 | GGAAGAUAUUUUAAGAGCAUUUU | Rat,Ms | [1382-1404] 3'UTR |
| 623 | 1222 | UCAAUGCCAUGACCUACCCCGGG | 1605 | CCCGGGGUAGGUCAUGGCAUUGA | | [685-707] ORF |
| 624 | 1223 | AUCAAUGCCAUGACCUACCCCGG | 1606 | CCGGGGUAGGUCAUGGCAUUGAU | | [684-706] ORF |
| 625 | 1224 | AUUCCAAGCUGGAGAAGGCGGAC | 1607 | GUCCGCCUUCUCCAGCUUGGAAU | Rat,GP,Chn | [451-473] ORF |
| 626 | 1225 | AUAUAAUGGAGAAAAAUUCCUCG | 1608 | CGAGGAAUUUUUCUCCAUUAUAU | Rat,Chn | [247-269] ORF |
| 627 | 1226 | AAAAUUCUUUUUCGUGAAGAACU | 1609 | AGUUCUUCACGAAAAAGAAUUUU | | [169-191] 5'UTR |
| 628 | 1227 | ACAAAAUAUAAUAAACCCUCAGC | 1610 | GCUGAGGGUUUAUUAUAUUUUGU | | [97-119] 5'UTR |
| 629 | 1228 | CUUUCCUCAUUCCCAACGGGGCC | 1611 | GGCCCCGUUGGGAAUGAGGAAAG | | [925-947] ORF |
| 630 | 1229 | GCUUCCUCAUUCCCAACGGGGGC | 1612 | GCCCCGUUGGGAAUGAGGAAGC | | [924-946] ORF |
| 631 | 1230 | GAUAUAAUGGAGAAAAAUUCCUC | 1613 | GAGGAAUUUUUCUCCAUUAUAUC | Rat,Ms,Chn | [246-268] ORF |
| 632 | 1231 | GCUGAUAACAGCGGAAUCCCCCG | 1614 | CGGGGGAUUCCGCUGUUAUCAGC | Ms | [24-46] 5'UTR |
| 633 | 1232 | UUAAUACCGAGGUGCGCACUCGG | 1615 | CCGAGUGCGCACCUCGGUAUUAA | | [628-650] ORF |
| 634 | 1233 | CUGAUAACAGCGGAAUCCCCGU | 1616 | ACGGGGGAUUCCGCUGUUAUCAG | Ms | [25-47] 5'UTR |
| 635 | 1234 | UAAAUACCGAGGUGCGCACUCGGC | 1617 | GCCGAGUGCGCACCUCGGUAUUA | | [629-651] ORF |
| 636 | 1235 | AAAAAUUCUUUUUCGUGAAGAAC | 1618 | GUUCUUCACGAAAAAGAAUUUUU | | [168-190] 5'UTR |
| 637 | 1236 | UUUCCUCAUUCCCAACGGGGCCU | 1619 | AGGCCCCGUUGGGAAUGAGGAAA | | [926-948] ORF |
| 638 | 1237 | CUACCUCUCUCCUUGGUCCUGGA | 1620 | UCCAGGACCAAGGAGAGAGGUAG | Rat,Ms | [48-70] 5'UTR |
| 639 | 1238 | UCUACCUCUCUCCUUGGUCCUGG | 1621 | CCAGGACCAAGGAGAGAGGUAGA | Rat,Ms | [47-69] 5'UTR |
| 640 | 1239 | UUUAUAUGUUCAUAUUGGAUUGCG | 1622 | CGCAAUCCAAUAUGAACAUAUAAA | | [1281-1303] 3'UTR |
| 641 | 1240 | AUGACAGUGAAGCACCUCCGGAA | 1623 | UUCCGGAGGUGCUUCACUGUCAU | Rat,GP,Chn | [483-505] ORF |
| 642 | 1241 | AAUGACAGUGAAGCACCUCCGGA | 1624 | UCCGGAGGUGCUUCACUGUCAUU | Rat,GP,Chn | [482-504] ORF |
| 643 | 1242 | AGAUUUCUUUUUAUGUGAUGCC | 1625 | GGCAUCACAUAAAAAGAAAUCU | | [1348-1370] 3'UTR |
| 644 | 1243 | UUUAUAUGUUCAUAUUGGAUUGC | 1626 | GCAAUCCAAUAUGAACAUAUAAA | Rat,Ms | [1280-1302] 3'UTR |

Table A2 HES5 - hairy and enhancer of split 5

| No. | SEQ ID NO. | Sense siRNA | SEQ ID NO. | AntiSense siRNA | Other Sp | Human-145301612 ORF:82-582 |
|---|---|---|---|---|---|---|
| 1 | 1627 | CCUCCACUAUGAUCCUUAA | 1884 | UUAAGGAUCAUAGUGGAGG | | [1160-1178] 3'UTR |
| 2 | 1628 | GCUGUAUCCUCAUAGGAAA | 1885 | UUUCCUAUGAGGAUACAGC | | [1027-1045] 3'UTR |
| 3 | 1629 | CCGAAGCCGCCAUAAUAAA | 1886 | UUUAUUAUGGCGGCUUCGG | | [1267-1285] 3'UTR |
| 4 | 1630 | CCGCCAUAAUAAAAUCUGA | 1887 | UCAGAUUUUAUUAUGGCGG | | [1273-1291] 3'UTR |
| 5 | 1631 | CGAAGCCGCCAUAAUAAAA | 1888 | UUUUAUUAUGGCGGCUUCG | | [1268-1286] 3'UTR |
| 6 | 1632 | CAGAGUCCCUGCCGUUUUA | 1889 | UAAAACGGCAGGGACUCUG | | [760-778] 3'UTR |

FIGURE 4 Continued

| | | | | | | | |
|---|---|---|---|---|---|---|---|
| 7 | 1633 | AGAUGAAGCUGCUGUACCA | 1890 | UGGUACAGCAGCUUCAUCU | | | [416-434] ORF |
| 8 | 1634 | CUACCUGAAGCACAGCAAA | 1891 | UUUGCUGUGCUUCAGGUAG | Rat,GP | | [282-300] ORF |
| 9 | 1635 | ACGACUUUGUACUCAGAAA | 1892 | UUUCUGAGUACAAAGUCGU | | | [1212-1230] 3'UTR |
| 10 | 1636 | GGUUGUUCUGUGUUUGCAU | 1893 | AUGCAAACACAGAACAACC | GP | | [822-840] 3'UTR |
| 11 | 1637 | CUCCGAAGCCGCCAUAAUA | 1894 | UAUUAUGGCGGCUUCGGAG | | | [1265-1283] 3'UTR |
| 12 | 1638 | CCAACUCCAAGCUGGAGAA | 1895 | UUCUCCAGCUUGGAGUUGG | Ms,GP,Chn | | [236-254] ORF |
| 13 | 1639 | AGAAAAACCGACUGCGGAA | 1896 | UUCCGCAGUCGGUUUUUCU | Ms | | [125-143] ORF |
| 14 | 1640 | CGCAGAUGAAGCUGCUGUA | 1897 | UACAGCAGCUUCAUCUGCG | | | [413-431] ORF |
| 15 | 1641 | CUUUGUACUCAGAAAUUGA | 1898 | UCAAUUUCUGAGUACAAAG | | | [1216-1234] 3'UTR |
| 16 | 1642 | GUUCUGUGUUUGCAUUUAA | 1899 | UUAAAUGCAAACACAGAAC | | | [826-844] 3'UTR |
| 17 | 1643 | CAGAGAAUGUGUGUGCAGA | 1900 | UCUGCACACACAUUCUCUG | | | [745-763] 3'UTR |
| 18 | 1644 | GCACGACUUUGUACUCAGA | 1901 | UCUGAGUACAAAGUCGUGC | | | [1210-1228] 3'UTR |
| 19 | 1645 | GGUUCUAUGAUAUUUGUAG | 1902 | CUACAAAUAUCAUAGAACC | Ms,GP,Chn | | [879-897] 3'UTR |
| 20 | 1646 | GCUACCUGAAGCACAGCAA | 1903 | UUGCUGUGCUUCAGGUAGC | Rat,GP,Chn | | [281-299] ORF |
| 21 | 1647 | AACUCUCAGUCACGUGGAA | 1904 | UUCCACGUGACUGAGAGUU | | | [1234-1252] 3'UTR |
| 22 | 1648 | CGACUUUGUACUCAGAAAU | 1905 | AUUUCUGAGUACAAAGUCG | | | [1213-1231] 3'UTR |
| 23 | 1649 | CCAAAAGGCUCCUGAGUGU | 1906 | ACACUCAGGAGCCUUUUGG | | | [1090-1108] 3'UTR |
| 24 | 1650 | CAAUCAGGGCCCAUCUUCU | 1907 | AGAAGAUGGGCCCUGAUUG | | | [782-800] 3'UTR |
| 25 | 1651 | CGCCAUAAUAAAAUCUGAU | 1908 | AUCAGAUUUUAUUAUGGCG | | | [1274-1292] 3'UTR |
| 26 | 1652 | GGGUUCUAUGAUAUUUGUA | 1909 | UACAAAUAUCAUAGAACCC | Ms,GP,Chn | | [878-896] 3'UTR |
| 27 | 1653 | UGGAGAUGGCUGUCAGCUA | 1910 | UAGCUGACAGCCAUCUCCA | | | [266-284] ORF |
| 28 | 1654 | CACGACUUUGUACUCAGAA | 1911 | UUCUGAGUACAAAGUCGUG | | | [1211-1229] 3'UTR |
| 29 | 1655 | CCUCAUAGGAAACAGUGAU | 1912 | AUCACUGUUUCCUAUGAGG | | | [1034-1052] 3'UTR |
| 30 | 1656 | GGGUUGUUCUGUGUUUGCA | 1913 | UGCAAACACAGAACAACCC | GP | | [821-839] 3'UTR |
| 31 | 1657 | GUGUGGGCACGACUUUGUA | 1914 | UACAAAGUCGUGCCCACAC | | | [1204-1222] 3'UTR |
| 32 | 1658 | GAAGCCGCCAUAAUAAAAU | 1915 | AUUUUAUUAUGGCGGCUUC | | | [1269-1287] 3'UTR |
| 33 | 1659 | CUCCACUAUGAUCCUUAAA | 1916 | UUUAAGGAUCAUAGUGGAG | | | [1161-1179] 3'UTR |
| 34 | 1660 | GAGAAAAACCGACUGCGGA | 1917 | UCCGCAGUCGGUUUUUCUC | Ms | | [124-142] ORF |
| 35 | 1661 | CUCAGAAAUUGAACUCUCA | 1918 | UGAGAGUUCAAUUUCUGAG | | | [1223-1241] 3'UTR |
| 36 | 1662 | CUAUGAUCCUUAAAGGAUU | 1919 | AAUCCUUUAAGGAUCAUAG | | | [1166-1184] 3'UTR |
| 37 | 1663 | AGCUGUAUCCUCAUAGGAA | 1920 | UUCCUAUGAGGAUACAGCU | | | [1026-1044] 3'UTR |
| 38 | 1664 | GCAUCAACAGCAGCAUCGA | 1921 | UCGAUGCUGCUGUUGAUGC | GP,Chn | | [173-191] ORF |
| 39 | 1665 | CCCUGCCGUUUUAGGACAA | 1922 | UUGUCCUAAAACGGCAGGG | | | [766-784] 3'UTR |
| 40 | 1666 | GCCUUUUGUGAAGGCCGAA | 1923 | UUCGGCCUUCACAAAAGGC | | | [1003-1021] 3'UTR |
| 41 | 1667 | CUAUGAUAUUUGUAGUGCC | 1924 | GGCACUACAAAUAUCAUAG | | | [883-901] 3'UTR |
| 42 | 1668 | AGGACUACAGCGAAGGCUA | 1925 | UAGCCUUCGCUGUAGUCCU | | | [338-356] ORF |
| 43 | 1669 | UCCGAAGCCGCCAUAAUAA | 1926 | UUAUUAUGGCGGCUUCGGA | | | [1266-1284] 3'UTR |
| 44 | 1670 | GCCUCCACUAUGAUCCUUA | 1927 | UAAGGAUCAUAGUGGAGGC | | | [1159-1177] 3'UTR |
| 45 | 1671 | GAACUCUCAGUCACGUGGA | 1928 | UCCACGUGACUGAGAGUUC | | | [1233-1251] 3'UTR |
| 46 | 1672 | GCACAUUUGCCUUUUGUGA | 1929 | UCACAAAAGGCAAAUGUGC | Ms | | [995-1013] 3'UTR |
| 47 | 1673 | AGCAAGUGACUUCUGGGAA | 1930 | UUCCCAGAAGUCACUUGCU | GP,Chn | | [844-862] 3'UTR |
| 48 | 1674 | CUGUCAGCUACCUGAAGCA | 1931 | UGCUUCAGGUAGCUGACAG | | | [275-293] ORF |
| 49 | 1675 | UGGCUGUCAGCUACCUGAA | 1932 | UUCAGGUAGCUGACAGCCA | | | [272-290] ORF |
| 50 | 1676 | CACAUUUGCCUUUUGUGAA | 1933 | UUCACAAAAGGCAAAUGUG | Ms | | [996-1014] 3'UTR |
| 51 | 1677 | GCCGUUUUAGGACAAUCAG | 1934 | CUGAUUGUCCUAAAACGGC | | | [770-788] 3'UTR |
| 52 | 1678 | CUCAGAGAAUGUGUGUGCA | 1935 | UGCACACACAUUCUCUGAG | | | [743-761] 3'UTR |
| 53 | 1679 | GACUUUGUACUCAGAAAUU | 1936 | AAUUUCUGAGUACAAAGUC | | | [1214-1232] 3'UTR |
| 54 | 1680 | CACUAUGAUCCUUAAAGGA | 1937 | UCCUUUAAGGAUCAUAGUG | | | [1164-1182] 3'UTR |
| 55 | 1681 | UUGUGAAGGCCGAACUCGA | 1938 | UCGAGUUCGGCCUUCACAA | | | [1008-1026] 3'UTR |
| 56 | 1682 | AGCUGCUGUACCACUUCCA | 1939 | UGGAAGUGGUACAGCAGCU | | | [422-440] ORF |
| 57 | 1683 | GCAAGUGACUUCUGGGAAG | 1940 | CUUCCCAGAAGUCACUUGC | GP,Chn | | [845-863] 3'UTR |
| 58 | 1684 | UGUUCUGUGUUUGCAUUUA | 1941 | UAAAUGCAAACACAGAACA | | | [825-843] 3'UTR |
| 59 | 1685 | CCAAAGAGAAAAACCGACU | 1942 | AGUCGGUUUUUCUCUUUGG | | | [119-137] ORF |
| 60 | 1686 | CCGUUUUAGGACAAUCAGG | 1943 | CCUGAUUGUCCUAAAACGG | | | [771-789] 3'UTR |
| 61 | 1687 | AGAGAAUGUGUGUGCAGAG | 1944 | CUCUGCACACACAUUCUCU | Ms | | [746-764] 3'UTR |
| 62 | 1688 | UCAGCUACCUGAAGCACAG | 1945 | CUGUGCUUCAGGUAGCUGA | Rat | | [278-296] ORF |
| 63 | 1689 | CUCGAGCUGUAUCCUCAUA | 1946 | UAUGAGGAUACAGCUCGAG | | | [1022-1040] 3'UTR |
| 64 | 1690 | GUUGUUCUGUGUUUGCAUU | 1947 | AAUGCAAACACAGAACAAC | GP | | [823-841] 3'UTR |
| 65 | 1691 | GAGAAUGUGUGUGCAGAGU | 1948 | ACUCUGCACACACAUUCUC | Ms | | [747-765] 3'UTR |
| 66 | 1692 | UGCCUUUUGUGAAGGCCGA | 1949 | UCGGCCUUCACAAAAGGCA | | | [1002-1020] 3'UTR |
| 67 | 1693 | GAAUGUGUGUGCAGAGUCC | 1950 | GGACUCUGCACACACAUUC | | | [749-767] 3'UTR |
| 68 | 1694 | AUGGCUGUCAGCUACCUGA | 1951 | UCAGGUAGCUGACAGCCAU | | | [271-289] ORF |
| 69 | 1695 | CAUAGGAAACAGUGAUCAC | 1952 | GUGAUCACUGUUUCCUAUG | | | [1037-1055] 3'UTR |
| 70 | 1696 | GGGCACGACUUUGUACUCA | 1953 | UGAGUACAAAGUCGUGCCC | | | [1208-1226] 3'UTR |
| 71 | 1697 | CGAGCUGUAUCCUCAUAGG | 1954 | CCUAUGAGGAUACAGCUCG | | | [1024-1042] 3'UTR |
| 72 | 1698 | ACUCGAGCUGUAUCCUCAU | 1955 | AUGAGGAUACAGCUCGAGU | | | [1021-1039] 3'UTR |
| 73 | 1699 | CUGUGUUUGCAUUUAAGCA | 1956 | UGCUUAAAUGCAAACACAG | | | [829-847] 3'UTR |
| 74 | 1700 | GAAAUUGAACUCUCAGUCA | 1957 | UGACUGAGAGUUCAAUUUC | | | [1227-1245] 3'UTR |

FIGURE 4 Continued

| | | | | | | | |
|---|---|---|---|---|---|---|---|
| 75 | 1701 | GAGCUGUAUCCUCAUAGGA | 1958 | UCCUAUGAGGAUACAGCUC | | [1025-1043] 3'UTR |
| 76 | 1702 | CGGGCACAUUUGCCUUUUG | 1959 | CAAAAGGCAAAUGUGCCCG | | [992-1010] 3'UTR |
| 77 | 1703 | CCCAAAGAGAAAAACCGAC | 1960 | GUCGGUUUUUCUCUUUGGG | | [118-136] ORF |
| 78 | 1704 | UCCUCAUAGGAAACAGUGA | 1961 | UCACUGUUUCCUAUGAGGA | | [1033-1051] 3'UTR |
| 79 | 1705 | AAGCAAGUGACUUCUGGGA | 1962 | UCCCAGAAGUCACUUGCUU | | [843-861] 3'UTR |
| 80 | 1706 | UGUGUUUGCAUUUAAGCAA | 1963 | UUGCUUAAAUGCAAACACA | | [830-848] 3'UTR |
| 81 | 1707 | CAUCUUCUGCCAAGUGUCU | 1964 | AGACACUUGGCAGAAGAUG | | [793-811] 3'UTR |
| 82 | 1708 | GGCACGACUUUGGUACUCAG | 1965 | CUGAGUACAAAGUCGUGCC | | [1209-1227] 3'UTR |
| 83 | 1709 | GGGCACAUUUGCCUUUUGU | 1966 | ACAAAAGGCAAAUGUGCCC | Ms | [993-1011] 3'UTR |
| 84 | 1710 | UUCUGUGUUUGCAUUUAAG | 1967 | CUUAAAUGCAAACACAGAA | | [827-845] 3'UTR |
| 85 | 1711 | UCUUCUGCCAAGUGUCUGA | 1968 | UCAGACACUUGGCAGAAGA | | [795-813] 3'UTR |
| 86 | 1712 | ACAUUUGCCUUUUGUGAAG | 1969 | CUUCACAAAAGGCAAAUGU | Ms | [997-1015] 3'UTR |
| 87 | 1713 | UCAACAGCAGCAUCGAGCA | 1970 | UGCUCGAUGCUGCUGUUGA | Chn | [176-194] ORF |
| 88 | 1714 | CGUUUUAGGACAAUCAGGG | 1971 | CCCGAUUGUCCUAAAACG | | [772-790] 3'UTR |
| 89 | 1715 | CCACUAUGAUCCUUAAAGG | 1972 | CCUUUAAGGAUCAUAGUGG | | [1163-1181] 3'UTR |
| 90 | 1716 | UGCCGUUUUAGGACAAUCA | 1973 | UGAUUGUCCUAAAACGGCA | | [769-787] 3'UTR |
| 91 | 1717 | GUCAGCUACCUGAAGCACA | 1974 | UGUGCUUCAGGUAGCUGAC | Rat | [277-295] ORF |
| 92 | 1718 | AACUCGAGCUGUAUCCUCA | 1975 | UGAGGAUACAGCUCGAGUU | | [1020-1038] 3'UTR |
| 93 | 1719 | GCGGGCACAUUUGCCUUUU | 1976 | AAAAGGCAAAUGUGCCCGC | | [991-1009] 3'UTR |
| 94 | 1720 | ACCUGUAGAGGACUUUCUU | 1977 | AAGAAAGUCCUCUACAGGU | | [926-944] 3'UTR |
| 95 | 1721 | CCUGCCGUUUUAGGACAAU | 1978 | AUUGUCCUAAAACGGCAGG | | [767-785] 3'UTR |
| 96 | 1722 | AGUCCCUGCCGUUUUAGGA | 1979 | UCCUAAAACGGCAGGGACU | | [763-781] 3'UTR |
| 97 | 1723 | CUGUAGAGGACUUUCUUCA | 1980 | UGAAGAAAGUCCUCUACAG | GP | [928-946] 3'UTR |
| 98 | 1724 | CAGAAAUUGAACUCUCAGU | 1981 | ACUGAGAGUUCAAUUUCUG | | [1225-1243] 3'UTR |
| 99 | 1725 | CCUUAAAGGAUUCCUCUGU | 1982 | ACAGAGGAAUCCUUUAAGG | | [1173-1191] 3'UTR |
| 100 | 1726 | CAAAGAGAAAAACCGACUG | 1983 | CAGUCGGUUUUUCUCUUUG | | [120-138] ORF |
| 101 | 1727 | CUUUUGUGAAGGCCGAACU | 1984 | AGUUCGGCCUUCACAAAAG | | [1005-1023] 3'UTR |
| 102 | 1728 | CCAUUCUCAGAAUGUGU | 1985 | ACACAUUCUCUGAGAAUGG | | [738-756] 3'UTR |
| 103 | 1729 | UGAAGCUGCUGUACCACUU | 1986 | AAGUGGUACAGCAGCUUCA | | [419-437] ORF |
| 104 | 1730 | UGAUAUUUGUAGUGCCGGG | 1987 | CCCGGCACUACAAAUAUCA | | [886-904] 3'UTR |
| 105 | 1731 | UGUUUGCAUUUAAGCAAGU | 1988 | ACUUGCUUAAAUGCAAACA | | [832-850] 3'UTR |
| 106 | 1732 | AUGUGUGCAGAGUCCCU | 1989 | AGGGACUCUGCACACACAU | | [751-769] 3'UTR |
| 107 | 1733 | ACACGCAGAUGAAGCUGCU | 1990 | AGCAGCUUCAUCUGCGUGU | Rat,Ms | [410-428] ORF |
| 108 | 1734 | CCAACCUGUAGAGGACUUU | 1991 | AAAGUCCUCUACAGGUUGG | | [923-941] 3'UTR |
| 109 | 1735 | CCCAACCUGUAGAGGACUU | 1992 | AAGUCCUCUACAGGUUGGG | | [922-940] 3'UTR |
| 110 | 1736 | GACAAUCAGGGCCCAUCUU | 1993 | AAGAUGGGCCCUGAUUGUC | | [780-798] 3'UTR |
| 111 | 1737 | UCAUAGGAAACAGUGAUCA | 1994 | UGAUCACUGUUUCCUAUGA | | [1036-1054] 3'UTR |
| 112 | 1738 | UAUGAUAUUUGUAGUGCCG | 1995 | CGGCACUACAAAUAUCAUA | | [884-902] 3'UTR |
| 113 | 1739 | UGAAGCACAGCAAAGCCUU | 1996 | AAGGCUUUGCUGUGCUUCA | Rat,GP | [287-305] ORF |
| 114 | 1740 | UGGGUGCCUCCACUAUGAU | 1997 | AUCAUAGUGGAGGCACCCA | | [1154-1172] 3'UTR |
| 115 | 1741 | GUGUUUGCAUUUAAGCAAG | 1998 | CUUGCUUAAAUGCAAACAC | | [831-849] 3'UTR |
| 116 | 1742 | CCAUCUUCUGCCAAGUGUC | 1999 | GACACUUGGCAGAAGAUGG | | [792-810] 3'UTR |
| 117 | 1743 | UCAGAAAUUGAACUCUCAG | 2000 | CUGAGAGUUCAAUUUCUGA | | [1224-1242] 3'UTR |
| 118 | 1744 | AUGGCCAAAAGGCUCCUGA | 2001 | UCAGGAGCCUUUUGGCCAU | | [1086-1104] 3'UTR |
| 119 | 1745 | UAUCCUCUAGGAAACAGU | 2002 | ACUGUUUCCUAUGAGGAUA | | [1031-1049] 3'UTR |
| 120 | 1746 | ACUUUCUUCAGGGCCCUGA | 2003 | UCAGGGCCCUGAAGAAAGU | | [937-955] 3'UTR |
| 121 | 1747 | GGCACAUUUGCCUUUUGUG | 2004 | CACAAAAGGCAAAUGUGCC | Ms | [994-1012] 3'UTR |
| 122 | 1748 | CAUCAACAGCAGCAUCGAG | 2005 | CUCGAUGCUGCUGUUGAUG | Chn | [174-192] ORF |
| 123 | 1749 | GCAUUUAAGCAAGUGACUU | 2006 | AAGUCACUUGCUUAAAUGC | | [837-855] 3'UTR |
| 124 | 1750 | UACAGCGAAGGCUACUCGU | 2007 | ACGAGUAGCCUUCGCUGUA | | [343-361] ORF |
| 125 | 1751 | GACUACAGCGAAGGCUACU | 2008 | AGUAGCCUUCGCUGUAGUC | | [340-358] ORF |
| 126 | 1752 | CCCAUCUUCUGCCAAGUGU | 2009 | ACACUUGGCAGAAGAUGGG | | [791-809] 3'UTR |
| 127 | 1753 | AAGCCGCCAUAAUAAAAUC | 2010 | GAUUUUAUUAUGGCGGCUU | | [1270-1288] 3'UTR |
| 128 | 1754 | AGGAAUUCCUCUGUGUGGGU | 2011 | ACCCACACAGAGGAAUCCU | | [1179-1197] 3'UTR |
| 129 | 1755 | CUUUAAAGGAUUCCUCUGUG | 2012 | CACAGAGGAAUCCUUUAAG | | [1174-1192] 3'UTR |
| 130 | 1756 | UCAGAGAAUGUGUGUGCAG | 2013 | CUGCACACACAUUCUCUGA | | [744-762] 3'UTR |
| 131 | 1757 | UUAGGACAAUCAGGGCCCA | 2014 | UGGGCCCUGAUUGUCCUAA | | [776-794] 3'UTR |
| 132 | 1758 | GAAGCACAGCAAAGCCUUC | 2015 | GAAGGCUUUGCUGUGCUUC | Rat | [288-306] ORF |
| 133 | 1759 | UGUACUCAGAAAUUGAACU | 2016 | AGUUCAAUUUCUGAGUACA | | [1219-1237] 3'UTR |
| 134 | 1760 | CGAACUCGAGCUGUAUCCU | 2017 | AGGAUACAGCUCGAGUUCG | | [1018-1036] 3'UTR |
| 135 | 1761 | AGAGGACUUUCUUCAGGGC | 2018 | GCCCUGAAGAAAGUCCUCU | Ms | [932-950] 3'UTR |
| 136 | 1762 | GUGCCUCCACUAUGAUCCU | 2019 | AGGAUCAUAGUGGAGGCAC | | [1157-1175] 3'UTR |
| 137 | 1763 | UGUAGAGGACUUUCUUCAG | 2020 | CUGAAGAAAGUCCUCUACA | | [929-947] 3'UTR |
| 138 | 1764 | UGCAUUUAAGCAAGUGACU | 2021 | AGUCACUUGCUUAAAUGCA | | [836-854] 3'UTR |
| 139 | 1765 | GAAAAACCGACUGCGGAAG | 2022 | CUUCCGCAGUCGGUUUUUC | Ms | [126-144] ORF |
| 140 | 1766 | CAACCUGUAGAGGACUUUC | 2023 | GAAAGUCCUCUACAGGUUG | | [924-942] 3'UTR |
| 141 | 1767 | CAAGUGACUUCUGGGAAGU | 2024 | ACUUCCCAGAAGUCACUUG | GP,Chn | [846-864] 3'UTR |
| 142 | 1768 | GUUUUAGGACAAUCAGGGC | 2025 | GCCCUGAUUGUCCUAAAAC | | [773-791] 3'UTR |

FIGURE 4 Continued

| | | | | | | |
|---|---|---|---|---|---|---|
| 143 | 1769 | GCCGCCAUAAUAAAAUCUG | 2026 | CAGAUUUAUUAUGGCGGC | | [1272-1290] 3'UTR |
| 144 | 1770 | AAUUGAACUCUCAGUCACG | 2027 | CGUGACUGAGAGUUCAAUU | | [1229-1247] 3'UTR |
| 145 | 1771 | ACCGCAUCAACAGCAGCAU | 2028 | AUGCUGCUGUUGAUGCGGU | Rat,Ms,Chn | [170-188] ORF |
| 146 | 1772 | UAGGACAAUCAGGGCCCAU | 2029 | AUGGGCCCUGAUUGUCCUA | | [777-795] 3'UTR |
| 147 | 1773 | UACCUGAAGCACAGCAAAG | 2030 | CUUUGCUGUGCUUCAGGUA | Rat,GP | [283-301] ORF |
| 148 | 1774 | UUAAAGGAUUCCUCUGUGU | 2031 | ACACAGAGGAAUCCUUUAA | | [1175-1193] 3'UTR |
| 149 | 1775 | ACAUCCUGGAGAUGGCUGU | 2032 | ACAGCCAUCUCCAGGAUGU | | [260-278] ORF |
| 150 | 1776 | UCCCUGCCGUUUUAGGACA | 2033 | UGUCCUAAAACGGCAGGGA | | [765-783] 3'UTR |
| 151 | 1777 | CAUUCUCAGAGAAUGUGUG | 2034 | CACACAUUCUCUGAGAAUG | | [739-757] 3'UTR |
| 152 | 1778 | AGAUGGCUGUCAGCUACCU | 2035 | AGGUAGCUGACAGCCAUCU | | [269-287] ORF |
| 153 | 1779 | CAAAAGGCUCCUGAGUGUG | 2036 | CACACUCAGGAGCCUUUUG | | [1091-1109] 3'UTR |
| 154 | 1780 | GUAGAGGACUUUCUUCAGG | 2037 | CCUGAAGAAAGUCCUCUAC | Ms | [930-948] 3'UTR |
| 155 | 1781 | CCUGUAGAGGACUUUCUUC | 2038 | GAAGAAAGUCCUCUACAGG | GP | [927-945] 3'UTR |
| 156 | 1782 | UUUGCAUUUAAGCAAGUGA | 2039 | UCACUUGCUUAAAUGCAAA | | [834-852] 3'UTR |
| 157 | 1783 | AGAGAAAAACCGACUGCGG | 2040 | CCGCAGUCGGUUUUUCUCU | | [123-141] ORF |
| 158 | 1784 | GCAGAUGAAGCUGCUGUAC | 2041 | GUACAGCAGCUUCAUCUGC | | [414-432] ORF |
| 159 | 1785 | AGCACAGCAAAGCCUUCGU | 2042 | ACGAAGGCUUUGCUGUGCU | | [290-308] ORF |
| 160 | 1786 | ACUUUGUACUCAGAAAUUG | 2043 | CAAUUUCUGAGUACAAAGU | | [1215-1233] 3'UTR |
| 161 | 1787 | GUGGGCACGACUUUGUACU | 2044 | AGUACAAAGUCGUGCCCAC | | [1206-1224] 3'UTR |
| 162 | 1788 | GAUCCUAAAAGGAUUCCUC | 2045 | GAGGAAUCCUUUAAGGAUC | | [1170-1188] 3'UTR |
| 163 | 1789 | UCCACUAUGAUCCUUAAAG | 2046 | CUUUAAGGAUCAUAGUGGA | | [1162-1180] 3'UTR |
| 164 | 1790 | CUCAUAGGAAACAGUGAUC | 2047 | GAUCACUGUUUCCUAUGAG | | [1035-1053] 3'UTR |
| 165 | 1791 | CUGUAUCCUCAUAGGAAAC | 2048 | GUUUCCUAUGAGGAUACAG | | [1028-1046] 3'UTR |
| 166 | 1792 | CAGAUGAAGCUGCUGUACC | 2049 | GGUACAGCAGCUUCAUCUG | | [415-433] ORF |
| 167 | 1793 | ACUAUGAUCCUUAAAGGAU | 2050 | AUCCUUUAAGGAUCAUAGU | | [1165-1183] 3'UTR |
| 168 | 1794 | GUAUCCUCAUAGGAAACAG | 2051 | CUGUUUCCUAUGAGGAUAC | | [1030-1048] 3'UTR |
| 169 | 1795 | AACCUGUAGAGGACUUUCU | 2052 | AGAAAGUCCUCUACAGGUU | | [925-943] 3'UTR |
| 170 | 1796 | AGAGUCCCUGCCGUUUUAG | 2053 | CUAAAACGGCAGGGACUCU | | [761-779] 3'UTR |
| 171 | 1797 | GAAGCUGCUGUACCACUUC | 2054 | GAAGUGGUACAGCAGCUUC | | [420-438] ORF |
| 172 | 1798 | ACGCAGAUGAAGCUGCUGU | 2055 | ACAGCAGCUUCAUCUGCGU | | [412-430] ORF |
| 173 | 1799 | AGCCGCCAUAAUAAAAUCU | 2056 | AGAUUUUAUUAUGGCGGCU | | [1271-1289] 3'UTR |
| 174 | 1800 | CAACUCCAAGCUGGAGAAG | 2057 | CUUCUCCAGCUUGGAGUUG | Ms,GP,Chn | [237-255] ORF |
| 175 | 1801 | AGCUACCUGAAGCACAGCA | 2058 | UGCUGUGCUUCAGGUAGCU | Rat,GP,Chn | [280-298] ORF |
| 176 | 1802 | AUUCCUCUGUGUGGGUGGA | 2059 | UCCACCCACACAGAGGAAU | | [1182-1200] 3'UTR |
| 177 | 1803 | UUUUGUGAAGGCCGAACUC | 2060 | GAGUUCGGCCUUCACAAAA | | [1006-1024] 3'UTR |
| 178 | 1804 | CUGAAGCACAGCAAAGCCU | 2061 | AGGCUUUGCUGUGCUUCAG | Rat,GP | [286-304] ORF |
| 179 | 1805 | AUUGAACUCUCAGUCACGU | 2062 | ACGUGACUGAGAGUUCAAU | | [1230-1248] 3'UTR |
| 180 | 1806 | UUGUUCUGUGUUUGCAUUU | 2063 | AAAUGCAAACACAGAACAA | GP | [824-842] 3'UTR |
| 181 | 1807 | AGAAUGUGUGUGCAGAGUC | 2064 | GACUCUGCACACACAUUCU | | [748-766] 3'UTR |
| 182 | 1808 | GAUGAAGCUGCUGUACCAC | 2065 | GUGGUACAGCAGCUUCAUC | | [417-435] ORF |
| 183 | 1809 | UGUGGGCACGACUUUGUAC | 2066 | GUACAAAGUCGUGCCCACA | | [1205-1223] 3'UTR |
| 184 | 1810 | CAUUUAAGCAAGUGACUUC | 2067 | GAAGUCACUUGCUUAAAUG | | [838-856] 3'UTR |
| 185 | 1811 | AAAUCUGAUUGUUCAGCCC | 2068 | GGGCUGAACAAUCAGAUUU | | [1284-1302] 3'UTR |
| 186 | 1812 | AAAUUGAACUCUCAGUCAC | 2069 | GUGACUGAGAGUUCAAUUU | | [1228-1246] 3'UTR |
| 187 | 1813 | CCUUUUGUGAAGGCCGAAC | 2070 | GUUCGGCCUUCACAAAAGG | | [1004-1022] 3'UTR |
| 188 | 1814 | ACAAUCAGGGCCCAUCUUC | 2071 | GAAGAUGGGCCCUGAUUGU | | [781-799] 3'UTR |
| 189 | 1815 | CCCAUUCUCAGAGAAUGUG | 2072 | CACAUUCUCUGAGAAUGGG | | [737-755] 3'UTR |
| 190 | 1816 | AAGAGAAAAACCGACUGCG | 2073 | CGCAGUCGGUUUUUCUCUU | | [122-140] ORF |
| 191 | 1817 | AAAGGAUUCCUCUGUGUGG | 2074 | CCACACAGAGGAAUCCUUU | | [1177-1195] 3'UTR |
| 192 | 1818 | AUCCUUAAAGGAUUCCUCU | 2075 | AGAGGAAUCCUUUAAGGAU | | [1171-1189] 3'UTR |
| 193 | 1819 | UGCCUCCACUAUGAUCCUU | 2076 | AAGGAUCAUAGUGGAGGCA | | [1158-1176] 3'UTR |
| 194 | 1820 | AUGAUAUUUGUAGUGCCGG | 2077 | CCGGCACUACAAAUAUCAU | | [885-903] 3'UTR |
| 195 | 1821 | AUUUAAGCAAGUGACUUCU | 2078 | AGAAGUCACUUGCUUAAAU | | [839-857] 3'UTR |
| 196 | 1822 | UUAAGCAAGUGACUUCUGG | 2079 | CCAGAAGUCACUUGCUUAA | | [841-859] 3'UTR |
| 197 | 1823 | GUUUGCAUUUAAGCAAGUG | 2080 | CACUUGCUUAAAUGCAAAC | | [833-851] 3'UTR |
| 198 | 1824 | CUGCCGUUUUAGGACAAUC | 2081 | GAUUGUCCUAAAACGGCAG | | [768-786] 3'UTR |
| 199 | 1825 | ACCUGAAGCACAGCAAAGC | 2082 | GCUUUGCUGUGCUUCAGGU | Rat,GP | [284-302] ORF |
| 200 | 1826 | AAAAGGCUCCUGAGUGUGC | 2083 | GCACACUCAGGAGCCUUUU | | [1092-1110] 3'UTR |
| 201 | 1827 | UAAGCAAGUGACUUCUGGG | 2084 | CCCAGAAGUCACUUGCUUA | | [842-860] 3'UTR |
| 202 | 1828 | AAUCAGGGCCCAUCUUCUG | 2085 | CAGAAGAUGGGCCCUGAUU | | [783-801] 3'UTR |
| 203 | 1829 | ACUCAGAAAUUGAACUCUC | 2086 | GAGAGUUCAAUUUCUGAGU | | [1222-1240] 3'UTR |
| 204 | 1830 | GAACUCGAGCUGUAUCCUC | 2087 | GAGGAUACAGCUCGAGUUC | | [1019-1037] 3'UTR |
| 205 | 1831 | AUGAAGCUGCUGUACCACU | 2088 | AGUGGUACAGCAGCUUCAU | | [418-436] ORF |
| 206 | 1832 | UUGUACUCAGAAAUUGAAC | 2089 | GUUCAAUUUCUGAGUACAA | | [1218-1236] 3'UTR |
| 207 | 1833 | UGGGCACGACUUUGUACUC | 2090 | GAGUACAAAGUCGUGCCCA | | [1207-1225] 3'UTR |
| 208 | 1834 | UCUAUGAUAUUUGUAGUGC | 2091 | GCACUACAAAUAUCAUAGA | | [882-900] 3'UTR |
| 209 | 1835 | UUGCAUUUAAGCAAGUGAC | 2092 | GUCACUUGCUUAAAUGCAA | | [835-853] 3'UTR |
| 210 | 1836 | AAAGAGAAAAACCGACUGC | 2093 | GCAGUCGGUUUUUCUCUUU | | [121-139] ORF |

FIGURE 4 Continued

| | | | | | | | |
|---|---|---|---|---|---|---|---|
| 211 | 1837 | UCGAGCUGUAUCCUCAUAG | 2094 | CUAUGAGGAUACAGCUCGA | | | [1023-1041] 3'UTR |
| 212 | 1838 | UAGAGGACUUUCUUCAGGG | 2095 | CCCUGAAGAAAGUCCUCUA | Ms | | [931-949] 3'UTR |
| 213 | 1839 | UGUCAGCUACCUGAAGCAC | 2096 | GUGCUUCAGGUAGCUGACA | | | [276-294] ORF |
| 214 | 1840 | AGAAAUUGAACUCUCAGUC | 2097 | GACUGAGAGUUCAAUUUCU | | | [1226-1244] 3'UTR |
| 215 | 1841 | UGAUCCUUAAAGGAUUCCU | 2098 | AGGAAUCCUUUAAGGAUCA | Ms | | [1169-1187] 3'UTR |
| 216 | 1842 | AUCCUGGAGAUGGCUGUCA | 2099 | UGACAGCCAUCUCCAGGAU | | | [262-280] ORF |
| 217 | 1843 | AUUCUCAGAGAAUGUGUGU | 2100 | ACACACAUUCUCUGAGAAU | | | [740-758] 3'UTR |
| 218 | 1844 | UCCUUAAAGGAUUCCUCUG | 2101 | CAGAGGAAUCCUUUAAGGA | | | [1172-1190] 3'UTR |
| 219 | 1845 | UAUGAUCCUUAAAGGAUUC | 2102 | GAAUCCUUUAAGGAUCAUA | | | [1167-1185] 3'UTR |
| 220 | 1846 | UGUAUCCUCAUAGGAAACA | 2103 | UGUUUCCUAUGAGGAUACA | | | [1029-1047] 3'UTR |
| 221 | 1847 | UCUCAGAGAAUGUGUGUGC | 2104 | GCACACACAUUCUCUGAGA | | | [742-760] 3'UTR |
| 222 | 1848 | UGAACUCUCAGUCACGUGG | 2105 | CCACGUGACUGAGAGUUCA | | | [1232-1250] 3'UTR |
| 223 | 1849 | GUACUCAGAAAUUGAACUC | 2106 | GAGUUCAAUUUCUGAGUAC | | | [1220-1238] 3'UTR |
| 224 | 1850 | AAAAUCUGAUUGUUCAGCC | 2107 | GGCUGAACAAUCAGAUUUU | | | [1283-1301] 3'UTR |
| 225 | 1851 | AAUGUGUGUGCAGAGUCCC | 2108 | GGGACUCUGCACACACAUU | | | [750-768] 3'UTR |
| 226 | 1852 | ACUACAGCGAAGGCUACUC | 2109 | GAGUAGCCUUCGCUGUAGU | | | [341-359] ORF |
| 227 | 1853 | AAGGAUUCCUCUGUGUGGG | 2110 | CCCACACAGAGGAAUCCUU | | | [1178-1196] 3'UTR |
| 228 | 1854 | UAAAGGAUUCCUCUGUGUG | 2111 | CACACAGAGGAAUCCUUUA | | | [1176-1194] 3'UTR |
| 229 | 1855 | UAGGAAACAGUGAUCACCC | 2112 | GGGUGAUCACUGUUUCCUA | | | [1039-1057] 3'UTR |
| 230 | 1856 | UUGCCUUUUGUGAAGGCCG | 2113 | CGGCCUUCACAAAAGGCAA | | | [1001-1019] 3'UTR |
| 231 | 1857 | UCUGUGUUUGCAUUUAAGC | 2114 | GCUUAAAUGCAAACACAGA | | | [828-846] 3'UTR |
| 232 | 1858 | AAAAACCGACUGCGGAAGC | 2115 | GCUUCCGCAGUCGGUUUUU | Ms | | [127-145] ORF |
| 233 | 1859 | AACUCCAAGCUGGAGAAGG | 2116 | CCUUCUCCAGCUUGGAGUU | Ms,GP,Chn | | [238-256] ORF |
| 234 | 1860 | CAUUUGCCUUUUGUGAAGG | 2117 | CCUUCACAAAAGGCAAAUG | Ms | | [998-1016] 3'UTR |
| 235 | 1861 | ACUCUCAGUCACGUGGAAG | 2118 | CUUCCACGUGACUGAGAGU | | | [1235-1253] 3'UTR |
| 236 | 1862 | UACUCAGAAAUUGAACUCU | 2119 | AGAGUUCAAUUUCUGAGUA | | | [1221-1239] 3'UTR |
| 237 | 1863 | UUUAAGCAAGUGACUUCUG | 2120 | CAGAAGUCACUUGCUUAAA | | | [840-858] 3'UTR |
| 238 | 1864 | AGUGACUUCUGGGAAGUCC | 2121 | GGACUUCCCAGAAGUCACU | GP,Chn | | [848-866] 3'UTR |
| 239 | 1865 | AAGUGACUUCUGGGAAGUC | 2122 | GACUUCCCAGAAGUCACUU | GP,Chn | | [847-865] 3'UTR |
| 240 | 1866 | AAGCUGCUGUACCACUUCC | 2123 | GGAAGUGGUACAGCAGCUU | | | [421-439] ORF |
| 241 | 1867 | UUCCUCUGUGUGGGUGGAU | 2124 | AUCCACCCACACAGAGGAA | | | [1183-1201] 3'UTR |
| 242 | 1868 | AUCCUCAUAGGAAACAGUG | 2125 | CACUGUUUCCUAUGAGGAU | | | [1032-1050] 3'UTR |
| 243 | 1869 | UUCUCAGAGAAUGUGUGUG | 2126 | CACACACAUUCUCUGAGAA | | | [741-759] 3'UTR |
| 244 | 1870 | AUAGGAAACAGUGAUCACC | 2127 | GGUGAUCACUGUUUCCUAU | | | [1038-1056] 3'UTR |
| 245 | 1871 | UUGAACUCUCAGUCACGUG | 2128 | CACGUGACUGAGAGUUCAA | | | [1231-1249] 3'UTR |
| 246 | 1872 | AUUUGCCUUUUGUGAAGGC | 2129 | GCCUUCACAAAAGGCAAAU | Ms | | [999-1017] 3'UTR |
| 247 | 1873 | CUUCUGCCAAGUGUCUGAC | 2130 | GUCAGACACUUGGCAGAAG | | | [796-814] 3'UTR |
| 248 | 1874 | AUCAACAGCAGCAUCGAGC | 2131 | GCUCGAUGCUGCUGUUGAU | Chn | | [175-193] ORF |
| 249 | 1875 | AUCUUCUGCCAAGUGUCUG | 2132 | CAGACACUUGGCAGAAGAU | | | [794-812] 3'UTR |
| 250 | 1876 | UUUUAGGACAAUCAGGGCC | 2133 | GGCCCUGAUUGUCCUAAAA | | | [774-792] 3'UTR |
| 251 | 1877 | AAGCACAGCAAAGCCUUCG | 2134 | CGAAGGCUUUGCUGUGCUU | Rat | | [289-307] ORF |
| 252 | 1878 | UUCUGCCAAGUGUCUGACC | 2135 | GGUCAGACACUUGGCAGAA | | | [797-815] 3'UTR |
| 253 | 1879 | UUUGUGAAGGCCGAACUCG | 2136 | CGAGUUCGGCCUUCACAAA | | | [1007-1025] 3'UTR |
| 254 | 1880 | UUUAGGACAAUCAGGGCCC | 2137 | GGGCCCUGAUUGUCCUAAA | | | [775-793] 3'UTR |
| 255 | 1881 | UAAAAUCUGAUUGUUCAGC | 2138 | GCUGAACAAUCAGAUUUUA | | | [1282-1300] 3'UTR |
| 256 | 1882 | UUUGCCUUUUGUGAAGGCC | 2139 | GGCCUUCACAAAAGGCAAA | | | [1000-1018] 3'UTR |
| 257 | 1883 | AUGAUCCUUAAAGGAUUCC | 2140 | GGAAUCCUUUAAGGAUCAU | Ms | | [1168-1186] 3'UTR |

Table A3 ID1 - inhibitor of DNA binding 1

| No. | SEQ ID NO. | Sense siRNA | SEQ ID NO. | AntiSense siRNA | Other Sp | Human-31317298 ORF:100-567 | Human-31317296 ORF:100-549 |
|---|---|---|---|---|---|---|---|
| 1 | 2141 | CAAUGAUCACCGACUGAAA | 2424 | UUUCAGUCGGUGAUCAUUG | | [901-919] 3'UTR | [1140-1158] 3'UTR |
| 2 | 2142 | CGGAUCUGAGGGAGAACAA | 2425 | UUGUUCUCCCUCAGAUCCG | | [656-674] 3'UTR | [895-913] 3'UTR |
| 3 | 2143 | AGGUAAACGUGCUGCUCUA | 2426 | UAGAGCAGCACGUUUACCU | Chp | [281-299] ORF | [281-299] ORF |
| 4 | 2144 | UGGACGAGCAGCAGGUAAA | 2427 | UUUACCUGCUGCUCGUCCA | Chp | [269-287] ORF | [269-287] ORF |
| 5 | 2145 | GCUGAACUCGGAAUCCGAA | 2428 | UUCGGAUUCCGAGUUCAGC | GP,Chp | [423-441] ORF | [423-441] ORF |
| 6 | 2146 | GUUGGAGCUGAACUCGGAA | 2429 | UUCCGAGUUCAGCUCCAAC | GP | [417-435] ORF | [417-435] ORF |
| 7 | 2147 | CGUUCUUAACUGUUCCAUU | 2430 | AAUGGAACAGUUAAGAACG | | [7-25] 5'UTR | [7-25] 5'UTR |
| 8 | 2148 | AGUUGGAGCUGAACUCGGA | 2431 | UCCGAGUUCAGCUCCAACU | GP | [416-434] ORF | [416-434] ORF |
| 9 | 2149 | AAUGAUCACCGACUGAAAA | 2432 | UUUUCAGUCGGUGAUCAUU | | [902-920] 3'UTR | [1141-1159] 3'UTR |
| 10 | 2150 | GAGGGAGAACAAGACCGAU | 2433 | AUCGGUCUUGUUCUCCCUC | | [663-681] 3'UTR | [902-920] 3'UTR |
| 11 | 2151 | GAUCUGAGGGAGAACAAGA | 2434 | UCUUGUUCUCCCUCAGAUC | | [658-676] 3'UTR | [897-915] 3'UTR |
| 12 | 2152 | CAGUCGCCAAGAAUCAUGA | 2435 | UCAUGAUUCUUGGCGACUG | | [85-103] 5'UTR+ORF | [85-103] 5'UTR+ORF |
| 13 | 2153 | AGUCGCCAAGAAUCAUGAA | 2436 | UUCAUGAUUCUUGGCGACU | | [86-104] 5'UTR+ORF | [86-104] 5'UTR+ORF |
| 14 | 2154 | GGAUCUGAGGGAGAACAAG | 2437 | CUUGUUCUCCCUCAGAUCC | | [657-675] 3'UTR | [896-914] 3'UTR |
| 15 | 2155 | ACUACAUCAGGGACCUUCA | 2438 | UGAAGGUCCCUGAUGUAGU | | [398-416] ORF | [398-416] ORF |
| 16 | 2156 | UGCUGCUCUACGACAUGAA | 2439 | UUCAUGUCGUAGAGCAGCA | GP,Chn,Chp | [290-308] ORF | [290-308] ORF |

FIGURE 4 Continued

| | | | | | | | |
|---|---|---|---|---|---|---|---|
| 17 | 2157 | UGAGGGAGAACAAGACCGA | 2440 | UCGGUCUUGUUCUCCCUCA | | [662-680] 3'UTR | [901-919] 3'UTR |
| 18 | 2158 | GCUUCCACCUCAUUUUUU | 2441 | AAAAAAAUGAGGUGGAAGC | | [43-61] 5'UTR | [43-61] 5'UTR |
| 19 | 2159 | CGCAUCUUGUGUCGCUGAA | 2442 | UUCAGCGACACAAGAUGCG | GP,Chn,Chp | [550-568] ORF+3'UTR | [789-807] 3'UTR |
| 20 | 2160 | AGCUGAACUCGGAAUCCGA | 2443 | UCGGAUUCCGAGUUCAGCU | GP,Chp | [422-440] ORF | [422-440] ORF |
| 21 | 2161 | GGGCUGUUUUUUGUUAUU | 2444 | AAUAACAAAAAAACAGCCC | Chp | [944-962] 3'UTR | [1183-1201] 3'UTR |
| 22 | 2162 | AGGUGGAGAUUCUCCAGCA | 2445 | UGCUGGAGAAUCUCCACCU | Chp | [371-389] ORF | [371-389] ORF |
| 23 | 2163 | GCAAGGUGGAGAUUCUCCA | 2446 | UGGAGAAUCUCCACCUUGC | Chp | [368-386] ORF | [368-386] ORF |
| 24 | 2164 | AGGUGAGCAAGGUGGAGAU | 2447 | AUCUCCACCUUGCUCACCU | Chp | [362-380] ORF | [362-380] ORF |
| 25 | 2165 | GCCAGUCGCCAAGAAUCAU | 2448 | AUGAUUCUUGGCGACUGGC | | [83-101] 5'UTR+ORF | [83-101] 5'UTR+ORF |
| 26 | 2166 | ACGUUUGGUGCUUCUCAGA | 2449 | UCUGAGAAGCACCAAACGU | Chp | [850-868] 3'UTR | [1089-1107] 3'UTR |
| 27 | 2167 | CACGUUUGGUGCUUCUCAG | 2450 | CUGAGAAGCACCAAACGUG | Chp | [849-867] 3'UTR | [1088-1106] 3'UTR |
| 28 | 2168 | CUCGGAAUCCGAAGUUGGA | 2451 | UCCAACUUCGGAUUCCGAG | | [429-447] ORF | [429-447] ORF |
| 29 | 2169 | AUAUUACAAUGAUCACCGA | 2452 | UCGGUGAUCAUUGUAAUAU | Chp | [895-913] 3'UTR | [1134-1152] 3'UTR |
| 30 | 2170 | CCAUUUUCCGUAUCUGCUU | 2453 | AAGCAGAUACGGAAAAUGG | | [21-39] 5'UTR | [21-39] 5'UTR |
| 31 | 2171 | CUUUGCCCAUUCUGUUUCA | 2454 | UGAAACAGAAUGGGCAAAG | Chp | [64-82] 5'UTR | [64-82] 5'UTR |
| 32 | 2172 | CGUUUGGUGCUUCUCAGAU | 2455 | AUCUGAGAAGCACCAAACG | Chp | [851-869] 3'UTR | [1090-1108] 3'UTR |
| 33 | 2173 | GAGAUUCUCCAGCACGUCA | 2456 | UGACGUGCUGGAGAAUCUC | Chp | [376-394] ORF | [376-394] ORF |
| 34 | 2174 | GUCGCCAAGAAUCAUGAAA | 2457 | UUUCAUGAUUCUUGGCGAC | Chp | [87-105] 5'UTR+ORF | [87-105] 5'UTR+ORF |
| 35 | 2175 | GAUCACCGACUGAAAAUAU | 2458 | AUAUUUUCAGUCGGUGAUC | | [905-923] 3'UTR | [1144-1162] 3'UTR |
| 36 | 2176 | CCUCUCUGCACACCUACUA | 2459 | UAGUAGGUGUGCAGAGAGG | Chp | [753-771] 3'UTR | [992-1010] 3'UTR |
| 37 | 2177 | CAAGAAUCAUGAAAGUCGC | 2460 | GCGACUUUCAUGAUUCUUG | Chp | [92-110] 5'UTR+ORF | [92-110] 5'UTR+ORF |
| 38 | 2178 | CGCUUUGCCCAUUCUGUUU | 2461 | AAACAGAAUGGGCAAAGCG | Chp | [62-80] 5'UTR | [62-80] 5'UTR |
| 39 | 2179 | UUCUCAGAUUUCUGAGGAA | 2462 | UUCCUCAGAAAUCUGAGAA | Chp | [861-879] 3'UTR | [1100-1118] 3'UTR |
| 40 | 2180 | ACCUUCAGUUGGAGCUGAA | 2463 | UUCAGCUCCAACUGAAGGU | | [410-428] ORF | [410-428] ORF |
| 41 | 2181 | GCUGUUACUCACGCCUCAA | 2464 | UUGAGGCGUGAGUAACAGC | | [311-329] ORF | [311-329] ORF |
| 42 | 2182 | UGAUCACCGACUGAAAAUA | 2465 | UAUUUUCAGUCGGUGAUCA | | [904-922] 3'UTR | [1143-1161] 3'UTR |
| 43 | 2183 | ACACCUACUAGUCACCAGA | 2466 | UCUGGUGACUAGUAGGUGU | Chp | [762-780] 3'UTR | [1001-1019] 3'UTR |
| 44 | 2184 | GAAUCAUGAAAGUCGCCAG | 2467 | CUGGCGACUUUCAUGAUUC | Chp | [95-113] 5'UTR+ORF | [95-113] 5'UTR+ORF |
| 45 | 2185 | CGGGCUUCCACCUCAUUUU | 2468 | AAAAUGAGGUGGAAGCCCG | | [40-58] 5'UTR | [40-58] 5'UTR |
| 46 | 2186 | AGAACCGCAAGGUGAGCAA | 2469 | UUGCUCACCUUGCGGUUCU | Chp | [353-371] ORF | [353-371] ORF |
| 47 | 2187 | GGAAUUACGUGCUCUGUGG | 2470 | CCACAGAGCACGUAAUUCC | Chp | [616-634] 3'UTR | [855-873] 3'UTR |
| 48 | 2188 | GUUACUCACGCCUCAAGGA | 2471 | UCCUUGAGGCGUGAGUAAC | | [314-332] ORF | [314-332] ORF |
| 49 | 2189 | GUUCUUAACUGUUCCAUUU | 2472 | AAAUGGAACAGUUAAGAAC | | [8-26] 5'UTR | [8-26] 5'UTR |
| 50 | 2190 | AGAAUUCUCCAGCACGUCAU | 2473 | AUGACGUGCUGGAGAAUCU | Chp | [377-395] ORF | [377-395] ORF |
| 51 | 2191 | ACGACAUGAACGGCUGCAU | 2474 | UAACAGCCGUUCAUGUCGU | Chp | [299-317] ORF | [299-317] ORF |
| 52 | 2192 | CCGACUGAAAAUAUUGUUU | 2475 | AAACAAUAUUUUCAGUCGG | | [910-928] 3'UTR | [1149-1167] 3'UTR |
| 53 | 2193 | CACCGACUGAAAAUAUUGU | 2476 | ACAAUAUUUUCAGUCGGUG | | [908-926] 3'UTR | [1147-1165] 3'UTR |
| 54 | 2194 | ACAAUGAUCACCGACUGAA | 2477 | UUCAGUCGGUGAUCAUUGU | | [900-918] 3'UTR | [1139-1157] 3'UTR |
| 55 | 2195 | CUCAGAUUUCUGAGGAAAU | 2478 | AUUUCCUCAGAAAUCUGAG | Chp | [863-881] 3'UTR | [1102-1120] 3'UTR |
| 56 | 2196 | AACUGUUCCAUUUUCCGUA | 2479 | UACGGAAAAUGGAACAGUU | | [14-32] 5'UTR | [14-32] 5'UTR |
| 57 | 2197 | UCGCUUUGCCCAUUCUGUU | 2480 | AACAGAAUGGGCAAAGCGA | Chp | [61-79] 5'UTR | [61-79] 5'UTR |
| 58 | 2198 | GGGCAAGAGGAAUUACGUG | 2481 | CACGUAAUUCCUCUUGCCC | Chp | [608-626] 3'UTR | [847-865] 3'UTR |
| 59 | 2199 | GCAUCUUGUGUCGCUGAAG | 2482 | CUUCAGCGACACAAGAUGC | GP,Chn,Chp | [551-569] ORF+3'UTR | [790-808] 3'UTR |
| 60 | 2200 | CGACUACAUCAGGGACCUU | 2483 | AAGGUCCCUGAUGUAGUCG | | [396-414] ORF | [396-414] ORF |
| 61 | 2201 | UCAUCGACUACAUCAGGGA | 2484 | UCCCUGAUGUAGUCGAUGA | Chn,Chp | [392-410] ORF | [392-410] ORF |
| 62 | 2202 | GGUGAGCAAGGUGGAGAUU | 2485 | AAUCUCCACCUUGCUCACC | Chp | [363-381] ORF | [363-381] ORF |
| 63 | 2203 | CUACGACAUGAACGGCUGU | 2486 | ACAGCCGUUCAUGUCGUAG | Chp | [297-315] ORF | [297-315] ORF |
| 64 | 2204 | CUCGUGUGUUUCUAUUUUU | 2487 | AAAAAUAGAAACACACGAG | Chp | [803-821] 3'UTR | [1042-1060] 3'UTR |
| 65 | 2205 | UAAACGUGCUGCUCUACGA | 2488 | UCGUAGAGCAGCACGUUUA | Chp | [284-302] ORF | [284-302] ORF |
| 66 | 2206 | CCACCUCAUUUUUUCGCU | 2489 | AGCGAAAAAAAUGAGGUGG | | [47-65] 5'UTR | [47-65] 5'UTR |
| 67 | 2207 | GAGGAAUUACGUGCUCUGU | 2490 | ACAGAGCACGUAAUUCCUC | Chp | [614-632] 3'UTR | [853-871] 3'UTR |
| 68 | 2208 | UCGGAAUCCGAAGUUGGAA | 2491 | UUCCAACUUCGGAUUCCGA | | [430-448] ORF | [430-448] ORF |
| 69 | 2209 | CUACAUCAGGGACCUUCAG | 2492 | CUGAAGGUCCCUGAUGUAG | | [399-417] ORF | [399-417] ORF |
| 70 | 2210 | UGUUUCAGCCAGUCGCCAA | 2493 | UUGGCGACUGGCUGAAACA | | [76-94] 5'UTR | [76-94] 5'UTR |
| 71 | 2211 | CACGUUCUUAACUGUUCCA | 2494 | UGGAACAGUUAAGAACGUG | | [5-23] 5'UTR | [5-23] 5'UTR |
| 72 | 2212 | GGGCUUCCACCUCAUUUUU | 2495 | AAAAAUGAGGUGGAAGCCC | | [41-59] 5'UTR | [41-59] 5'UTR |
| 73 | 2213 | ACUGUUCCAUUUUCCGUAU | 2496 | AUACGGAAAAUGGAACAGU | | [15-33] 5'UTR | [15-33] 5'UTR |
| 74 | 2214 | UGGAGAUUCUCCAGCACGU | 2497 | ACGUGCUGGAGAAUCUCCA | Chp | [374-392] ORF | [374-392] ORF |
| 75 | 2215 | AGCCAGUCGCCAAGAAUCA | 2498 | UGAUUCUUGGCGACUGGCU | | [82-100] 5'UTR | [82-100] 5'UTR |
| 76 | 2216 | CUAGUCACCAGAGACUUUA | 2499 | UAAAGUCUCUGGUGACUAG | Chp | [769-787] 3'UTR | [1008-1026] 3'UTR |
| 77 | 2217 | UACAAUGAUCACCGACUGA | 2500 | UCAGUCGGUGAUCAUUGUA | | [899-917] 3'UTR | [1138-1156] 3'UTR |
| 78 | 2218 | ACUCGUGUGUUUCUAUUUU | 2501 | AAAAUAGAAACACACGAGU | | [802-820] 3'UTR | [1041-1059] 3'UTR |
| 79 | 2219 | ACGUGCUGCUCUACGACAU | 2502 | AUGUCGUAGAGCAGCACGU | GP,Chn,Chp | [287-305] ORF | [287-305] ORF |
| 80 | 2220 | CCAUUCUGUUUCAGCCAGU | 2503 | ACUGGCUGAAACAGAAUGG | | [70-88] 5'UTR | [70-88] 5'UTR |
| 81 | 2221 | CCACGUUCUUAACUGUUCC | 2504 | GGAACAGUUAAGAACGUGG | | [4-22] 5'UTR | [4-22] 5'UTR |
| 82 | 2222 | AUCACCGACUGAAAAUAUU | 2505 | AAUAUUUUCAGUCGGUGAU | | [906-924] 3'UTR | [1145-1163] 3'UTR |
| 83 | 2223 | ACCUACUAGUCACCAGAGA | 2506 | UCUCUGGUGACUAGUAGGU | Chp | [764-782] 3'UTR | [1003-1021] 3'UTR |
| 84 | 2224 | CUCUCUGCACACCUACUAG | 2507 | CUAGUAGGUGUGCAGAGAG | Chp | [754-772] 3'UTR | [993-1011] 3'UTR |

FIGURE 4 Continued

| # | ID | Seq1 | ID2 | Seq2 | Species | Pos1 | Pos2 |
|---|---|---|---|---|---|---|---|
| 85 | 2225 | CGGAAUCCGAAGUUGGAAC | 2508 | GUUCCAACUUCGGAUUCCG | | [431-449] ORF | [431-449] ORF |
| 86 | 2226 | GAUUCUCCAGCACGUCAUC | 2509 | GAUGACGUGCUGGAGAAUC | Chp | [378-396] ORF | [378-396] ORF |
| 87 | 2227 | CAAGGUGGAGAUUCUCCAG | 2510 | CUGGAGAAUCUCCACCUUG | Chp | [369-387] ORF | [369-387] ORF |
| 88 | 2228 | GCUGCUCUACGACAUGAAC | 2511 | GUUCAUGUCGUAGAGCAGC | GP,Chn,Chp | [291-309] ORF | [291-309] ORF |
| 89 | 2229 | UCAGCCAGUCGCCAAGAAU | 2512 | AUUCUUGGCGACUGGCUGA | | [80-98] 5'UTR | [80-98] 5'UTR |
| 90 | 2230 | GUGCUUCUCAGAUUUCUGA | 2513 | UCAGAAAUCUGAGAAGCAC | Rat,Chp | [857-875] 3'UTR | [1096-1114] 3'UTR |
| 91 | 2231 | ACUAGUCACCAGAGACUUU | 2514 | AAAGUCUCUGGUGACUAGU | Chp | [768-786] 3'UTR | [1007-1025] 3'UTR |
| 92 | 2232 | GCCCAUUCUGUUUCAGCCA | 2515 | UGGCUGAAACAGAAUGGGC | | [68-86] 5'UTR | [68-86] 5'UTR |
| 93 | 2233 | ACCUCAUUUUUUUCGCUUU | 2516 | AAAGCGAAAAAAAUGAGGU | | [49-67] 5'UTR | [49-67] 5'UTR |
| 94 | 2234 | UGGUGCUUCUCAGAUUUCU | 2517 | AGAAAUCUGAGAAGCACCA | Chp | [855-873] 3'UTR | [1094-1112] 3'UTR |
| 95 | 2235 | UCAUGAAAGUCGCCAGUGG | 2518 | CCACUGGCGACUUUCAUGA | Chp | [98-116] 5'UTR+ORF | [98-116] 5'UTR+ORF |
| 96 | 2236 | AUGAUCACCGACUGAAAAU | 2519 | AUUUUCAGUCGGUGAUCAU | | [903-921] 3'UTR | [1142-1160] 3'UTR |
| 97 | 2237 | UCUCAGAUUUCUGAGGAAA | 2520 | UUUCCUCAGAAAUCUGAGA | Chp | [862-880] 3'UTR | [1101-1119] 3'UTR |
| 98 | 2238 | UCACGUUUGGUGCUUCUCA | 2521 | UGAGAAGCACCAAACGUGA | Chp | [848-866] 3'UTR | [1087-1105] 3'UTR |
| 99 | 2239 | AAAAAAUGGUCACGUUUGG | 2522 | CCAAACGUGACCAUUUUUU | | [839-857] 3'UTR | [1078-1096] 3'UTR |
| 100 | 2240 | CGUGUGUUUCUAUUUUUUG | 2523 | CAAAAAAUAGAAACACACG | Chp | [805-823] 3'UTR | [1044-1062] 3'UTR |
| 101 | 2241 | UCGCAUCUUGUGUCGCUGA | 2524 | UCAGCGACACAAGAUGCGA | Ms,GP,Chn,Chp | [549-567] ORF | [788-806] 3'UTR |
| 102 | 2242 | CAUCGACUACAUCAGGGAC | 2525 | GUCCCUGAUGUAGUCGAUG | Chn,Chp | [393-411] ORF | [393-411] ORF |
| 103 | 2243 | GAGCAAGGUGGAGAUUCUC | 2526 | GAGAAUCUCCACCUUGCUC | Chp | [366-384] ORF | [366-384] ORF |
| 104 | 2244 | UCGCCAAGAAUCAUGAAAG | 2527 | CUUUCAUGAUUCUUGGCGA | Chp | [88-106] 5'UTR+ORF | [88-106] 5'UTR+ORF |
| 105 | 2245 | CCUCAUUUUUUUCGCUUUG | 2528 | CAAAGCGAAAAAAAUGAGG | | [50-68] 5'UTR | [50-68] 5'UTR |
| 106 | 2246 | UCCACUCGUGUGUUUCUAU | 2529 | AUAGAAACACACGAGUGGA | | [799-817] 3'UTR | [1038-1056] 3'UTR |
| 107 | 2247 | GGGAUUCCACUCGUGUGUU | 2530 | AACACACGAGUGGAAUCCC | | [794-812] 3'UTR | [1033-1051] 3'UTR |
| 108 | 2248 | CACACCUACUAGUCACCAG | 2531 | CUGGUGACUAGUAGGUGUG | Chp | [761-779] 3'UTR | [1000-1018] 3'UTR |
| 109 | 2249 | AGCACGUCAUCGACUACAU | 2532 | AUGUAGUCGAUGACGUGCU | GP,Chn,Chp | [386-404] ORF | [386-404] ORF |
| 110 | 2250 | CCAAGAAUCAUGAAAGUCG | 2533 | CGACUUUCAUGAUUCUUGG | Chp | [91-109] 5'UTR+ORF | [91-109] 5'UTR+ORF |
| 111 | 2251 | UUUUUUUCGCUUUGCCCAU | 2534 | AUGGGCAAAGCGAAAAAAA | | [55-73] 5'UTR | [55-73] 5'UTR |
| 112 | 2252 | GUUUUACAAUAGUUCUGUG | 2535 | CACAGAACUAUUGUAAAAC | Chp | [925-943] 3'UTR | [1164-1182] 3'UTR |
| 113 | 2253 | GAUUUCUGAGGAAAUUGCU | 2536 | AGCAAUUUCCUCAGAAAUC | Chp | [867-885] 3'UTR | [1106-1124] 3'UTR |
| 114 | 2254 | GGUGCUUCUCAGAUUUCUG | 2537 | CAGAAAUCUGAGAAGCACC | Chp | [856-874] 3'UTR | [1095-1113] 3'UTR |
| 115 | 2255 | AUUCCACGUUCUUAACAGU | 2538 | ACAGUUAAGAACGUGGAAU | | [1-19] 5'UTR | [1-19] 5'UTR |
| 116 | 2256 | AAUCAUGAAAGUCGCCAGU | 2539 | ACUGGCGACUUUCAUGAUU | Chp | [96-114] 5'UTR+ORF | [96-114] 5'UTR+ORF |
| 117 | 2257 | CCAGUCGCCAAGAAUCAUG | 2540 | CAUGAUUCUUGGCGACUGG | | [84-102] 5'UTR+ORF | [84-102] 5'UTR+ORF |
| 118 | 2258 | AUUUUUUUCGCUUUGCCCA | 2541 | UGGGCAAAGCGAAAAAAAU | | [54-72] 5'UTR | [54-72] 5'UTR |
| 119 | 2259 | CUUCUCAGAUUUCUGAGGA | 2542 | UCCUCAGAAAUCUGAGAAG | Chp | [860-878] 3'UTR | [1099-1117] 3'UTR |
| 120 | 2260 | UCCUCUCUGCACACCUACU | 2543 | AGUAGGUGUGCAGAGAGGA | Chp | [752-770] 3'UTR | [991-1009] 3'UTR |
| 121 | 2261 | CAAGAGGAAUUACGUGCUC | 2544 | GAGCACGUAAUUCCUCUUG | Chp | [611-629] 3'UTR | [850-868] 3'UTR |
| 122 | 2262 | GACCUUCAGUUGGAGCUGA | 2545 | UCAGCUCCAACUGAAGGUC | | [409-427] ORF | [409-427] ORF |
| 123 | 2263 | ACAUCAGGGACCUUCAGUU | 2546 | AACUGAAGGUCCCUGAUGU | | [401-419] ORF | [401-419] ORF |
| 124 | 2264 | CACGUCAUCGACUACAUCA | 2547 | UGAUGUAGUCGAUGACGUG | GP,Chn,Chp | [388-406] ORF | [388-406] ORF |
| 125 | 2265 | UCAGAUUUCUGAGGAAAUU | 2548 | AAUUUCCUCAGAAAUCUGA | Chp | [864-882] 3'UTR | [1103-1121] 3'UTR |
| 126 | 2266 | ACUGCGCCCUUAACUGCAU | 2549 | AUGCAGUUAAGGGCGCAGU | Chp | [690-708] 3'UTR | [929-947] 3'UTR |
| 127 | 2267 | UUCAGCCAGUCGCCAAGAA | 2550 | UUCUUGGCGACUGGCUGAA | | [79-97] 5'UTR | [79-97] 5'UTR |
| 128 | 2268 | GCAAGAGGAAUUACGUGCU | 2551 | AGCACGUAAUUCCUCUUGC | Chp | [610-628] 3'UTR | [849-867] 3'UTR |
| 129 | 2269 | CACCUCAUUUUUUUCGCUU | 2552 | AAGCGAAAAAAAUGAGGUG | | [48-66] 5'UTR | [48-66] 5'UTR |
| 130 | 2270 | ACCGACUGAAAAUAUUGUU | 2553 | AACAAUAUUUUCAGUCGGU | | [909-927] 3'UTR | [1148-1166] 3'UTR |
| 131 | 2271 | AUCUGAGGGAGAACAAGAC | 2554 | GUCUUGUUCUCCCUCAGAU | | [659-677] 3'UTR | [898-916] 3'UTR |
| 132 | 2272 | CCUUCAGUUGGAGCUGAAC | 2555 | GUUCAGCUCCAACUGAAGG | | [411-429] ORF | [411-429] ORF |
| 133 | 2273 | UCGACUACAUCAGGGACCU | 2556 | AGGUCCCUGAUGUAGUCGA | Rat,Ms,Chn,Chp | [395-413] ORF | [395-413] ORF |
| 134 | 2274 | GGUAAACGUGCUGCUCUAC | 2557 | GUAGAGCAGCACGUUUACC | Chp | [282-300] ORF | [282-300] ORF |
| 135 | 2275 | AGGAAUUACGUGCUCUGUG | 2558 | CACAGAGCACGUAAUUCCU | Chp | [615-633] 3'UTR | [854-872] 3'UTR |
| 136 | 2276 | UUCUCCAGCACGUCAUCGA | 2559 | UCGAUGACGUGCUGGAGAA | Chp | [380-398] ORF | [380-398] ORF |
| 137 | 2277 | AUGAAAGUCGCCAGUGGCA | 2560 | UGCCACUGGCGACUUUCAU | Chp | [100-118] ORF | [100-118] ORF |
| 138 | 2278 | UUCGCUUUGCCCAUUCUGU | 2561 | ACAGAAUGGGCAAAGCGAA | Chp | [60-78] 5'UTR | [60-78] 5'UTR |
| 139 | 2279 | GGCUUCCACCUCAUUUUUU | 2562 | AAAAAAUGAGGUGGAAGCC | | [42-60] 5'UTR | [42-60] 5'UTR |
| 140 | 2280 | CACUCGUGUGUUUCUAUUU | 2563 | AAAUAGAAACACACGAGUG | | [801-819] 3'UTR | [1040-1058] 3'UTR |
| 141 | 2281 | CGUCAUCGACUACAUCAGG | 2564 | CCUGAUGUAGUCGAUGACG | Chn,Chp | [390-408] ORF | [390-408] ORF |
| 142 | 2282 | CAGGUAACGUGCUGCUCUC | 2565 | AGAGCAGCACGUUAACCUG | Chp | [280-298] ORF | [280-298] ORF |
| 143 | 2283 | CCUACUAGUCACCAGAGAC | 2566 | GUCUCUGGUGACUAGUAGG | Chp | [765-783] 3'UTR | [1004-1022] 3'UTR |
| 144 | 2284 | UCUGCACACCUACUAGUCA | 2567 | UGACUAGUAGGUGUGCAGA | Chp | [757-775] 3'UTR | [996-1014] 3'UTR |
| 145 | 2285 | GAAUUACGUGCUCUGUGGG | 2568 | CCCACAGAGCACGUAAUUC | Chp | [617-635] 3'UTR | [856-874] 3'UTR |
| 146 | 2286 | ACGAGCAGCAGGUAAACGU | 2569 | ACGUUUACCUGCUGCUCGU | Chp | [272-290] ORF | [272-290] ORF |
| 147 | 2287 | UCACCGACUGAAAAUAUUG | 2570 | CAAUAUUUUCAGUCGGUGA | | [907-925] 3'UTR | [1146-1164] 3'UTR |
| 148 | 2288 | GAUCGCAUCUUGUGUCGCU | 2571 | AGCGACACAAGAUGCGAUC | Ms,GP,Chn,Chp | [547-565] ORF | [786-804] 3'UTR |
| 149 | 2289 | UCCAUUUCCGUAUCUGCU | 2572 | AGCAGAUACGGAAAAUGGA | | [20-38] 5'UTR | [20-38] 5'UTR |
| 150 | 2290 | GUUCCAUUUCCGUAUCUG | 2573 | CAGAUACGGAAAAUGGAAC | | [18-36] 5'UTR | [18-36] 5'UTR |
| 151 | 2291 | UGUUCCAUUUCCGUAUCU | 2574 | AGAUACGGAAAAUGGAACA | | [17-35] 5'UTR | [17-35] 5'UTR |
| 152 | 2292 | UCUACGACAUGAACGGCUG | 2575 | CAGCCGUUCAUGUCGUAGA | Rat,Ms,Chn,Chp | [296-314] ORF | [296-314] ORF |

FIGURE 4 Continued

| # | ID | Sequence 1 | ID2 | Sequence 2 | Target | Pos1 | Pos2 |
|---|---|---|---|---|---|---|---|
| 153 | 2293 | AAAAAUGGUCACGUUUGGU | 2576 | ACCAAACGUGACCAUUUUU | Chp | [840-858] 3'UTR | [1079-1097] 3'UTR |
| 154 | 2294 | UUACGUGCUCUGUGGGUCU | 2577 | AGACCCACAGAGCACGUAA | Chp | [620-638] 3'UTR | [859-877] 3'UTR |
| 155 | 2295 | CAUUUUUUUCGCUUUGCCC | 2578 | GGGCAAAGCGAAAAAAAUG | | [53-71] 5'UTR | [53-71] 5'UTR |
| 156 | 2296 | UUACAAUGAUCACCGACUG | 2579 | CAGUCGGUGAUCAUUGUAA | | [898-916] 3'UTR | [1137-1155] 3'UTR |
| 157 | 2297 | CUACUAGUCACCAGAGACU | 2580 | AGUCUCUGGUGACUAGUAG | Chp | [766-784] 3'UTR | [1005-1023] 3'UTR |
| 158 | 2298 | UGAACUCGGAAUCCGAAGU | 2581 | ACUUCGGAUUCCGAGUUCA | GP,Chp | [425-443] ORF | [425-443] ORF |
| 159 | 2299 | AUGAACGGCUGUUACUCAC | 2582 | GUGAGUAACAGCCGUUCAU | Chp | [304-322] ORF | [304-322] ORF |
| 160 | 2300 | AGAAUCAUGAAAGUCGCCA | 2583 | UGGCGACUUUCAUGAUUCU | Chp | [94-112] 5'UTR+ORF | [94-112] 5'UTR+ORF |
| 161 | 2301 | CAUUCUGUUUCAGCCAGUC | 2584 | GACUGGCUGAAACAGAAUG | | [71-89] 5'UTR | [71-89] 5'UTR |
| 162 | 2302 | GCACACCUACUAGUCACCA | 2585 | UGGUGACUAGUAGGUGUGC | Chp | [760-778] 3'UTR | [999-1017] 3'UTR |
| 163 | 2303 | CAUUUUCCGUAUCUGCUUC | 2586 | GAAGCAGAUACGGAAAAUG | | [22-40] 5'UTR | [22-40] 5'UTR |
| 164 | 2304 | CUGAACUCGGAAUCCGAAG | 2587 | CUUCGGAUUCCGAGUUCAG | GP,Chp | [424-442] ORF | [424-442] ORF |
| 165 | 2305 | UUCCACUCGUGUGUUUCUA | 2588 | UAGAAACACACGAGUGGAA | | [799-816] 3'UTR | [1037-1055] 3'UTR |
| 166 | 2306 | UAGUCACCAGAGACUUUAG | 2589 | CUAAAGUCUCUGGUGACUA | Chp | [770-788] 3'UTR | [1009-1027] 3'UTR |
| 167 | 2307 | AGAGGAAUUACGUGCUCUG | 2590 | CAGAGCACGUAAUUCCUCU | Chp | [613-631] 3'UTR | [852-870] 3'UTR |
| 168 | 2308 | ACGUCAUCGACUACAUCAG | 2591 | CUGAUGUAGUCGAUGACGU | GP,Chn,Chp | [389-407] ORF | [389-407] ORF |
| 169 | 2309 | AACGUGCUGCUCUACGACA | 2592 | UGUCGUAGAGCAGCACGUU | GP,Chn,Chp | [286-304] ORF | [286-304] ORF |
| 170 | 2310 | CUUCCACCUCAUUUUUUUC | 2593 | GAAAAAAAUGAGGUGGAAG | | [44-62] 5'UTR | [44-62] 5'UTR |
| 171 | 2311 | UUCGGGCUUCCACCUCAUU | 2594 | AAUGAGGUGGAAGCCCGAA | | [38-56] 5'UTR | [38-56] 5'UTR |
| 172 | 2312 | CCUUAACUGCAUCCAGCCU | 2595 | AGGCUGGAUGCAGUUAAGG | | [697-715] 3'UTR | [936-954] 3'UTR |
| 173 | 2313 | UUGGAGCUGAACUCGGAAU | 2596 | AUUCCGAGUUCAGCUCCAA | GP | [418-436] ORF | [418-436] ORF |
| 174 | 2314 | AAGGUGAGCAAGGUGGAGA | 2597 | UCUCCACCUUGCUCACCUU | Chp | [361-379] ORF | [361-379] ORF |
| 175 | 2315 | CUGUUACUCACGCCUCAAG | 2598 | CUUGAGGCGUGAGUAACAG | | [312-330] ORF | [312-330] ORF |
| 176 | 2316 | UAACUGUUCCAUUUUCCGU | 2599 | ACGGAAAAUGGAACAGUUA | | [13-31] 5'UTR | [13-31] 5'UTR |
| 177 | 2317 | CUCUACGACAUGAACGGCU | 2600 | AGCCGUUCAUGUCGUAGAG | Rat,Ms,Chn,Chp | [295-313] ORF | [295-313] ORF |
| 178 | 2318 | ACGUUCUUAACUGUUCCAU | 2601 | AUGGAACAGUUAAGAACGU | | [6-24] 5'UTR | [6-24] 5'UTR |
| 179 | 2319 | AUUUCUGAGGAAAUUGCUU | 2602 | AAGCAAUUUCCUCAGAAAU | Chp | [868-886] 3'UTR | [1107-1125] 3'UTR |
| 180 | 2320 | AAUGGUCACGUUUGGUGCU | 2603 | AGCACCAAACGUGACCAUU | Chp | [843-861] 3'UTR | [1082-1100] 3'UTR |
| 181 | 2321 | CACCUACUAGUCACCAGAG | 2604 | CUCUGGUGACUAGUAGGUG | Chp | [763-781] 3'UTR | [1002-1020] 3'UTR |
| 182 | 2322 | CUGCACACCUACUAGUCAC | 2605 | GUGACUAGUAGGUGUGCAG | Chp | [758-776] 3'UTR | [997-1015] 3'UTR |
| 183 | 2323 | AAUUACGUGCUCUGUGGGU | 2606 | ACCCACAGAGCACGUAAUU | Chp | [618-636] 3'UTR | [857-875] 3'UTR |
| 184 | 2324 | UCUUAACUGUUCCAUUUUC | 2607 | GAAAAUGGAACAGUUAAGA | | [10-28] 5'UTR | [10-28] 5'UTR |
| 185 | 2325 | AUUACAAUGAUCACCGACU | 2608 | AGUCGGUGAUCAUUGUAAU | | [897-915] 3'UTR | [1136-1154] 3'UTR |
| 186 | 2326 | UCGGGCUUCCACCUCAUUU | 2609 | AAAUGAGGUGGAAGCCCGA | | [39-57] 5'UTR | [39-57] 5'UTR |
| 187 | 2327 | UAAAAAUGGUCACGUUUG | 2610 | CAAACGUGACCAUUUUUUA | Chn | [838-856] 3'UTR | [1077-1095] 3'UTR |
| 188 | 2328 | UGGGAUUCCACUCGUGUGU | 2611 | ACACACGAGUGGAAUCCCA | | [793-811] 3'UTR | [1032-1050] 3'UTR |
| 189 | 2329 | CUUCAGUGCUGGAACU | 2612 | AGUUCAGCUCCAACUGAAG | | [412-430] ORF | [412-430] ORF |
| 190 | 2330 | AGAUUUCUGAGGAAAUUGC | 2613 | GCAAUUUCCUCAGAAAUCU | Chp | [866-884] 3'UTR | [1105-1123] 3'UTR |
| 191 | 2331 | UUAACUGCAUCCAGCCUGG | 2614 | CCAGGCUGGAUGCAGUUAA | | [699-717] 3'UTR | [938-956] 3'UTR |
| 192 | 2332 | ACAUGAACGGCUGUUACUC | 2615 | GAGUAACAGCCGUUCAUGU | Chp | [302-320] ORF | [302-320] ORF |
| 193 | 2333 | CUUAACUGUUCCAUUUUCC | 2616 | GGAAAAUGGAACAGUUAAG | | [11-29] 5'UTR | [11-29] 5'UTR |
| 194 | 2334 | UUUCAGCCAGCGCCAAGA | 2617 | UCUUGGCGCUGGCUGAAA | | [78-96] 5'UTR | [78-96] 5'UTR |
| 195 | 2335 | CCCAUUCUGUUUCAGCCAG | 2618 | CUGGCUGAAACAGAAUGGG | | [69-87] 5'UTR | [69-87] 5'UTR |
| 196 | 2336 | AUUCCACUCGUGUGUUUCU | 2619 | AGAAACACACGAGUGGAAU | | [797-815] 3'UTR | [1036-1054] 3'UTR |
| 197 | 2337 | CAUCUUGUGUCGCUGAAGC | 2620 | GCUUCAGCGACACAAGAUG | Chp | [552-570] ORF+3'UTR | [791-809] 3'UTR |
| 198 | 2338 | GAACUCGGAAUCCGAAGUU | 2621 | AACUUCGGAUUCCGAGUU | Chp | [426-444] ORF | [426-444] ORF |
| 199 | 2339 | AAACGUGCUGCUCUACGAC | 2622 | GUCGUAGAGCAGCACGUUU | Chp | [285-303] ORF | [285-303] ORF |
| 200 | 2340 | UCAUUUUUUUCGCUUUGCC | 2623 | GGCAAAGCGAAAAAAAUGA | | [52-70] 5'UTR | [52-70] 5'UTR |
| 201 | 2341 | UUUCUGAGGAAAUUGCUUU | 2624 | AAAGCAAUUUCCUCAGAAA | Chp | [869-887] 3'UTR | [1108-1126] 3'UTR |
| 202 | 2342 | CAGCACGUCAUCGACUACA | 2625 | UGUAGUCGAUGACGUGCUG | GP,Chn,Chp | [385-403] ORF | [385-403] ORF |
| 203 | 2343 | UUUUUUCGCUUUGCCCAUU | 2626 | AAUGGGCAAAGCGAAAAAA | | [56-74] 5'UTR | [56-74] 5'UTR |
| 204 | 2344 | UUCUGAGGAAAUUGCUUUG | 2627 | CAAAGCAAUUUCCUCAGAA | | [870-888] 3'UTR | [1109-1127] 3'UTR |
| 205 | 2345 | UCUCUGCACACCUACUAGU | 2628 | ACUAGUAGGUGUGCAGAGA | Chp | [755-773] 3'UTR | [994-1012] 3'UTR |
| 206 | 2346 | ACUCGGAAUCCGAAGUUGG | 2629 | CCAACUUCGGAUUCCGAGU | Chp | [428-446] ORF | [428-446] ORF |
| 207 | 2347 | GUCAUCGACUACAUCAGGG | 2630 | CCCUGAUGUAGUCGAUGAC | Chn,Chp | [391-409] ORF | [391-409] ORF |
| 208 | 2348 | AGCAGGUAAACGUGCUGCU | 2631 | AGCAGCACGUUUACCUGCU | Chp | [278-296] ORF | [278-296] ORF |
| 209 | 2349 | AGCAGCAGGUAAACGUGCU | 2632 | AGCACGUUUACCUGCUGCU | Chp | [275-293] ORF | [275-293] ORF |
| 210 | 2350 | CUCUGCACACCUACUAGUC | 2633 | GACUAGUAGGUGUGCAGAG | Chp | [756-774] 3'UTR | [995-1013] 3'UTR |
| 211 | 2351 | UCUGAGGGAGAACAAGACC | 2634 | GGUCUUGUUCUCCCUCAGA | | [660-678] 3'UTR | [899-917] 3'UTR |
| 212 | 2352 | UCCACGUUCUUAACUGUUC | 2635 | GAACAGUUAAGAACGUGGA | | [3-21] 5'UTR | [3-21] 5'UTR |
| 213 | 2353 | UUUUCGCUUUGCCCAUUCU | 2636 | AGAAUGGGCAAAGCGAAA | | [58-76] 5'UTR | [58-76] 5'UTR |
| 214 | 2354 | CAGAUUUCUGAGGAAAUUG | 2637 | CAAUUUCCUCAGAAAUCUG | Chp | [865-883] 3'UTR | [1104-1122] 3'UTR |
| 215 | 2355 | UGGUCACGUUUGGUGCUUC | 2638 | GAAGCACCAAACGUGACCA | Chp | [845-863] 3'UTR | [1084-1102] 3'UTR |
| 216 | 2356 | UGUUACUCACGCCUCAAGG | 2639 | CCUUGAGGCGUGAGUAACA | | [313-331] ORF | [313-331] ORF |
| 217 | 2357 | GUAAACGUGCUGCUCUACG | 2640 | CGUAGAGCAGCACGUUUAC | Chp | [283-301] ORF | [283-301] ORF |
| 218 | 2358 | UACUAGUCACCAGAGACUU | 2641 | AAGUCUCUGGUGACUAGUA | Chp | [767-785] 3'UTR | [1006-1024] 3'UTR |
| 219 | 2359 | GACUACAUCAGGGACCUUC | 2642 | GAAGGUCCCUGAUGUAGUC | | [397-415] ORF | [397-415] ORF |
| 220 | 2360 | GCCAAGAAUCAUGAAAGUC | 2643 | GACUUUCAUGAUUCUUGGC | Chp | [90-108] 5'UTR+ORF | [90-108] 5'UTR+ORF |

FIGURE 4 Continued

| | | | | | | | |
|---|---|---|---|---|---|---|---|
| 221 | 2361 | UAUUACAAUGAUCACCGAC | 2644 | GUCGGUGAUCAUUGUAAUA | | [896-914] 3'UTR | [1135-1153] 3'UTR |
| 222 | 2362 | GCUUCUCAGAUUUCUGAGG | 2645 | CCUCAGAAAUCUGAGAAGC | Chp | [859-877] 3'UTR | [1098-1116] 3'UTR |
| 223 | 2363 | UGGAGCUGAACUCGGAAUC | 2646 | GAUUCCGAGUUCAGCUCCA | GP | [419-437] ORF | [419-437] ORF |
| 224 | 2364 | CUGUUCCAUUUUCCGUAUC | 2647 | GAUACGGAAAAUGGAACAG | | [16-34] 5'UTR | [16-34] 5'UTR |
| 225 | 2365 | UUAACUGUUCCAUUUUCCG | 2648 | CGGAAAAUGGAACAGUUAA | | [12-30] 5'UTR | [12-30] 5'UTR |
| 226 | 2366 | UUCCACGUUCUUAACUGUU | 2649 | AACAGUUAAGAACGUGGAA | | [2-20] 5'UTR | [2-20] 5'UTR |
| 227 | 2367 | GCUUUGCCCAUUCUGUUUC | 2650 | GAAACAGAAUGGGCAAAGC | Chp | [63-81] 5'UTR | [63-81] 5'UTR |
| 228 | 2368 | GUAUAUUACAAUGAUCACC | 2651 | GGUGAUCAUUGUAAUAUAC | Chp | [893-911] 3'UTR | [1132-1150] 3'UTR |
| 229 | 2369 | GAUUCCACUCGUGUGUUUC | 2652 | GAAACACACGAGUGGAAUC | | [796-814] 3'UTR | [1035-1053] 3'UTR |
| 230 | 2370 | AAGAGGAAUUACGUGCUCU | 2653 | AGAGCACGUAAUUCCUCUU | Chp | [612-630] 3'UTR | [851-869] 3'UTR |
| 231 | 2371 | GUGAGCAAGGUGGAGAUUC | 2654 | GAAUCUCCACCUUGCUCAC | Chp | [364-382] ORF | [364-382] ORF |
| 232 | 2372 | UGCUCUACGACAUGAACGG | 2655 | CCGUUCAUGUCGUAGAGCA | Rat,Ms,GP,Chn,Chp | [293-311] ORF | [293-311] ORF |
| 233 | 2373 | AAGAAUCAUGAAAAGUCGCC | 2656 | GGCGACUUUCAUGAUUCUU | Chp | [93-111] 5'UTR+ORF | [93-111] 5'UTR+ORF |
| 234 | 2374 | UGCUUCUCAGAUUUCUGAG | 2657 | CUCAGAAAUCUGAGAAGCA | Rat,Chp | [858-876] 3'UTR | [1097-1115] 3'UTR |
| 235 | 2375 | UAUCUGCUUCGGGCUUCCA | 2658 | UGGAAGCCCGAAGCAGAUA | | [31-49] 5'UTR | [31-49] 5'UTR |
| 236 | 2376 | UGCCCAUUCUGUUUCAGCC | 2659 | GGCUGAAACAGAAUGGGCA | Chp | [67-85] 5'UTR | [67-85] 5'UTR |
| 237 | 2377 | UCUGAGGAAAUUGCUUUGU | 2660 | ACAAAGCAAUUUCCUCAGA | | [871-889] 3'UTR | [1110-1128] 3'UTR |
| 238 | 2378 | AAAUGGUCACGUUUGGUGC | 2661 | GCACCAAACGUGACCAUUU | Chp | [842-860] 3'UTR | [1081-1099] 3'UTR |
| 239 | 2379 | GGCAAGAGGAAUUACGUGC | 2662 | GCACGUAAUUCCUCUUGCC | Chp | [609-627] 3'UTR | [848-866] 3'UTR |
| 240 | 2380 | UUCCAUUUUCCGUAUCUGC | 2663 | GCAGAUACGGAAAAUGGAA | | [19-37] 5'UTR | [19-37] 5'UTR |
| 241 | 2381 | AUCGCAUCUUGUGUCGCUG | 2664 | CAGCGACACAAGAUGCGAU | Ms,GP,Chn,Chp | [548-566] ORF | [787-805] 3'UTR |
| 242 | 2382 | UACGACAUGAACGGCUGUU | 2665 | AACAGCCGUUCAUGUCGUA | Chp | [298-316] ORF | [298-316] ORF |
| 243 | 2383 | CUCAUUUUUUCGCUUUGC | 2666 | GCAAAGCGAAAAAAAUGAG | | [51-69] 5'UTR | [51-69] 5'UTR |
| 244 | 2384 | CUUAACUGCAUCCAGCCUG | 2667 | CAGGCUGGAUGCAGUUAAG | | [698-716] 3'UTR | [937-955] 3'UTR |
| 245 | 2385 | GGAAUCCGAAGUUGGAACC | 2668 | GGUUCCAACUUCGGAUUCC | | [432-450] ORF | [432-450] ORF |
| 246 | 2386 | UACAUCAGGGACCUUCAGU | 2669 | ACUGAAGGUCCCUGAUGUA | | [400-418] ORF | [400-418] ORF |
| 247 | 2387 | UUACUCACGCCUCAAGGAG | 2670 | CUCCUUGAGGCGUGAGUAA | | [315-333] ORF | [315-333] ORF |
| 248 | 2388 | AGUCACCAGAGACUUUAGG | 2671 | CCUAAAGUCUCUGGUGACU | Chp | [771-789] 3'UTR | [1010-1028] 3'UTR |
| 249 | 2389 | GACGAUCGCAUCUUGUGUC | 2672 | GACACAAGAUGCGAUCGUC | Ms,GP,Chn,Chp | [544-562] ORF | [783-801] 3'UTR |
| 250 | 2390 | AACUCGGAAUCCGAAGUUG | 2673 | CAACUUCGGAUUCCGAGUU | Chp | [427-445] ORF | [427-445] ORF |
| 251 | 2391 | AUCAGGGACCUUCAGUUGG | 2674 | CCAACUGAAGGUCCCUGAU | | [403-421] ORF | [403-421] ORF |
| 252 | 2392 | CUGCUCUACGACAUGAACG | 2675 | CGUUCAUGUCGUAGAGCAG | Rat,Ms,GP,Chn,Chp | [292-310] ORF | [292-310] ORF |
| 253 | 2393 | UCCACCUCAUUUUUUCGC | 2676 | GCGAAAAAAAUGAGGUGGA | | [46-64] 5'UTR | [46-64] 5'UTR |
| 254 | 2394 | AUGGUCACGUUUGGUGCUU | 2677 | AAGCACCAAACGUGACCAU | Chp | [844-862] 3'UTR | [1083-1101] 3'UTR |
| 255 | 2395 | UGAACGGCUGUUACUCACG | 2678 | CGUGAGUAACAGCCGUUCA | Chp | [305-323] ORF | [305-323] ORF |
| 256 | 2396 | UUCUGUUUCAGCCAGUCGC | 2679 | GCGACUGGCUGAAACAGAA | | [73-91] 5'UTR | [73-91] 5'UTR |
| 257 | 2397 | UUUGCCCAUUCUGUUUCAG | 2680 | CUGAAACAGAAUGGGCAAA | Chp | [65-83] 5'UTR | [65-83] 5'UTR |
| 258 | 2398 | UAUAUUACAAUGAUCACCG | 2681 | CGGUGAUCAUUGUAAUAUA | Chp | [894-912] 3'UTR | [1133-1151] 3'UTR |
| 259 | 2399 | GUCACGUUUGGUGCUUCUC | 2682 | GAGAAGCACCAAACGUGAC | Chp | [847-865] 3'UTR | [1086-1104] 3'UTR |
| 260 | 2400 | UUUCGCUUUGCCCAUUCUG | 2683 | CAGAAUGGGCAAAGCGAAA | Chp | [59-77] 5'UTR | [59-77] 5'UTR |
| 261 | 2401 | GAAUCCGAAGUUGGAACCC | 2684 | GGGUUCCAACUUCGGAUUC | | [433-451] ORF | [433-451] ORF |
| 262 | 2402 | UUUACAAUAGUUCUGUGGG | 2685 | CCCACAGAACUAUUGUAAA | Chp | [927-945] 3'UTR | [1166-1184] 3'UTR |
| 263 | 2403 | UUCAGUUGGAGCUGAACUC | 2686 | GAGUUCAGCUCCAACUGAA | | [413-431] ORF | [413-431] ORF |
| 264 | 2404 | UUGGUGCUUCUCAGAUUUC | 2687 | GAAAUCUGAGAAGCACCAA | Chp | [854-872] 3'UTR | [1093-1111] 3'UTR |
| 265 | 2405 | AGCAAGGUGGAGAUUCUCC | 2688 | GGAGAAUCUCCACCUUGCU | Chp | [367-385] ORF | [367-385] ORF |
| 266 | 2406 | AUUACGUGCUCUGUGGGUC | 2689 | GACCCACAGAGCACGUAAU | Chp | [619-637] 3'UTR | [858-876] 3'UTR |
| 267 | 2407 | ACGAUCGCAUCUUGUGUCG | 2690 | CGACACAAGAUGCGAUCGU | Ms,GP,Chn,Chp | [545-563] ORF | [784-802] 3'UTR |
| 268 | 2408 | AAGGUGGAGAUUCUCCAGC | 2691 | GCUGGAGAAUCUCCACCUU | Chp | [370-388] ORF | [370-388] ORF |
| 269 | 2409 | AAAAUGGUCACGUUUGGUG | 2692 | CACCAAACGUGACCAUUUU | Chp | [841-859] 3'UTR | [1080-1098] 3'UTR |
| 270 | 2410 | UGCACACCUACUAGUCACC | 2693 | GGUGACUAGUAGGUGUGCA | Chp | [759-777] 3'UTR | [998-1016] 3'UTR |
| 271 | 2411 | UCAGUUGGAGCUGAACUCG | 2694 | CGAGUUCAGCUCCAACUGA | | [414-432] ORF | [414-432] ORF |
| 272 | 2412 | UUUUACAAUAGUUCUGUGG | 2695 | CCACAGAACUAUUGUAAAA | Chp | [926-944] 3'UTR | [1165-1183] 3'UTR |
| 273 | 2413 | AUCUUGUGUCGCUGAAGCG | 2696 | CGCUUCAGCGACACAAGCG | Chp | [553-571] ORF+3'UTR | [792-810] 3'UTR |
| 274 | 2414 | AUUCUGUUUCAGCCAGUCG | 2697 | CGACUGGCUGAAACAGAAU | | [72-90] 5'UTR | [72-90] 5'UTR |
| 275 | 2415 | AUCAUGAAAGUCGCCAGUG | 2698 | CACUGGCGACUUUCAUGAU | Chp | [97-115] 5'UTR+ORF | [97-115] 5'UTR+ORF |
| 276 | 2416 | UUUUUCGCUUUGCCCAUUC | 2699 | GAAUGGGCAAAGCGAAAAA | | [57-75] 5'UTR | [57-75] 5'UTR |
| 277 | 2417 | AUUUUCCGUAUCUGCUUCG | 2700 | CGAAGCAGAUACGGAAAAU | Chp | [23-41] 5'UTR | [23-41] 5'UTR |
| 278 | 2418 | AUCGACUACAUCAGGGACC | 2701 | GGUCCCUGAUGUAGUCGAU | Rat,Ms,Chn,Chp | [394-412] ORF | [394-412] ORF |
| 279 | 2419 | UUUCCGUAUCUGCUUCGGG | 2702 | CCCGAAGCAGAUACGGAAA | Chp | [25-43] 5'UTR | [25-43] 5'UTR |
| 280 | 2420 | UUGCCCAUUCUGUUUCAGC | 2703 | GCUGAAACAGAAUGGGCAA | Chp | [66-84] 5'UTR | [66-84] 5'UTR |
| 281 | 2421 | AUUCUCCAGCACGUCAUCG | 2704 | CGAUGACGUGCUGGAGAAU | Chp | [379-397] ORF | [379-397] ORF |
| 282 | 2422 | UUUUCCGUAUCUGCUUCGG | 2705 | CCGAAGCAGAUACGGAAAA | Chp | [24-42] 5'UTR | [24-42] 5'UTR |
| 283 | 2423 | UUCCACCUCAUUUUUUUCG | 2706 | CGAAAAAAAUGAGGUGGAA | | [45-63] 5'UTR | [45-63] 5'UTR |

Table A4 ID2 - inhibitor of DNA binding 2

| No. | SEQ ID NO. | Sense siRNA | SEQ ID NO. | AntiSense siRNA | Other Sp | Human-33946335 ORF:184-588 |
|---|---|---|---|---|---|---|

FIGURE 4 Continued

| # | | | | | | |
|---|---|---|---|---|---|---|
| 1 | 2707 | UGCUAUACAACAUGAACGA | 3207 | UCGUUCAUGUUGUAUAGCA | | [287-305] ORF |
| 2 | 2708 | AUGAACGACUGCUACUCCA | 3208 | UGGAGUAGCAGUCGUUCAU | Rat,Ms,GP,Chn | [298-316] ORF |
| 3 | 2709 | ACAACAUGAACGACUGCUA | 3209 | UAGCAGUCGUUCAUGUUGU | Rat,Ms,GP | [293-311] ORF |
| 4 | 2710 | UGUUAUAACUGAACCCAAA | 3210 | UUUGGGUUCAGUUAUAACA | Ms | [1284-1302] 3'UTR |
| 5 | 2711 | GCCUGCUAUACAACAUGAA | 3211 | UUCAUGUUGUAUAGCAGGC | | [284-302] ORF |
| 6 | 2712 | CCUUCUGAGUUAAUGUCAA | 3212 | UUGACAUUAACUCAGAAGG | | [544-562] ORF |
| 7 | 2713 | GUCUAUUUCUGCAUUCAAA | 3213 | UUUGAAUGCAGAAAUAGAC | | [1115-1133] 3'UTR |
| 8 | 2714 | CGAAAACGUUAAAAUCACA | 3214 | UGUGAUUUUAACGUUUUCG | | [874-892] 3'UTR |
| 9 | 2715 | UGAACGACUGCUACUCCAA | 3215 | UUGGAGUAGCAGUCGUUCA | Rat,Ms,GP,Chn | [299-317] ORF |
| 10 | 2716 | CAACAUGAACGACUGCUAC | 3216 | GUAGCAGUCGUUCAUGUUG | Rat,Ms,GP | [294-312] ORF |
| 11 | 2717 | CUAUACAACAUGAACGACU | 3217 | AGUCGUUCAUGUUGUAUAG | | [289-307] ORF |
| 12 | 2718 | UAUACAACAUGAACGACUG | 3218 | CAGUCGUUCAUGUUGUAUA | | [290-308] ORF |
| 13 | 2719 | CGUUAAAAUCACAAGGAAU | 3219 | AUUCCUUGUGAUUUUAACG | | [880-898] 3'UTR |
| 14 | 2720 | GAAGGAAAACUAAGAAUGA | 3220 | UCAUUCUUAGUUUUCCUUC | | [735-753] 3'UTR |
| 15 | 2721 | GAAUCUUUUAAGUGCUGAA | 3221 | UUCAGCACUUAAAAGAUUC | | [649-667] 3'UTR |
| 16 | 2722 | GACUUUGCCUUUUUUUCAAA | 3222 | UUUGAAAAAAGGCAAAGUC | | [914-932] 3'UTR |
| 17 | 2723 | CGGUCAGCAUGAAAGCCUU | 3223 | AAGGCUUUCAUGCUGACCG | | [176-194] 5'UTR+ORF |
| 18 | 2724 | ACGUUAAAAUCACAAGGAA | 3224 | UUCCUUGUGAUUUUAACGU | | [879-897] 3'UTR |
| 19 | 2725 | GGGUGUUCUCUUACUUGGA | 3225 | UCCAAGUAAGAGAACACCC | | [765-783] 3'UTR |
| 20 | 2726 | CCUACUGAAUGCUGUGUAU | 3226 | AUACACAGCAUUCAGUAGG | Ms | [1016-1034] 3'UTR |
| 21 | 2727 | GAAGUCUUUUGGUCAGAAA | 3227 | UUUCUGACCAAAAGACUUC | | [979-997] 3'UTR |
| 22 | 2728 | CCAGUAUUCAGUCACUUAA | 3228 | UUAAGUGACUGAAUACUGG | | [958-976] 3'UTR |
| 23 | 2729 | CAGUAUUCAGUCACUUAAA | 3229 | UUUAAGUGACUGAAUACUG | | [959-977] 3'UTR |
| 24 | 2730 | CAAGGAAUUGCCCAAUCUA | 3230 | UAGAUUGGGCAAUUCCUUG | | [891-909] 3'UTR |
| 25 | 2731 | GAACGACUGCUACUCCAAG | 3231 | CUUGGAGUAGCAGUCGUUC | Rat,Ms,GP,Chn | [300-318] ORF |
| 26 | 2732 | GGAGCGAAAACGUUAAAAU | 3232 | AUUUUAACGUUUUCGCUCC | | [870-888] 3'UTR |
| 27 | 2733 | GAACCCAAAUAAAUACAAG | 3233 | CUUGUAUUUAUUUGGGUUC | | [1294-1312] 3'UTR |
| 28 | 2734 | GCUAUACAACAUGAACGAC | 3234 | GUCGUUCAUGUUGUAUAGC | | [288-306] ORF |
| 29 | 2735 | AAGGAAUUGCCCAAUCUAA | 3235 | UUAGAUUGGGCAAUUCCUU | | [892-910] 3'UTR |
| 30 | 2736 | AGAAGGUGAGCAAGAUGGA | 3236 | UCCAUCUUGCUCACCUUCU | GP,Chn | [353-371] ORF |
| 31 | 2737 | ACUGCUACUCCAAGCUCAA | 3237 | UUGAGCUUGGAGUAGCAGU | Rat,Ms | [305-323] ORF |
| 32 | 2738 | GGGAGCGAAAACGUUAAAA | 3238 | UUUUAACGUUUUCGCUCCC | | [869-887] 3'UTR |
| 33 | 2739 | GGACUGUGAUAUUCGUUAU | 3239 | AUAACGAAUAUCACAGUCC | | [781-799] 3'UTR |
| 34 | 2740 | CCAGUGCUUUGAUUUUUAU | 3240 | AUAAAAAUCAAAGCACUGG | | [1258-1276] 3'UTR |
| 35 | 2741 | CAUGAACGACUGCUACUCC | 3241 | GGAGUAGCAGUCGUUCAUG | Rat,Ms,GP | [297-315] ORF |
| 36 | 2742 | CCUUUUUGCACACAAGCCUA | 3242 | UAGGCUUGUGUCAAAAAGG | | [1001-1019] 3'UTR |
| 37 | 2743 | GUCCUUGCAGGCUUCUGAA | 3243 | UUCAGAAGCCUGCAAGGAC | | [522-540] ORF |
| 38 | 2744 | UGAGGUCCGUUAGGAAAAA | 3244 | UUUUUCCUAACGGACCUCA | Rat,Ms | [203-221] ORF |
| 39 | 2745 | GGAAAACUAAGAAUGAUCA | 3245 | UGAUCAUUCUUAGUUUUCC | | [738-756] 3'UTR |
| 40 | 2746 | GUGAGGUCCGUUAGGAAAA | 3246 | UUUUCCUAACGGACCUCAC | Rat,Ms | [202-220] ORF |
| 41 | 2747 | GUUGGAAGGUUUUCUUUAU | 3247 | AUAAAGAAAACCUUCCAAC | Ms | [833-851] 3'UTR |
| 42 | 2748 | CAUUCACAAGGAGGACAA | 3248 | UUGUCCUCCUUGUGAAAUG | | [681-699] 3'UTR |
| 43 | 2749 | GGAAAAACAGCCUGUCGGA | 3249 | UCCGACAGGCUGUUUUUCC | Rat,Ms | [215-233] ORF |
| 44 | 2750 | AGGUGAGCAAGAUGGAAAU | 3250 | AUUUCCAUCUUGCUCACCU | GP,Chn | [356-374] ORF |
| 45 | 2751 | GGUGAUUGCCUGCUUUAUU | 3251 | AAUAAAGCAGGCAAUCACC | | [1231-1249] 3'UTR |
| 46 | 2752 | UGAUGUACUUAUUCAUGCU | 3252 | AGCAUGAAUAAGUACAUCA | | [1141-1159] 3'UTR |
| 47 | 2753 | CUUGUAUAGUGGCAGAGAU | 3253 | AUCUCUGCCACUAUACAAG | | [1096-1114] 3'UTR |
| 48 | 2754 | CCUUGUGAACUCUUUAAUU | 3254 | AAUUAAAGAGUUCACAAGG | | [1069-1087] 3'UTR |
| 49 | 2755 | AGCCUGCUAUACAACAUGA | 3255 | UCAUGUUGUAUAGCAGGCU | | [283-301] ORF |
| 50 | 2756 | GCCCUUUCUGCAGUUGGAA | 3256 | UUCCAACUGCAGAAAGGGC | | [821-839] 3'UTR |
| 51 | 2757 | CAACAACAAAUUCACGGAA | 3257 | UUCCGUGAAUUUGUUGUUG | | [633-651] 3'UTR |
| 52 | 2758 | CUGAAUAAGCGGUGUUCAU | 3258 | AUGAACACCGCUUAUUCAG | | [585-603] ORF+3'UTR |
| 53 | 2759 | GAGUUAAUGUCAAAUGACA | 3259 | UGUCAUUUGACAUUAACUC | | [550-568] ORF |
| 54 | 2760 | AUGUUAUAACUGAACCCAA | 3260 | UUGGGUUCAGUUAUAACAU | Ms | [1283-1301] 3'UTR |
| 55 | 2761 | UGUCUAUUUCUGCAUUCAA | 3261 | UUGAAUGCAGAAAUAGACA | | [1114-1132] 3'UTR |
| 56 | 2762 | GCGUGAAUACCAGAAGGAU | 3262 | AUCCUUCUGGUAUUCACGC | | [939-957] 3'UTR |
| 57 | 2763 | CAAAGGUGGAGCGUGAAUA | 3263 | UAUUCACGCUCCACCUUUG | | [929-947] 3'UTR |
| 58 | 2764 | CCUGCUAUACAACAUGAA | 3264 | GUUCAUGUUGUAUAGCAGG | | [285-303] ORF |
| 59 | 2765 | GAUGUACUUAUUCAUGCUA | 3265 | UAGCAUGAAUAAGUACAUC | | [1142-1160] 3'UTR |
| 60 | 2766 | GAAGGAUCCAGUAUUCAGU | 3266 | ACUGAAUACUGGAUCCUUC | | [951-969] 3'UTR |
| 61 | 2767 | ACCAGUGCUUUGAUUUUUA | 3267 | UAAAAAUCAAAGCACUGGU | | [1257-1275] 3'UTR |
| 62 | 2768 | GACCAGUGCUUUGAUUUUU | 3268 | AAAAAUCAAAGCACUGGUC | | [1255-1273] 3'UTR |
| 63 | 2769 | UGUGUUUAUUGAAUGGUGA | 3269 | UCACCAUUCAAUAAACACA | | [1217-1235] 3'UTR |
| 64 | 2770 | GACUGCUACUCCAAGCUCA | 3270 | UGAGCUGGAGUAGCAGUC | Rat,Ms | [304-322] ORF |
| 65 | 2771 | UCUGCAUUCAAAAGUGUAA | 3271 | UUACACUUUUGAAUGCAGA | | [1122-1140] 3'UTR |
| 66 | 2772 | CUUUGCACAACAACAACAA | 3272 | UUGUUGUUGUUGUGCAAAG | | [617-635] 3'UTR |
| 67 | 2773 | AAUGUCAAAUGACAGCAAA | 3273 | UUUGCUGUCAUUUGACAUU | | [555-573] ORF |
| 68 | 2774 | GCUUUAUUUCAGAGGACCA | 3274 | UGGUCCUCUGAAAUAAAGC | | [1242-1260] 3'UTR |

FIGURE 4 Continued

| | | | | | | | |
|---|---|---|---|---|---|---|---|
| 69 | 2775 | ACUGAAUGCUGUGUAUAUA | 3275 | UAUAUACACAGCAUUCAGU | Ms | | [1019-1037] 3'UTR |
| 70 | 2776 | ACCCGAUGAGCCUGCUAUA | 3276 | UAUAGCAGGCUCAUCGGGU | | | [275-293] ORF |
| 71 | 2777 | AGAGGACCAGUGCUUUGAU | 3277 | AUCAAAGCACUGGUCCUCU | | | [1252-1270] 3'UTR |
| 72 | 2778 | AAACCUUGUGAACUCUUUA | 3278 | UAAAGAGUUCACAAGGUUU | | | [1066-1084] 3'UTR |
| 73 | 2779 | AACAUGAACGACUGCUACU | 3279 | AGUAGCAGUCGUUCAUGUU | Rat,Ms,GP | | [295-313] ORF |
| 74 | 2780 | AGUUGGAAGGUUUUCUUUA | 3280 | UAAAGAAAACCUUCCAACU | Ms | | [832-850] 3'UTR |
| 75 | 2781 | CUUGGACUGUGAUAUUCGU | 3281 | ACGAAUAUCACAGUCCAAG | | | [778-796] 3'UTR |
| 76 | 2782 | CCAGGGUGUUCUCUUACUU | 3282 | AAGUAAGAGAACACCCUGG | | | [762-780] 3'UTR |
| 77 | 2783 | CACAAGGAGGACAAGUUGA | 3283 | UCAACUUGUCCUCCUUGUG | | | [686-704] 3'UTR |
| 78 | 2784 | ACAUGAACGACUGCUACUC | 3284 | GAGUAGCAGUCGUUCAUGU | Rat,Ms,GP | | [296-314] ORF |
| 79 | 2785 | GCAAGAUGGAAAUCCUGCA | 3285 | UGCAGGAUUUCCAUCUUGC | | | [362-380] ORF |
| 80 | 2786 | GAAACCUUGUGAACUCUUU | 3286 | AAAGAGUUCACAAGGUUUC | | | [1065-1083] 3'UTR |
| 81 | 2787 | GCAGUUGGAAGGUUUUCUU | 3287 | AAGAAAACCUUCCAACUGC | | | [830-848] 3'UTR |
| 82 | 2788 | CUAUUGUCAGCCUGCAUCA | 3288 | UGAUGCAGGCUGACAAUAG | | | [434-452] ORF |
| 83 | 2789 | CCACUAUUGUCAGCCUGCA | 3289 | UGCAGGCUGACAAUAGUGG | | | [431-449] ORF |
| 84 | 2790 | AGAGAUGUCUAUUUCUGCA | 3290 | UGCAGAAAUAGACAUCUCU | | | [1109-1127] 3'UTR |
| 85 | 2791 | CUGAAUGCUGUGUAUAUAU | 3291 | AUAUAUACACAGCAUUCAG | Ms | | [1020-1038] 3'UTR |
| 86 | 2792 | UUGACACAAGCCUACUGAA | 3292 | UUCAGUAGGCUUGUGUCAA | | | [1006-1024] 3'UTR |
| 87 | 2793 | UGCACAACAACAACAACAA | 3293 | UUGUUGUUGUUGUUGUGCA | | | [620-638] 3'UTR |
| 88 | 2794 | GUUAUAAACUGAACCCAAAU | 3294 | AUUUGGGUUCAGUUUAUAAC | Ms | | [1285-1303] 3'UTR |
| 89 | 2795 | UUGAGUGAAACCUUGUGAA | 3295 | UUCACAAGGUUUCACUCAA | | | [1059-1077] 3'UTR |
| 90 | 2796 | UUUCAAAGGUGGAGCGUGA | 3296 | UCACGCUCCACCUUUGAAA | | | [926-944] 3'UTR |
| 91 | 2797 | GAAUGAUCAUCUUCCCAGG | 3297 | CCUGGGAAGAUGAUCAUUC | | | [748-766] 3'UTR |
| 92 | 2798 | AAAGCACUGUGUGGCUGAA | 3298 | UUCAGCCACACAGUGCUUU | | | [571-589] ORF+3'UTR |
| 93 | 2799 | UUGUCAGCCUGCAUCACCA | 3299 | UGGUGAUGCAGGCUGACAA | | | [437-455] ORF |
| 94 | 2800 | AGAUGGAAAUCCUGCAGCA | 3300 | UGCUGCAGGAUUUCCAUCU | Rat,Ms | | [365-383] ORF |
| 95 | 2801 | GAGGACCAGUGCUUUGAUU | 3301 | AAUCAAAGCACUGGUCCUC | | | [1253-1271] 3'UTR |
| 96 | 2802 | GAUCCAGUAUUCAGUCACU | 3302 | AGUGACUGAAUACUGGAUC | | | [955-973] 3'UTR |
| 97 | 2803 | GGUCCGUUAGGAAAAACAG | 3303 | CUGUUUUUCCUAACGGACC | Rat,Ms | | [206-224] ORF |
| 98 | 2804 | GUGAUUGCCUGCUUUAUUU | 3304 | AAAUAAAGCAGGCAAUCAC | | | [1232-1250] 3'UTR |
| 99 | 2805 | GAAUGGUGAUUGCCUGCUU | 3305 | AAGCAGGCAAUCACCAUUC | | | [1227-1245] 3'UTR |
| 100 | 2806 | GUGUUUAUUGAAUGGUGAU | 3306 | AUCACCAUUCAAUAAACAC | | | [1218-1236] 3'UTR |
| 101 | 2807 | AGACUUUGCCUUUUUUCAA | 3307 | UUGAAAAAAGGCAAAGUCU | | | [913-931] 3'UTR |
| 102 | 2808 | UCUCUUACUUGGACUGUGA | 3308 | UCACAGUCCAAGUAAGAGA | | | [771-789] 3'UTR |
| 103 | 2809 | GGCAGAGAUGUCUAUUUCU | 3309 | AGAAAUAGACAUCUCUGCC | | | [1106-1124] 3'UTR |
| 104 | 2810 | CAAAGCACUGUGUGGCUGA | 3310 | UCAGCCACACAGUGCUUUG | | | [570-588] ORF |
| 105 | 2811 | CAAGCCUACUGAAUGCUGU | 3311 | ACAGCAUUCAGUAGGCUUG | | | [1012-1030] 3'UTR |
| 106 | 2812 | UGGAGCUGAAUACCAGAA | 3312 | UUCUGGUAUUCACGCUCCA | | | [935-953] 3'UTR |
| 107 | 2813 | UUCCCAGGGUGUUCUCUUA | 3313 | UAAGAGAACACCCUGGGAA | | | [759-777] 3'UTR |
| 108 | 2814 | UAAUGUCAAAUGACAGCAA | 3314 | UUGCUGUCAUUUGACAUUA | | | [554-572] ORF |
| 109 | 2815 | CAGAGGACCAGUGCUUUGA | 3315 | UCAAAGCACUGGUCCUCUG | | | [1251-1269] 3'UTR |
| 110 | 2816 | GGAGCGUGAAUACCAGAAG | 3316 | CUUCUGGUAUUCACGCUCC | | | [936-954] 3'UTR |
| 111 | 2817 | AGCGAAAACGUUAAAAUCA | 3317 | UGAUUUUAACGUUUUCGCU | | | [872-890] 3'UTR |
| 112 | 2818 | GAGCGAAAACGUUAAAAUC | 3318 | GAUUUUAACGUUUUCGCUC | | | [871-889] 3'UTR |
| 113 | 2819 | CAGUUGGAAGGUUUUCUUU | 3319 | AAAGAAAACCUUCCAACUG | Ms | | [831-849] 3'UTR |
| 114 | 2820 | UGGACUGUGAUAUUCGUUA | 3320 | UAACGAAUAUCACAGUCCA | | | [780-798] 3'UTR |
| 115 | 2821 | CCCAGGGUGUUCUCUUACU | 3321 | AGUAAGAGAACACCCUGGG | | | [761-779] 3'UTR |
| 116 | 2822 | GGAAUCUUUUAAGUGCUGA | 3322 | UCAGCACUUAAAAGAUUCC | | | [648-666] 3'UTR |
| 117 | 2823 | CAAAUGACAGCAAAGCACU | 3323 | AGUGCUUUGCUGUCAUUUG | Chn | | [560-578] ORF |
| 118 | 2824 | GAUUGCCUGCUUUAUUUCA | 3324 | UGAAAUAAAGCAGGCAAUC | | | [1234-1252] 3'UTR |
| 119 | 2825 | GUUGUAAACUUAACCCUUU | 3325 | AAAGGGUUAAGUUUACAAC | Ms | | [1180-1198] 3'UTR |
| 120 | 2826 | AACCUUGUGAACUCUUUAA | 3326 | UUAAAGAGUUCACAAGGUU | | | [1067-1085] 3'UTR |
| 121 | 2827 | UACUGAAUGCUGUGUAUAU | 3327 | AUAUACACAGCAUUCAGUA | Ms | | [1018-1036] 3'UTR |
| 122 | 2828 | AAGUCUUUUGGUCAGAAAU | 3328 | AUUUCUGACCAAAAGACUU | | | [980-998] 3'UTR |
| 123 | 2829 | UGCCCUUUCUGCAGUUGGA | 3329 | UCCAACUGCAGAAAGGGCA | | | [820-838] 3'UTR |
| 124 | 2830 | UGGAAGGAAAACUAAGAAU | 3330 | AUUCUUAGUUUUCCUUCCA | | | [733-751] 3'UTR |
| 125 | 2831 | AGUUGUAAACUUAACCCUU | 3331 | AAGGGUUAAGUUUACAACU | Ms | | [1179-1197] 3'UTR |
| 126 | 2832 | GCCUACUGAAUGCUGUGUA | 3332 | UACACAGCAUUCAGUAGGC | Ms | | [1015-1033] 3'UTR |
| 127 | 2833 | AAAUGAAGUCUUUUGGUCA | 3333 | UGACCAAAAGACUUCAUUU | | | [975-993] 3'UTR |
| 128 | 2834 | CAGACUUUGCCUUUUUUCA | 3334 | UGAAAAAAGGCAAAGUCUG | | | [912-930] 3'UTR |
| 129 | 2835 | ACAAAUUCACGGAAUCUUU | 3335 | AAAGAUUCCGUGAAUUUGU | | | [638-656] 3'UTR |
| 130 | 2836 | GGUGUUCAUGAUUUCUUUU | 3336 | AAAAGAAAUCAUGAACACC | | | [595-613] 3'UTR |
| 131 | 2837 | AGGUCCGUUAGGAAAAACA | 3337 | UGUUUUUCCUAACGGACCU | Rat,Ms | | [205-223] ORF |
| 132 | 2838 | ACUACAUCUUGGACCUGCA | 3338 | UGCAGGUCCAAGAUGUAGU | | | [392-410] ORF |
| 133 | 2839 | CCUGCUUUAUUUCGAGGA | 3339 | UCCUCGAAAUAAAGCAGG | | | [1239-1257] 3'UTR |
| 134 | 2840 | AGAUGUCUAUUUCUGCAUU | 3340 | AAUGCAGAAAUAGACAUCU | | | [1111-1129] 3'UTR |
| 135 | 2841 | CUAUUUGAGUGAAACCUUG | 3341 | CAAGGUUUCACUCAAAUAG | | | [1055-1073] 3'UTR |
| 136 | 2842 | GUGGAGCGUGAAUACCAGA | 3342 | UCUGGUAUUCACGCUCCAC | | | [934-952] 3'UTR |

FIGURE 4 Continued

| | | | | | | | |
|---|---|---|---|---|---|---|---|
| 137 | 2843 | GCCUUUUUCAAAGGUGGA | 3343 | UCCACCUUUGAAAAAGGC | | [920-938] 3'UTR |
| 138 | 2844 | CUCUUACUUGGACUGUGAU | 3344 | AUCACAGUCCAAGUAAGAG | | [772-790] 3'UTR |
| 139 | 2845 | UCAUCGACUACAUCUUGGA | 3345 | UCCAAGAUGUAGUCGAUGA | | [386-404] ORF |
| 140 | 2846 | GAACAAGAAGGUGAGCAAG | 3346 | CUUGCUCACCUUCUUGUUC | GP,Chn | [348-366] ORF |
| 141 | 2847 | CUGCAUUCAAAAGUGUAAU | 3347 | AUUACACUUUUGAAUGCAG | | [1123-1141] 3'UTR |
| 142 | 2848 | AGGUGGAGCGUGAAUACCA | 3348 | UGGUAUUCACGCUCCACCU | | [932-950] 3'UTR |
| 143 | 2849 | UCUUACUUGGACUGUGAUA | 3349 | UAUCACAGUCCAAGUAAGA | | [773-791] 3'UTR |
| 144 | 2850 | CCAUUUCACAAGGAGGACA | 3350 | UGUCCUCCUUGUGAAAUGG | | [680-698] 3'UTR |
| 145 | 2851 | CCCUUCUGAGUUAAUGUCA | 3351 | UGACAUUAACUCAGAAGGG | | [543-561] ORF |
| 146 | 2852 | UCCAGUAUUCAGUCACUUA | 3352 | UAAGUGACUGAAUACUGGA | | [957-975] 3'UTR |
| 147 | 2853 | UCUGCAGUUGGAAGGUUUU | 3353 | AAAACCUUCCAACUGCAGA | | [827-845] 3'UTR |
| 148 | 2854 | GACUGUGAUAUUCGUUAUU | 3354 | AAUAACGAAUAUCACAGUC | | [782-800] 3'UTR |
| 149 | 2855 | CCCUCAACACGGAUAUCAG | 3355 | CUGAUAUCCGUGUUGAGGG | | [497-515] ORF |
| 150 | 2856 | GCUACUCCAAGCUCAAGGA | 3356 | UCCUUGAGCUUGGAGUAGC | Rat,Ms | [308-326] ORF |
| 151 | 2857 | GUCUUUUGGUCAGAAAUUA | 3357 | UAAUUUCUGACCAAAAGAC | | [982-1000] 3'UTR |
| 152 | 2858 | AUACCAGAAGGAUCCAGUA | 3358 | UACUGGAUCCUUCUGGUAU | | [945-963] 3'UTR |
| 153 | 2859 | UCUUUUAAGUGCUGAACUU | 3359 | AAGUUCAGCACUUAAAAGA | | [652-670] 3'UTR |
| 154 | 2860 | ACAACAACAAAUUCACGGA | 3360 | UCCGUGAAUUUGUUGUUGU | | [632-650] 3'UTR |
| 155 | 2861 | AAAUCCUGCAGCACGUCAU | 3361 | AUGACGUGCUGCAGGAUUU | Rat,Ms | [371-389] ORF |
| 156 | 2862 | CCCAAAUAAAUACAAGUUC | 3362 | GAACUUGUAUUUAUUUGGG | | [1297-1315] 3'UTR |
| 157 | 2863 | CUACUGAAUGCUGUGUAUA | 3363 | UAUACACAGCAUUCAGUAG | Ms | [1017-1035] 3'UTR |
| 158 | 2864 | GGUCAGAAAUUACCUUUUU | 3364 | AAAAAGGUAAUUUCUGACC | | [989-1007] 3'UTR |
| 159 | 2865 | UGAAGUCUUUUGGUCAGAA | 3365 | UUCUGACCAAAAGACUUCA | | [978-996] 3'UTR |
| 160 | 2866 | AGAAGGAUCCAGUAUUCAG | 3366 | CUGAAUACUGGAUCCUUCU | | [950-968] 3'UTR |
| 161 | 2867 | UCAAAGGUGGAGCGUGAAU | 3367 | AUUCACGCUCCACCUUUGA | | [928-946] 3'UTR |
| 162 | 2868 | UUCAAAGGUGGAGCGUGAA | 3368 | UUCACGCUCCACCUUUGAA | | [927-945] 3'UTR |
| 163 | 2869 | GGAAGGAAAACUAAGAAUG | 3369 | CAUUCUUAGUUUUCCUUCC | | [734-752] 3'UTR |
| 164 | 2870 | GCUGAAUAAGCGGUGUUCA | 3370 | UGAACACCGCUUAUUCAGC | | [584-602] ORF+3'UTR |
| 165 | 2871 | CACUGUGUGGCUGAAUAAG | 3371 | CUUAUUCAGCCACACAGUG | | [575-593] ORF+3'UTR |
| 166 | 2872 | CAGGCUUCUGAAUUCCCUU | 3372 | AAGGGAAUUCAGAAGCCUG | | [529-547] ORF |
| 167 | 2873 | GAAACCUGCAGCACGUCA | 3373 | UGACGUGCUGCAGGAUUUC | Rat,Ms | [370-388] ORF |
| 168 | 2874 | AAUGGUGAUUGCCUGCUUU | 3374 | AAAGCAGGCAAUCACCAUU | | [1228-1246] 3'UTR |
| 169 | 2875 | UUUCUUGUAUAGUGGCAGA | 3375 | UCUGCCACUAUACAAGAAA | Ms | [1093-1111] 3'UTR |
| 170 | 2876 | CAGAAAUUACCUUUUUGAC | 3376 | GUCAAAAGGUAAUUUCUG | | [992-1010] 3'UTR |
| 171 | 2877 | GCAGGCUUCUGAAUUCCCU | 3377 | AGGGAAUUCAGAAGCCUGC | | [528-546] ORF |
| 172 | 2878 | UCAGCAUCCUGUCCUUGCA | 3378 | UGCAAGGACAGGAUGCUGA | Rat,Ms,GP,Chn | [512-530] ORF |
| 173 | 2879 | CACUAUUGUCAGCCUGCAU | 3379 | AUGCAGGCUGACAAUAGUG | | [432-450] ORF |
| 174 | 2880 | UCUUGUAUAGUGGCAGAGA | 3380 | UCUCUGCCACUAUACAAGA | | [1095-1113] 3'UTR |
| 175 | 2881 | AAAGGUGGAGCGUGAAUAC | 3381 | GUAUUCACGCUCCACCUUU | | [930-948] 3'UTR |
| 176 | 2882 | AUCACAAGGAAUUGCCCAA | 3382 | UUGGGCAAUUCCUUGUGAU | Ms | [887-905] 3'UTR |
| 177 | 2883 | GCGAAAACGUUAAAAUCAC | 3383 | GUGAUUUUAACGUUUUCGC | | [873-891] 3'UTR |
| 178 | 2884 | CAAAUUCACGGAAUCUUUU | 3384 | AAAAGAUUCCGUGAAUUUG | | [639-657] 3'UTR |
| 179 | 2885 | AUAUCAGCAUCCUGUCCUU | 3385 | AAGGACAGGAUGCUGAUAU | | [509-527] ORF |
| 180 | 2886 | CCUCAACACGGAUAUCAGC | 3386 | GCUGAUAUCCGUGUUGAGG | | [498-516] ORF |
| 181 | 2887 | UGGAAAUCCUGCAGCACGU | 3387 | ACGUGCUGCAGGAUUUCCA | Rat,Ms | [368-386] ORF |
| 182 | 2888 | GUGUGUUUAUUGAAUGGUG | 3388 | CACCAUUCAAUAAACACAC | | [1216-1234] 3'UTR |
| 183 | 2889 | GCAUUCAAAAGUGUAAUGA | 3389 | UCAUUACACUUUUGAAUGC | | [1125-1143] 3'UTR |
| 184 | 2890 | GAGUGAAACCUUGUGAACU | 3390 | AGUUCACAAGGUUUCACUC | | [1061-1079] 3'UTR |
| 185 | 2891 | AGGAAUUGCCCAAUCUAAG | 3391 | CUUAGAUUGGGCAAUUCCU | | [893-911] 3'UTR |
| 186 | 2892 | AACCAUUUCACAAGGAGGA | 3392 | UCCUCCUUGUGAAAUGGUU | | [678-696] 3'UTR |
| 187 | 2893 | CAACCAUUUCACAAGGAGG | 3393 | CCUCCUUGUGAAAUGGUUG | | [677-695] 3'UTR |
| 188 | 2894 | GCGGUGUUCAUGAUUUCUU | 3394 | AAGAAAUCAUGAACACCGC | | [593-611] 3'UTR |
| 189 | 2895 | CCUUGCAGGCUUCUGAAUU | 3395 | AAUUCAGAAGCCUGCAAGG | | [524-542] ORF |
| 190 | 2896 | CCACCCUCAACACGGAUAU | 3396 | AUAUCCGUGUUGAGGGUGG | | [494-512] ORF |
| 191 | 2897 | ACAUCUUGGACCUGCAGAU | 3397 | AUCUGCAGGUCCAAGAUGU | Ms | [395-413] ORF |
| 192 | 2898 | CCCUUUCUGCAGUUGGAAG | 3398 | CUUCCAACUGCAGAAAGGG | | [822-840] 3'UTR |
| 193 | 2899 | UAUUCUUUGCACAACAACA | 3399 | UGUUGUUGUGCAAAGAAUA | | [613-631] 3'UTR |
| 194 | 2900 | UGUCCUUGCAGGCUUCUGA | 3400 | UCAGAAGCCUGCAAGGACA | | [521-539] ORF |
| 195 | 2901 | UCAACACGGAUAUCAGCAU | 3401 | AUGCUGAUAUCCGUGUUGA | | [500-518] ORF |
| 196 | 2902 | CUGAACCCAAAUAAAUACA | 3402 | UGUAUUUAUUUGGGUUCAG | | [1292-1310] 3'UTR |
| 197 | 2903 | CAAGUGUGUUUAUUGAAUG | 3403 | CAUUCAAUAAACACACUUG | Ms | [1213-1231] 3'UTR |
| 198 | 2904 | GAGAUGUCUAUUUCUGCAU | 3404 | AUGCAGAAAUAGACAUCUC | | [1110-1128] 3'UTR |
| 199 | 2905 | GUUUUCUUGUAUAGUGGCA | 3405 | UGCCACUAUACAAGAAAAC | Ms | [1091-1109] 3'UTR |
| 200 | 2906 | ACCUUGUGAACUCUUUUAU | 3406 | AUUAAAGAGUUCACAAGGU | | [1068-1086] 3'UTR |
| 201 | 2907 | CCCAAUCUAAGCAGACUUU | 3407 | AAAGUCUGCUUAGAUUGGG | | [901-919] 3'UTR |
| 202 | 2908 | ACUUUUAAAUGCCCUUUCU | 3408 | AGAAAGGGCAUUUAAAAGU | | [811-829] 3'UTR |
| 203 | 2909 | GUGCUGAACUUAUUUUUCA | 3409 | UGAAAAAUAAGUUCAGCAC | | [660-678] 3'UTR |
| 204 | 2910 | CGGAAUCUUUUAAGUGCUG | 3410 | CAGCACUUAAAAGAUUCCG | | [647-665] 3'UTR |

FIGURE 4 Continued

| | | | | | | |
|---|---|---|---|---|---|---|
| 205 | 2911 | GUCAAAUGACAGCAAAGCA | 3411 | UGCUUUGCUGUCAUUUGAC | Chn | [558-576] ORF |
| 206 | 2912 | UGGUGAUUGCCUGCUUUAU | 3412 | AUAAAGCAGGCAAUCACCA | | [1230-1248] 3'UTR |
| 207 | 2913 | AUGGUGAUUGCCUGCUUUA | 3413 | UAAAGCAGGCAAUCACCAU | | [1229-1247] 3'UTR |
| 208 | 2914 | GUGGCAGAGAUGACUAUUU | 3414 | AAAUAGCAUCUCUGCCAC | | [1104-1122] 3'UTR |
| 209 | 2915 | GAGUUUUCUUGUAUAGUGG | 3415 | CCACUAUACAAGAAAACUC | Ms | [1089-1107] 3'UTR |
| 210 | 2916 | AGUCUUUUGGUCAGAAAUU | 3416 | AAUUUCUGACCAAAAGACU | | [981-999] 3'UTR |
| 211 | 2917 | AUACAACAUGAACGACGC | 3417 | GCAGUCGUUCAUGUUGUAU | | [291-309] ORF |
| 212 | 2918 | GGUGUUCUCUUACUUGGAC | 3418 | GUCCAAGUAAGAGAACACC | | [766-784] 3'UTR |
| 213 | 2919 | CAGGGUGUUCUCUUACUUG | 3419 | CAAGUAAGAGAACACCCUG | | [763-781] 3'UTR |
| 214 | 2920 | AAAACAGCCUGUCGGACCA | 3420 | UGGUCCGACAGGCUGUUUU | Rat,Ms,GP | [218-236] ORF |
| 215 | 2921 | CACAACAACAACAACAACA | 3421 | UGUUGUUGUUGUUGUUGUG | | [622-640] 3'UTR |
| 216 | 2922 | GACCAGUGCUUUGAUUUUU | 3422 | AAAAAUCAAAGCACUGGUC | | [1256-1274] 3'UTR |
| 217 | 2923 | CAGCAUGAAAGCCUUCAGU | 3423 | ACUGAAGGCUUUCAUGCUG | Rat,Ms | [180-198] 5'UTR+ORF |
| 218 | 2924 | ACGGAAUCUUUUAAGUGCU | 3424 | AGCACUUAAAAGAUUCCGU | | [646-664] 3'UTR |
| 219 | 2925 | AACAACAACAAUUCACGGAAU | 3425 | AUUCCGUGAAUUUGUUGUU | | [634-652] 3'UTR |
| 220 | 2926 | CAACAACAACAAAUUCACG | 3426 | CGUGAAUUUGUUGUUGUUG | | [630-648] 3'UTR |
| 221 | 2927 | ACAACAACAACAAAUUCAC | 3427 | GUGAAUUUGUUGUUGUUGU | | [629-647] 3'UTR |
| 222 | 2928 | AUUCUUUGCACAACAACAA | 3428 | UUGUUGUUGUGCAAAGAAU | | [614-632] 3'UTR |
| 223 | 2929 | AACAAGAAGGUGAGCAAGA | 3429 | UCUUGCUCACCUUCUUGUU | GP,Chn | [349-367] ORF |
| 224 | 2930 | GCAUGAAAGCCUUCAGCC | 3430 | GGACUGAAGGCUUUCAUGC | Rat,Ms | [182-200] 5'UTR+ORF |
| 225 | 2931 | UUGCCUGCUUUAUUUCAGA | 3431 | UCUGAAAUAAAGCAGGCAA | | [1236-1254] 3'UTR |
| 226 | 2932 | AGGAUCCAGUAUUCAGUCA | 3432 | UGACUGAAUACUGGAUCCU | | [953-971] 3'UTR |
| 227 | 2933 | CAGAAGGAUCCAGUAUUCA | 3433 | UGAAUACUGGAUCCUUCUG | | [949-967] 3'UTR |
| 228 | 2934 | CCAGAAGGAUCCAGUAUUC | 3434 | GAAUACUGGAUCCUUCUGG | | [948-966] 3'UTR |
| 229 | 2935 | AGCAGACUUUGCCUUUUUU | 3435 | AAAAAAGGCAAAGUCUGCU | | [910-928] 3'UTR |
| 230 | 2936 | CACGGAUAUCAGCAUCCUG | 3436 | CAGGAUGCUGAUAUCCGUG | | [504-522] ORF |
| 231 | 2937 | GAAAAUACCUUUUUGACAC | 3437 | GUGUCAAAAAGGUAAUUUC | | [994-1012] 3'UTR |
| 232 | 2938 | UGAGCCUGCUAUACAACAU | 3438 | AUGUUGUAUAGCAGGCUCA | | [281-299] ORF |
| 233 | 2939 | GAUGAGCCUGCUAUACAAC | 3439 | GUUGUAUAGCAGGCUCAUC | | [279-297] ORF |
| 234 | 2940 | CUUACUUGGACUGUGAUAU | 3440 | AUAUCACAGUCCAAGUAAG | | [774-792] 3'UTR |
| 235 | 2941 | CUUCCCAGGGUGUUCUCUU | 3441 | AAGAGAACACCCUGGGAAG | | [758-776] 3'UTR |
| 236 | 2942 | CUUUUAAGUGCUGAACUUA | 3442 | UAAGUUCAGCACUUAAAAG | | [653-671] 3'UTR |
| 237 | 2943 | GCUUCUGAAUUCCCUUCCG | 3443 | CAGAAGGGAAUUCAGAAGC | | [532-550] ORF |
| 238 | 2944 | GAGCAAGAUGGAAAUCCUG | 3444 | CAGGAUUUCCAUCUUGCUC | | [360-378] ORF |
| 239 | 2945 | AGGACCAGUGCUUUGAUUU | 3445 | AAAUCAAAGCACUGGUCCU | | [1254-1272] 3'UTR |
| 240 | 2946 | CUGCUUUAUUUCAGAGGAC | 3446 | GUCCUCUGAAAUAAAGCAG | | [1240-1258] 3'UTR |
| 241 | 2947 | UAGUGGCAGAGAUGUCUAU | 3447 | AUAGACAUCUCUGCCACUA | | [1102-1120] 3'UTR |
| 242 | 2948 | UCUAUUUGAGUGAAACCUU | 3448 | AAGGUUUCACUCAAAUAGA | | [1054-1072] 3'UTR |
| 243 | 2949 | GUCAGAAAUUACCUUUUUG | 3449 | CAAAAAGGUAAUUUCUGAC | | [990-1008] 3'UTR |
| 244 | 2950 | CGUGAAUACCAGAAGGAUC | 3450 | GAUCCUUCUGGUAUUCACG | | [940-958] 3'UTR |
| 245 | 2951 | AUUGCCCAAUCUAAGCAGA | 3451 | UCUGCUUAGAUUGGGCAAU | | [897-915] 3'UTR |
| 246 | 2952 | AACGUUAAAAUCACAAGGA | 3452 | UCCUUGUGAUUUUAACGUU | | [878-896] 3'UTR |
| 247 | 2953 | UAUAUACUAUUCCCACCAU | 3453 | AUGGUGGGAAUAGUAUAUA | Ms | [849-867] 3'UTR |
| 248 | 2954 | CUUUAUAUACUAUUCCCAC | 3454 | GUGGGAAUAGUAUAUAAAG | Ms | [846-864] 3'UTR |
| 249 | 2955 | UUACUUGGACUGUGAUAUU | 3455 | AAUAUCACAGUCCAAGUAA | | [775-793] 3'UTR |
| 250 | 2956 | GUGUUCUCUUACUUGGACU | 3456 | AGUCCAAGUAAGAGAACAC | | [767-785] 3'UTR |
| 251 | 2957 | CUCAACACGGAUAUCAGCA | 3457 | UGCUGAUAUCCGUGUUGAG | | [499-517] ORF |
| 252 | 2958 | UCGACUACAUCUUGGACCU | 3458 | AGGUCCAAGAUGUAGUCGA | | [389-407] ORF |
| 253 | 2959 | AAAGCCUUCAGUCCCGUGA | 3459 | UCACGGGACUGAAGGCUUU | | [187-205] ORF |
| 254 | 2960 | AGCACGCAUCGACUACAU | 3460 | AUGUAGUCGAUGCGUGCU | | [380-398] ORF |
| 255 | 2961 | AUGUCUAUUUCUGCAUUCA | 3461 | UGAAUGCAGAAAUAGACAU | | [1113-1131] 3'UTR |
| 256 | 2962 | AGAGUUUUCUUGUAUAGUG | 3462 | CACUAUACAAGAAAACUCU | Ms | [1088-1106] 3'UTR |
| 257 | 2963 | GAGCGUGAAUACCAGAAGG | 3463 | CCUUCUGGUAUUCACGCUC | | [937-955] 3'UTR |
| 258 | 2964 | CUAAGCAGACUUUGCCUUU | 3464 | AAAGGCAAAGUCUGCUUAG | | [907-925] 3'UTR |
| 259 | 2965 | UUCUGCAGUUGGAAGGUUU | 3465 | AAACCUUCCAACUGCAGAA | | [826-844] 3'UTR |
| 260 | 2966 | ACAACAAAUUCACGGAAUC | 3466 | GAUUCCGUGAAUUUGUUGU | | [635-653] 3'UTR |
| 261 | 2967 | AAUUCCCUUCUGAGUUAAU | 3467 | AUUAACUCAGAAGGGAAUU | | [539-557] ORF |
| 262 | 2968 | CAUCGACUACAUCUUGGAC | 3468 | GUCCAAGAUGUAGUCGAUG | | [387-405] ORF |
| 263 | 2969 | UGCAGCACGUCAUCGACUA | 3469 | UAGUCGAUGACGUGCUGCA | | [377-395] ORF |
| 264 | 2970 | UGACACAAGCCUACUGAAU | 3470 | AUUCAGUAGGCUUGUGUCA | | [1007-1025] 3'UTR |
| 265 | 2971 | UCUUUGCACAACAACAACA | 3471 | UGUUGUUGUUGUGCAAAGA | | [616-634] 3'UTR |
| 266 | 2972 | GUGGCUGAAUAAGCGGUGU | 3472 | ACACCGCUUAUUCAGCCAC | | [581-599] ORF+3'UTR |
| 267 | 2973 | ACGGAUAUCAGCAUCCUGU | 3473 | ACAGGAUGCUGAUAUCCGU | | [505-523] ORF |
| 268 | 2974 | ACUCGCAUCCCACUAUUGU | 3474 | ACAAUAGUGGGAUGCGAGU | | [422-440] ORF |
| 269 | 2975 | UGAGUGAAACCUUGUGAAC | 3475 | GUUCACAAGGUUUCACUCA | | [1060-1078] 3'UTR |
| 270 | 2976 | UCUUUUGGUCAGAAAUUAC | 3476 | GUAAUUUCUGACCAAAAGA | | [983-1001] 3'UTR |
| 271 | 2977 | GGAUCCAGUAUUCAGUCAC | 3477 | GUGACUGAAUACUGGAUCC | | [954-972] 3'UTR |
| 272 | 2978 | GAUCAUCUUCCCAGGGUGU | 3478 | ACACCCUGGGAAGAUGAUC | | [752-770] 3'UTR |

FIGURE 4 Continued

| | | | | | | | |
|---|---|---|---|---|---|---|---|
| 273 | 2979 | CACGGAAUCUUUUAAGUGC | 3479 | GCACUUAAAAGAUUCCGUG | | | [645-663] 3'UTR |
| 274 | 2980 | GUUAGGAAAAACAGCCUGU | 3480 | ACAGGCUGUUUUUCCUAAC | Rat,Ms | | [211-229] ORF |
| 275 | 2981 | CGGAUAUCAGCAUCCUGUC | 3481 | GACAGGAUGCUGAUAUCCG | | | [506-524] ORF |
| 276 | 2982 | CAGAACAAGAAGGUGAGCA | 3482 | UGCUCACCUUCUUGUUCUG | GP,Chn | | [346-364] ORF |
| 277 | 2983 | GUAUAGUGGCAGAGAUGUC | 3483 | GACAUCUCUGCCACUAUAC | | | [1099-1117] 3'UTR |
| 278 | 2984 | AUGAAGUCUUUUGGUCAGA | 3484 | UCUGACCAAAAGACUUCAU | | | [977-995] 3'UTR |
| 279 | 2985 | GCCCAAUCUAAGCAGACUU | 3485 | AAGUCUGCUUAGAUUGGGC | | | [900-918] 3'UTR |
| 280 | 2986 | GAGCCUGCUAUACAACAUG | 3486 | CAUGUUGUAUAGCAGGCUC | | | [282-300] ORF |
| 281 | 2987 | CCGUUAGGAAAAACAGCCU | 3487 | AGGCUGUUUUUCCUAACGG | Rat,Ms | | [209-227] ORF |
| 282 | 2988 | CUCGCAUCCCACUAUUGUC | 3488 | GACAAUAGUGGGAUGCGAG | | | [423-441] ORF |
| 283 | 2989 | CCCAGAACAAGAAGGUGAG | 3489 | CUCACCUUCUUGUUCUGGG | GP,Chn | | [344-362] ORF |
| 284 | 2990 | ACUCCAAGCUCAAGGAGCU | 3490 | AGCUCCUUGAGCUUGGAGU | | | [311-329] ORF |
| 285 | 2991 | UAUUUGAGUGAAACCUUGU | 3491 | ACAAGGUUUCACUCAAAUA | | | [1056-1074] 3'UTR |
| 286 | 2992 | CUUUUUGACACAAGCCUAC | 3492 | GUAGGCUUGUGUCAAAAAG | | | [1002-1020] 3'UTR |
| 287 | 2993 | AAUGAAGUCUUUUGGUCAG | 3493 | CUGACCAAAAGACUUCAUU | | | [976-994] 3'UTR |
| 288 | 2994 | UACAACAUGAACGACUGCU | 3494 | AGCAGUCGUUCAUGUUGUA | Rat,Ms,GP | | [292-310] ORF |
| 289 | 2995 | AAUCACAAGGAAUUGCCCA | 3495 | UGGGCAAUUCCUUGUGAUU | Ms | | [886-904] 3'UTR |
| 290 | 2996 | AAAUGCCCUUUCUGCAGUU | 3496 | AACUGCAGAAAGGGCAUUU | | | [817-835] 3'UTR |
| 291 | 2997 | AGGGUGUUCUCUUACUUGG | 3497 | CCAAGUAAGAGAACACCCU | | | [764-782] 3'UTR |
| 292 | 2998 | CUGUGUGGCUGAAUAAGCG | 3498 | CGCUUAUUCAGCCACACAG | | | [577-595] ORF+3'UTR |
| 293 | 2999 | AGUUAAUGCAAAUGACAG | 3499 | CUGUCAUUUGACAUUAACU | | | [551-569] ORF |
| 294 | 3000 | CUGAAUUCCCUUCUGAGUU | 3500 | AACUCAGAAGGGAAUUCAG | | | [536-554] ORF |
| 295 | 3001 | GACUCGCAUCCCACUAUUG | 3501 | CAAUAGUGGGAUGCGAGUC | | | [421-439] ORF |
| 296 | 3002 | AGUGGCAGAGAUGUCUAUU | 3502 | AAUAGACAUCUCUGCCACU | | | [1103-1121] 3'UTR |
| 297 | 3003 | UGUAUAGUGGCAGAGAUGU | 3503 | ACAUCUCUGCCACUAUACA | | | [1098-1116] 3'UTR |
| 298 | 3004 | UCAGUCACUUAAAUGAAGU | 3504 | ACUUCAUUUAAGUGACUGA | | | [965-983] 3'UTR |
| 299 | 3005 | UCAGCAUGAAAGCCUUCAG | 3505 | CUGAAGGCUUUCAUGCUGA | | | [179-197] 5'UTR+ORF |
| 300 | 3006 | UCAAAUGACAGCAAAGCAC | 3506 | GUGCUUUGCUGUCAUUUGA | Chn | | [559-577] ORF |
| 301 | 3007 | UACAUCUUGGACCUGCAGA | 3507 | UCUGCAGGUCCAAGAUGUA | Ms | | [394-412] ORF |
| 302 | 3008 | GGUCAGCAUGAAAGCCUUC | 3508 | GAAGGCUUUCAUGCUGACC | | | [177-195] 5'UTR+ORF |
| 303 | 3009 | ACGUCAUCGACUACAUCUU | 3509 | AAGAUGUAGUCGAUGACGU | | | [383-401] ORF |
| 304 | 3010 | CUUUAUUGCAGGAGGACCAG | 3510 | CUGGUCCUCUGAAAUAAAG | | | [1243-1261] 3'UTR |
| 305 | 3011 | AUAUGGCAGAGAUGUCUA | 3511 | UAGACAUCUCUGCCACUAU | | | [1101-1119] 3'UTR |
| 306 | 3012 | UUUGAGUGAAACCUUGUGA | 3512 | UCACAAGGUUUCACUCAAA | | | [1058-1076] 3'UTR |
| 307 | 3013 | CUUUUAAAUGCCCUUUCUG | 3513 | CAGAAAGGGCAUUUAAAAG | | | [812-830] 3'UTR |
| 308 | 3014 | UGAUCAUCUUCCCAGGGUG | 3514 | CACCCUGGGAAGAUGAUCA | | | [751-769] 3'UTR |
| 309 | 3015 | AGGAAAACUAAGAAUGAUC | 3515 | GAUCAUUCUUAGUUUUCCU | | | [737-755] 3'UTR |
| 310 | 3016 | ACUGAACCCAAAUAAAUAC | 3516 | GUAUUUAUUUGGGUUCAGU | Ms | | [1291-1309] 3'UTR |
| 311 | 3017 | AUUUCAGAGGACCAGUGCU | 3517 | AGCACUGGUCCUCUGAAAU | | | [1247-1265] 3'UTR |
| 312 | 3018 | AGCUGAAUACCAGAAGGA | 3518 | UCCUUCUGGUAUUCACGCU | | | [938-956] 3'UTR |
| 313 | 3019 | ACAAGGAAUUGCCCAAUCU | 3519 | AGAUUGGGCAAUUCCUUGU | | | [890-908] 3'UTR |
| 314 | 3020 | UUCACAAGGAGGACAAGUU | 3520 | AACUUGUCCUCCUUGUGAA | | | [684-702] 3'UTR |
| 315 | 3021 | AUUUCACAAGGAGGACAAG | 3521 | CUUGUCCUCCUUGUGAAAU | | | [682-700] 3'UTR |
| 316 | 3022 | UCAACCAUUUCACAAGGAG | 3522 | CUCCUUGUGAAAUGGUUGA | | | [676-694] 3'UTR |
| 317 | 3023 | AGCGGUGUUCAUGAUUUCU | 3523 | AGAAAUCAUGAACACCGCU | | | [592-610] 3'UTR |
| 318 | 3024 | UGACAGCAAAGCACUGUGU | 3524 | ACACAGUGCUUUGCUGUCA | | | [564-582] ORF |
| 319 | 3025 | CGUCAUCGACUACAUCUUG | 3525 | CAAGAUGUAGUCGAUGACG | | | [384-402] ORF |
| 320 | 3026 | AAGUGUGUUUAUUGAAUGG | 3526 | CCAUUCAAUAAACACACUU | | | [1214-1232] 3'UTR |
| 321 | 3027 | ACGACUGCUACUCCAAGCU | 3527 | AGCUUGGAGUAGCAGUCGU | Rat,Ms,GP,Chn | | [302-320] ORF |
| 322 | 3028 | UGGUCAGAAAUUACCCUUU | 3528 | AAAAGGUAAUUUCUGACCA | | | [988-1006] 3'UTR |
| 323 | 3029 | ACCAGAAGGAUCCAGUAUU | 3529 | AAUACUGGAUCCUUCUGGU | | | [947-965] 3'UTR |
| 324 | 3030 | CUGCUAUACAACAUGAACG | 3530 | CGUUCAUGUUGUAUAGCAG | | | [286-304] ORF |
| 325 | 3031 | GGAAUUGCCCAAUCUAAGC | 3531 | GCUUAGAUUGGGCAAUUCC | | | [894-912] 3'UTR |
| 326 | 3032 | CUUUCUGCAGUUGGAAGGU | 3532 | ACCUUCCAACUGCAGAAAG | | | [824-842] 3'UTR |
| 327 | 3033 | GUGUGGCUGAAUAAGCGGU | 3533 | ACCGCUUAUUCAGCCACAC | | | [579-597] ORF+3'UTR |
| 328 | 3034 | UCAGAGGACCAGUGCUUUG | 3534 | CAAAGCACUGGUCCUCUGA | | | [1250-1268] 3'UTR |
| 329 | 3035 | UUCAGAGGACCAGUGCUUU | 3535 | AAAGCACUGGUCCUCUGAA | | | [1249-1267] 3'UTR |
| 330 | 3036 | AUUGAAUGGUGAUUGCCUG | 3536 | CAGGCAAUCACCAUUCAAU | | | [1224-1242] 3'UTR |
| 331 | 3037 | AUGAUGUACUUAUUCAUGC | 3537 | GCAUGAAUAAGUACAUCAU | | | [1140-1158] 3'UTR |
| 332 | 3038 | GCAGAGAUGUCUAUUUCUG | 3538 | CAGAAAUAGACAUCUCUGC | | | [1107-1125] 3'UTR |
| 333 | 3039 | UUGUAUAGUGGCAGAGAUG | 3539 | CAUCUCUGCCACUAUACAA | | | [1097-1115] 3'UTR |
| 334 | 3040 | UUCAGUCACUUAAAUGAAG | 3540 | CUUCAUUUAAGUGACUGAA | | | [964-982] 3'UTR |
| 335 | 3041 | GUAUUCAGUCACUUAAAUG | 3541 | CAUUUAAGUGACUGAAUAC | | | [961-979] 3'UTR |
| 336 | 3042 | UGAAUACCAGAAGGAUCCA | 3542 | UGGAUCCUUCUGGUAUUCA | | | [942-960] 3'UTR |
| 337 | 3043 | GCAGACUUUGCCUUUUUUC | 3543 | GAAAAAAGGCAAAGUCUGC | | | [911-929] 3'UTR |
| 338 | 3044 | CAUCUUCCCAGGGUGUUCU | 3544 | AGAACACCCUGGGAAGAUG | | | [755-773] 3'UTR |
| 339 | 3045 | UUCACGGAAUCUUUUAAGU | 3545 | ACUUAAAAGAUUCCGUGAA | | | [643-661] 3'UTR |
| 340 | 3046 | UUCUGAAUUCCCUUCUGAG | 3546 | CUCAGAAGGGAAUUCAGAA | | | [534-552] ORF |

FIGURE 4 Continued

| | | | | | | | |
|---|---|---|---|---|---|---|---|
| 341 | 3047 | UGGACUCGCAUCCCACUAU | 3547 | AUAGUGGGAUGCGAGUCCA | Ms | [419-437] ORF | |
| 342 | 3048 | CUGCUACUCCAAGCUCAAG | 3548 | CUUGAGCUUGGAGUAGCAG | Rat,Ms | [306-324] ORF | |
| 343 | 3049 | GAAUUGCCCAAUCUAAGCA | 3549 | UGCUUAGAUUGGGCAAUUC | | [895-913] 3'UTR | |
| 344 | 3050 | UGCAGUUGGAAGGUUUUCU | 3550 | AGAAAACCUUCCAACUGCA | | [829-847] 3'UTR | |
| 345 | 3051 | UUUAAAUGCCCUUUCUGCA | 3551 | UGCAGAAAGGGCAUUUAAA | | [814-832] 3'UTR | |
| 346 | 3052 | AUAAGCGGUGUUCAUGAUU | 3552 | AAUCAUGAACACCGCUUAU | | [589-607] 3'UTR | |
| 347 | 3053 | GUCAGCAUGAAAGCCUUCA | 3553 | UGAAGGCUUUCAUGCUGAC | | [178-196] 5'UTR+ORF | |
| 348 | 3054 | GAGGUCCGUUAGGAAAAAC | 3554 | GUUUUUCCUAACGGACCUC | Rat,Ms | [204-222] ORF | |
| 349 | 3055 | GCUAUGUUAUAACUGAACC | 3555 | GGUUCAGUUAUAACAUAGC | Ms | [1280-1298] 3'UTR | |
| 350 | 3056 | UUCUGCAUUCAAAAGUGUA | 3556 | UACACUUUUGAAUGCAGAA | | [1121-1139] 3'UTR | |
| 351 | 3057 | CAGAGAUGUCUAUUUCUGC | 3557 | GCAGAAAUAGACAUCUCUG | | [1108-1126] 3'UTR | |
| 352 | 3058 | UAUAGUGGCAGAGAUGUCU | 3558 | AGACAUCUCUGCCACUAUA | | [1100-1118] 3'UTR | |
| 353 | 3059 | UUAUAUACUAUUCCCACCA | 3559 | UGGUGGGAAUAGUAUAUAA | Ms | [848-866] 3'UTR | |
| 354 | 3060 | AAGAAUGAUCAUCUUCCCA | 3560 | UGGGAAGAUGAUCAUUCUU | | [746-764] 3'UTR | |
| 355 | 3061 | AGUGCUGAACUUAUUUUUC | 3561 | GAAAAAUAAGUUCAGCACU | | [659-677] 3'UTR | |
| 356 | 3062 | AUGUCAAAUGACAGCAAAG | 3562 | CUUUGCUGUCAUUUGACAU | | [556-574] ORF | |
| 357 | 3063 | GAUGUCUAUUUCUGCAUUC | 3563 | GAAUGCAGAAAUAGACAUC | | [1112-1130] 3'UTR | |
| 358 | 3064 | UUUGACACAAGCCUACUGA | 3564 | UCAGUAGGCUUGUGUCAAA | | [1005-1023] 3'UTR | |
| 359 | 3065 | CUUAAAUGAAGUCUUUUGG | 3565 | CCAAAAGACUUCAUUUAAG | | [972-990] 3'UTR | |
| 360 | 3066 | GUCACUUAAAUGAAGUCUU | 3566 | AAGACUUCAUUUAAGUGAC | | [968-986] 3'UTR | |
| 361 | 3067 | CAAUCUAAGCAGACUUUGC | 3567 | GCAAAGUCUGCUUAGAUUG | | [903-921] 3'UTR | |
| 362 | 3068 | CCAAUCUAAGCAGACUUUG | 3568 | CAAAGUCUGCUUAGAUUGG | | [902-920] 3'UTR | |
| 363 | 3069 | AAACGUUUAAAAUCACAAGG | 3569 | CCUUGUGAUUUUAAACGUUU | | [877-895] 3'UTR | |
| 364 | 3070 | AUAUACUAUUCCCACCAUG | 3570 | CAUGGUGGGAAUAGUAUAU | Ms | [850-868] 3'UTR | |
| 365 | 3071 | AUGAGCCUGCUAUACAACA | 3571 | UGUUGUAUAGCAGGCUCAU | | [280-298] ORF | |
| 366 | 3072 | UGAAUAAGCGGUGUUCAUG | 3572 | CAUGAACACCGCUUAUUCA | | [586-604] ORF+3'UTR | |
| 367 | 3073 | UGGCAGAGAUGUCUAUUUC | 3573 | GAAAUAGACAUCUCUGCCA | | [1105-1123] 3'UTR | |
| 368 | 3074 | GACACAAGCCUACUGAAUG | 3574 | CAUUCAGUAGGCUUGUGUC | | [1008-1026] 3'UTR | |
| 369 | 3075 | CAGUCACUUAAAUGAAGUC | 3575 | GACUUCAUUUAAGUGACUG | | [966-984] 3'UTR | |
| 370 | 3076 | AAGCAGACUUUGCCUUUUU | 3576 | AAAAAGGCAAAGUCUGCUU | | [909-927] 3'UTR | |
| 371 | 3077 | UGGCUGAAUAAGCGGUGUU | 3577 | AACACCGCUUAUUCAGCCA | | [582-600] ORF+3'UTR | |
| 372 | 3078 | UCUGAAUUCCCUUCUGAGU | 3578 | ACUCAGAAGGGAAUUCAGA | | [535-553] ORF | |
| 373 | 3079 | UCCUUGCAGGCUUCUGAAU | 3579 | AUUCAGAAGCCUGCAAGGA | | [523-541] ORF | |
| 374 | 3080 | CGACUACAUCUUUGGACCUG | 3580 | CAGGUCCAAGAUGUAGUCG | | [390-408] ORF | |
| 375 | 3081 | CAAGAUGGAAAUCCUGCAG | 3581 | CUGCAGGAUUUCCAUCUUG | Rat,Ms | [363-381] ORF | |
| 376 | 3082 | CAUGAAAGCCUUCAGUCCC | 3582 | GGGACUGAAGGCUUUCAUG | | [183-201] 5'UTR+ORF | |
| 377 | 3083 | CUAUGUUAUAACUGAACCC | 3583 | GGGUUCAGUUAUAACAUAG | Ms | [1281-1299] 3'UTR | |
| 378 | 3084 | CUAUUUCUGCAUUCAAAAG | 3584 | CUUUUGAAUGCAGAAAUAG | | [1117-1135] 3'UTR | |
| 379 | 3085 | UCACAAGGAAUUGCCCAAU | 3585 | AUUGGGCAAUUCCUUGUGA | Ms | [888-906] 3'UTR | |
| 380 | 3086 | GACUUUUAAAUGCCCUUUC | 3586 | GAAAGGGCAUUUAAAAGUC | | [810-828] 3'UTR | |
| 381 | 3087 | UUCAACCAUUUCACAAGGA | 3587 | UCCUUGUGAAAUGGUUGAA | | [675-693] 3'UTR | |
| 382 | 3088 | CAACAAAUUCACGGAAUCU | 3588 | AGAUUCCGUGAAUUUGUUG | | [636-654] 3'UTR | |
| 383 | 3089 | CGUUAGGAAAAACAGCCUG | 3589 | CAGGCUGUUUUUCCUAACG | Rat,Ms | [210-228] ORF | |
| 384 | 3090 | AGCAAAGCACUGUGUGGCU | 3590 | AGCCACACAGUGCUUUGCU | | [568-586] ORF | |
| 385 | 3091 | GUCCGUUAGGAAAAACAGC | 3591 | GCUGUUUUUCCUAACGGAC | Rat,Ms | [207-225] ORF | |
| 386 | 3092 | CUACAUCUUGGACCUGCAG | 3592 | CUGCAGGUCCAAGAUGUAG | | [393-411] ORF | |
| 387 | 3093 | UAUGUUAUAACUGAACCCA | 3593 | UGGGUUCAGUUAUAACAUA | Ms | [1282-1300] 3'UTR | |
| 388 | 3094 | UUUCAGAGGACCAGUGCUU | 3594 | AAGCACUGGUCCUCUGAAA | | [1248-1266] 3'UTR | |
| 389 | 3095 | CAAAAGUGUAAUGAUGUAC | 3595 | GUACAUCAUUACACUUUUG | | [1130-1148] 3'UTR | |
| 390 | 3096 | GUGAACUCUUUAAUUAGAG | 3596 | CUCUAAUUAAAGAGUUCAC | | [1073-1091] 3'UTR | |
| 391 | 3097 | GUGAAACCUUGUGAACUCU | 3597 | AGAGUUCACAAGGUUUCAC | | [1063-1081] 3'UTR | |
| 392 | 3098 | UUUGGUCAGAAAUUACCUU | 3598 | AAGGUAAUUUCUGACCAAA | | [986-1004] 3'UTR | |
| 393 | 3099 | UGCCUUUUUUCAAAGGUGG | 3599 | CCACCUUUGAAAAAAGGCA | | [919-937] 3'UTR | |
| 394 | 3100 | AAGCAUUUUAAAUGCCCUU | 3600 | AAGGGCAUUUAAAAUGCUU | | [808-826] 3'UTR | |
| 395 | 3101 | ACUGGACUGUGAUAUUCG | 3601 | CGAAUAUCACAGUCCAAGU | | [777-795] 3'UTR | |
| 396 | 3102 | AAAUGACAGCAAAGCACUG | 3602 | CAGUGCUUUGCUGUCAUUU | | [561-579] ORF | |
| 397 | 3103 | UUUAUUCAGAGGACCAGU | 3603 | ACUGGUCCUCUGAAAUAAA | | [1244-1262] 3'UTR | |
| 398 | 3104 | GUACUUAUUCAUGCUAAAC | 3604 | GUUUAGCAUGAAUAAGUAC | | [1145-1163] 3'UTR | |
| 399 | 3105 | AACGACUGCUACUCCAAGC | 3605 | GCUUGGAGUAGCAGUCGUU | Rat,Ms,GP,Chn | [301-319] ORF | |
| 400 | 3106 | UUUUCAACCAUUUCACAAG | 3606 | CUUGUGAAAUGGUUGAAAA | | [673-691] 3'UTR | |
| 401 | 3107 | AUCUUUUAAGUGCUGAACU | 3607 | AGUUCAGCACUUAAAAGAU | | [651-669] 3'UTR | |
| 402 | 3108 | UGAGUUAAUGUCAAAUGAC | 3608 | GUCAUUUGACAUUAACUCA | | [549-567] ORF | |
| 403 | 3109 | UUCCCUUCUGAGUUAAUGU | 3609 | ACAUUAACUCAGAAGGGAA | | [541-559] ORF | |
| 404 | 3110 | ACACGGAUAUCAGCAUCCU | 3610 | AGGAUGCUGAUAUCCGUGU | | [503-521] ORF | |
| 405 | 3111 | CGCAUCCCACUAUUGUCAG | 3611 | CUGACAAUAGUGGGAUGCG | | [425-443] ORF | |
| 406 | 3112 | GAUGGAAAUCCUGCAGCAC | 3612 | GUGCUGCAGGAUUUCCAUC | Rat,Ms | [366-384] ORF | |
| 407 | 3113 | CCAGAACAAGAAGGUGAGC | 3613 | GCUCACCUUCUUGUUCUGG | GP,Chn | [345-363] ORF | |
| 408 | 3114 | UAUUGAAUGGUGAUUGCCU | 3614 | AGGCAAUCACCAUUCAAUA | | [1223-1241] 3'UTR | |

FIGURE 4 Continued

| | | | | | | | |
|---|---|---|---|---|---|---|---|
| 409 | 3115 | AUUUCUGCAUUCAAAAGUG | 3615 | CACUUUUGAAUGCAGAAAU | | [1119-1137] 3'UTR |
| 410 | 3116 | AAUACCAGAAGGAUCCAGU | 3616 | ACUGGAUCCUUCUGGUAUU | | [944-962] 3'UTR |
| 411 | 3117 | UGCCCAAUCUAAGCAGACU | 3617 | AGUCUGCUUAGAUUGGGCA | | [899-917] 3'UTR |
| 412 | 3118 | GGCUGAAUAAGCGGUGUUC | 3618 | GAACACCGCUUAUUCAGCC | | [583-601] ORF+3'UTR |
| 413 | 3119 | GUCAUCGACUACAUCUUGG | 3619 | CCAAGAUGUAGUCGAUGAC | | [385-403] ORF |
| 414 | 3120 | CACGUCAUCGACUACAUCU | 3620 | AGAUGUAGUCGAUGACGUG | | [382-400] ORF |
| 415 | 3121 | AAUCCUGCAGCACGUCAUC | 3621 | GAUGACGUGCUGCAGGAUU | Rat,Ms | [372-390] ORF |
| 416 | 3122 | AGUGAAACCUUGUGAACUC | 3622 | GAGUUCACAAGGUUUCACU | | [1062-1080] 3'UTR |
| 417 | 3123 | UAAGCAGACUUUGCCUUUU | 3623 | AAAAGGCAAAGUCUGCUUA | Ms | [908-926] 3'UTR |
| 418 | 3124 | UUGGACUGUGAUAUUCGUU | 3624 | AACGAAUAUCACAGUCCAA | | [779-797] 3'UTR |
| 419 | 3125 | GCUGAACUUAUUUUUCAAC | 3625 | GUUGAAAAAUAAGUUCAGC | | [662-680] 3'UTR |
| 420 | 3126 | ACCACCUCAACACGGAUA | 3626 | UAUCCGUGUUGAGGGUGGU | | [493-511] ORF |
| 421 | 3127 | UGAAACCUUGUGAACUCUU | 3627 | AAGAGUUCACAAGGUUUCA | | [1064-1082] 3'UTR |
| 422 | 3128 | AAGGAUCCAGUAUUCAGUC | 3628 | GACUGAAUACUGGAUCCUU | | [952-970] 3'UTR |
| 423 | 3129 | AAAUCACAAGGAAUUGCCC | 3629 | GGGCAAUUCCUUGUGAUUU | Ms | [885-903] 3'UTR |
| 424 | 3130 | CUUUUAUUCUUUGCACAAC | 3630 | GUUGUGCAAAGAAUAAAAG | | [609-627] 3'UTR |
| 425 | 3131 | AAGCACUGUGUGGCUGAAU | 3631 | AUUCAGCCACACAGUGCUU | | [572-590] ORF+3'UTR |
| 426 | 3132 | AUCCUGUCCUUGCAGGCUU | 3632 | AAGCCUGCAAGGACAGGAU | | [517-535] ORF |
| 427 | 3133 | CAACACGGAUAUCAGCAUC | 3633 | GAUGCUGAUAUCCGUGUUG | | [501-519] ORF |
| 428 | 3134 | CAGCACGUCAUCGACUACA | 3634 | UGUAGUCGAUGACGUGCUG | | [379-397] ORF |
| 429 | 3135 | UGAAAGCCUUCAGUCCCGU | 3635 | ACGGGACUGAAGGCUUUCA | | [185-203] ORF |
| 430 | 3136 | UGAUUGCCUGCUUUAUUUC | 3636 | GAAAUAAAGCAGGCAAUCA | | [1233-1251] 3'UTR |
| 431 | 3137 | UGCAUUCAAAAGUGUAAUG | 3637 | CAUUACACUUUUGAAUGCA | | [1124-1142] 3'UTR |
| 432 | 3138 | UACCAGAAGGAUCCAGUAU | 3638 | AUACUGGAUCCUUCUGGUA | | [946-964] 3'UTR |
| 433 | 3139 | UAAAUGCCCUUUCUGCAGU | 3639 | ACUGCAGAAAGGGCAUUUA | | [816-834] 3'UTR |
| 434 | 3140 | CUAAGAAGAAUCAUCUUCC | 3640 | GGAAGAUGAUCAUUCUUAG | | [744-762] 3'UTR |
| 435 | 3141 | GCAUCCACUAUUGUCAGC | 3641 | GCUGACAAUAGUGGGAUGC | | [426-444] ORF |
| 436 | 3142 | AAGAAGGUGAGCAAGAUGG | 3642 | CCAUCUUGCUCACCUUCUU | GP,Chn | [352-370] ORF |
| 437 | 3143 | AUUUGAGUGAAACCUUGUG | 3643 | CACAAGGUUUCACUCAAAU | | [1057-1075] 3'UTR |
| 438 | 3144 | ACACAAGCCUACUGAAUGC | 3644 | GCAUUCAGUAGGCUUGUGU | | [1009-1027] 3'UTR |
| 439 | 3145 | CUGCAGUUGGAAGGUUUUC | 3645 | GAAAACCUUCCAACUGCAG | | [828-846] 3'UTR |
| 440 | 3146 | ACAGCAAAGCACUGUGUGG | 3646 | CCACACAGUGCUUUGCUGU | | [566-584] ORF |
| 441 | 3147 | GACAGCAAAGCACUGUGUG | 3647 | CACACAGUGCUUUGCUGUC | | [565-583] ORF |
| 442 | 3148 | GGCUUCUGAAUUCCCUUCU | 3648 | AGAAGGGAAUUCAGAAGCC | | [531-549] ORF |
| 443 | 3149 | UAUUGUCAGCCUGCAUCAC | 3649 | GUGAUGCAGGCUGACAAUA | | [435-453] ORF |
| 444 | 3150 | AUCCCACUAUUGUCAGCCU | 3650 | AGGCUGACAAUAGUGGGAU | | [428-446] ORF |
| 445 | 3151 | UUUAUUGAAUGGUGAUUGC | 3651 | GCAAUCACCAUUCAAUAAA | | [1221-1239] 3'UTR |
| 446 | 3152 | AAGCCUACUGAAUGCUGUG | 3652 | CACAGCAUUCAGUAGGCUU | | [1013-1031] 3'UTR |
| 447 | 3153 | UUUUGGUCAGAAAUUACCU | 3653 | AGGUAAUUUCUGACCAAAA | | [985-1003] 3'UTR |
| 448 | 3154 | CCUUUUUUCAAAGGUGGAG | 3654 | CUCCACCUUUGAAAAAAGG | | [921-939] 3'UTR |
| 449 | 3155 | ACUUUGCCUUUUUUCAAAG | 3655 | CUUUGAAAAAAGGCAAAGU | | [915-933] 3'UTR |
| 450 | 3156 | UCCCAGGGUGUUCUCUUAC | 3656 | GUAAGAGAACACCCUGGGA | | [760-778] 3'UTR |
| 451 | 3157 | UCAUCUUCCCAGGGUGUUC | 3657 | GAACACCCUGGGAAGAUGA | | [754-772] 3'UTR |
| 452 | 3158 | GAAAAACAGCCUGUCGGAC | 3658 | GUCCGACAGGCUGUUUUUC | Rat,Ms,GP | [216-234] ORF |
| 453 | 3159 | AUUCACGGAAUCUUUUAAG | 3659 | CUUAAAAGAUUCCGUGAAU | | [642-660] 3'UTR |
| 454 | 3160 | UGUGGCUGAAUAAGCGGUG | 3660 | CACCGCUUAUUCAGCCACA | | [580-598] ORF+3'UTR |
| 455 | 3161 | GUUAAUGUCAAAUGACAGC | 3661 | GCUGUCAUUUGACAUUAAC | | [552-570] ORF |
| 456 | 3162 | GAUAUCAGCAUCCUGUCCU | 3662 | AGGACAGGAUGCUGAUAUC | | [508-526] ORF |
| 457 | 3163 | AGUUUCUUGUAUAGUGGC | 3663 | GCCACUAUACAAGAAAACU | Ms | [1090-1108] 3'UTR |
| 458 | 3164 | AAAGACUUUUAAAUGCCCU | 3664 | AGGGCAUUUAAAAGUCUUU | | [807-825] 3'UTR |
| 459 | 3165 | UAAGAAUGAUCAUCUUCCC | 3665 | GGGAAGAUGAUCAUUCUUA | | [745-763] 3'UTR |
| 460 | 3166 | ACCAUUUCACAAGGAGGAC | 3666 | GUCCUCCUUGUGAAAUGGU | | [679-697] 3'UTR |
| 461 | 3167 | UGUGUGGCUGAAUAAGCGG | 3667 | CCGCUUAUUCAGCCACACA | | [578-596] ORF+3'UTR |
| 462 | 3168 | GGUGAGCAAGAUGGAAAUC | 3668 | GAUUUCCAUCUUGCUCACC | | [357-375] ORF |
| 463 | 3169 | GUUUAUUGAAUGGUGAUUG | 3669 | CAAUCACCAUUCAAUAAAC | | [1220-1238] 3'UTR |
| 464 | 3170 | UGUUCUCUUACUUGGACUG | 3670 | CAGUCCAAGUAAGAGAACA | | [768-786] 3'UTR |
| 465 | 3171 | GGAUAUCAGCAUCCUGUCC | 3671 | GGACAGGAUGCUGAUAUCC | | [507-525] ORF |
| 466 | 3172 | ACUAUUGUCAGCCUGCAUC | 3672 | GAUGCAGGCUGACAAUAGU | | [433-451] ORF |
| 467 | 3173 | UGCUAUGUUAUAACUGAAC | 3673 | GUUCAGUUAUAACAUAGCA | Ms | [1279-1297] 3'UTR |
| 468 | 3174 | AGUGUGUUUAUUGAAUGGU | 3674 | ACCAUUCAAUAAACACACU | | [1215-1233] 3'UTR |
| 469 | 3175 | UUGCCUUUUUUCAAAGGUG | 3675 | CACCUUUGAAAAAAGGCAA | | [918-936] 3'UTR |
| 470 | 3176 | CCUUUCUGCAGUUGGAAGG | 3676 | CCUUCCAACUGCAGAAAGG | | [823-841] 3'UTR |
| 471 | 3177 | UUUCACAAGGAGGACAAGU | 3677 | ACUUGUCCUCCUUGUGAAA | | [683-701] 3'UTR |
| 472 | 3178 | UUUCAACCAUUUCACAAGG | 3678 | CCUUGUGAAAUGGUUGAAA | | [674-692] 3'UTR |
| 473 | 3179 | AGGAAAAACAGCCUGUCGG | 3679 | CCGACAGGCUGUUUUUCCU | Rat,Ms | [214-232] ORF |
| 474 | 3180 | GACUACAUCUUGGACCUGC | 3680 | GCAGGUCCAAGAUGUAGUC | | [391-409] ORF |
| 475 | 3181 | UGCUUUAUUUCAGAGGACC | 3681 | GGUCCUCUGAAAUAAAGCA | | [1241-1259] 3'UTR |
| 476 | 3182 | UAUCUAUUUGAGUGAAACC | 3682 | GGUUUCACUCAAAUAGAUA | | [1052-1070] 3'UTR |

FIGURE 4 Continued

| | | | | | | | |
|---|---|---|---|---|---|---|---|
| 477 | 3183 | ACCUUUUUGACACAAGCCU | 3683 | AGGCUUGUGUCAAAAAGGU | | | [1000-1018] 3'UTR |
| 478 | 3184 | UUACCUUUUUGACACAAGC | 3684 | GCUUGUGUCAAAAAGGUAA | | | [998-1016] 3'UTR |
| 479 | 3185 | UAAAUGAAGUCUUUUGGUC | 3685 | GACCAAAAGACUUCAUUUA | | | [974-992] 3'UTR |
| 480 | 3186 | AUCUAAGCAGACUUUGCCU | 3686 | AGGCAAAGUCUGCUUAGAU | | | [905-923] 3'UTR |
| 481 | 3187 | GUUCUCUUACUUGGACUGU | 3687 | ACAGUCCAAGUAAGAGAAC | | | [769-787] 3'UTR |
| 482 | 3188 | AACAAAUUCACGGAAUCUU | 3688 | AAGAUUCCGUGAAUUUGUU | | | [637-655] 3'UTR |
| 483 | 3189 | UUAUUUCAGAGGACCAGUG | 3689 | CACUGGUCCUCUGAAAUAA | | | [1245-1263] 3'UTR |
| 484 | 3190 | UUUCUGCAUUCAAAAGUGU | 3690 | ACACUUUUGAAUGCAGAAA | | | [1120-1138] 3'UTR |
| 485 | 3191 | AGACUUUUAAAUGCCCUUU | 3691 | AAAGGGCAUUUAAAAGUCU | | | [809-827] 3'UTR |
| 486 | 3192 | UUCUCUUACUUGGACUGUG | 3692 | CACAGUCCAAGUAAGAGAA | | | [770-788] 3'UTR |
| 487 | 3193 | UCUUCCCAGGGUGUUCUCU | 3693 | AGAGAACACCCUGGGAAGA | | | [757-775] 3'UTR |
| 488 | 3194 | AGAAUGAUCAUCUUCCCAG | 3694 | CUGGGAAGAUGAUCAUUCU | | | [747-765] 3'UTR |
| 489 | 3195 | AAUCUUUUAAGUGCUGAAC | 3695 | GUUCAGCACUUAAAAGAUU | | | [650-668] 3'UTR |
| 490 | 3196 | AUGGAAAUCCUGCAGCACG | 3696 | CGUGCUGCAGGAUUUCCAU | Rat,Ms | | [367-385] ORF |
| 491 | 3197 | UUUUUGACACAAGCCUACU | 3697 | AGUAGGCUUGUGUCAAAAA | | | [1003-1021] 3'UTR |
| 492 | 3198 | UUGGUCAGAAAUUACCUUU | 3698 | AAAGGUAAUUUCUGACCAA | | | [987-1005] 3'UTR |
| 493 | 3199 | GAAUACCAGAAGGAUCCAG | 3699 | CUGGAUCCUUCUGGUAUUC | | | [943-961] 3'UTR |
| 494 | 3200 | UUGCACAACAACAACAACA | 3700 | UGUUGUUGUUGUUGUGCAA | | | [619-637] 3'UTR |
| 495 | 3201 | UUCUUUGCACAACAACAAC | 3701 | GUUGUUGUUGUGCAAAGAA | | | [615-633] 3'UTR |
| 496 | 3202 | UUAAUGUCAAAUGACAGCA | 3702 | UGCUGUCAUUUGACAUUAA | | | [553-571] ORF |
| 497 | 3203 | CACCCUCAACACGGAUAUC | 3703 | GAUAUCCGUGUUGAGGGUG | | | [495-513] ORF |
| 498 | 3204 | CUACUCCAAGCUCAAGGAG | 3704 | CUCCUUGAGCUUGGAGUAG | | | [309-327] ORF |
| 499 | 3205 | UUUCUGCAGUUGGAAGGUU | 3705 | AACCUUCCAACUGCAGAAA | | | [825-843] 3'UTR |
| 500 | 3206 | UAGUUGUAAACUUAACCCU | 3706 | AGGGUUAAGUUUACAACUA | Ms | | [1178-1196] 3'UTR |

Table A5 ID3 - inhibitor of DNA binding 3

| No. | SEQ ID NO. | Sense siRNA | SEQ ID NO. | AntiSense siRNA | Other Sp | Human-156119620 ORF:406-765 |
|---|---|---|---|---|---|---|
| 1 | 3707 | GACUUCUUUUGGUUUUCUU | 4064 | AAGAAAACCAAAAGAAGUC | | [353-371] 5'UTR |
| 2 | 3708 | GGGCCAUUUUGAAUAAAGA | 4065 | UCUUUAUUCAAAAUGGCCC | Chp | [261-279] 5'UTR |
| 3 | 3709 | GGAGGAAGCCUGUUUGCAA | 4066 | UUGCAAACAGGCUUCCUCC | Chp | [194-212] 5'UTR |
| 4 | 3710 | GGACUUCUUUUGGUUUUCU | 4067 | AGAAAACCAAAAGAAGUCC | | [352-370] 5'UTR |
| 5 | 3711 | AGCAAAUUCUGGAAGUUAA | 4068 | UUAACUUCCAGAAUUUGCU | Chp | [61-79] 5'UTR |
| 6 | 3712 | GCAAAUUCUGGAAGUUAAU | 4069 | AUUAACUUCCAGAAUUUGC | Chp | [62-80] 5'UTR |
| 7 | 3713 | CCCACUUGACUUCACCAAA | 4070 | UUUGGUGAAGUCAAGUGGG | Chp | [882-900] 3'UTR |
| 8 | 3714 | CUUUUUGGUUUUCUUUCUCU | 4071 | AGAGAAAGAAAACCAAAAG | | [358-376] 5'UTR |
| 9 | 3715 | GCUUGCUGGACGACAUGAA | 4072 | UUCAUGUCGUCCAGCAAGC | Chp | [521-539] ORF |
| 10 | 3716 | AAGCCUGUUUGCAAUUUAA | 4073 | UUAAAUUGCAAACAGGCUU | Chp | [199-217] 5'UTR |
| 11 | 3717 | GGAAGUUAAUGGUUUUGAG | 4074 | CUCAAAACCAUUAACUUCC | Chp | [71-89] 5'UTR |
| 12 | 3718 | GGAAAAAGCAAAUUCUGGA | 4075 | UCCAGAAUUUGCUUUUUCC | Chp | [55-73] 5'UTR |
| 13 | 3719 | GAGGAAGCCUGUUUGCAAU | 4076 | AUUGCAAACAGGCUUCCUC | Chp | [195-213] 5'UTR |
| 14 | 3720 | CCCUGAUUUUAGAAACUCUA | 4077 | UAGAGUUCUAAAAUCAGGG | Chp | [1136-1154] 3'UTR |
| 15 | 3721 | AGGAGCGAAGGACUGUGAA | 4078 | UUCACAGUCCUUCGCUCCU | Chp | [930-948] 3'UTR |
| 16 | 3722 | CGGAACUUGUCAUCUCCAA | 4079 | UUGGAGAUGACAAGUUCCG | Chp | [722-740] ORF |
| 17 | 3723 | CGGGACUUCUUUUGGUUUU | 4080 | AAAACCAAAAGAAGUCCCG | | [350-368] 5'UTR |
| 18 | 3724 | GCGGGCCAUUUUGAAUAAA | 4081 | UUUAUUCAAAAUGGCCCGC | Chp | [259-277] 5'UTR |
| 19 | 3725 | CAGGGAAGCUCAAAGAUCU | 4082 | AGAUCUUUGAGCUUCCCUG | | [24-42] 5'UTR |
| 20 | 3726 | GAAAAAGCAAAUUCUGGAA | 4083 | UUCCAGAAUUUGCUUUUUC | Chp | [56-74] 5'UTR |
| 21 | 3727 | UGAGCUUGCUGGACGACAU | 4084 | AUGUCGUCCAGCAAGCUCA | Chp | [518-536] ORF |
| 22 | 3728 | GGCGGGCCAUUUUGAAUAA | 4085 | UUAUUCAAAAUGGCCCGCC | Chp | [258-276] 5'UTR |
| 23 | 3729 | AAUUUAAGCGGGCUGUGAA | 4086 | UUCACAGCCCGCUUAAAUU | Chp | [211-229] 5'UTR |
| 24 | 3730 | GCGGGACUUCUUUUGGUUU | 4087 | AAACCAAAAGAAGUCCCGC | | [349-367] 5'UTR |
| 25 | 3731 | AGGUGACUUUCUGUAACAA | 4088 | UUGUUACAGAAAGUCACCU | Chp | [1192-1210] 3'UTR |
| 26 | 3732 | GAAGCCUGUUUGCAAUUUA | 4089 | UAAAUUGCAAACAGGCUUC | Chp | [198-216] 5'UTR |
| 27 | 3733 | GGUGACUUUCUGUAACAAU | 4090 | AUUGUUACAGAAAGUCACC | Chp | [1193-1211] 3'UTR |
| 28 | 3734 | UGAACUUGUGGCCUGAAGA | 4091 | UCUUCAGGCCACAAGUUCA | Chp | [945-963] 3'UTR |
| 29 | 3735 | CUGUGAACUUGUGGCCUGA | 4092 | UCAGGCCACAAGUUCACAG | Chp | [942-960] 3'UTR |
| 30 | 3736 | CCAGGAAAAAGCAAAUUCU | 4093 | AGAAUUUGCUUUUUCCUGG | Chp | [52-70] 5'UTR |
| 31 | 3737 | CUUCCAGGCAGGCUCUAUA | 4094 | UAUAGAGCCUGCCUGGAAG | | [287-305] 5'UTR |
| 32 | 3738 | CUUCUUUUGGUUUUCUUUC | 4095 | GAAAGAAAACCAAAAGAAG | | [355-373] 5'UTR |
| 33 | 3739 | AGUUAAUGGUUUUGAGUGA | 4096 | UCACUCAAAACCAUUAACU | Chp | [74-92] 5'UTR |
| 34 | 3740 | AGCGGGACUUCUUUUGGUU | 4097 | AACCAAAAGAAGUCCCGCU | | [348-366] 5'UTR |
| 35 | 3741 | GCUGCCAGGAAAAAGCAAA | 4098 | UUUGCUUUUUCCUGGCAGC | Chp | [48-66] 5'UTR |
| 36 | 3742 | CCAAAUCCCUUCCUGGAGA | 4099 | UCUCCAGGAAGGGAUUUGG | | [896-914] 3'UTR |

FIGURE 4 Continued

| | | | | | | |
|---|---|---|---|---|---|---|
| 37 | 3743 | GCCAGGUGGAAAUCCUACA | 4100 | UGUAGGAUUUCCACCUGGC | Chp | [599-617] ORF |
| 38 | 3744 | CAAUUUAAGCGGGCUGUGA | 4101 | UCACAGCCCGCUUAAAUUG | Chp | [210-228] 5'UTR |
| 39 | 3745 | GAGGCGGGCCAUUUUGAAU | 4102 | AUUCAAAAUGGCCCGCCUC | Chp | [256-274] 5'UTR |
| 40 | 3746 | CUGUAACAAUGCGAUGUAU | 4103 | AUACAUCGCAUUGUUACAG | Chp | [1202-1220] 3'UTR |
| 41 | 3747 | CUGUUGCCCUGAUUUAUGA | 4104 | UCAUAAAUCAGGGCAACAG | Chp | [1130-1148] 3'UTR |
| 42 | 3748 | AGCUUAGCCAGGUGGAAAU | 4105 | AUUUCCACCUGGCUAAGCU | Rat,Ms,GP,Chn,Chp | [593-611] ORF |
| 43 | 3749 | GCGCUUCCUCAUUCUUUGA | 4106 | UCAAAGAAUGAGGAAGCGC | Chp | [139-157] 5'UTR |
| 44 | 3750 | CGAUUUUUAAACACUUGUG | 4107 | CACAAGUGUUUAAAAAUCG | Chp | [1260-1278] 3'UTR |
| 45 | 3751 | GUUCUGUUGCCCUGAUUUA | 4108 | UAAAUCAGGGCAACAGAAC | Chp | [1127-1145] 3'UTR |
| 46 | 3752 | GGUUCUGUUGCCCUGAUUU | 4109 | AAAUCAGGGCAACAGAACC | Chp | [1126-1144] 3'UTR |
| 47 | 3753 | UCUUUUGGUUUUCUUUCUC | 4110 | GAGAAAGAAAACCAAAAGA | | [357-375] 5'UTR |
| 48 | 3754 | CUUUUUUACAGGAAGGUGA | 4111 | UCACCUUCCUGUAAAAAAG | Ms,Chp | [1179-1197] 3'UTR |
| 49 | 3755 | GCCCACUUGACUUCACCAA | 4112 | UUGGUGAAGUCAAGUGGGC | Chp | [881-899] 3'UTR |
| 50 | 3756 | ACGACAUGAACCACUGCUA | 4113 | UAGCAGUGGUUCAUGUCGU | Rat,Ms,GP,Chn,Chp | [530-548] ORF |
| 51 | 3757 | CCAGGCAGGCUCUAUAAGU | 4114 | ACUUAUAGAGCCUGCCUGG | | [290-308] 5'UTR |
| 52 | 3758 | CGGGCCAUUUUGAAUAAAG | 4115 | CUUUAUUCAAAAUGGCCCG | Chp | [260-278] 5'UTR |
| 53 | 3759 | GGUAUCAGCGCUUCCUCAU | 4116 | AUGAGGAAGCGCUGAUACC | | [132-150] 5'UTR |
| 54 | 3760 | AGGCAGGCUCUAUAAGUGA | 4117 | UCACUUAUAGAGCCUGCCU | | [292-310] 5'UTR |
| 55 | 3761 | CUUGGAGAAAGGUUCUGUU | 4118 | AACAGAACCUUUCUCCAAG | Chp | [1116-1134] 3'UTR |
| 56 | 3762 | CGACAUGAACCACUGCUAC | 4119 | GUAGCAGUGGUUCAUGUCG | Rat,Ms,GP,Chn,Chp | [531-549] ORF |
| 57 | 3763 | UCUGGAAGUUAAUGGUUUU | 4120 | AAAACCAUUAACUUCCAGA | Chp | [68-86] 5'UTR |
| 58 | 3764 | CCUGGAGACUAAACCUGGU | 4121 | ACCAGGUUUAGUCUCCAGG | | [907-925] 3'UTR |
| 59 | 3765 | GGCCAUUUUGAAUAAAGAG | 4122 | CUCUUUAUUCAAAAUGGCC | Chp | [262-280] 5'UTR |
| 60 | 3766 | CUUUCUGUAACAAUGCGAU | 4123 | AUCGCAUUGUUACAGAAAG | Chp | [1198-1216] 3'UTR |
| 61 | 3767 | GAAGUUAAUGGUUUUGAGU | 4124 | ACUCAAAACCAUUAACUUC | Chp | [72-90] 5'UTR |
| 62 | 3768 | GCUCUCCAAACUAUGCCAA | 4125 | UUGGCAUAGUUUGGAGAGC | Chp | [1068-1086] 3'UTR |
| 63 | 3769 | UGUCAUCUCCAACGACAAA | 4126 | UUUGUCGUUGGAGAUGACA | Chp | [729-747] ORF |
| 64 | 3770 | UAGCCAGGUGGAAAUCCUA | 4127 | UAGGAUUUCCACCUGGCUA | Chp | [597-615] ORF |
| 65 | 3771 | CUGCCAGGAAAAAGCAAAU | 4128 | AUUUGCUUUUUCCUGGCAG | Chp | [49-67] 5'UTR |
| 66 | 3772 | CACUGUAGCGGGACUUCUU | 4129 | AAGAAGUCCCGCUACAGUG | | [342-360] 5'UTR |
| 67 | 3773 | GGCAGGGAAGCUCAAAGAU | 4130 | AUCUUUGAGCUUCCCUGCC | | [22-40] 5'UTR |
| 68 | 3774 | UGUGAACUUGUGGCCUGAA | 4131 | UUCAGGCCACAAGUUCACA | Chp | [943-961] 3'UTR |
| 69 | 3775 | UGUCCUGACACCUCCAGAA | 4132 | UUCUGGAGGUGUCAGGACA | | [774-792] 3'UTR |
| 70 | 3776 | UUGUCAUCUCCAACGACAA | 4133 | UUGUCGUUGGAGAUGACAA | Chp | [728-746] ORF |
| 71 | 3777 | CAGGAAAAAGCAAAUUCUG | 4134 | CAGAAUUUGCUUUUUCCUG | Chp | [53-71] 5'UTR |
| 72 | 3778 | GGGACUUCUUUUGGUUUUC | 4135 | GAAAACCAAAAGAAGUCCC | | [351-369] 5'UTR |
| 73 | 3779 | AGGAAGGUGACUUUCUGUA | 4136 | UACAGAAAGUCACCUUCCU | Rat,Ms,Chp | [1188-1206] 3'UTR |
| 74 | 3780 | GGCUGCUCUCCAAACUAUG | 4137 | CAUAGUUUGGAGAGCAGCC | Chp | [1064-1082] 3'UTR |
| 75 | 3781 | CUUGCUGGACGACAUGAAC | 4138 | GUUCAUGUCGUCCAGCAAG | Chp | [522-540] ORF |
| 76 | 3782 | UGCUGCCAGGAAAAAGCAA | 4139 | UUGCUUUUUCCUGGCAGCA | | [47-65] 5'UTR |
| 77 | 3783 | GUUCUAAGGUCUCUUCAGA | 4140 | UCUGAAGAGACCUUAGAAC | | [1024-1042] 3'UTR |
| 78 | 3784 | CAGCGCUUCCUCAUUCUUU | 4141 | AAAGAAUGAGGAAGCGCUG | Chp | [137-155] 5'UTR |
| 79 | 3785 | GACUAAACCUGGUGCUCAG | 4142 | CUGAGCACCAGGUUUAGUC | | [913-931] 3'UTR |
| 80 | 3786 | GGAGCUUUUGCCACUGACU | 4143 | AGUCAGUGGCAAAAGCUCC | Chp | [749-767] |
| 81 | 3787 | UUCCAGGCAGGCUCUAUAA | 4144 | UUAUAGAGCCUGCCUGGAA | | [288-306] 5'UTR |
| 82 | 3788 | UGUACCUUUUUUACAGGAA | 4145 | UUCCUGUAAAAAAGGUACA | Ms,Chp | [1174-1192] 3'UTR |
| 83 | 3789 | GUGGCUGCUCUCCAAACUA | 4146 | UAGUUUGGAGAGCAGCCAC | Chp | [1062-1080] 3'UTR |
| 84 | 3790 | CACCAAAUCCCUUCCUGGA | 4147 | UCCAGGAAGGGAUUUGGUG | | [894-912] 3'UTR |
| 85 | 3791 | CCGGAACUUGUCAUCUCCA | 4148 | UGGAGAUGACAAGUUCCGG | Chp | [721-739] ORF |
| 86 | 3792 | GCGUCAUCGACUACAUUCU | 4149 | AGAAUGUAGUCGAUGACGC | Chp | [620-638] ORF |
| 87 | 3793 | AGCGCGUCAUCGACUACAU | 4150 | AUGUAGUCGAUGACGCGCU | GP,Chn,Chp | [617-635] ORF |
| 88 | 3794 | UCAGCUUAGCCAGGUGGAA | 4151 | UUCCACCUGGCUAAGCUGA | Rat,Ms,GP,Chp | [591-609] ORF |
| 89 | 3795 | CAGGCAGGCUCUAUAAGUG | 4152 | CACUUAUAGAGCCUGCCUG | | [291-309] 5'UTR |
| 90 | 3796 | GUCUUCUGGUCUCCUUGGA | 4153 | UCCAAGGAGACCAGAAGAC | Chp | [1103-1121] 3'UTR |
| 91 | 3797 | CCAAGUUCUAAGGUCUCUU | 4154 | AAGAGACCUUAGAACUUGG | | [1020-1038] 3'UTR |
| 92 | 3798 | AGCGAAGGACUGUGAACUU | 4155 | AAGUUCACAGUCCUUCGCU | Chp | [933-951] 3'UTR |
| 93 | 3799 | AUCCCUUCCUGGAGACUAA | 4156 | UUAGUCUCCAGGAAGGGAU | | [900-918] 3'UTR |
| 94 | 3800 | CUGUAGCGGGACUUCUUUU | 4157 | AAAAGAAGUCCCGCUACAG | | [344-362] 5'UTR |
| 95 | 3801 | ACUGUAGCGGGACUUCUUU | 4158 | AAAGAAGUCCCGCUACAGU | | [343-361] 5'UTR |
| 96 | 3802 | GAGUAUAUAGGUUUUGUAC | 4159 | GUACAAAACCUAUAUACUC | Chp | [1160-1178] 3'UTR |
| 97 | 3803 | CUCACUCCGGAACUUGUCA | 4160 | UGACAAGUUCCGGAGUGAG | | [715-733] ORF |
| 98 | 3804 | ACUACAUUCUCGACCUGCA | 4161 | UGCAGGUCGAGAAUGUAGU | Chp | [629-647] ORF |

FIGURE 4 Continued

| | | | | | | | |
|---|---|---|---|---|---|---|---|
| 99 | 3805 | GGAGACUAAACCUGGUGCU | 4162 | AGCACCAGGUUUAGUCUCC | | | [910-928] 3'UTR |
| 100 | 3806 | AGCGCUUCCUCAUUCUUUG | 4163 | CAAAGAAUGAGGAAGCGCU | Chp | | [138-156] 5'UTR |
| 101 | 3807 | UCUGGUCUCCUUGGAGAAA | 4164 | UUUCUCCAAGGAGACCAGA | Chp | | [1107-1125] 3'UTR |
| 102 | 3808 | CAACGACAAAAGGAGCUUU | 4165 | AAAGCUCCUUUUGUCGUUG | Chp | | [738-756] ORF |
| 103 | 3809 | GGCAGGCUCUAUAAGUGAC | 4166 | GUCACUUAUAGAGCCUGCC | | | [293-311] 5'UTR |
| 104 | 3810 | GCUUCCUCAUUCUUUGAAU | 4167 | AUUCAAAGAAUGAGGAAGC | Chp | | [141-159] 5'UTR |
| 105 | 3811 | GUACCUUUUUUACAGGAAG | 4168 | CUUCCUGUAAAAAGGUAC | Ms,Chp | | [1175-1193] 3'UTR |
| 106 | 3812 | UGUUGCCCUGAUUUAUGAA | 4169 | UUCAUAAAUCAGGGCAACA | Chp | | [1131-1149] 3'UTR |
| 107 | 3813 | CUUCUGGUCUCCUUGGAGA | 4170 | UCUCCAAGGAGACCAGAAG | Chp | | [1105-1123] 3'UTR |
| 108 | 3814 | AAGCAAAUUCUGGAAGUUA | 4171 | UAACUUCCAGAAUUUGCUU | Chp | | [60-78] 5'UTR |
| 109 | 3815 | GAAAUCCUACAGCGCGUCA | 4172 | UGACGCGCUGUAGGAUUUC | Chp | | [607-625] ORF |
| 110 | 3816 | GACAUGAACCACUGCUACU | 4173 | AGUAGCAGUGGUUCAUGUC | Rat,Ms,GP,Chn,Chp | | [532-550] ORF |
| 111 | 3817 | GGUUUUCUUUCUCUUUGGG | 4174 | CCCAAAGAGAAAGAAAACC | | | [363-381] 5'UTR |
| 112 | 3818 | CAGGAAGGUGACUUUCUGU | 4175 | ACAGAAAGUCACCUUCCUG | Rat,Ms,Chp | | [1187-1205] 3'UTR |
| 113 | 3819 | GUUAAUGGUUUUGAGUGAU | 4176 | AUCACUCAAAACCAUUAAC | Chp | | [75-93] 5'UTR |
| 114 | 3820 | GUGAACUUGUGGCCUGAAG | 4177 | CUUCAGGCCACAAGUUCAC | | | [944-962] 3'UTR |
| 115 | 3821 | AGGCGGGCCAUUUUGAAUA | 4178 | UAUUCAAAAUGGCCCGCCU | Chp | | [257-275] 5'UTR |
| 116 | 3822 | GUGCUGCCAGGAAAAAGCA | 4179 | UGCUUUUUCCUGGCAGCAC | | | [46-64] 5'UTR |
| 117 | 3823 | AAGUUCUAAGGUCUCUUCA | 4180 | UGAAGAGACCUUAGAACUU | | | [1022-1040] 3'UTR |
| 118 | 3824 | CGACUACAUUCUCGACCUG | 4181 | CAGGUCGAGAAUGUAGUCG | Chp | | [627-645] ORF |
| 119 | 3825 | GAGCGAAGGACUGUGAACU | 4182 | AGUUCACAGUCCUUCGCUC | Chp | | [932-950] 3'UTR |
| 120 | 3826 | CUUGUCAUCUCCAACGACA | 4183 | UGUCGUUGGAGAUGACAAG | Chp | | [727-745] ORF |
| 121 | 3827 | GAAUAAAGAGGCGUGCCUU | 4184 | AAGGCACGCCUCUUUAUUC | Chp | | [271-289] 5'UTR |
| 122 | 3828 | AGGGAAGCUCAAAGAUCUG | 4185 | CAGAUCUUUGAGCUUCCCU | | | [25-43] 5'UTR |
| 123 | 3829 | GGAACUUGUCAUCUCCAAC | 4186 | GUUGGAGAUGACAAGUUCC | Chp | | [723-741] ORF |
| 124 | 3830 | AAAAGCAAAUUCUGGAAGU | 4187 | ACUUCCAGAAUUUGCUUUU | Chp | | [58-76] 5'UTR |
| 125 | 3831 | UGGUUUUCUUUCUCUUUGG | 4188 | CCAAAGAGAAAGAAAACCA | | | [362-380] 5'UTR |
| 126 | 3832 | AACUUGUCAUCUCCAACGA | 4189 | UCGUUGGAGAUGACAAGUU | Chp | | [725-743] ORF |
| 127 | 3833 | AGCUCACUCCGGAACUUGU | 4190 | ACAAGUUCCGGAGUGAGCU | Rat,Ms | | [713-731] ORF |
| 128 | 3834 | CAUUCUCGACCUGCAGGUA | 4191 | UACCUGCAGGUCGAGAAUG | Chp | | [633-651] ORF |
| 129 | 3835 | UAGCGGGACUUCUUUUGGU | 4192 | ACCAAAAGAAGUCCCGCUA | | | [347-365] 5'UTR |
| 130 | 3836 | UGGUCUCCUUGGAGAAAGG | 4193 | CCUUUCUCCAAGGAGACCA | Chp | | [1109-1127] 3'UTR |
| 131 | 3837 | UUCUGGUCUCCUUGGAGAA | 4194 | UUCUCCAAGGAGACCAGAA | Chp | | [1106-1124] 3'UTR |
| 132 | 3838 | AGUGGCUGCUCUCCAAACU | 4195 | AGUUUGGAGAGCAGCCACU | Chp | | [1061-1079] 3'UTR |
| 133 | 3839 | AAUUCUGGAAGUUAAUGGU | 4196 | ACCAUUAACUUCCAGAAUU | Chp | | [65-83] 5'UTR |
| 134 | 3840 | ACAAAAGGAGCUUUUGCCA | 4197 | UGGCAAAAGCUCCUUUUGU | Chp | | [743-761] ORF |
| 135 | 3841 | UGCUGGACGACAUGAACCA | 4198 | UGGUUCAUGUCGUCCAGCA | Chp | | [524-542] ORF |
| 136 | 3842 | UAAAGAGGCGUGCCUUCCA | 4199 | UGGAAGGCACGCCUCUUUA | | | [274-292] 5'UTR |
| 137 | 3843 | AUUUACACAGGAAGGUGACUUUCUGU | 4200 | GUUCACAGCCCGCUUAAAU | Chp | | [212-230] 5'UTR |
| 138 | 3844 | CGCUUCCUCAUUCUUUGAA | 4201 | UUCAAAGAAUGAGGAAGCG | Chp | | [140-158] 5'UTR |
| 139 | 3845 | GGAAGCUCAAAGAUCUGGG | 4202 | CCCAGAUCUUUGAGCUUCC | Chp | | [27-45] 5'UTR |
| 140 | 3846 | GUAUCAGCGCUUCCUCAUU | 4203 | AAUGAGGAAGCGCUGAUAC | Chp | | [133-151] 5'UTR |
| 141 | 3847 | ACACUUGUGUAUAUGAUGA | 4204 | UCAUCAUAUACAAGUGU | | | [1270-1288] 3'UTR |
| 142 | 3848 | ACUUUCUGUAACAAUGCGA | 4205 | UCGCAUUGUUACAGAAAGU | Chp | | [1197-1215] 3'UTR |
| 143 | 3849 | CCAACGACAAAAGGAGCUU | 4206 | AAGCUCCUUUUGUCGUUGG | Chp | | [737-755] ORF |
| 144 | 3850 | UCAUCGACUACAUUCUCGA | 4207 | UCGAGAAUGUAGUCGAUGA | | | [623-641] ORF |
| 145 | 3851 | UGGAAAUCCUACAGCGCGU | 4208 | ACGCGCUGUAGGAUUUCCA | Chp | | [605-623] ORF |
| 146 | 3852 | AGCUUGCUGGACGACAUGA | 4209 | UCAUGUCGUCCAGCAAGCU | Chp | | [520-538] ORF |
| 147 | 3853 | CAUUUUGAAUAAAGAGGCG | 4210 | CGCCUCUUUAUUCAAAAUG | Chp | | [265-283] 5'UTR |
| 148 | 3854 | AAAGCAAAUUCUGGAAGUU | 4211 | AACUUCCAGAAUUUGCUUU | Chp | | [59-77] 5'UTR |
| 149 | 3855 | UUUACAGGAAGGUGACUUU | 4212 | AAAGUCACCUUCCUGUAAA | Rat,Ms,Chp | | [1183-1201] 3'UTR |
| 150 | 3856 | GGUUUUGUACCUUUUUUAC | 4213 | GUAAAAAAGGUACAAAACC | Chp | | [1169-1187] 3'UTR |
| 151 | 3857 | AGGUUCUGUUGCCCUGAUU | 4214 | AAUCAGGGCAACAGAACCU | Chp | | [1125-1143] 3'UTR |
| 152 | 3858 | UGGAAGUUAAUGGUUUUGA | 4215 | UCAAAACCAUUAACUUCCA | Chp | | [70-88] 5'UTR |
| 153 | 3859 | UCCCUUCCUGGAGACUAAA | 4216 | UUUAGUCUCCAGGAAGGGA | | | [901-919] 3'UTR |
| 154 | 3860 | AGGUGGAAAUCCUACAGCG | 4217 | CGCUGUAGGAUUUCCACCU | Chp | | [602-620] ORF |
| 155 | 3861 | AGGAAAAAGCAAAUUCUGG | 4218 | CCAGAAUUUGCUUUUUCCU | Chp | | [54-72] 5'UTR |
| 156 | 3862 | GCAAUUUAAGCGGGCUGUG | 4219 | CACAGCCCGCUUAAAUUGC | Chp | | [209-227] 5'UTR |
| 157 | 3863 | GGAAGCCUGUUUGCAAUUU | 4220 | AAAUUGCAAACAGGCUUCC | Chp | | [197-215] 5'UTR |
| 158 | 3864 | CUCCUUGGAGAAAGGUUCU | 4221 | AGAACCUUUCUCCAAGGAG | Chp | | [1113-1131] 3'UTR |
| 159 | 3865 | AGGAAGCCUGUUUGCAAUU | 4222 | AAUUGCAAACAGGCUUCCU | Chp | | [196-214] 5'UTR |
| 160 | 3866 | UUCUGUUGCCCUGAUUUAU | 4223 | AUAAAUCAGGGCAACAGAA | Chp | | [1128-1146] 3'UTR |

FIGURE 4 Continued

| | | | | | | |
|---|---|---|---|---|---|---|
| 161 | 3867 | AGAGCUGGUCUUCUGGUCU | 4224 | AGACCAGAAGACCAGCUCU | Chp | [1096-1114] 3'UTR |
| 162 | 3868 | UUCUGGAAGUUAAUGGUUU | 4225 | AAACCAUUAACUUCCAGAA | Chp | [67-85] 5'UTR |
| 163 | 3869 | AAAUCCUACAGCGCGUCAU | 4226 | AUGACGCGCUGUAGGAUUU | Chp | [608-626] ORF |
| 164 | 3870 | UUAAAUCCUUGCUGGCGGA | 4227 | UCCGCCAGCAAGGAUUUAA | Chp | [96-114] 5'UTR |
| 165 | 3871 | GAAAGGUUCUGUUGCCCUG | 4228 | CAGGGCAACAGAACCUUUC | Chp | [1122-1140] 3'UTR |
| 166 | 3872 | UAAGGUCUCUUCAGAGCGU | 4229 | ACGCUCUGAAGAGACCUUA | | [1028-1046] 3'UTR |
| 167 | 3873 | AACGACAAAAGGAGCUUUU | 4230 | AAAAGCUCCUUUUGUCGUU | Chp | [739-757] ORF |
| 168 | 3874 | GUCAUCUCCAACGACAAAA | 4231 | UUUUGUCGUUGGAGAUGAC | Chp | [730-748] ORF |
| 169 | 3875 | CCAGGUGGAAAUCCUACAG | 4232 | CUGUAGGAUUUCCACCUGG | Chp | [600-618] ORF |
| 170 | 3876 | CCAUUUUGAAUAAAGAGGC | 4233 | GCCUCUUUAUUCAAAAUGG | | [264-282] 5'UTR |
| 171 | 3877 | UCAGCGCUUCCUCAUUCUU | 4234 | AAGAAUGAGGAAGCGCUGA | Chp | [136-154] 5'UTR |
| 172 | 3878 | GGAGAAAGGUUCUGUUGCC | 4235 | GGCAACAGAACCUUUCUCC | Chp | [1119-1137] 3'UTR |
| 173 | 3879 | UGCCCACUUGACUUCACCA | 4236 | UGGUGAAGUCAAGUGGGCA | Chp | [880-898] 3'UTR |
| 174 | 3880 | CUACAUUCUCGACCUGCAG | 4237 | CUGCAGGUCGAGAAUGUAG | Chp | [630-648] ORF |
| 175 | 3881 | GCAGGGAAGCUCAAAGAUC | 4238 | GAUCUUUGAGCUUCCCUGC | | [23-41] 5'UTR |
| 176 | 3882 | AAAUCCUUGCUGGCGGAGA | 4239 | UCUCCGCCAGCAAGGAUUU | Chp | [98-116] 5'UTR |
| 177 | 3883 | GUAUAUAGGUUUUGUACCU | 4240 | AGGUACAAAACCUAUAUAC | Chp | [1162-1180] 3'UTR |
| 178 | 3884 | AAGGUUCUGUUGCCCUGAU | 4241 | AUCAGGGCAACAGAACCUU | Chp | [1124-1142] 3'UTR |
| 179 | 3885 | GACUGUGAACUUGUGGCCU | 4242 | AGGCCACAAGUUCACAGUC | Chp | [940-958] 3'UTR |
| 180 | 3886 | UUGACUUCACCAAAUCCCU | 4243 | AGGGAUUUGGUGAAGUCAA | | [887-905] 3'UTR |
| 181 | 3887 | GGUCUCCUUGGAGAAAGGU | 4244 | ACCUUUCUCCAAGGAGACC | Chp | [1110-1128] 3'UTR |
| 182 | 3888 | UGGUCUUCUGGUCUCCUUG | 4245 | CAAGGAGACCAGAAGACCA | Chp | [1101-1119] 3'UTR |
| 183 | 3889 | UGCUCUCCAAACUAUGCCA | 4246 | UGGCAUAGUUUGGAGAGCA | Chp | [1067-1085] 3'UTR |
| 184 | 3890 | UAAACCUGGUGCUCAGGAG | 4247 | CUCCUGAGCACCAGGUUUA | | [916-934] 3'UTR |
| 185 | 3891 | CUUCCUGGAGACUAAACCU | 4248 | AGGUUUAGUCUCCAGGAAG | | [904-922] 3'UTR |
| 186 | 3892 | UCACUCCGGAACUUGUCAU | 4249 | AUGACAAGUUCCGGAGUGA | | [716-734] ORF |
| 187 | 3893 | UUGGUUUUCUUUCUCUUUG | 4250 | CAAAGAGAAAGAAAACCAA | | [361-379] 5'UTR |
| 188 | 3894 | GCCUGUUUGCAAUUUAAGC | 4251 | GCUUAAAUUGCAAACAGGC | Chp | [201-219] 5'UTR |
| 189 | 3895 | GACUUUCUGUAACAAUGCG | 4252 | CGCAUUGUUACAGAAAGUC | Chp | [1196-1214] 3'UTR |
| 190 | 3896 | AAAGGUUCUGUUGCCCUGA | 4253 | UCAGGGCAACAGAACCUUU | Chp | [1123-1141] 3'UTR |
| 191 | 3897 | CAAGUUCUAAGGUCUCUUC | 4254 | GAAGAGACCUUAGAACUUG | | [1021-1039] 3'UTR |
| 192 | 3898 | AGACUAAACCUGGUGCUCA | 4255 | UGAGCACCAGGUUUAGUCU | | [912-930] 3'UTR |
| 193 | 3899 | UGACUUCACCAAAUCCCUU | 4256 | AAGGGAUUUGGUGAAGUCA | | [888-906] 3'UTR |
| 194 | 3900 | AGGAGCUUUUGCCACUGAC | 4257 | GUCAGUGGCAAAAGCUCCU | Ms,Chp | [748-766] |
| 195 | 3901 | AAGGAGCUUUUGCCACUGA | 4258 | UCAGUGGCAAAAGCUCCUU | Chp | [747-765] ORF |
| 196 | 3902 | CGACAAAAGGAGCUUUUGC | 4259 | GCAAAAGCUCCUUUUGUCG | Chp | [741-759] ORF |
| 197 | 3903 | UACAGGAAGGUGACUUUCU | 4260 | AGAAAGUCACCUUCCUGUA | Rat,Ms,Chp | [1185-1203] 3'UTR |
| 198 | 3904 | AGUUCUAAGGUCUCUUCAG | 4261 | CUGAAGAGACCUUAGAACU | | [1023-1041] 3'UTR |
| 199 | 3905 | CUCCGGAACUUGUCAUCUC | 4262 | GAGAUGACAAGUUCCGGAG | Chp | [719-737] ORF |
| 200 | 3906 | GACGACAUGAACCACUGCU | 4263 | AGCAGUGGUUCAUGUCGUC | Rat,Ms,GP,Chn,Chp | [529-547] ORF |
| 201 | 3907 | AAAAGGAGCUUUUGCCACU | 4264 | AGUGGCAAAAGCUCCUUUU | Chp | [745-763] ORF |
| 202 | 3908 | AAUCCUACAGCGCGUCAUC | 4265 | GAUGACGCGCUGUAGGAUU | Chp | [609-627] ORF |
| 203 | 3909 | AGCCUGUUUGCAAUUUAAG | 4266 | CUUAAAUUGCAAACAGGCU | Chp | [200-218] 5'UTR |
| 204 | 3910 | AUCAGCGCUUCCUCAUUCU | 4267 | AGAAUGAGGAAGCGCUGAU | Chp | [135-153] 5'UTR |
| 205 | 3911 | UUUUUUACAGGAAGGUGAC | 4268 | GUCACCUUCCUGUAAAAAA | Rat,Ms,Chp | [1180-1198] 3'UTR |
| 206 | 3912 | CCUUGGAGAAAGGUUCUGU | 4269 | ACAGAACCUUUCUCCAAGG | Chp | [1115-1133] 3'UTR |
| 207 | 3913 | GCUGCUCCAAACUAUGCGC | 4270 | GCAUAGUUUGGAGAGCAGC | Chp | [1065-1083] 3'UTR |
| 208 | 3914 | GCCAUUUUGAAUAAAGAGG | 4271 | CCUCUUUAUUCAAAAUGGC | | [263-281] 5'UTR |
| 209 | 3915 | CUGGUCUCCUUGGAGAAAG | 4272 | CUUUCUCCAAGGAGACCAG | Chp | [1108-1126] 3'UTR |
| 210 | 3916 | CUAAACCUGGUGCUCAGGA | 4273 | UCCUGAGCACCAGGUUUAG | | [915-933] 3'UTR |
| 211 | 3917 | CAAAUUCUGGAAGUUAAUG | 4274 | CAUUAACUUCCAGAAUUUG | Chp | [63-81] 5'UTR |
| 212 | 3918 | UUCUCGACCUGCAGGUAGU | 4275 | ACUACCUGCAGGUCGAGAA | Chp | [635-653] ORF |
| 213 | 3919 | CAUCGACUACAUUCUCGAC | 4276 | GUCGAGAAUGUAGUCGAUG | Chp | [624-642] ORF |
| 214 | 3920 | GCUUAGCCAGGUGGAAAUC | 4277 | GAUUUCCACCUGGCUAAGC | Rat,Ms,GP,Chn,Chp | [594-612] ORF |
| 215 | 3921 | UGGACGACAUGAACCACUG | 4278 | CAGUGGUUCAUGUCGUCCA | Rat,Ms,GP,Chn,Chp | [527-545] ORF |
| 216 | 3922 | GAUUUUAAAUCCUUGCUG | 4279 | CAGCAAGGAUUUAAAAAUC | Chp | [91-109] 5'UTR |
| 217 | 3923 | GUCUCCUUGGAGAAAGGUU | 4280 | AACCUUUCUCCAAGGAGAC | | [1111-1129] 3'UTR |
| 218 | 3924 | CUCUCCAAACUAUGCCAAG | 4281 | CUUGGCAUAGUUUGGAGAG | Chp | [1069-1087] 3'UTR |
| 219 | 3925 | UCAUCUCCAACGACAAAAG | 4282 | CUUUUGUCGUUGGAGAUGA | Chp | [731-749] ORF |
| 220 | 3926 | CACUCCGGAACUUGUCAUC | 4283 | GAUGACAAGUUCCGGAGUG | | [717-735] ORF |
| 221 | 3927 | CGUCAUCGACUACAUUCUC | 4284 | GAGAAUGUAGUCGAUGACG | Chp | [621-639] ORF |
| 222 | 3928 | CCUCAUUCUUUGAAUCCGC | 4285 | GCGGAUUCAAAGAAUGAGG | | [145-163] 5'UTR |

FIGURE 4 Continued

| | | | | | | |
|---|---|---|---|---|---|---|
| 223 | 3929 | AUCUCCAACGACAAAAGGA | 4286 | UCCUUUUGUCGUUGGAGAU | Chp | [733-751] ORF |
| 224 | 3930 | CGCGUCAUCGACUACAUUC | 4287 | GAAUGUAGUCGAUGACGCG | Chp | [619-637] ORF |
| 225 | 3931 | GUAGCGGGACUUCUUUUGG | 4288 | CCAAAAGAAGUCCCGCUAC | | [346-364] 5'UTR |
| 226 | 3932 | CUCAUUCUUUGAAUCCGCG | 4289 | CGCGGAUUCAAAGAAUGAG | | [146-164] 5'UTR |
| 227 | 3933 | UCUGUUGCCCUGAUUUAUG | 4290 | CAUAAAUCAGGGCAACAGA | Chp | [1129-1147] 3'UTR |
| 228 | 3934 | CCCAAGUUCUAAGGUCUCU | 4291 | AGAGACCUUAGAACUUGGG | | [1019-1037] 3'UTR |
| 229 | 3935 | UCUCCAACGACAAAAGGAG | 4292 | CUCCUUUUGUCGUUGGAGA | Chp | [734-752] ORF |
| 230 | 3936 | UGGAGAAAGGUUCUGUUGC | 4293 | GCAACAGAACCUUUCUCCA | Chp | [1118-1136] 3'UTR |
| 231 | 3937 | UGAAGAGCCAGAGCUAGCU | 4294 | AGCUAGCUCUGGCUCUUCA | Chp | [958-976] 3'UTR |
| 232 | 3938 | UCGACUACAUUCUCGACCU | 4295 | AGGUCGAGAAUGUAGUCGA | Chp | [626-644] ORF |
| 233 | 3939 | UUAGCCAGGUGGAAAUCCU | 4296 | AGGAUUCCACCUGGCUAA | Rat,Ms,GP,Chn,Chp | [596-614] ORF |
| 234 | 3940 | AAUAAAGAGGCGUGCCUUC | 4297 | GAAGGCACGCCUCUUUAUU | Chp | [272-290] 5'UTR |
| 235 | 3941 | UGAAUAAAGAGGCGUGCCU | 4298 | AGGCACGCCUCUUUAUUCA | Chp | [270-288] 5'UTR |
| 236 | 3942 | GGGAAGCUCAAAGAUCUGG | 4299 | CCAGAUCUUUGAGCUUCCC | Chp | [26-44] 5'UTR |
| 237 | 3943 | UGACUUUCUGUAACAAUGC | 4300 | GCAUUGUUACAGAAAGUCA | Chp | [1195-1213] 3'UTR |
| 238 | 3944 | ACUGUGAACUUGUGGCCUG | 4301 | CAGGCCACAAGUUCACAGU | Chp | [941-959] 3'UTR |
| 239 | 3945 | CUGGACGACAUGAACCACU | 4302 | AGUGGUUCAUGUCGUCCAG | GP,Chn,Chp | [526-544] ORF |
| 240 | 3946 | AUUCUGGAAGUUAAUGGUU | 4303 | AACCAUUAACUUCCAGAAU | Chp | [66-84] 5'UTR |
| 241 | 3947 | CAAAUCCCUUCCUGGAGAC | 4304 | GUCUCCAGGAAGGGAUUUG | | [897-915] 3'UTR |
| 242 | 3948 | CAAAAGGAGCUUUUGCCAC | 4305 | GUGGCAAAAGCUCCUUUUG | Chp | [744-762] ORF |
| 243 | 3949 | CAGGUGGAAAUCCUACAGC | 4306 | GCUGUAGGAUUUCCACCUG | Chp | [601-619] ORF |
| 244 | 3950 | GUUUGCAAUUUAAGCGGGC | 4307 | GCCCGCUUAAAUUGCAAAC | Chp | [205-223] 5'UTR |
| 245 | 3951 | AGCCAGGUGGAAAUCCUAC | 4308 | GUAGGAUUUCCACCUGGCU | Chp | [598-616] ORF |
| 246 | 3952 | AAUCCCUUCCUGGAGACUA | 4309 | UAGUCUCCAGGAAGGGAUU | | [899-917] 3'UTR |
| 247 | 3953 | UGUAGCGGGACUUCUUUUG | 4310 | CAAAAGAAGUCCCGCUACA | | [345-363] 5'UTR |
| 248 | 3954 | AGAAAGGUUCUGUUGCCCU | 4311 | AGGGCAACAGAACCUUUCU | Chp | [1121-1139] 3'UTR |
| 249 | 3955 | UCUCCAAACUAUGCCAAGG | 4312 | CCUUGGCAUAGUUUGGAGA | Chp | [1070-1088] 3'UTR |
| 250 | 3956 | AGGACUGUGAACUUGUGGC | 4313 | GCCACAAGUUCACAGUCCU | Chp | [938-956] 3'UTR |
| 251 | 3957 | ACUUGUCAUCUCCAACGAC | 4314 | GUCGUUGGAGAUGACAAGU | Chp | [726-744] ORF |
| 252 | 3958 | CAUUCUUUGAAUCCGCGGC | 4315 | GCCGCGGAUUCAAAGAAUG | | [148-166] 5'UTR |
| 253 | 3959 | UUGUACCUUUUUUACAGGA | 4316 | UCCUGUAAAAAAGGUACAA | Ms,Chp | [1173-1191] 3'UTR |
| 254 | 3960 | AAGUUAAUGGUUUUGAGUG | 4317 | CACUCAAAACCAUUAACUU | Chp | [73-91] 5'UTR |
| 255 | 3961 | UCACCAAAUCCCUUCCUGG | 4318 | CCAGGAAGGGAUUUGGUGA | | [893-911] 3'UTR |
| 256 | 3962 | CAUCUCCAACGACAAAAGG | 4319 | CCUUUUGUCGUUGGAGAUG | Chp | [732-750] ORF |
| 257 | 3963 | ACAUUCUCGACCUGCAGGU | 4320 | ACCUGCAGGUCGAGAAUGU | Chp | [632-650] ORF |
| 258 | 3964 | UCACUGUAGCGGGACUUCU | 4321 | AGAAGUCCCGCUACAGUGA | | [341-359] 5'UTR |
| 259 | 3965 | UUUCUGUAACAAUGCGAUG | 4322 | CAUCGCAUUGUUACAGAAA | Chp | [1199-1217] 3'UTR |
| 260 | 3966 | UCUUCUGGUCUCCUUGGAG | 4323 | CUCCAAGGAGACCAGAAGA | Chp | [1104-1122] 3'UTR |
| 261 | 3967 | ACUCCGGAACUUGUCAUCU | 4324 | AGAUGACAAGUUCCGGAGU | | [718-736] ORF |
| 262 | 3968 | GCCAGGAAAAAGCAAAUUC | 4325 | GAAUUUGCUUUUUCCUGGC | Chp | [51-69] 5'UTR |
| 263 | 3969 | UUUUGAAUAAAGAGGCGUG | 4326 | CACGCCUCUUUAUUCAAAA | Chp | [267-285] 5'UTR |
| 264 | 3970 | CUUCCUCAUUCUUUGAAUC | 4327 | GAUUCAAAGAAUGAGGAAG | Chp | [142-160] 5'UTR |
| 265 | 3971 | AACACUUGUGUAUAUGAUG | 4328 | CAUCAUAUACACAAGUGUU | | [1269-1287] 3'UTR |
| 266 | 3972 | UUUUUACAGGAAGGUGACU | 4329 | AGUCACCUUCCUGUAAAAA | Rat,Ms,Chp | [1181-1199] 3'UTR |
| 267 | 3973 | CCUUUUUUACAGGAAGGUG | 4330 | CACCUUCCUGUAAAAAAGG | Ms,Chp | [1178-1196] 3'UTR |
| 268 | 3974 | GCCCUGAUUUAUGAACUCU | 4331 | AGAGUUCAUAAAUCAGGGC | Chp | [1135-1153] 3'UTR |
| 269 | 3975 | CUGGAGACUAAACCUGGUG | 4332 | CACCAGGUUUAGUCUCCAG | | [908-926] 3'UTR |
| 270 | 3976 | CCUUCCUGGAGACUAAACC | 4333 | GGUUUAGUCUCCAGGAAGG | | [903-921] 3'UTR |
| 271 | 3977 | CUUCACCAAAUCCCUUCCU | 4334 | AGGAAGGGAUUUGGUGAAG | | [891-909] 3'UTR |
| 272 | 3978 | ACGACAAAAGGAGCUUUUG | 4335 | CAAAAGCUCCUUUUGUCGU | Chp | [740-758] ORF |
| 273 | 3979 | CUCCAACGACAAAAGGAGC | 4336 | GCUCCUUUUGUCGUUGGAG | Chp | [735-753] ORF |
| 274 | 3980 | CUGUUUGCAAUUUAAGCGG | 4337 | CCGCUUAAAUUGCAAACAG | Chp | [203-221] 5'UTR |
| 275 | 3981 | UACCUUUUUUACAGGAAGG | 4338 | CCUUCCUGUAAAAAAGGUA | Ms,Chp | [1176-1194] 3'UTR |
| 276 | 3982 | UUGGAGAAAGGUUCUGUUG | 4339 | CAACAGAACCUUUCUCCAA | Chp | [1117-1135] 3'UTR |
| 277 | 3983 | CUGGAAGUUAAUGGUUUUG | 4340 | CAAAACCAUUAACUUCCAG | Chp | [69-87] 5'UTR |
| 278 | 3984 | CUAAGGUCUCUUCAGAGCG | 4341 | CGCUCUGAAGAGACCUUAG | | [1027-1045] 3'UTR |
| 279 | 3985 | AAGAGCCAGAGCUAGCUCU | 4342 | AGAGCUAGCUCUGGCUCUU | Chp | [960-978] 3'UTR |
| 280 | 3986 | AAGGACUGUGAACUUGUGG | 4343 | CCACAAGUUCACAGUCCUU | Chp | [937-955] 3'UTR |
| 281 | 3987 | UCCUGGAGACUAAACCUGG | 4344 | CCAGGUUUAGUCUCCAGGA | | [906-924] 3'UTR |
| 282 | 3988 | AAAAAGCAAAUUCUGGAAG | 4345 | CUUCCAGAAUUUGCUUUUU | Chp | [57-75] 5'UTR |
| 283 | 3989 | ACAUGAACCACUGCUACUC | 4346 | GAGUAGCAGUGGUUCAUGU | Rat,Ms,GP,Chn,Chp | [533-551] ORF |
| 284 | 3990 | GCAGGCUCUAUAAGUGACC | 4347 | GGUCACUUAUAGAGCCUGC | | [294-312] 5'UTR |

FIGURE 4 Continued

| | | | | | | | |
|---|---|---|---|---|---|---|---|
| 285 | 3991 | AUUCUUUGAAUCCGCGGCU | 4348 | AGCCGCGGAUUCAAAGAAU | | [149-167] 5'UTR |
| 286 | 3992 | GUGAUUUUUAAAUCCUUGC | 4349 | GCAAGGAUUUAAAAAUCAC | Chp | [89-107] 5'UTR |
| 287 | 3993 | UGCCCUGAUUUAUGAACUC | 4350 | GAGUUCAUAAAUCAGGGCA | Chp | [1134-1152] 3'UTR |
| 288 | 3994 | GACAAAAGGAGCUUUUGCC | 4351 | GGCAAAAGCUCCUUUUGUC | Chp | [742-760] ORF |
| 289 | 3995 | UGCCAGGAAAAAGCAAAUU | 4352 | AAUUUGCUUUUUCCUGGCA | Chp | [50-68] 5'UTR |
| 290 | 3996 | GAACUUGUCAUCUCCAACG | 4353 | CGUUGGAGAUGACAAGUUC | Chp | [724-742] ORF |
| 291 | 3997 | UGUUUGCAAUUUAAGCGGG | 4354 | CCCGCUUAAAUUGCAAACA | Chp | [204-222] 5'UTR |
| 292 | 3998 | UCUCCUUGGAGAAAGGUUC | 4355 | GAACCUUUCUCCAAGGAGA | Chp | [1112-1130] 3'UTR |
| 293 | 3999 | AAAUUCUGGAAGUUAAUGG | 4356 | CCAUUAACUUCCAGAAUUU | Chp | [64-82] 5'UTR |
| 294 | 4000 | ACCAAAUCCCUUCCUGGAG | 4357 | CUCCAGGAAGGGAUUUGGU | | [895-913] 3'UTR |
| 295 | 4001 | UGCAAUUUAAGCGGGCUGU | 4358 | ACAGCCCGCUUAAAUUGCA | Chp | [208-226] 5'UTR |
| 296 | 4002 | UCAUUCUUUGAAUCCGCGG | 4359 | CCGCGGAUUCAAAGAAUGA | | [147-165] 5'UTR |
| 297 | 4003 | UUCUAAGGUCUCUUCAGAG | 4360 | CUCUGAAGAGACCUUAGAA | | [1025-1043] 3'UTR |
| 298 | 4004 | CCCUUCCUGGAGACUAAAC | 4361 | GUUUAGUCUCCAGGAAGGG | | [902-920] 3'UTR |
| 299 | 4005 | UCCGGAACUUGUCAUCUCC | 4362 | GGAGAUGACAAGUUCCGGA | Chp | [720-738] ORF |
| 300 | 4006 | UUUGCAAUUUAAGCGGGCU | 4363 | AGCCCGCUUAAAUUGCAAA | Chp | [206-224] 5'UTR |
| 301 | 4007 | GAGCUUUUGCCACUGACUC | 4364 | GAGUCAGUGGCAAAAGCUC | Chp | [750-768] |
| 302 | 4008 | CAUGAACCACUGCUACUCC | 4365 | GGAGUAGCAGUGGUUCAUG | Chp | [534-552] ORF |
| 303 | 4009 | CAGGCUCUAUAAGUGACCG | 4366 | CGGUCACUUAUAGAGCCUG | | [295-313] 5'UTR |
| 304 | 4010 | CCUGUUUGCAAUUUAAGCG | 4367 | CGCUUAAAUUGCAAACAGG | Chp | [202-220] 5'UTR |
| 305 | 4011 | UUGCCCUGAUUUAUGAACU | 4368 | AGUUCAUAAAUCAGGGCAA | Chp | [1133-1151] 3'UTR |
| 306 | 4012 | GAGACUAAACCUGGUGCUC | 4369 | GAGCACCAGGUUUAGUCUC | | [911-929] 3'UTR |
| 307 | 4013 | UUCUGUAACAAUGCGAUGU | 4370 | ACAUCGCAUUGUUACAGAA | Chp | [1200-1218] 3'UTR |
| 308 | 4014 | AAGGUCUCUUCAGAGCGUG | 4371 | CACGCUCUGAAGAGACCUU | | [1029-1047] 3'UTR |
| 309 | 4015 | AAAGGAGCUUUUGCCACUG | 4372 | CAGUGGCAAAAGCUCCUUU | Chp | [746-764] ORF |
| 310 | 4016 | GACUACAUUCUCGACCUGC | 4373 | GCAGGUCGAGAAUGUAGUC | | [628-646] ORF |
| 311 | 4017 | GAGAAAGGUUCUGUUGCCC | 4374 | GGGCAACAGAACCUUUCUC | Chp | [1120-1138] 3'UTR |
| 312 | 4018 | UUCACCAAAUCCCUUCCUG | 4375 | CAGGAAGGGAUUUGGUGAA | | [892-910] 3'UTR |
| 313 | 4019 | ACUUCACCAAAUCCCUUCC | 4376 | GGAAGGGAUUUGGUGAAGU | | [890-908] 3'UTR |
| 314 | 4020 | AUUUUUAAAUCCUUGCUGG | 4377 | CCAGCAAGGAUUUAAAAAU | Chp | [92-110] 5'UTR |
| 315 | 4021 | CUUGACUUCACCAAAUCCC | 4378 | GGGAUUUGGUGAAGUCAAG | | [886-904] 3'UTR |
| 316 | 4022 | AUUUUGAAUAAAGAGGCGU | 4379 | ACGCCUCUUUAUUCAAAAU | Chp | [266-284] 5'UTR |
| 317 | 4023 | UCCUCAUUCUUUGAAUCCG | 4380 | CGGAUUCAAAGAAUGAGGA | | [144-162] 5'UTR |
| 318 | 4024 | UUACAGGAAGGUGACUUUC | 4381 | GAAAGUCACCUUCCUGUAA | Rat,Ms,Chp | [1184-1202] 3'UTR |
| 319 | 4025 | ACCUUUUUUACAGGAAGGU | 4382 | ACCUUCCUGUAAAAAAGGU | Ms,Chp | [1177-1195] 3'UTR |
| 320 | 4026 | UACAUUCUCGACCUGCAGG | 4383 | CCUGCAGGUCGAGAAUGUA | Chp | [631-649] ORF |
| 321 | 4027 | UUUUACAGGAAGGUGACUU | 4384 | AAGUCACCUUCCUGUAAAA | Rat,Ms,Chp | [1182-1200] 3'UTR |
| 322 | 4028 | AGUAUAUAGGGUUUUGUACC | 4385 | GGUACAAAACCUAUAUACU | Chp | [1161-1179] 3'UTR |
| 323 | 4029 | UCCAAACUAUGCCAAGGCG | 4386 | CGCCUUGGCAUAGUUUGGA | Chp | [1072-1090] 3'UTR |
| 324 | 4030 | GACUUCACCAAAUCCCUUC | 4387 | GAAGGGAUUUGGUGAAGUC | | [889-907] 3'UTR |
| 325 | 4031 | ACUUGACUUCACCAAAUCC | 4388 | GGAUUUGGUGAAGUCAAGU | | [885-903] 3'UTR |
| 326 | 4032 | GUUGCCCUGAUUUAUGAAC | 4389 | GUUCAUAAAUCAGGGCAAC | Chp | [1132-1150] 3'UTR |
| 327 | 4033 | AGCUUUUGCCACUGACUCG | 4390 | CGAGUCAGUGGCAAAAGCU | Chp | [751-769] |
| 328 | 4034 | UUGCUGGACGACAUGAACC | 4391 | GGUUCAUGUCGUCCAGCAA | Chp | [523-541] ORF |
| 329 | 4035 | UUUGAAUAAAGAGGCGUGC | 4392 | GCACGCCUCUUUAUUCAAA | Chp | [268-286] 5'UTR |
| 330 | 4036 | UCUAAGGUCUCUUCAGAGC | 4393 | GCUCUGAAGAGACCUUAGA | | [1026-1044] 3'UTR |
| 331 | 4037 | UUGCAAUUUAAGCGGGCUG | 4394 | CAGCCCGCUUAAAUUGCAA | Chp | [207-225] 5'UTR |
| 332 | 4038 | GUCAUCGACUACAUUCUCG | 4395 | CGAGAAUGUAGUCGAUGAC | Chp | [622-640] ORF |
| 333 | 4039 | CUGCUCUCCAAACUAUGCC | 4396 | GGCAUAGUUUGGAGAGCAG | Chp | [1066-1084] 3'UTR |
| 334 | 4040 | ACUAAACCUGGUGCUCAGG | 4397 | CCUGAGCACCAGGUUUAGU | | [914-932] 3'UTR |
| 335 | 4041 | UGGAGACUAAACCUGGUGC | 4398 | GCACCAGGUUUAGUCUCCA | | [909-927] 3'UTR |
| 336 | 4042 | AAAUCCCUUCCUGGAGACU | 4399 | AGUCUCCAGGAAGGGAUUU | | [898-916] 3'UTR |
| 337 | 4043 | UCCAACGACAAAAGGAGCU | 4400 | AGCUCCUUUUGUCGUUGGA | Chp | [736-754] ORF |
| 338 | 4044 | UAUCAGCGCUUCCUCAUUC | 4401 | GAAUGAGGAAGCGCUGAUA | Chp | [134-152] 5'UTR |
| 339 | 4045 | UUUAAAUCCUUGCUGGCGG | 4402 | CCGCCAGCAAGGAUUUAAA | Chp | [95-113] 5'UTR |
| 340 | 4046 | AUUCUCGACCUGCAGGUAG | 4403 | CUACCUGCAGGUCGAGAAU | Chp | [634-652] ORF |
| 341 | 4047 | CUCCAAACUAUGCCAAGGC | 4404 | GCCUUGGCAUAGUUUGGAG | Chp | [1071-1089] 3'UTR |
| 342 | 4048 | UUUGUACCUUUUUUACAGG | 4405 | CCUGUAAAAAAGGUACAAA | Ms,Chp | [1172-1190] 3'UTR |
| 343 | 4049 | UUCCUGGAGACUAAACCUG | 4406 | CAGGUUUAGUCUCCAGGAA | | [905-923] 3'UTR |
| 344 | 4050 | AUGAACCACUGCUACUCCC | 4407 | GGGAGUAGCAGUGGUUCAU | Chp | [535-553] ORF |
| 345 | 4051 | UUUUUAAAUCCUUGCUGGC | 4408 | GCCAGCAAGGAUUUAAAAA | | [93-111] 5'UTR |
| 346 | 4052 | AGGCUCUAUAAGUGACCGC | 4409 | GCGGUCACUUAUAGAGCCU | | [296-314] 5'UTR |

FIGURE 4 Continued

| No. | SEQ ID NO. | Sense siRNA | SEQ ID NO. | AntiSense siRNA | Other Sp | Human-17978497 ORF:466-1062 |
|---|---|---|---|---|---|---|
| 347 | 4053 | AACUUGUGGCCUGAAGAGC | 4410 | GCUCUUCAGGCCACAAGUU | Chp | [947-965] 3'UTR |
| 348 | 4054 | UUUAAGCGGGCUGUGAACG | 4411 | CGUUCACAGCCCGCUUAAA | Chp | [213-231] 5'UTR |
| 349 | 4055 | UCCUUGGAGAAAGGUUCUG | 4412 | CAGAACCUUUCUCCAAGGA | Chp | [1114-1132] 3'UTR |
| 350 | 4056 | CUUAGCCAGGUGGAAAUCC | 4413 | GGAUUUCCACCUGGCUAAG | Rat,Ms,GP,Chn,Chp | [595-613] ORF |
| 351 | 4057 | UUCUUUGAAUCCGCGGCUC | 4414 | GAGCCGCGGAUUCAAAGAA | | [150-168] 5'UTR |
| 352 | 4058 | UAAAUCCUUGCUGGCGGAG | 4415 | CUCCGCCAGCAAGGAUUUA | Chp | [97-115] 5'UTR |
| 353 | 4059 | UUUUAAAUCCUUGCUGGCG | 4416 | CGCCAGCAAGGAUUUAAAA | Chp | [94-112] 5'UTR |
| 354 | 4060 | AUAAAGAGGCGUGCCUUCC | 4417 | GGAAGGCACGCCUCUUUAU | Chp | [273-291] 5'UTR |
| 355 | 4061 | UUGAAUAAAGAGGCGUGCC | 4418 | GGCACGCCUCUUUAUUCAA | Chp | [269-287] 5'UTR |
| 356 | 4062 | AUCGACUACAUUCUCGACC | 4419 | GGUCGAGAAUGUAGUCGAU | Chp | [625-643] ORF |
| 357 | 4063 | UUCCUCAUUCUUUGAAUCC | 4420 | GGAUUCAAAGAAUGAGGAA | | [143-161] 5'UTR |

Table A6 CDKN1B - cyclin-dependent kinase inhibitor 1B (p27, Kip1)

| No. | SEQ ID NO. | Sense siRNA | SEQ ID NO. | AntiSense siRNA | Other Sp | Human-17978497 ORF:466-1062 |
|---|---|---|---|---|---|---|
| 1 | 4421 | AAACAAAAGAGCCAACAGA | 4921 | UCUGUUGGCUCUUUUGUUU | | [954-972] ORF |
| 2 | 4422 | CCGGGAGAAAGAUGUCAAA | 4922 | UUUGACAUCUUUCUCCCGG | | [455-473] 5'UTR+ORF |
| 3 | 4423 | CCAUAUUGGGCCACUAAAA | 4923 | UUUUAGUGGCCCAAUAUGG | | [20-38] 5'UTR |
| 4 | 4424 | CAAAACAAAAGAGCCAACA | 4924 | UGUUGGCUCUUUUGUUUUG | | [952-970] ORF |
| 5 | 4425 | GGUGCUUGGGAGUUUUGAA | 4925 | UUCAAAACUCCCAAGCACC | | [1792-1810] 3'UTR |
| 6 | 4426 | GGUGGACCACGAAGAGUUA | 4926 | UAACUCUUCGUGGUCCACC | | [570-588] ORF |
| 7 | 4427 | AACAAAAGAGCCAACAGAA | 4927 | UUCUGUUGGCUCUUUUGUU | | [955-973] ORF |
| 8 | 4428 | GCAUGUGGCUUUUUUAAAA | 4928 | UUUUAAAAAAGCCACAUGC | | [1658-1676] 3'UTR |
| 9 | 4429 | CCUGUAUAAGCACUGAAAA | 4929 | UUUUCAGUGCUUAUACAGG | | [1181-1199] 3'UTR |
| 10 | 4430 | CCAACAGAACAGAAGAAAA | 4930 | UUUUCUUCUGUUCUGUUGG | Rat,Ms | [965-983] ORF |
| 11 | 4431 | CGCAUUUGGUGGACCCAAA | 4931 | UUUGGGUCCACCAAAUGCG | | [848-866] ORF |
| 12 | 4432 | AAAUGAUCGUGCCUCUAAA | 4932 | UUUUAGAGGCAGAUCAUUU | | [1237-1255] 3'UTR |
| 13 | 4433 | CAUAUUGGGCCACUAAAAA | 4933 | UUUUUAGUGGCCCAAUAUG | | [21-39] 5'UTR |
| 14 | 4434 | CGAUUUCAGAAUCACAAA | 4934 | UUUGUGAUUCUGAAAAUCG | | [651-669] ORF |
| 15 | 4435 | CUGUAUAAGCACUGAAAAA | 4935 | UUUUUCAGUGCUUAUACAG | | [1182-1200] 3'UTR |
| 16 | 4436 | AAAACAAAAGAGCCAACAG | 4936 | CUGUUGGCUCUUUUGUUUU | | [953-971] ORF |
| 17 | 4437 | UGGGAGUUUUGAAUGUUAA | 4937 | UUAACAUUCAAAACUCCCA | | [1798-1816] 3'UTR |
| 18 | 4438 | CAUUGCCUGUGUAUGGAAA | 4938 | UUUCCAUACACAGGCAAUG | | [2092-2110] 3'UTR |
| 19 | 4439 | UCAAAACAAAAGAGCCAAC | 4939 | GUUGGCUCUUUUGUUUUGA | | [951-969] ORF |
| 20 | 4440 | GUGUGAAAAGAUGCCAAU | 4940 | AUUGGCAUCUUUUUCACAC | Ms | [2341-2359] 3'UTR |
| 21 | 4441 | CAUGUUUUGUGCAUUUGUA | 4941 | UACAAAUGCACAAAACAUG | Ms | [2224-2242] 3'UTR |
| 22 | 4442 | AAGUGAAAUGGAUACUACA | 4942 | UGUAGUAUCCAUUUCACUU | Ms | [2057-2075] 3'UTR |
| 23 | 4443 | CCCGGGAGAAAGAUGUCAA | 4943 | UUGACAUCUUUCUCCCGGG | | [454-472] 5'UTR+ORF |
| 24 | 4444 | CAGAAGACGUCAAACGUAA | 4944 | UUACGUUUGACGUCUUCUG | | [1044-1062] ORF |
| 25 | 4445 | CUGUGUAAACACAGUCAAA | 4945 | UUUGACUGUGUUUACACAG | | [1881-1899] 3'UTR |
| 26 | 4446 | AGUAAUUACUCAGCAGAA | 4946 | UUCUGCUGAGUAAUUAACU | | [1736-1754] 3'UTR |
| 27 | 4447 | CGUAAACAGCUCGAAUUAA | 4947 | UUAAUUCGAGCUGUUUACG | | [1058-1076] ORF+3'UTR |
| 28 | 4448 | GCCAUAUUGGGCCACUAAA | 4948 | UUUAGUGGCCCAAUAUGGC | | [19-37] 5'UTR |
| 29 | 4449 | GUAGGAUAAGUGAAAAUGGA | 4949 | UCCAUUUCACUUAUCCUAC | | [2050-2068] 3'UTR |
| 30 | 4450 | ACUUGUAGGAUAAGUGAAA | 4950 | UUUCACUUAUCCUACAAGU | | [2046-2064] 3'UTR |
| 31 | 4451 | CAAUGCGCAGGAAUAAGGA | 4951 | UCCUUAUUCCUGCGCAUUG | | [904-922] ORF |
| 32 | 4452 | GGAAUUUCGAUUUUCAGAA | 4952 | UUCUGAAAAUCGAAAUUCC | GP,Chn | [644-662] ORF |
| 33 | 4453 | CAUACUGAGCCAAGUAUAA | 4953 | UUAUACUUGGCUCAGUAUG | Ms | [2311-2329] 3'UTR |
| 34 | 4454 | UGCUGUGUUGGGUAGAAUA | 4954 | UAUUCUACCCAACACAGCA | | [2245-2263] 3'UTR |
| 35 | 4455 | CUUGGAGAAGCACUGCAGA | 4955 | UCUGCAGUGCUUCUCCAAG | GP,Chn | [597-615] ORF |
| 36 | 4456 | CGAGGUGCUUGGGAGUUUU | 4956 | AAAACUCCCAAGCACCUCG | | [1789-1807] 3'UTR |
| 37 | 4457 | CUGAAAAACAACAACACAA | 4957 | UUGUGUUGUUGUUUUUCAG | | [1193-1211] 3'UTR |
| 38 | 4458 | CCUUGUUUAUCAGAUACAU | 4958 | AUGUAUCUGAUAAACAAGG | Chn | [1087-1105] 3'UTR |
| 39 | 4459 | AUAAUUCUAAAUCCCUCGA | 4959 | UCGAGGGAUUUAGAAUUAU | | [1900-1918] 3'UTR |
| 40 | 4460 | CCUUUUGAUGUAGCACAUA | 4960 | UAUGUGCUACAUCAAAAGG | | [1330-1348] 3'UTR |
| 41 | 4461 | AGAAGACGUCAAACGUAAA | 4961 | UUUACGUUUGACGUCUUCU | | [1045-1063] ORF+3'UTR |
| 42 | 4462 | AGUGGAAUUUCGAUUUUCA | 4962 | UGAAAAUCGAAAUUCCACU | GP,Chn | [641-659] ORF |
| 43 | 4463 | GCCAAUUAUUGUUACACAU | 4963 | AUGUGUAACAAUAAUUGGC | Ms | [2354-2372] 3'UTR |
| 44 | 4464 | GCUGCAUGUGGCUUUUUUA | 4964 | UAAAAAAGCCACAUGCAGC | | [1655-1673] 3'UTR |
| 45 | 4465 | GUAUAAGCACUGAAAAACA | 4965 | UGUUUUCAGUGCUUAUAC | | [1184-1202] 3'UTR |
| 46 | 4466 | AGACAAUAUACAAGCCAAA | 4966 | UUUGGCUUGUAUAUUGUCU | Ms | [2201-2219] 3'UTR |
| 47 | 4467 | CUCUGUAAAAACACUGAAA | 4967 | UUUCAGUGUUUUUACAGAG | | [2140-2158] 3'UTR |

FIGURE 4 Continued

| | | | | | | |
|---|---|---|---|---|---|---|
| 48 | 4468 | AGAGAAAAGCACACUUGUA | 4968 | UACAAGUGUGCUUUUCUCU | | [2034-2052] 3'UTR |
| 49 | 4469 | GGAUGUAGCAUUAUGCAAU | 4969 | AUUGCAUAAUGCUACAUCC | | [1261-1279] 3'UTR |
| 50 | 4470 | UCCUGUAUAAGCACUGAAA | 4970 | UUUCAGUGCUUAUACAGGA | GP,Chn | [1180-1198] 3'UTR |
| 51 | 4471 | GCGCAAGUGGAAUUUCGAU | 4971 | AUCGAAAUUCCACUUGCGC | GP,Chn | [636-654] ORF |
| 52 | 4472 | CGCCAUAUUGGGCCACUAA | 4972 | UUAGUGGCCCAAUAUGGCG | | [18-36] 5'UTR |
| 53 | 4473 | GGGAGUUUUGAAUGUUAAG | 4973 | CUUAACAUUCAAAACUCCC | | [1799-1817] 3'UTR |
| 54 | 4474 | AGCGCAAGUGGAAUUUCGA | 4974 | UCGAAAUUCCACUUGCGCU | Rat,Ms,GP,Chn | [635-653] ORF |
| 55 | 4475 | UCAUGUAGAGAAAAGCACA | 4975 | UGUGCUUUUCUCUACAUGA | | [2028-2046] 3'UTR |
| 56 | 4476 | AAAUUUGAACACUGGCUAA | 4976 | UUAGCCAGUGUUCAAAUUU | | [1550-1568] 3'UTR |
| 57 | 4477 | CGGUUUUGUUUUUUUGAGA | 4977 | UCUCAAAAAAACAAAACCG | | [411-429] 5'UTR |
| 58 | 4478 | GAGCCAACAGAACAGAAGA | 4978 | UCUUCUGUUCUGUUGGCUC | | [962-980] ORF |
| 59 | 4479 | AGGAUAAGUGAAAUGGAUA | 4979 | UAUCCAUUUCACUUAUCCU | | [2052-2070] 3'UTR |
| 60 | 4480 | GGGUUUGAAUUGUUUUCUU | 4980 | AAGAAAACAAUUCAAACCC | | [1475-1493] 3'UTR |
| 61 | 4481 | GCUUCAUUGUACUACCUGU | 4981 | ACAGGUAGUACAAUGAAGC | Rat,GP,Chn | [1297-1315] 3'UTR |
| 62 | 4482 | GCAAUUAGGUUUUUCCUUA | 4982 | UAAGGAAAAACCUAAUUGC | Rat,GP,Chn | [1275-1293] 3'UTR |
| 63 | 4483 | AGUGGCAAGAGGUGGAGAA | 4983 | UUCUCCACCUCUUGCCACU | | [689-707] ORF |
| 64 | 4484 | GCAUACUGAGCCAAGUAUA | 4984 | UAUACUUGGCUCAGUAUGC | Ms | [2310-2328] 3'UTR |
| 65 | 4485 | UAGACAAUAUACAAGCCAA | 4985 | UUGGCUUGUAUAUUGUCUA | Ms | [2200-2218] 3'UTR |
| 66 | 4486 | UAUUGGGCCACUAAAAAAA | 4986 | UUUUUUUAGUGGCCCAAUA | | [23-41] 5'UTR |
| 67 | 4487 | AGUUUAUUCUCAUUUGGGA | 4987 | UCCCAAAUGAGAAUAAACU | | [1596-1614] 3'UTR |
| 68 | 4488 | CAUUGUACUACCUGUGUAU | 4988 | AUACACAGGUAGUACAAUG | Rat,GP,Chn | [1301-1319] 3'UTR |
| 69 | 4489 | CCUUAUUUGCUUCAUUGUA | 4989 | UACAAUGAAGCAAAUAAGG | Rat,GP,Chn | [1289-1307] 3'UTR |
| 70 | 4490 | GCUCGCCAGUCCAUUUGAU | 4990 | AUCAAAUGGACUGGCGAGC | | [234-252] 5'UTR |
| 71 | 4491 | AGUGUACCUGUGUACAUAA | 4991 | UUAUGUACACAGGUACACU | | [2121-2139] 3'UTR |
| 72 | 4492 | CCCUCGAUAUUUUAAAGA | 4992 | UCUUUAAAAAUAUCGAGGG | | [1912-1930] 3'UTR |
| 73 | 4493 | UGACCAUCUGCUUUUAUUA | 4993 | UAAUAAAAGCAGAUGGUCA | | [1821-1839] 3'UTR |
| 74 | 4494 | AUAUUGGGCCACUAAAAAA | 4994 | UUUUUUAGUGGCCCAAUAU | | [22-40] 5'UTR |
| 75 | 4495 | CUGUACAUAACUCUGUA | 4995 | UACAGAGUUAUGUACACAG | | [2128-2146] 3'UTR |
| 76 | 4496 | GAAUGUUAAGAAUUGACCA | 4996 | UGGUCAAUUCUUAACAUUC | | [1808-1826] 3'UTR |
| 77 | 4497 | AACACUGGCUAAAGAUAAU | 4997 | AUUAUCUUUAGCCAGUGUU | | [1557-1575] 3'UTR |
| 78 | 4498 | GGUUUUUCCUUAUUUGCUU | 4998 | AAGCAAAUAAGGAAAAACC | Rat,GP,Chn | [1282-1300] 3'UTR |
| 79 | 4499 | GCACUGAAAAACAACAACA | 4999 | UGUUGUUGUUUUUCAGUGC | | [1190-1208] 3'UTR |
| 80 | 4500 | GGCCUCAGAAGACGUCAAA | 5000 | UUUGACGUCUUCUGAGGCC | | [1039-1057] ORF |
| 81 | 4501 | ACAAAGAGCCAACAGAAC | 5001 | GUUCUGUUGGCUCUUUUGU | | [956-974] ORF |
| 82 | 4502 | GGGUAUGAAGAGCUUGCUU | 5002 | AAGCAAGCUCUUCAUACCC | | [1398-1416] 3'UTR |
| 83 | 4503 | AAGAGCCAACAGAACAGAA | 5003 | UUCUGUUCUGUUGGCUCUU | | [960-978] ORF |
| 84 | 4504 | GCAUGUUUUGUGCAUUUGU | 5004 | ACAAAUGCACAAAACAUGC | Ms | [2223-2241] 3'UTR |
| 85 | 4505 | CUCUGUCCAUUUAUCCACA | 5005 | UGUGGAUAAAUGGACAGAG | | [1983-2001] 3'UTR |
| 86 | 4506 | AGAUCUGUAAGUAACUUCA | 5006 | UGAAGUUACUUACAGAUCU | | [1928-1946] 3'UTR |
| 87 | 4507 | GGCUGUGUAAACACAGUCA | 5007 | UGACUGUGUUUACACAGCC | | [1879-1897] 3'UTR |
| 88 | 4508 | GAUUCUUCUACUCAAAACA | 5008 | UGUUUUGAGUAGAAGAAUC | | [940-958] ORF |
| 89 | 4509 | ACUGCAGAGACAUGGAAGA | 5009 | UCUUCCAUGUCUCUGCAGU | GP,Chn | [608-626] ORF |
| 90 | 4510 | CAGUUAAUUACUCAGCAGA | 5010 | UCUGCUGAGUAAUUAACUG | | [1735-1753] 3'UTR |
| 91 | 4511 | AGAUGUAAUGUCCCUUUCA | 5011 | UGAAAGGGACAUUACAUCU | | [1497-1515] 3'UTR |
| 92 | 4512 | GAUGUAGCAUUAUGCAAUU | 5012 | AAUUGCAUAAUGCUACAUC | | [1262-1280] 3'UTR |
| 93 | 4513 | ACUGAAAAACAACAACACA | 5013 | UGUGUUGUUGUUUUUCAGU | | [1192-1210] 3'UTR |
| 94 | 4514 | AAACGUAAACAGCUCGAAU | 5014 | AUUCGAGCUGUUUACGUUU | | [1055-1073] ORF+3'UTR |
| 95 | 4515 | ACGAUUCUUCUACUCAAAA | 5015 | UUUUGAGUAGAAGAAUCGU | | [938-956] ORF |
| 96 | 4516 | GCAACCGACGAUUCUUCUA | 5016 | UAGAAGAAUCGUCGGUUGC | | [931-949] ORF |
| 97 | 4517 | AAUGCGCAGGAAUAAGGAA | 5017 | UUCCUUAUUCCUGCGCAUU | | [905-923] ORF |
| 98 | 4518 | UGCCAAUUAUUGUUACACA | 5018 | UGUGUAACAAUAAUUGGCA | Ms | [2353-2371] 3'UTR |
| 99 | 4519 | GAUGCCAAUUAUUGUUACA | 5019 | UGUAACAAUAAUUGGCAUC | Ms | [2351-2369] 3'UTR |
| 100 | 4520 | AAGUGUACCUGUGUACAUA | 5020 | UAUGUACACAGGUACACUU | | [2120-2138] 3'UTR |
| 101 | 4521 | AUUCUAAAUCCCUCGAUAU | 5021 | AUAUCGAGGGAUUUAGAAU | | [1903-1921] 3'UTR |
| 102 | 4522 | GCUGUGUAAACACAGUCAA | 5022 | UUGACUGUGUUUACACAGC | | [1880-1898] 3'UTR |
| 103 | 4523 | CUGCAUGUGGCUUUUUUAA | 5023 | UUAAAAAAGCCACAUGCAG | | [1656-1674] 3'UTR |
| 104 | 4524 | GAGACAGCUGAUACUUCAU | 5024 | AUGAAGUAUCAGCUGUCUC | | [1516-1534] 3'UTR |
| 105 | 4525 | CAUCCUGUAUAAGCACUGA | 5025 | UCAGUGCUUAUACAGGAUG | Rat,Ms,GP,Chn | [1178-1196] 3'UTR |
| 106 | 4526 | CAGAUACAUCACUGCUUGA | 5026 | UCAAGCAGUGAUGUAUCUG | | [1097-1115] 3'UTR |
| 107 | 4527 | GGGUCUGUGUCUUUUGGCU | 5027 | AGCCAAAAGACACAGACCC | | [330-348] 5'UTR |
| 108 | 4528 | CUCAAAACAAAAGAGCCAA | 5028 | UUGGCUCUUUUGUUUUGAG | | [950-968] ORF |
| 109 | 4529 | AGCACUGCAGAGACAUGGA | 5029 | UCCAUGUCUCUGCAGUGCU | GP,Chn | [605-623] ORF |

FIGURE 4 Continued

| | | | | | | | |
|---|---|---|---|---|---|---|---|
| 110 | 4530 | AAUAAUUCUAAAUCCCUCG | 5030 | CGAGGGAUUUAGAAUUAUU | | [1899-1917] 3'UTR |
| 111 | 4531 | CGGGCUGUGUAAACACAGU | 5031 | ACUGUGUUUACACAGCCCG | | [1877-1895] 3'UTR |
| 112 | 4532 | UGGUGAUCUCCCAAGCUAU | 5032 | AUAGCUUGGGAGAUCACCA | | [1619-1637] 3'UTR |
| 113 | 4533 | AGAUCGGUGAUCUCCCAA | 5033 | UUGGGAGAUCACCAGAUCU | | [1614-1632] 3'UTR |
| 114 | 4534 | GAAGGGUUUGAAUUGUUUU | 5034 | AAAACAAUUCAAACCCUUC | | [1472-1490] 3'UTR |
| 115 | 4535 | CGUUGGAUGUAGCAUUAUG | 5035 | CAUAAUGCUACAUCCAACG | | [1257-1275] 3'UTR |
| 116 | 4536 | AAGCAAGGAAGAUAUACAU | 5036 | AUGUAUAUCUUCCUUGCUU | Ms,GP,Chn | [1118-1136] 3'UTR |
| 117 | 4537 | UGGCCUCAGAAGACGUCAA | 5037 | UUGACGUCUUCUGAGGCCA | | [1038-1056] ORF |
| 118 | 4538 | AUAAGGAAGCGACCUGCAA | 5038 | UUGCAGGUCGCUUCCUUAU | | [916-934] ORF |
| 119 | 4539 | GCUUGCCCGAGUUCUACUA | 5039 | UAGUAGAACUCGGGCAAGC | Rat,Ms | [713-731] ORF |
| 120 | 4540 | CCAUUUGAAGUGUACCUGU | 5040 | ACAGGUACACUUCAAAUGG | | [2113-2131] 3'UTR |
| 121 | 4541 | GCUUACUCUGUCCAUUUAU | 5041 | AUAAAUGGACAGAGUAAGC | | [1978-1996] 3'UTR |
| 122 | 4542 | UUGGGAGUUUUGAAUGUUA | 5042 | UAACAUUCAAAACUCCCAA | | [1797-1815] 3'UTR |
| 123 | 4543 | UGAUUUACAGCAAGUAGAU | 5043 | AUCUACUUGCUGUAAAUCA | | [1417-1435] 3'UTR |
| 124 | 4544 | CUUAAAUGAUCUGCCUCUA | 5044 | UAGAGGCAGAUCAUUUAAG | | [1234-1252] 3'UTR |
| 125 | 4545 | GCCCGAGUUCUACUACAGA | 5045 | UCUGUAGUAGAACUCGGGC | Rat,GP,Chn | [717-735] ORF |
| 126 | 4546 | GUAAAUGCUGUGUUGGGUA | 5046 | UACCCAACACAGCAUUUAC | | [2240-2258] 3'UTR |
| 127 | 4547 | CACUUGUAGGAUAAGUGAA | 5047 | UUCACUUAUCCUACAAGUG | | [2045-2063] 3'UTR |
| 128 | 4548 | UGGAUGUAGCAUUAUGCAA | 5048 | UUGCAUAAUGCUACAUCCA | | [1260-1278] 3'UTR |
| 129 | 4549 | UGGAAUUUCGAUUUUCAGA | 5049 | UCUGAAAAUCGAAAUUCCA | GP,Chn | [643-661] ORF |
| 130 | 4550 | UGUGUGAAAAAGAUGCCAA | 5050 | UUGGCAUCUUUUUCACACA | Ms | [2340-2358] 3'UTR |
| 131 | 4551 | AAUGCUGUGUUGGGUAGAA | 5051 | UUCUACCCAACACAGCAUU | | [2243-2261] 3'UTR |
| 132 | 4552 | GUAUGGAAAAACCAUUUGA | 5052 | UCAAAUGGUUUUUCCAUAC | | [2102-2120] 3'UTR |
| 133 | 4553 | CUGUGUAUGGAAAAACCAU | 5053 | AUGGUUUUUCCAUACACAG | | [2098-2116] 3'UTR |
| 134 | 4554 | UCAUUGCCUGUGUAUGGAA | 5054 | UUCCAUACACAGGCAAUGA | | [2091-2109] 3'UTR |
| 135 | 4555 | CUUGUAGGAUAAGUGAAAU | 5055 | AUUUCACUUAUCCUACAAG | | [2047-2065] 3'UTR |
| 136 | 4556 | GUUCAUGUAGAGAAAAGCA | 5056 | UGCUUUUCUCUACAUGAAC | | [2026-2044] 3'UTR |
| 137 | 4557 | CUAAAUCCCUCGAUAUUUU | 5057 | AAAAUAUCGAGGGAUUUAG | | [1906-1924] 3'UTR |
| 138 | 4558 | GUGUAAACACAGUCAAAAU | 5058 | AUUUUGACUGUGUUUACAC | | [1883-1901] 3'UTR |
| 139 | 4559 | GCUUGGGAGUUUUGAAUGU | 5059 | ACAUUCAAAACUCCCAAGC | | [1795-1813] 3'UTR |
| 140 | 4560 | GUGCUUGGGAGUUUUGAAU | 5060 | AUUCAAAACUCCCAAGCAC | | [1793-1811] 3'UTR |
| 141 | 4561 | AGGUGCUUGGGAGUUUUGA | 5061 | UCAAAACUCCCAAGCACCU | | [1791-1809] 3'UTR |
| 142 | 4562 | CGCUUUGUUUUGUUCGGUU | 5062 | AACCGAACAAAACAAAGCG | | [397-415] 5'UTR |
| 143 | 4563 | AUGAAGCAAGGAAGAUAUA | 5063 | UAUAUCUUCCUUGCUUCAU | Ms,GP,Chn | [1115-1133] 3'UTR |
| 144 | 4564 | AAAAGAGCCAACAGAACAG | 5064 | CUGUUCUGUUGGCUCUUUU | | [958-976] ORF |
| 145 | 4565 | GCAGGAAUAAGGAAGCGAC | 5065 | GUCGCUUCCUUAUUCCUGC | | [910-928] ORF |
| 146 | 4566 | GUGAAAAAGAUGCCAAUUA | 5066 | UAAUUGGCAUCUUUUUCAC | Ms | [2343-2361] 3'UTR |
| 147 | 4567 | UUCACUUCGGGCUGUGUAA | 5067 | UUACACAGCCCGAAGUGAA | | [1870-1888] 3'UTR |
| 148 | 4568 | GGAGUUUUGAAUGUUAAGA | 5068 | UCUUAACAUUCAAAACUCC | | [1800-1818] 3'UTR |
| 149 | 4569 | GAUUUACAGCAAGUAGAUA | 5069 | UAUCUACUUGCUGUAAAUC | | [1418-1436] 3'UTR |
| 150 | 4570 | AAGCACUGAAAAACAACAA | 5070 | UUGUUGUUUUUCAGUGCUU | | [1188-1206] 3'UTR |
| 151 | 4571 | CAUUUGGUGGACCCAAAGA | 5071 | UCUUUGGGUCCACCAAAUG | | [850-868] ORF |
| 152 | 4572 | AUUGCCUGUGUAUGGAAAA | 5072 | UUUUCCAUACACAGGCAAU | | [2093-2111] 3'UTR |
| 153 | 4573 | GUGGACCACGAAGAGUUAA | 5073 | UUAACUCUUCGUGGUCCAC | | [571-589] ORF |
| 154 | 4574 | AAUUGACCAUCUGCUUUUA | 5074 | UAAAAGCAGAUGGUCAAUU | | [1818-1836] 3'UTR |
| 155 | 4575 | AGUCUCUCUUAAAGUUGGA | 5075 | UCCAACUUUAAGAGAGACU | | [1710-1728] 3'UTR |
| 156 | 4576 | ACAGCUGAUACUUCAUUUA | 5076 | UAAAUGAAGUAUCAGCUGU | | [1519-1537] 3'UTR |
| 157 | 4577 | UCAAUUGUACUACCUGUGUA | 5077 | UACACAGGUAGUACAAUGA | Rat,GP,Chn | [1300-1318] 3'UTR |
| 158 | 4578 | CAUGGAAUGGACAUCCUGU | 5078 | ACAGGAUGUCCAUUCCAUG | GP,Chn | [1167-1185] 3'UTR |
| 159 | 4579 | CUUGAUGAAGCAAGGAAGA | 5079 | UCUUCCUUGCUUCAUCAAG | Chn | [1111-1129] 3'UTR |
| 160 | 4580 | GCUCGAAUUAAGAAUAUGU | 5080 | ACAUAUUCUUAAUUCGAGC | | [1066-1084] 3'UTR |
| 161 | 4581 | AAGAAGCCUGGCCUCAGAA | 5081 | UUCUGAGGCCAGGCUUCUU | | [1030-1048] ORF |
| 162 | 4582 | UGGCUAUGCUUAAAAAGGUU | 5082 | AACCUUUUAAGCAUAGCCA | | [2291-2309] 3'UTR |
| 163 | 4583 | CCUGUGUAUGGAAAAACCA | 5083 | UGGUUUUUCCAUACACAGG | | [2097-2115] 3'UTR |
| 164 | 4584 | AGUGAAAUGGAUACUACAU | 5084 | AUGUAGUAUCCAUUUCACU | Ms | [2058-2076] 3'UTR |
| 165 | 4585 | AGAUGUCAAACGUGCGAGU | 5085 | ACUCGCACGUUUGACAUCU | | [464-482] 5'UTR+ORF |
| 166 | 4586 | AAAAGCAACAGAAACCUAU | 5086 | AUAGGUUUCUGUUGCUUUU | | [1675-1693] 3'UTR |
| 167 | 4587 | UGGCUAAAGAUAAUUGCUA | 5087 | UAGCAAUUAUCUUUUAGCCA | | [1562-1580] 3'UTR |
| 168 | 4588 | CAUGAAGAGAAGCAAUUUU | 5088 | AAAAUUGCUUCUCUUCAUG | GP | [1450-1468] 3'UTR |
| 169 | 4589 | GCUUGAUGAAGCAAGGAAG | 5089 | CUUCCUUGCUUCAUCAAGC | Chn | [1110-1128] 3'UTR |
| 170 | 4590 | AGAAGAAAAUGUUUCAGAC | 5090 | GUCUGAAACAUUUUCUUCU | Rat,Ms,GP,Chn | [975-993] ORF |
| 171 | 4591 | GCCAACAGAACAGAAGAAA | 5091 | UUUCUUCUGUUCUGUUGGC | Rat,Ms | [964-982] ORF |

FIGURE 4 Continued

| | | | | | | | |
|---|---|---|---|---|---|---|---|
| 172 | 4592 | AGCCAACAGAACAGAAGAA | 5092 | UUCUUCUGUUCUGUUGGCU | | [963-981] ORF |
| 173 | 4593 | CAAAGACUGAUCCGUCGGA | 5093 | UCCGACGGAUCAGUCUUUG | | [863-881] ORF |
| 174 | 4594 | CUGAGGACACGCAUUUGGU | 5094 | ACCAAAUGCGUGUCCUCAG | | [839-857] ORF |
| 175 | 4595 | GGUUGCAUACUGAGCCAAG | 5095 | CUUGGCUCAGUAUGCAACC | Ms | [2306-2324] 3'UTR |
| 176 | 4596 | AGUUAACCCGGGACUUGGA | 5096 | UCCAAGUCCCGGGUUAACU | GP,Chn | [584-602] ORF |
| 177 | 4597 | GGAUAAGUGAAAUGGAUAC | 5097 | GUAUCCAUUUCACUUAUCC | | [2053-2071] 3'UTR |
| 178 | 4598 | AAGGUUCAUGUAGAGAAAA | 5098 | UUUUCUCUACAUGAACCUU | | [2023-2041] 3'UTR |
| 179 | 4599 | GCAAAAAUCCGAGGUGCUU | 5099 | AAGCACCUCGGAUUUUUGC | | [1780-1798] 3'UTR |
| 180 | 4600 | AAAAAGCAACAGAAACCUA | 5100 | UAGGUUUCUGUUGCUUUUU | | [1674-1692] 3'UTR |
| 181 | 4601 | CAUUUGGGAGAUCUGGUGA | 5101 | UCACCAGAUCUCCCAAAUG | | [1606-1624] 3'UTR |
| 182 | 4602 | UUGACUUGCAUGAAGAGAA | 5102 | UUCUCUUCAUGCAAGUCAA | | [1442-1460] 3'UTR |
| 183 | 4603 | UGUUUUUUGAGAGUGCGA | 5103 | UCGCACUCUCAAAAAACA | | [417-435] 5'UTR |
| 184 | 4604 | GCAUUAUGCAAUUAGGUUU | 5104 | AAACCUAAUUGCAUAAUGC | | [1268-1286] 3'UTR |
| 185 | 4605 | CCUGCAACCGACGAUUCUU | 5105 | AAGAAUCGUCGGUUGCAGG | | [928-946] ORF |
| 186 | 4606 | UGGUGGACCCAAAGACUGA | 5106 | UCAGUCUUUGGGUCCACCA | | [854-872] ORF |
| 187 | 4607 | GUGGAAUUUCGAUUUCAG | 5107 | CUGAAAAUCGAAAUUCCAC | GP,Chn | [642-660] ORF |
| 188 | 4608 | GGCUAUGCUUAAAAGGUUG | 5108 | CAACCUUUUAAGCAUAGCC | | [2292-2310] 3'UTR |
| 189 | 4609 | AAGCCAAAGUGGCAUGUUU | 5109 | AAACAUGCCACUUUGGCUU | Ms | [2212-2230] 3'UTR |
| 190 | 4610 | UUGCCUGUGUAUGGAAAAA | 5110 | UUUUUCCAUACACAGGCAA | | [2094-2112] 3'UTR |
| 191 | 4611 | UUCUAAAUCCCUCGAUAUU | 5111 | AAUAUCGAGGGAUUUAGAA | | [1904-1922] 3'UTR |
| 192 | 4612 | CCAGUUAAUUACUCAGCAG | 5112 | CUGCUGAGUAAUUAACUGG | | [1734-1752] 3'UTR |
| 193 | 4613 | AUCUCCCAAGCUAUCAAA | 5113 | UUUAGAUAGCUUGGGAGAU | | [1624-1642] 3'UTR |
| 194 | 4614 | GCGUUGGAUGUAGCAUUAU | 5114 | AUAAUGCUACAUCCAACGC | | [1256-1274] 3'UTR |
| 195 | 4615 | ACAACAACACAAUAACACU | 5115 | AGUGUUAUUGUGUUGUUGU | | [1200-1218] 3'UTR |
| 196 | 4616 | UAAGCACUGAAAAACAACA | 5116 | UGUUGUUUUUCAGUGCUUA | | [1187-1205] 3'UTR |
| 197 | 4617 | UAUCGCUGACUUCAUGGAA | 5117 | UUCCAUGAAGUCAGCGAUA | | [1155-1173] 3'UTR |
| 198 | 4618 | AGAAAAUGUUUCAGACGGU | 5118 | ACCGUCUGAAACAUUUUCU | Rat,Ms,GP,Chn | [978-996] ORF |
| 199 | 4619 | ACUCAAAACAAAAGAGCCA | 5119 | UGGCUCUUUUGUUUUGAGU | | [949-967] ORF |
| 200 | 4620 | CGAUUCUUCUACUCAAAAC | 5120 | GUUUUGAGUAGAAGAAUCG | | [939-957] ORF |
| 201 | 4621 | CUAACUCUGAGGACACGCA | 5121 | UGCGUGUCCUCAGAGUUAG | | [833-851] ORF |
| 202 | 4622 | GACUUGGAGAAGCACUGCA | 5122 | UGCAGUGCUUCUCCAAGUC | GP,Chn | [595-613] ORF |
| 203 | 4623 | UAGAGAAAAGCACACUUGU | 5123 | ACAAGUGUGCUUUUCUCUA | | [2033-2051] 3'UTR |
| 204 | 4624 | GAGAUCUGGGUGAUCUCCCA | 5124 | UGGGAGAUCACCAGAUCUC | | [1613-1631] 3'UTR |
| 205 | 4625 | GCUUUGUUUUGUUCGGUUU | 5125 | AAACCGAACAAAACAAAGC | | [398-416] 5'UTR |
| 206 | 4626 | UGGACAUCCUGUAUAAGCA | 5126 | UGCUUAUACAGGAUGUCCA | Rat,Ms,GP,Chn | [1174-1192] 3'UTR |
| 207 | 4627 | AUGGAAUGGACAUCCUGUA | 5127 | UACAGGAUGUCCAUUCCAU | GP,Chn | [1168-1186] 3'UTR |
| 208 | 4628 | CUGUGUCUUUUGGCUCCGA | 5128 | UCGGAGCCAAAAGACACAG | | [334-352] 5'UTR |
| 209 | 4629 | CAAACGUAAACAGCUCGAA | 5129 | UUCGAGCUGUUUACGUUUG | | [1054-1072] ORF+3'UTR |
| 210 | 4630 | GAAAAUGUUUCAGACGGUU | 5130 | AACCGUCUGAAACAUUUUC | Rat,Ms,GP,Chn | [979-997] ORF |
| 211 | 4631 | CAGAAGAAAAUGUUUCAGA | 5131 | UCUGAAACAUUUUCUUCUG | Rat,Ms,GP,Chn | [974-992] ORF |
| 212 | 4632 | CCGACGAUUCUUCUACUCA | 5132 | UGAGUAGAAGAAUCGUCGG | | [935-953] ORF |
| 213 | 4633 | GGUGGACCCAAAGACUGAU | 5133 | AUCAGUCUUUGGGUCCACC | | [855-873] ORF |
| 214 | 4634 | GUUGCAUACUGAGCCAAGU | 5134 | ACUUGGCUCAGUAUGCAAC | Ms | [2307-2325] 3'UTR |
| 215 | 4635 | UGGAGAAGCACUGCAGAGA | 5135 | UCUCUGCAGUGCUUCUCCA | GP,Chn | [599-617] ORF |
| 216 | 4636 | CCAUUUAUCCACAGGAAAG | 5136 | CUUUCCUGUGGAUAAAUGG | | [1989-2007] 3'UTR |
| 217 | 4637 | UCCAUUUAUCCACAGGAAA | 5137 | UUUCCUGUGGAUAAAUGGA | | [1988-2006] 3'UTR |
| 218 | 4638 | UCAGCAGAAUGGUGAUCAC | 5138 | GUGAUCACCAUUCUGCUGA | | [1746-1764] 3'UTR |
| 219 | 4639 | GUAGCAUUAUGCAAUUAGG | 5139 | CCUAAUUGCAUAAUGCUAC | | [1265-1283] 3'UTR |
| 220 | 4640 | CACUAAAAUUUUAGGCACU | 5140 | AGUGCCUAAAAUUUUAGUG | Ms,GP,Chn | [1215-1233] 3'UTR |
| 221 | 4641 | GGACAUCCUGUAUAAGCAC | 5141 | GUGCUUAUACAGGAUGUCC | Rat,Ms,GP,Chn | [1175-1193] 3'UTR |
| 222 | 4642 | AAGACUGAUCCGUCGGACA | 5142 | UGUCCGACGGAUCAGUCUU | | [865-883] ORF |
| 223 | 4643 | UCGAUUUCAGAAUCACAA | 5143 | UUGUGAUUCUGAAAAUCGA | GP,Chn | [650-668] ORF |
| 224 | 4644 | CGCAAGUGGAAUUUCGAUU | 5144 | AAUCGAAAUUCCACUUGCG | GP,Chn | [637-655] ORF |
| 225 | 4645 | AAGGAAGGUUCAUGUAGAG | 5145 | CUCUACAUGAACCUUCCUU | | [2019-2037] 3'UTR |
| 226 | 4646 | UAUCCACAGGAAAGUGUUA | 5146 | UAACACUUUCCUGUGGAUA | | [1994-2012] 3'UTR |
| 227 | 4647 | ACUUCGGGCUGUGUAAACA | 5147 | UGUUUACACAGCCCGAAGU | | [1873-1891] 3'UTR |
| 228 | 4648 | UUUUUUUGAGAGUGCGAGA | 5148 | UCUCGCACUCUCAAAAAAA | | [419-437] 5'UTR |
| 229 | 4649 | AAAAGCGUUGGAUGUAGCA | 5149 | UGCUACAUCCAACGCUUUU | | [1252-1270] 3'UTR |
| 230 | 4650 | AAGGUUGCAUACUGAGCCA | 5150 | UGGCUCAGUAUGCAACCUU | Ms | [2304-2322] 3'UTR |
| 231 | 4651 | UGUUGGGUAGAAUAGGUUU | 5151 | AAACCUAUUCUACCCAACA | | [2250-2268] 3'UTR |
| 232 | 4652 | UGUGUUGGGUAGAAUAGGU | 5152 | ACCUAUUCUACCCAACACA | | [2248-2266] 3'UTR |
| 233 | 4653 | ACGAAGAGUUAACCCGGGA | 5153 | UCCCGGGUUAACUCUUCGU | GP,Chn | [578-596] ORF |

FIGURE 4 Continued

| | | | | | | | |
|---|---|---|---|---|---|---|---|
| 234 | 4654 | ACACUUGUAGGAUAAGUGA | 5154 | UCACUUAUCCUACAAGUGU | | [2044-2062] 3'UTR |
| 235 | 4655 | UGUGUAAACACAGUCAAAA | 5155 | UUUUGACUGUGUUUACACA | | [1882-1900] 3'UTR |
| 236 | 4656 | CUCUCUUAAAGUUGGAAUU | 5156 | AAUUCCAACUUUAAGAGAG | | [1713-1731] 3'UTR |
| 237 | 4657 | CAACAGAAACCUAUCCUCA | 5157 | UGAGGAUAGGUUUCUGUUG | | [1680-1698] 3'UTR |
| 238 | 4658 | AGUUUGUUAGAUAGCUGCA | 5158 | UGCAGCUAUCUAACAAACU | | [1642-1660] 3'UTR |
| 239 | 4659 | AAAAUUUGAACACUGGCUA | 5159 | UAGCCAGUGUUCAAAUUUU | | [1549-1567] 3'UTR |
| 240 | 4660 | AAGAGCUUGCUUUGAUUUA | 5160 | UAAAUCAAAGCAAGCUCUU | | [1405-1423] 3'UTR |
| 241 | 4661 | AAGCGUUGGAUGUAGCAUU | 5161 | AAUGCUACAUCCAACGCUU | | [1254-1272] 3'UTR |
| 242 | 4662 | GUUUCCUUGUUUAUCAGAU | 5162 | AUCUGAUAAACAAGGAAAC | Chn | [1083-1101] 3'UTR |
| 243 | 4663 | GCAUUUGGUGGACCCAAAG | 5163 | CUUUGGGUCCACCAAAUGC | | [849-867] ORF |
| 244 | 4664 | CACUGCAGAGACAUGGAAG | 5164 | CUUCCAUGUCUCUGCAGUG | GP,Chn | [607-625] ORF |
| 245 | 4665 | GAAGCACUGCAGAGACAUG | 5165 | CAUGUCUCUGCAGUGCUUC | GP,Chn | [603-621] ORF |
| 246 | 4666 | GUGCAUUUGUAAAUGCUGU | 5166 | ACAGCAUUUACAAAUGCAC | Ms | [2232-2250] 3'UTR |
| 247 | 4667 | GAAGUGUACCUGUGUACAU | 5167 | AUGUACACAGGUACACUUC | | [2119-2137] 3'UTR |
| 248 | 4668 | UUUGAAGUGUACCUGUGUA | 5168 | UACACAGGUACACUUCAAA | | [2116-2134] 3'UTR |
| 249 | 4669 | UAAUUCUAAAUCCCUCGAU | 5169 | AUCGAGGGAUUUAGAAUUA | | [1901-1919] 3'UTR |
| 250 | 4670 | UGUUAAGAAUUGACCAUCU | 5170 | AGAUGGUCAAUUCUUAACA | | [1811-1829] 3'UTR |
| 251 | 4671 | CAGAAUGGUGAUCACUCCA | 5171 | UGGAGUGAUCACCAUUCUG | | [1750-1768] 3'UTR |
| 252 | 4672 | AAUUUGAACACUGGCUAAA | 5172 | UUUAGCCAGUGUUCAAAUU | | [1551-1569] 3'UTR |
| 253 | 4673 | CCCUUUCAGAGACAGCUGA | 5173 | UCAGCUGUCUCUGAAAGGG | | [1508-1526] 3'UTR |
| 254 | 4674 | AUGUAAUGUCCCUUUCAGA | 5174 | UCUGAAAGGGACAUUACAU | | [1499-1517] 3'UTR |
| 255 | 4675 | UGACUUCAUGGAAUGGACA | 5175 | UGUCCAUUCCAUGAAGUCA | | [1161-1179] 3'UTR |
| 256 | 4676 | AUCGCUGACUUCAUGGAAU | 5176 | AUUCCAUGAAGUCAGCGAU | | [1156-1174] 3'UTR |
| 257 | 4677 | GCUGUGUUGGGUAGAAUAG | 5177 | CUAUUCUACCCAACACAGC | | [2246-2264] 3'UTR |
| 258 | 4678 | GCACACUUGUAGGAUAAGU | 5178 | ACUUAUCCUACAAGUGUGC | | [2042-2060] 3'UTR |
| 259 | 4679 | UGUAGAGAAAAGCACACUU | 5179 | AAGUGUGCUUUUCUCUACA | | [2031-2049] 3'UTR |
| 260 | 4680 | AAGAAUUGACCAUCUGCUU | 5180 | AAGCAGAUGGUCAAUUCUU | | [1815-1833] 3'UTR |
| 261 | 4681 | GUCUCUCUUAAAGUUGGAA | 5181 | UUCCAACUUUAAGAGAGAC | | [1711-1729] 3'UTR |
| 262 | 4682 | CUUGCAUGAAGAGAAGCAA | 5182 | UUGCUUCUCUUCAUGCAAG | GP | [1446-1464] 3'UTR |
| 263 | 4683 | CUCUAAAAGCGUUGGAUGU | 5183 | ACAUCCAACGCUUUUAGAG | | [1248-1266] 3'UTR |
| 264 | 4684 | CAAAUGCCGGUUCUGUGGA | 5184 | UCCACAGAACCGGCAUUUG | | [1001-1019] ORF |
| 265 | 4685 | UAACUCUGAGGACACGCAU | 5185 | AUGCGUGUCCUCAGAGUUA | | [834-852] ORF |
| 266 | 4686 | CUAGAGGGCAAGUACGAGU | 5186 | ACUCGUACUUGCCCUCUAG | | [673-691] ORF |
| 267 | 4687 | UCGCCAGUCCAUUUGAUCA | 5187 | UGAUCAAAUGGACUGGCGA | | [236-254] 5'UTR |
| 268 | 4688 | CAGCGCAAGUGGAAUUUCG | 5188 | CGAAAUUCCACUUGCGCUG | Rat,Ms,GP,Chn | [634-652] ORF |
| 269 | 4689 | GUGUACAUAACUCUGUAAA | 5189 | UUUACAGAGUUAUGUACAC | | [2130-2148] 3'UTR |
| 270 | 4690 | GUGUAUGGAAAAACCAUUU | 5190 | AAAUGGUUUUUCCAUACAC | | [2100-2118] 3'UTR |
| 271 | 4691 | AACCGACGAUUCUUCUACU | 5191 | AGUAGAAGAAUCGUCGGUU | | [933-951] ORF |
| 272 | 4692 | AGUACGAGUGGCAAGAGGU | 5192 | ACCUCUUGCCACUCGUACU | | [683-701] ORF |
| 273 | 4693 | CUGAGCCAAGUAUAAUUUU | 5193 | AAAAUUAUACUUGGCUCAG | Ms | [2315-2333] 3'UTR |
| 274 | 4694 | UGGCAUGUUUUGUGCAUUU | 5194 | AAAUGCACAAAACAUGCCA | Ms | [2221-2239] 3'UTR |
| 275 | 4695 | AGUGGCAUGUUUUGUGCAU | 5195 | AUGCACAAAACAUGCCACU | Ms | [2219-2237] 3'UTR |
| 276 | 4696 | ACUCUGUAAAAACACUGAA | 5196 | UUCAGUGUUUUUACAGAGU | | [2139-2157] 3'UTR |
| 277 | 4697 | GGAUACUACAUCUUUAAAC | 5197 | GUUUAAAGAUGUAGUAUCC | Ms | [2066-2084] 3'UTR |
| 278 | 4698 | UGGUGAUCACUCCAGGUAG | 5198 | CUACCUGGAGUGAUCACCA | | [1755-1773] 3'UTR |
| 279 | 4699 | AAAGAUGUCAAACGUGCGA | 5199 | UCGCACGUUUGACAUCUUU | | [462-480] 5'UTR+ORF |
| 280 | 4700 | GGGAGAAAGAUGUCAAACG | 5200 | CGUUUGACAUCUUUCUCCC | | [457-475] 5'UTR+ORF |
| 281 | 4701 | GUUUGUUAGAUAGCUGCAU | 5201 | AUGCAGCUAUCUAACAAAC | | [1643-1661] 3'UTR |
| 282 | 4702 | CUGGCUAAAGAUAAUUGCU | 5202 | AGCAAUUAUCUUUAGCCAG | | [1561-1579] 3'UTR |
| 283 | 4703 | CCCUAAAAGCGUUGGAUG | 5203 | CAUCCAACGCUUUUAGAGG | | [1247-1265] 3'UTR |
| 284 | 4704 | CUGACUUCAUGGAAUGGAC | 5204 | GUCCAUUCCAUGAAGUCAG | | [1160-1178] 3'UTR |
| 285 | 4705 | UACAUAUCGCUGACUUCAU | 5205 | AUGAAGUCAGCGAUAUGUA | | [1151-1169] 3'UTR |
| 286 | 4706 | ACGCAUUUGGUGGACCCAA | 5206 | UUGGGUCCACCAAAUGCGU | | [847-865] ORF |
| 287 | 4707 | UAACCCGGGACUUGGAGAA | 5207 | UUCUCCAAGUCCCGGGUUA | Rat,Ms,GP,Chn | [587-605] ORF |
| 288 | 4708 | GAAAGAUGUCAAACGUGCG | 5208 | CGCACGUUUGACAUCUUUC | | [461-479] 5'UTR+ORF |
| 289 | 4709 | AGACCCGGAGAAAGAUGU | 5209 | ACAUCUUUCUCCGGGUCU | | [451-469] 5'UTR+ORF |
| 290 | 4710 | CUUUCAGAGACAGCUGAUA | 5210 | UAUCAGCUGUCUCUGAAAG | | [1510-1528] 3'UTR |
| 291 | 4711 | UUGAUUUACAGCAAGUAGA | 5211 | UCUACUUGCUGUAAAUCAA | | [1416-1434] 3'UTR |
| 292 | 4712 | UUUAGGCACUCUUAAAUGA | 5212 | UCAUUUAAGAGUGCCUAAA | GP,Chn | [1224-1242] 3'UTR |
| 293 | 4713 | AUCCUGUAUAAGCACUGAA | 5213 | UUCAGUGCUUAUACAGGAU | GP,Chn | [1179-1197] 3'UTR |
| 294 | 4714 | AAUAAGGAAGCGACUGCA | 5214 | UGCAGGUCGCUUCCUUAUU | | [915-933] ORF |
| 295 | 4715 | AGGACACGCAUUUGGUGGA | 5215 | UCCACCAAAUGCGUGUCCU | | [842-860] ORF |

FIGURE 4 Continued

| | | | | | | |
|---|---|---|---|---|---|---|
| 296 | 4716 | AACUCUGAGGACACGCAUU | 5216 | AAUGCGUGUCCUCAGAGUU | | [835-853] ORF |
| 297 | 4717 | AUAUGGCUAUGCUUAAAAG | 5217 | CUUUUAAGCAUAGCCAUAU | | [2288-2306] 3'UTR |
| 298 | 4718 | GUGUUGGGUAGAAUAGGUU | 5218 | AACCUAUUCUACCCAACAC | | [2249-2267] 3'UTR |
| 299 | 4719 | AACUCUGUAAAAACACUGA | 5219 | UCAGUGUUUUUACAGAGUU | | [2138-2156] 3'UTR |
| 300 | 4720 | AGGUUCAUGUAGAGAAAAG | 5220 | CUUUUCUCUACAUGAACCU | | [2024-2042] 3'UTR |
| 301 | 4721 | GAAUGGUGAUCACUCCAGG | 5221 | CCUGGAGUGAUCACCAUUC | | [1752-1770] 3'UTR |
| 302 | 4722 | CAGUCUCUCUUAAAGUUGG | 5222 | CCAACUUUAAGAGAGACUG | | [1709-1727] 3'UTR |
| 303 | 4723 | UGAAGAGAAGCAAUUUUGG | 5223 | CCAAAAUUGCUUCUCUUCA | | [1452-1470] 3'UTR |
| 304 | 4724 | CAGAACAGAAGAAAAUGUU | 5224 | AACAUUUUCUUCUGUUCUG | Rat,Ms,GP,Chn | [969-987] ORF |
| 305 | 4725 | CCAUUUGAUCAGCGGAGAC | 5225 | GUCUCCGCUGAUCAAAUGG | | [244-262] 5'UTR |
| 306 | 4726 | AUGCUGUGUUGGGUAGAAU | 5226 | AUUCUACCCAACACAGCAU | | [2244-2262] 3'UTR |
| 307 | 4727 | GGCAAAAAUCCGAGGUGCU | 5227 | AGCACCUCGGAUUUUUGCC | | [1779-1797] 3'UTR |
| 308 | 4728 | CUCAUUUGGGAGAUCUGGU | 5228 | ACCAGAUCUCCCAAAUGAG | | [1604-1622] 3'UTR |
| 309 | 4729 | CACAAAAAUUUGAACACUG | 5229 | CAGUGUUCAAAUUUUUGUG | | [1545-1563] 3'UTR |
| 310 | 4730 | GCUUUGAUUUACAGCAAGU | 5230 | ACUUGCUGUAAAUCAAAGC | | [1413-1431] 3'UTR |
| 311 | 4731 | ACUCUUAAAUGAUCUGCCU | 5231 | AGGCAGAUCAUUUAAGAGU | | [1231-1249] 3'UTR |
| 312 | 4732 | AGAGCCAACAGAACAGAAG | 5232 | CUUCUGUUCUGUUGGCUCU | | [961-979] ORF |
| 313 | 4733 | AAAGAGCCAACAGAACAGA | 5233 | UCUGUUCUGUUGGCUCUUU | | [959-977] ORF |
| 314 | 4734 | AGGUUGCAUACUGAGCCAA | 5234 | UUGGCUCAGUAUGCAACCU | Ms | [2305-2323] 3'UTR |
| 315 | 4735 | GCUUAAAAGGUUGCAUACU | 5235 | AGUAUGCAACCUUUUAAGC | Ms | [2298-2316] 3'UTR |
| 316 | 4736 | GUUGGGUAGAAUAGGUUUU | 5236 | AAAACCUAUUCUACCCAAC | | [2251-2269] 3'UTR |
| 317 | 4737 | AGUAUUUCAUUGCCUGUGU | 5237 | ACACAGGCAAUGAAAUACU | | [2085-2103] 3'UTR |
| 318 | 4738 | GGUUCAUGUAGAGAAAAGC | 5238 | GCUUUUCUCUACAUGAACC | | [2025-2043] 3'UTR |
| 319 | 4739 | CAUUUAUCCACAGGAAAGU | 5239 | ACUUUCCUGUGGAUAAAUG | | [1990-2008] 3'UTR |
| 320 | 4740 | UACUCUGUCCAUUUAUCCA | 5240 | UGGAUAAAUGGACAGAGUA | | [1981-1999] 3'UTR |
| 321 | 4741 | AUCUGUAAGUAACUUCACA | 5241 | UGUGAAGUUACUUACAGAU | | [1930-1948] 3'UTR |
| 322 | 4742 | AAUGGUGAUCACUCCAGGU | 5242 | ACCUGGAGUGAUCACCAUU | | [1753-1771] 3'UTR |
| 323 | 4743 | CAGCAGAAUGGUGAUCACU | 5243 | AGUGAUCACCAUUCUGCUG | | [1747-1765] 3'UTR |
| 324 | 4744 | ACCAGUUAAUUACUCAGCA | 5244 | UGCUGAGUAAUUAACUGGU | | [1733-1751] 3'UTR |
| 325 | 4745 | CGGGAGAAAGAUGUCAAAC | 5245 | GUUUGACAUCUUUCUCCCG | | [456-474] 5'UTR+ORF |
| 326 | 4746 | UGAUCUCCCAAGCUAUCUA | 5246 | UAGAUAGCUUGGGAGAUCA | | [1622-1640] 3'UTR |
| 327 | 4747 | GCUGACUUCAUGGAAUGGA | 5247 | UCCAUUCCAUGAAGUCAGC | | [1159-1177] 3'UTR |
| 328 | 4748 | GGCGCUUUGUUUUGUUCGG | 5248 | CCGAACAAAACAAAGCGCC | | [395-413] 5'UTR |
| 329 | 4749 | AGACGUCAAACGUAAACAG | 5249 | CUGUUUACGUUUGACGUCU | Chn | [1048-1066] ORF+3'UTR |
| 330 | 4750 | AGAUGCCAAUUAUUGUUAC | 5250 | GUAACAAUAAUUGGCAUCU | Ms | [2350-2368] 3'UTR |
| 331 | 4751 | AACUGUGUGUUGGGUAGA | 5251 | UCUACCCAACACAGCAUUU | | [2242-2260] 3'UTR |
| 332 | 4752 | GUGGCAUGUUUUGUGCAUU | 5252 | AAUGCACAAAACAUGCCAC | Ms | [2220-2238] 3'UTR |
| 333 | 4753 | CCAAAGUGGCAUGUUUUGU | 5253 | ACAAAACAUGCCACUUUGG | Ms | [2215-2233] 3'UTR |
| 334 | 4754 | CAUUUGAAGUGUACCUGUG | 5254 | CACAGGUACACUUCAAAUG | | [2114-2132] 3'UTR |
| 335 | 4755 | GAAAAACCAUUUGAAGUGU | 5255 | ACACUUCAAAUGGUUUUUC | | [2107-2125] 3'UTR |
| 336 | 4756 | AGGAAGGUUCAUGUAGAGA | 5256 | UCUCUACAUGAACCUUCCU | | [2020-2038] 3'UTR |
| 337 | 4757 | UCACUUCGGGCUGUGUAAA | 5257 | UUUACACAGCCCGAAGUGA | | [1871-1889] 3'UTR |
| 338 | 4758 | GAGAAAGAUGUCAAACGUG | 5258 | CACGUUUGACAUCUUUCUC | | [459-477] 5'UTR+ORF |
| 339 | 4759 | CUUUGAUUUACAGCAAGUA | 5259 | UACUUGCUGUAAAUCAAAG | | [1414-1432] 3'UTR |
| 340 | 4760 | UUGCUUUGAUUUACAGCAA | 5260 | UUGCUGUAAAUCAAAGCAA | | [1411-1429] 3'UTR |
| 341 | 4761 | CUAAAAGCGUUGGAUGUAG | 5261 | CUACAUCCAACGCUUUUAG | | [1250-1268] 3'UTR |
| 342 | 4762 | GACUUCAUGGAAUGGACAU | 5262 | AUGUCCAUUCCAUGAAGUC | | [1162-1180] 3'UTR |
| 343 | 4763 | AGAGACAUGGAAGAGGCGA | 5263 | UCGCCUCUUCCAUGUCUCU | Chn | [613-631] ORF |
| 344 | 4764 | CAAAGUGGCAUGUUUUGUG | 5264 | CACAAAACAUGCCACUUUG | Ms | [2216-2234] 3'UTR |
| 345 | 4765 | AGCCAAAGUGGCAUGUUUU | 5265 | AAAACAUGCCACUUUGGCU | Ms | [2213-2231] 3'UTR |
| 346 | 4766 | UGCAUGUGGCUUUUUUAAA | 5266 | UUUAAAAAAGCCACAUGCA | | [1657-1675] 3'UTR |
| 347 | 4767 | UCUAAAAGCGUUGGAUGUA | 5267 | UACAUCCAACGCUUUUAGA | | [1249-1267] 3'UTR |
| 348 | 4768 | GCCUCUAAAAGCGUUGGAU | 5268 | AUCCAACGCUUUUAGAGGC | | [1246-1264] 3'UTR |
| 349 | 4769 | AGGCACUCUUAAAUGAUCU | 5269 | AGAUCAUUUAAGAGUGCCU | | [1227-1245] 3'UTR |
| 350 | 4770 | GCGCUUUGUUUUGUUCGGU | 5270 | ACCGAACAAAACAAAGCGC | | [396-414] 5'UTR |
| 351 | 4771 | UACAUCACUGCUUGAUGAA | 5271 | UUCAUCAAGCAGUGAUGUA | | [1101-1119] 3'UTR |
| 352 | 4772 | AUACAUCACUGCUUGAUGA | 5272 | UCAUCAAGCAGUGAUGUAU | | [1100-1118] 3'UTR |
| 353 | 4773 | AACAGCUCGAAUUAAGAAU | 5273 | AUUCUUAAUUCGAGCUGUU | | [1062-1080] 3'UTR |
| 354 | 4774 | CGCAGGAAUAAGGAAGCGA | 5274 | UCGCUUCCUUAUUCCUGCG | | [909-927] ORF |
| 355 | 4775 | AGUCCAUUUGAUCAGCGGA | 5275 | UCCGCUGAUCAAAUGGACU | | [241-259] 5'UTR |
| 356 | 4776 | CGCCAGUCCAUUUGAUCAG | 5276 | CUGAUCAAAUGGACUGGCG | | [237-255] 5'UTR |
| 357 | 4777 | UUCGAUUUUCAGAAUCACA | 5277 | UGUGAUUCUGAAAAUCGAA | GP,Chn | [649-667] ORF |

FIGURE 4 Continued

| | | | | | | | |
|---|---|---|---|---|---|---|---|
| 358 | 4778 | AGAAGCACUGCAGAGACAU | 5278 | AUGUCUCUGCAGUGCUUCU | GP,Chn | | [602-620] ORF |
| 359 | 4779 | UUGCAUACUGAGCCAAGUA | 5279 | UACUUGGCUCAGUAUGCAA | Ms | | [2308-2326] 3'UTR |
| 360 | 4780 | CAUUUGUAAAUGCUGUGUU | 5280 | AACACAGCAUUUACAAAUG | | | [2235-2253] 3'UTR |
| 361 | 4781 | ACUUGGAGAAGCACUGCAG | 5281 | CUGCAGUGCUUCUCCAAGU | GP,Chn | | [596-614] ORF |
| 362 | 4782 | GACAAUAUACAAGCCAAAG | 5282 | CUUUGGCUUGUAUAUUGUC | Ms | | [2202-2220] 3'UTR |
| 363 | 4783 | GGAAAAACCAUUUGAAGUG | 5283 | CACUUCAAAUGGUUUUUCC | | | [2106-2124] 3'UTR |
| 364 | 4784 | UGUGUAUGGAAAAACCAUU | 5284 | AAUGGUUUUUCCAUACACA | | | [2099-2117] 3'UTR |
| 365 | 4785 | GCCUGUGUAUGGAAAAACC | 5285 | GGUUUUUCCAUACACAGGC | | | [2096-2114] 3'UTR |
| 366 | 4786 | AGAAAAGCACACUUGUAGG | 5286 | CCUACAAGUGUGCUUUUCU | | | [2036-2054] 3'UTR |
| 367 | 4787 | CACAGGAAAGUGUUAUUUU | 5287 | AAAAUAACACUUUCCUGUG | | | [1998-2016] 3'UTR |
| 368 | 4788 | UCCACAGGAAAGUGUUAUU | 5288 | AAUAACACUUUCCUGUGGA | | | [1996-2014] 3'UTR |
| 369 | 4789 | UUGACCAUCUGCUUUUAUU | 5289 | AAUAAAAGCAGAUGGUCAA | | | [1820-1838] 3'UTR |
| 370 | 4790 | CUUGGGAGUUUUGAAUGUU | 5290 | AACAUUCAAAACUCCCAAG | | | [1796-1814] 3'UTR |
| 371 | 4791 | UUUUUGAGAGUGCGAGAGA | 5291 | UCUCUCGCACUCUCAAAAA | | | [421-439] 5'UTR |
| 372 | 4792 | GAAGAGAAGCAAUUUUGGG | 5292 | CCCAAAAUUGCUUCUCUUC | | | [1453-1471] 3'UTR |
| 373 | 4793 | AGCUUGCUUUGAUUUACAG | 5293 | CUGUAAAUCAAAGCAAGCU | | | [1408-1426] 3'UTR |
| 374 | 4794 | GUUCGGUUUUGUUUUUUUG | 5294 | CAAAAAAACAAAACCGAAC | | | [408-426] 5'UTR |
| 375 | 4795 | AACGUAAACAGCUCGAAUU | 5295 | AAUUCGAGCUGUUUACGUU | | | [1056-1074] ORF+3'UTR |
| 376 | 4796 | UCAGAAGACGUCAAACGUA | 5296 | UACGUUUGACGUCUUCUGA | | | [1043-1061] ORF |
| 377 | 4797 | ACCUGCAACCGACGAUUCU | 5297 | AGAAUCGUCGGUUGCAGGU | | | [927-945] ORF |
| 378 | 4798 | AGCUUGCCCGAGUUCUACU | 5298 | AGUAGAACUCGGGCAAGCU | Rat,Ms | | [712-730] ORF |
| 379 | 4799 | UCCCUUCCACCGCCAUAUU | 5299 | AAUAUGGCGGUGGAAGGGA | Ms | | [8-26] 5'UTR |
| 380 | 4800 | UGUGAAAAAGAUGCCAAUU | 5300 | AAUUGGCAUCUUUUUCACA | Ms | | [2342-2360] 3'UTR |
| 381 | 4801 | AUGUGUGAAAAAGAUGCCA | 5301 | UGGCAUCUUUUUCACACAU | Ms | | [2339-2357] 3'UTR |
| 382 | 4802 | CUUAAAAGGUUGCAUACUG | 5302 | CAGUAUGCAACCUUUUAAG | Ms | | [2299-2317] 3'UTR |
| 383 | 4803 | UGUAAAUGCUGUGUUGGGU | 5303 | ACCCAACACAGCAUUUACA | | | [2239-2257] 3'UTR |
| 384 | 4804 | ACAAUAUACAAGCCAAAGU | 5304 | ACUUUGGCUUGUAUAUUGU | Ms | | [2203-2221] 3'UTR |
| 385 | 4805 | GAAGAGUUAACCCGGGACU | 5305 | AGUCCCGGGUUAACUCUUC | GP,Chn | | [580-598] ORF |
| 386 | 4806 | GAGGUGCUUGGGGAGUUUUG | 5306 | CAAAACUCCCAAGCACCUC | | | [1790-1808] 3'UTR |
| 387 | 4807 | GCAGAAUGGUGAUCACUCC | 5307 | GGAGUGAUCACCAUUCUGC | | | [1749-1767] 3'UTR |
| 388 | 4808 | AGCUGCAUGUGGCUUUUUU | 5308 | AAAAAAGCCACAUGCAGCU | | | [1654-1672] 3'UTR |
| 389 | 4809 | ACAAAAAUUUGAACACUGG | 5309 | CCAGUGUUCAAAUUUUUGU | | | [1546-1564] 3'UTR |
| 390 | 4810 | CCUUUCAGAGACAGCUGAU | 5310 | AUCAGCUGUCUCUGAAAGG | | | [1509-1527] 3'UTR |
| 391 | 4811 | AGAGCUUGCUUUGAUUUAC | 5311 | GUAAAUCAAAGCAAGCUCU | | | [1406-1424] 3'UTR |
| 392 | 4812 | GGUUUUGUUUUUUUGAGAG | 5312 | CUCUCAAAAAAACAAAACC | | | [412-430] 5'UTR |
| 393 | 4813 | UUGUACUACCUGUGUAUAU | 5313 | AUAUACACAGGUAGUACAA | Rat,Ms,GP,Chn | | [1303-1321] 3'UTR |
| 394 | 4814 | UGUUUUGUUCGGUUUUGUU | 5314 | AACAAAACCGAACAAAACA | | | [402-420] 5'UTR |
| 395 | 4815 | UUAGGCACUCUUAAAUGAU | 5315 | AUCAUUUAAGAGUGCCUAA | | | [1225-1243] 3'UTR |
| 396 | 4816 | GUUUAUCAGAUACAUCACU | 5316 | AGUGAUGUAAUCUGAUAAAC | | | [1091-1109] 3'UTR |
| 397 | 4817 | UCCUUGUUUAUCAGAUACA | 5317 | UGUAUCUGAUAAACAAGGA | Chn | | [1086-1104] 3'UTR |
| 398 | 4818 | CAGUCCAUUUGAUCAGCGG | 5318 | CCGCUGAUCAAAUGGACUG | | | [240-258] 5'UTR |
| 399 | 4819 | GUAAUGUGUGAAAAAGAUG | 5319 | CAUCUUUUUCACACAUUAC | Ms | | [2338-2354] 3'UTR |
| 400 | 4820 | AUGCUUAAAAGGUUGCAUA | 5320 | UAUGCAACCUUUUAAGCAU | | | [2296-2314] 3'UTR |
| 401 | 4821 | UAUACAAGCCAAAGUGGCA | 5321 | UGCCACUUUGGCUUGUAUA | Ms | | [2207-2225] 3'UTR |
| 402 | 4822 | UGAAGUGUACCUGUGUACA | 5322 | UGUACACAGGUACACUUCA | | | [2118-2136] 3'UTR |
| 403 | 4823 | CUUACUCUGUCCAUUUAUC | 5323 | GAUAAAUGGACAGAGUAAG | | | [1979-1997] 3'UTR |
| 404 | 4824 | AACCUAUCCUCACUGCCCU | 5324 | AGGGCAGUGAGGAUAGGUU | | | [1687-1705] 3'UTR |
| 405 | 4825 | GCAACAGAAACCUAUCCUC | 5325 | GAGGAUAGGUUUCUGUUGC | | | [1679-1697] 3'UTR |
| 406 | 4826 | ACCCGGGAGAAAGAUGUCA | 5326 | UGACAUCUUUCUCCCGGGU | | | [453-471] 5'UTR+ORF |
| 407 | 4827 | CAAAAAUUUGAACACUGGC | 5327 | GCCAGUGUUCAAAUUUUUG | | | [1547-1565] 3'UTR |
| 408 | 4828 | AAAGAUGUAAUGUCCCUUU | 5328 | AAAGGGACAUUACAUCUUU | | | [1495-1513] 3'UTR |
| 409 | 4829 | AUAUUUGACUUGCAUGAAG | 5329 | CUUCAUGCAAGUCAAAUAU | | | [1438-1456] 3'UTR |
| 410 | 4830 | UAUGAAGAGCUUGCUUUGA | 5330 | UCAAAGCAAGCUCUUCAUA | | | [1401-1419] 3'UTR |
| 411 | 4831 | CUAAAAUUUUAGGCACUCU | 5331 | AGAGUGCCUAAAAUUUUAG | Ms,GP,Chn | | [1217-1235] 3'UTR |
| 412 | 4832 | AGCACUGAAAAACAACAAC | 5332 | GUUGUUGUUUUUCAGUGCU | | | [1189-1207] 3'UTR |
| 413 | 4833 | UGGAAUGGACAUCCUGUAU | 5333 | AUACAGGAUGUCCAUUCCA | GP,Chn | | [1169-1187] 3'UTR |
| 414 | 4834 | CUCAGAAGACGUCAAACGU | 5334 | ACGUUUGACGUCUUCUGAG | | | [1042-1060] ORF |
| 415 | 4835 | UUGCCCGAGUUCUACUACA | 5335 | UGUAGUAGAACUCGGGCAA | Rat,Ms,GP,Chn | | [715-733] ORF |
| 416 | 4836 | UAAAGGUUGCAUACUGAG | 5336 | CUCAGUAUGCAACCUUUUA | Ms | | [2301-2319] 3'UTR |
| 417 | 4837 | AUUUGUAAAUGCUGUGUUG | 5337 | CAACACAGCAUUUACAAAU | | | [2238-2254] 3'UTR |
| 418 | 4838 | AUUUGAAGUGUACCUGUGU | 5338 | ACACAGGUACACUUCAAAU | | | [2115-2133] 3'UTR |
| 419 | 4839 | UAUUUCAUUGCCUGUGUAU | 5339 | AUACACAGGCAAUGAAAUA | | | [2087-2105] 3'UTR |

FIGURE 4 Continued

| | | | | | | | |
|---|---|---|---|---|---|---|---|
| 420 | 4840 | CUGUAAGUAACUUCACAUU | 5340 | AAUGUGAAGUUACUUACAG | | [1932-1950] 3'UTR |
| 421 | 4841 | GGUGAUCUCCCAAGCUAUC | 5341 | GAUAGCUUGGGAGAUCACC | | [1620-1638] 3'UTR |
| 422 | 4842 | CUUUAAAGAUGUAAUGUCC | 5342 | GGACAUUACAUCUUUAAAG | | [1491-1509] 3'UTR |
| 423 | 4843 | AUCACUGCUUGAUGAAGCA | 5343 | UGCUUCAUCAAGCAGUGAU | | [1104-1122] 3'UTR |
| 424 | 4844 | UGUUUAUCAGAUACAUCAC | 5344 | GUGAUGUAUCUGAUAAACA | | [1090-1108] 3'UTR |
| 425 | 4845 | CGUCAAACGUAAACAGCUC | 5345 | GAGCUGUUUACGUUUGACG | Chn | [1051-1069] ORF+3'UTR |
| 426 | 4846 | UAAGGAAGCGACCUGCAAC | 5346 | GUUGCAGGUCGCUUCCUUA | | [917-935] ORF |
| 427 | 4847 | UGCCAUUUAUCCACAGGA | 5347 | UCCUGUGGAUAAAUGGACA | | [1986-2004] 3'UTR |
| 428 | 4848 | AUUGGGCCACUAAAAAAAG | 5348 | CUUUUUUUAGUGGCCCAAU | | [24-42] 5'UTR |
| 429 | 4849 | UAAGAAUUGACCAUCUGCU | 5349 | AGCAGAUGGUCAAUUCUUA | | [1814-1832] 3'UTR |
| 430 | 4850 | GUUAGAUAGCUGCAUGUGG | 5350 | CCACAUGCAGCUAUCUAAC | | [1647-1665] 3'UTR |
| 431 | 4851 | CUCCCAAGCUAUCUAAAGU | 5351 | ACUUUAGAUAGCUUGGGAG | | [1626-1644] 3'UTR |
| 432 | 4852 | AUUUGACUUGCAUGAAGAG | 5352 | CUCUUCAUGCAAGUCAAAU | | [1440-1458] 3'UTR |
| 433 | 4853 | UACCUUUUAUGUAGCACAU | 5353 | AUGUGCUACAUAAAAGGUA | | [1328-1346] 3'UTR |
| 434 | 4854 | AUUGUACUACCUGUGUAUA | 5354 | UAUACACAGGUAGUACAAU | Rat,GP,Chn | [1302-1320] 3'UTR |
| 435 | 4855 | UAGCAUUAUGCAAUUAGGU | 5355 | ACCUAAUUGCAUAAUGCUA | | [1266-1284] 3'UTR |
| 436 | 4856 | GAUCUGCCUCUAAAAGCGU | 5356 | ACGCUUUUAGAGGCAGAUC | | [1241-1259] 3'UTR |
| 437 | 4857 | AUACAUAUCGCUGACUUCA | 5357 | UGAAGUCAGCGAUAUGUAU | | [1150-1168] 3'UTR |
| 438 | 4858 | AAAUGCCGGUUCUGUGGAG | 5358 | CUCCACAGAACCGGCAUUU | | [1002-1020] ORF |
| 439 | 4859 | ACUCUGAGGACACGCAUUU | 5359 | AAAUGCGUGUCCUCAGAGU | | [836-854] ORF |
| 440 | 4860 | CAAGUACGAGUGGCAAGAG | 5360 | CUCUUGCCACUCGUACUUG | | [681-699] ORF |
| 441 | 4861 | GAUUUUCAGAAUCACAAAC | 5361 | GUUUGUGAUUCUGAAAAUC | | [652-670] ORF |
| 442 | 4862 | UGUGUACAUAACUCGUAA | 5362 | UUACAGAGUUAUGUACACA | | [2129-2147] 3'UTR |
| 443 | 4863 | AAGAGUUAACCCGGGACUU | 5363 | AAGUCCCGGGUUAACUCUU | GP,Chn | [581-599] ORF |
| 444 | 4864 | AUGUCAAACGUGCGAGUGU | 5364 | ACACUCGCACGUUUGACAU | | [466-484] ORF |
| 445 | 4865 | GAUCACUCCAGGUAGUUUG | 5365 | CAAACUACCUGGAGUGAUC | | [1759-1777] 3'UTR |
| 446 | 4866 | AGAAAGAUGUCAAACGUGC | 5366 | GCACGUUUGACAUCUUUCU | | [460-478] 5'UTR+ORF |
| 447 | 4867 | AUAGCUGCAUGUGGCUUUU | 5367 | AAAAGCCACAUGCAGCUAU | | [1652-1670] 3'UTR |
| 448 | 4868 | UUUUGAGAGUGCGAGAGAG | 5368 | CUCUCUCGCACUCUCAAAA | | [422-440] 5'UTR |
| 449 | 4869 | GGCACUCUUAAAUGAUCUG | 5369 | CAGAUCAUUUAAGAGUGCC | | [1228-1246] 3'UTR |
| 450 | 4870 | AUAUCGCUGACUUCAUGGA | 5370 | UCCAUGAAGUCAGCGAUAU | | [1154-1172] 3'UTR |
| 451 | 4871 | AAAAAUACAUAUCGCUGAC | 5371 | GUCAGCGAUAUGUAUUUUU | | [1146-1164] 3'UTR |
| 452 | 4872 | UGCAACCGACGAUUCUUCU | 5372 | AGAAGAAUCGUCGGUUGCA | | [930-948] ORF |
| 453 | 4873 | CAGGAAUAAGGAAGCGACC | 5373 | GGUCGCUUCCUUAUUCCUG | | [911-929] ORF |
| 454 | 4874 | UACUGAGCCAAGUAUAAUU | 5374 | AAUUAUACUUGGCUCAGUA | Ms | [2313-2331] 3'UTR |
| 455 | 4875 | AAAACCAUUUGAAGUGUAC | 5375 | GUACACUUCAAAUGGUUUU | | [2109-2127] 3'UTR |
| 456 | 4876 | AAACAGUAUUUCAUUGCCU | 5376 | AGGCAAUGAAAUACUGUUU | | [2081-2099] 3'UTR |
| 457 | 4877 | UUAUCCACAGGAAAGUGUU | 5377 | AACACUUUCCUGUGGAUAA | | [1993-2011] 3'UTR |
| 458 | 4878 | UUCGGGCUGUGUAAACACA | 5378 | UGUGUUUACACAGCCCGAA | | [1875-1893] 3'UTR |
| 459 | 4879 | CAAAAAUCCGAGGUGCUUG | 5379 | CAAGCACCUCGGAUUUUUG | | [1781-1799] 3'UTR |
| 460 | 4880 | UCUCUCUUAAAGUUGGAAU | 5380 | AUUCCAACUUUAAGAGAGA | | [1712-1730] 3'UTR |
| 461 | 4881 | CUUGCUUUGAUUUACAGCA | 5381 | UGCUGUAAAUCAAAGCAAG | | [1410-1428] 3'UTR |
| 462 | 4882 | UCCUUAUUUGCUUCAUUGU | 5382 | ACAAUGAAGCAAAUAAGGA | Rat,GP,Chn | [1288-1306] 3'UTR |
| 463 | 4883 | AAAGCGUUGGAUGUAGCAU | 5383 | AUGCUACAUCCAACGCUUU | | [1253-1271] 3'UTR |
| 464 | 4884 | GACAUCCUGUAUAAGCACU | 5384 | AGUGCUUAUACAGGAUGUC | Rat,Ms,GP,Chn | [1176-1194] 3'UTR |
| 465 | 4885 | UGUGUCUUUGGCUCCGAG | 5385 | CUCGGAGCCAAAAGACACA | | [335-353] 5'UTR |
| 466 | 4886 | GAAGAAAAUGUUUCAGACG | 5386 | CGUCUGAAACAUUUUCUUC | Rat,Ms,GP,Chn | [976-994] ORF |
| 467 | 4887 | UCCAUUUGAUCAGCGGAGA | 5387 | UCUCCGCUGAUCAAAUGGA | | [243-261] 5'UTR |
| 468 | 4888 | CCCGAGUUCUACUACAGAC | 5388 | GUCUGUAGUAGAACUCGGG | Rat,GP,Chn | [718-736] ORF |
| 469 | 4889 | ACUGAGCCAAGUAUAAUUU | 5389 | AAAUUAUACUUGGCUCAGU | Ms | [2314-2332] 3'UTR |
| 470 | 4890 | ACCUGUGUACAAUACUCUG | 5390 | CAGAGUUAUGUACACAGGU | | [2126-2144] 3'UTR |
| 471 | 4891 | GUAGAGAAAAGCACACUUG | 5391 | CAAGUGUGCUUUUCUCUAC | | [2032-2050] 3'UTR |
| 472 | 4892 | UUUAAAGGAAGGUUCAUGU | 5392 | ACAUGAACCUUCCUUUAAA | | [2015-2033] 3'UTR |
| 473 | 4893 | UCUAAAUCCCUCGAUAUUU | 5393 | AAAUAUCGAGGGAUUUAGA | | [1905-1923] 3'UTR |
| 474 | 4894 | UUUCACUUCGGGCUGUGUA | 5394 | UACACAGCCCGAAGUGAAA | | [1869-1887] 3'UTR |
| 475 | 4895 | AAGUUGGAAUUUACCAGUU | 5395 | AACUGGUAAAUUCCAACUU | | [1721-1739] 3'UTR |
| 476 | 4896 | ACCUUUUAUGUAGCACAUA | 5396 | UAUGUGCUACAUAAAAGGU | | [1329-1347] 3'UTR |
| 477 | 4897 | GUUUUGUUCGGUUUUGUUU | 5397 | AAACAAAACCGAACAAAAC | | [403-421] 5'UTR |
| 478 | 4898 | AGCUCGAAUUAAGAAUAUG | 5398 | CAUAUUCUUAAUUCGAGCU | | [1065-1083] 3'UTR |
| 479 | 4899 | ACGUCAAACGUAAACAGCU | 5399 | AGCUGUUUACGUUUGACGU | Chn | [1050-1068] ORF+3'UTR |
| 480 | 4900 | CUCUGAGGACACGCAUUUG | 5400 | CAAAUGCGUGUCCUCAGAG | | [837-855] ORF |
| 481 | 4901 | GCCAAAGUGGCAUGUUUUG | 5401 | CAAAACAUGCCACUUUGGC | Ms | [2214-2232] 3'UTR |

FIGURE 4 Continued

| No. | SEQ ID NO | Sense siRNA | SEQ ID NO. | AntiSense siRNA | Other Sp | Human-47132606 ORF:213-683 | Human-98965803 ORF:213-563 | Human-47132605 ORF:38-559 |
|---|---|---|---|---|---|---|---|---|
| 482 | 4902 | UUAACCCGGGACUUGGAGA | 5402 | UCUCCAAGUCCCGGGUUAA | GP,Chn | [586-604] ORF | | |
| 483 | 4903 | UUCAUUGCCUGUGUAUGGA | 5403 | UCCAUACACAGGCAAUGAA | | [2090-2108] 3'UTR | | |
| 484 | 4904 | UGGACCACGAAGAGUUAAC | 5404 | GUUAACUCUUCGUGGUCCA | | [572-590] ORF | | |
| 485 | 4905 | AAAGUUGGAAUUUACCAGU | 5405 | ACUGGUAAAUUCCAACUUU | | [1720-1738] 3'UTR | | |
| 486 | 4906 | UUGUUAGAUAGCUGCAUGU | 5406 | ACAUGCAGCUAUCUAACAA | | [1645-1663] 3'UTR | | |
| 487 | 4907 | AAAGUUUGUUAGAUAGCUG | 5407 | CAGCUAUCUAACAAACUUU | | [1640-1658] 3'UTR | | |
| 488 | 4908 | UUGGAUGUAGCAUUAUGCA | 5408 | UGCAUAAUGCUACAUCCAA | | [1259-1277] 3'UTR | | |
| 489 | 4909 | UCAUGGAAUGGACAUCCUG | 5409 | CAGGAUGUCCAUUCCAUGA | | [1166-1184] 3'UTR | | |
| 490 | 4910 | CUUGUUUAUCAGAUACAUC | 5410 | GAUGUAUCUGAUAAACAAG | | [1088-1106] 3'UTR | | |
| 491 | 4911 | AAGACGUCAAACGUAAACA | 5411 | UGUUUACGUUUGACGUCUU | Chn | [1047-1065] ORF+3'UTR | | |
| 492 | 4912 | GAAGACGUCAAACGUAAAC | 5412 | GUUUACGUUUGACGUCUUC | Chn | [1046-1064] ORF+3'UTR | | |
| 493 | 4913 | CAACCGACGAUUCUUCUAC | 5413 | GUAGAAGAAUCGUCGGUUG | | [932-950] ORF | | |
| 494 | 4914 | AAGUACGAGUGGCAAGAGG | 5414 | CCUCUUGCCACUCGUACUU | | [682-700] ORF | | |
| 495 | 4915 | UGGAAAAACCAUUUGAAGU | 5415 | ACUUCAAAUGGUUUUUCCA | | [2105-2123] 3'UTR | | |
| 496 | 4916 | GAUAAGUGAAAUGGAUACU | 5416 | AGUAUCCAUUUCACUUAUC | | [2054-2072] 3'UTR | | |
| 497 | 4917 | AGCACACUUGUAGGAUAAG | 5417 | CUUAUCCUACAAGUGUGCU | | [2041-2059] 3'UTR | | |
| 498 | 4918 | AAACGUGCGAGUGUCUAAC | 5418 | GUUAGACACUCGCACGUUU | | [471-489] ORF | | |
| 499 | 4919 | UACUCAGCAGAAUGGUGAU | 5419 | AUCACCAUUCUGCUGAGUA | | [1743-1761] 3'UTR | | |
| 500 | 4920 | AAUGAUCUGCCUCUAAAAG | 5420 | CUUUUAGAGGCAGAUCAUU | | [1238-1256] 3'UTR | | |

Table A7 CDKN2A - cyclin-dependent kinase inhibitor 2A (melanoma, p16, inhibits CDK4)

| No. | SEQ ID NO | Sense siRNA | SEQ ID NO. | AntiSense siRNA | Other Sp | Human-47132606 ORF:213-683 | Human-98965803 ORF:213-563 | Human-47132605 ORF:38-559 |
|---|---|---|---|---|---|---|---|---|
| 1 | 5421 | CCGUAAAUGUCCAUUUAUA | 5632 | UAUAAAUGGACAUUUACGG | | [860-878] 3'UTR | [1134-1152] 3'UTR | [851-869] 3'UTR |
| 2 | 5422 | AGCAAAUGGCAGAACCAAA | 5633 | UUUGGUUCUGCCAUUUGCU | Chp | [1103-1121] 3'UTR | [1377-1395] 3'UTR | [1094-1112] 3'UTR |
| 3 | 5423 | GCCUUUUAACGUAGAUAUA | 5634 | UAUAUCUACGUUAAAAGGC | Chp | [826-844] 3'UTR | [1100-1118] 3'UTR | [817-835] 3'UTR |
| 4 | 5424 | CCCGAUUGAAAGAACCAGA | 5635 | UCUGGUUCUUUCAAUCGGG | Chp | [675-693] ORF+3'UTR | [949-967] 3'UTR | [666-684] 3'UTR |
| 5 | 5425 | CGAUUGAAAGAACCAGAGA | 5636 | UCUCUGGUUCUUUCAAUCG | Chp | [677-695] ORF+3'UTR | [951-969] 3'UTR | [668-686] 3'UTR |
| 6 | 5426 | GGGAAACUUAGAUCAUCAG | 5637 | CUGAUGAUCUAAGUUUCCC | | [712-730] 3'UTR | [986-1004] 3'UTR | [703-721] 3'UTR |
| 7 | 5427 | CUCGGGAAACUUAGAUCAU | 5638 | AUGAUCUAAGUUUCCCGAG | | [709-727] 3'UTR | [983-1001] 3'UTR | [700-718] 3'UTR |
| 8 | 5428 | AAAAUGUCCUGCCUUUUAA | 5639 | UUAAAAGGCAGGACAUUUU | | [816-834] 3'UTR | [1090-1108] 3'UTR | [807-825] 3'UTR |
| 9 | 5429 | CAGUAACCAUGCCCGCAUA | 5640 | UAUGCGGGCAUGGUUACUG | Chp | [629-647] ORF | [903-921] 3'UTR | [620-638] 3'UTR |
| 10 | 5430 | GGAAACUUAGAUCAUCAGU | 5641 | ACUGAUGAUCUAAGUUUCC | Chp | [713-731] 3'UTR | [987-1005] 3'UTR | [704-722] 3'UTR |
| 11 | 5431 | CAUUUUGUGAACUAGGGAA | 5642 | UUCCCUAGUUCACAAAAUG | Chp | [1045-1063] 3'UTR | [1319-1337] 3'UTR | [1036-1054] 3'UTR |
| 12 | 5432 | CUCUGAGAAACCUCGGGAA | 5643 | UUCCCGAGGUUUCUCAGAG | | [698-716] 3'UTR | [972-990] 3'UTR | [689-707] 3'UTR |
| 13 | 5433 | GCAUUUGUGAACUAGGGAA | 5644 | UCCCUAGUUCACAAAAUGC | Chp | [1044-1062] 3'UTR | [1318-1336] 3'UTR | [1035-1053] 3'UTR |
| 14 | 5434 | CGGAAGCUGUCGACUUCAU | 5645 | AUGAAGUCGACAGCUUCCG | Chp | [1020-1038] 3'UTR | [1294-1312] 3'UTR | [1011-1029] 3'UTR |
| 15 | 5435 | CCAGAGAGGCUCUGAGAAA | 5646 | UUUCUCAGAGCCUCUCUGG | Chp | [689-707] 3'UTR | [963-981] 3'UTR | [680-698] 3'UTR |
| 16 | 5436 | AAACCUCGGGAAACUUAGA | 5647 | UCUAAGUUUCCCGAGGUUU | | [705-723] 3'UTR | [979-997] 3'UTR | [696-714] 3'UTR |
| 17 | 5437 | GGUUACUGGCUUCUCUUGA | 5648 | UCAAGAGAAGCCAGUAACC | Chp | [1073-1091] 3'UTR | [1347-1365] 3'UTR | [1064-1082] 3'UTR |
| 18 | 5438 | CAUUCAUGUGGGCAUUUCU | 5649 | AGAAAUGCCCACAUGAAUG | | [983-1001] 3'UTR | [1257-1275] 3'UTR | [974-992] 3'UTR |
| 19 | 5439 | UGUCCUGCCUUUUAACGUA | 5650 | UACGUUAAAAGGCAGGACU | | [820-838] 3'UTR | [1094-1112] 3'UTR | [811-829] 3'UTR |
| 20 | 5440 | CCGCUUUCGUAGUUUUCAU | 5651 | AUGAAAACUACGAAAGCGG | | [778-796] 3'UTR | [1052-1070] 3'UTR | [769-787] 3'UTR |
| 21 | 5441 | CCUCGGGAAACUUAGAUCA | 5652 | UGAUCUAAGUUUCCCGAGG | | [708-726] 3'UTR | [982-1000] 3'UTR | [699-717] 3'UTR |
| 22 | 5442 | UACCGUAAAUGUCCAUUUA | 5653 | UAAAUGGACAUUUACGGUA | | [858-876] 3'UTR | [1132-1150] 3'UTR | [849-867] 3'UTR |
| 23 | 5443 | UCGACUUCAUGACAAGCAU | 5654 | AUGCUUGUCAUGAAGUCGA | | [1029-1047] 3'UTR | [1303-1321] 3'UTR | [1020-1038] 3'UTR |
| 24 | 5444 | CCUGCCUUUUAACGUAGAU | 5655 | AUCUACGUUAAAAGGCAGG | Chp | [823-841] 3'UTR | [1097-1115] 3'UTR | [814-832] 3'UTR |
| 25 | 5445 | CGACUUCAUGACAAGCAUU | 5656 | AAUGCUUGUCAUGAAGUCG | | [1030-1048] 3'UTR | [1304-1322] 3'UTR | [1021-1039] 3'UTR |
| 26 | 5446 | GAAACCUCGGGAAACUUAG | 5657 | CUAAGUUUCCCGAGGUUUC | | [704-722] 3'UTR | [978-996] 3'UTR | [695-713] 3'UTR |
| 27 | 5447 | CACCAGAGGCAGUAACCAU | 5658 | AUGGUUACUGCCUCUGGUG | Chp | [620-638] ORF | [894-912] 3'UTR | [611-629] 3'UTR |
| 28 | 5448 | GCCUUUUCACUGUGUUGGA | 5659 | UCCAACACAGUGAAAAGGC | Chp | [930-948] 3'UTR | [1204-1222] 3'UTR | [921-939] 3'UTR |
| 29 | 5449 | GCUGUCGACUUCAUGACAA | 5660 | UUGUCAUGAAGUCGACAGC | Chp | [1025-1043] 3'UTR | [1299-1317] 3'UTR | [1016-1034] 3'UTR |
| 30 | 5450 | GAAGCUGUCGACUUCAUGA | 5661 | UCAUGAAGUCGACAGCUUC | Chp | [1022-1040] 3'UTR | [1296-1314] 3'UTR | [1013-1031] 3'UTR |
| 31 | 5451 | GAGUUUUCUGGAGUGAGCA | 5662 | UGCUCACUCCAGAAAACUC | Chp | [947-965] 3'UTR | [1221-1239] 3'UTR | [938-956] 3'UTR |
| 32 | 5452 | CCACUACCGUAAAUGUCCA | 5663 | UGGACAUUUACGGUAGUGG | | [854-872] 3'UTR | [1128-1146] 3'UTR | [845-863] 3'UTR |
| 33 | 5453 | UGAGUCACACUGCUAGCAA | 5664 | UUGCUAGCAGUGUGACUCA | Chp | [1089-1107] 3'UTR | [1363-1381] 3'UTR | [1080-1098] 3'UTR |
| 34 | 5454 | CGCACAUUCAUGUGGGCAU | 5665 | AUGCCCACAUGAAUGUGCG | | [979-997] 3'UTR | [1253-1271] 3'UTR | [970-988] 3'UTR |
| 35 | 5455 | CCGAUUGAAAGAACCAGAG | 5666 | CUCUGGUUCUUUCAAUCGG | Chp | [676-694] ORF+3'UTR | [950-968] 3'UTR | [667-685] 3'UTR |
| 36 | 5456 | UAACCAUGCCCGCAUAGAU | 5667 | AUCUAUGCGGGCAUGGUUA | Chp | [632-650] ORF | [906-924] 3'UTR | [623-641] 3'UTR |

FIGURE 4 Continued

| # | ID | Sequence 1 | ID2 | Sequence 2 | Chp | Range 1 | Range 2 | Range 3 |
|---|---|---|---|---|---|---|---|---|
| 37 | 5457 | ACAAGCAUUUGUGAACUA | 5668 | UAGUUCACAAAAUGCUUGU | | [1040-1058] 3'UTR | [1314-1332] 3'UTR | [1031-1049] 3'UTR |
| 38 | 5458 | GCUUCUGCCUUUUCACUGU | 5669 | ACAGUGAAAAGGCAGAAGC | Chp | [924-942] 3'UTR | [1198-1216] 3'UTR | [915-933] 3'UTR |
| 39 | 5459 | CUAGCAAAUGGCAGAACCA | 5670 | UGGUUCUGCCAUUUGCUAG | Chp | [1101-1119] 3'UTR | [1375-1393] 3'UTR | [1092-1110] 3'UTR |
| 40 | 5460 | GGAGUUUUCUGGAGUGAGC | 5671 | GCUCACUCCAGAAAACUCC | | [946-964] 3'UTR | [1220-1238] 3'UTR | [937-955] 3'UTR |
| 41 | 5461 | CUCUUGAGUCACACUGCUA | 5672 | UAGCAGUGUGACUCAAGAG | Chp | [1085-1103] 3'UTR | [1359-1377] 3'UTR | [1076-1094] 3'UTR |
| 42 | 5462 | CAUGACAAGCAUUUUGUGA | 5673 | UCACAAAAUGCUUGUCAUG | | [1036-1054] 3'UTR | [1310-1328] 3'UTR | [1027-1045] 3'UTR |
| 43 | 5463 | AAAAAUGCCUGCCUUUUA | 5674 | UAAAAGGCAGGACAUUUUU | | [815-833] 3'UTR | [1089-1107] 3'UTR | [806-824] 3'UTR |
| 44 | 5464 | CAAGCAUUUUGUGAACUAG | 5675 | CUAGUUCACAAAAUGCUUG | | [1041-1059] 3'UTR | [1315-1333] 3'UTR | [1032-1050] 3'UTR |
| 45 | 5465 | UGUGUUGGAGUUUUCUGGA | 5676 | UCCAGAAAACUCCAACACA | Chp | [940-958] 3'UTR | [1214-1232] 3'UTR | [931-949] 3'UTR |
| 46 | 5466 | AGAUCAUCAGUCACCGAAG | 5677 | CUUCGGUGACUGAUGAUCU | Chp | [721-739] 3'UTR | [995-1013] 3'UTR | [712-730] 3'UTR |
| 47 | 5467 | AACCAGAGAGGCUCUGAGA | 5678 | UCUCAGAGCCUCUCUGGUU | Chp | [687-705] 3'UTR | [961-979] 3'UTR | [678-696] 3'UTR |
| 48 | 5468 | GCUUCUCUUGAGUCACACU | 5679 | AGUGUGACUCAAGAGAAGC | Chp | [1081-1099] 3'UTR | [1355-1373] 3'UTR | [1072-1090] 3'UTR |
| 49 | 5469 | AUGACAAGCAUUUUGUGAA | 5680 | UUCACAAAAUGCUUGUCAU | | [1037-1055] 3'UTR | [1311-1329] 3'UTR | [1028-1046] 3'UTR |
| 50 | 5470 | CGCUUUCGUAGUUUUCAUU | 5681 | AAUGAAAACUACGAAAGCG | Chp | [779-797] 3'UTR | [1053-1071] 3'UTR | [770-788] 3'UTR |
| 51 | 5471 | GAUUGAAAGAACCAGAGAG | 5682 | CUCUCUGGUUCUUUCAAUC | Chp | [678-696] ORF+3'UTR | [952-970] 3'UTR | [669-687] 3'UTR |
| 52 | 5472 | ACUGGCUUCUCUUGAGUCA | 5683 | UGACUCAAGAGAAGCCAGU | Chp | [1077-1095] 3'UTR | [1351-1369] 3'UTR | [1068-1086] 3'UTR |
| 53 | 5473 | CCCUAAGCGCACAUUCAUG | 5684 | CAUGAAUGUGCGCUUAGGG | | [972-990] 3'UTR | [1246-1264] 3'UTR | [963-981] 3'UTR |
| 54 | 5474 | CUGCCUUUUAACGUAGAUA | 5685 | UAUCUACGUUAAAAGGCAG | | [824-842] 3'UTR | [1098-1116] 3'UTR | [815-833] 3'UTR |
| 55 | 5475 | UGCCUUUUAACGUAGAUAU | 5686 | AUAUCUACGUUAAAAGGCA | Chp | [825-843] 3'UTR | [1099-1117] 3'UTR | [816-834] 3'UTR |
| 56 | 5476 | UCCUGCCUUUUAACGUAGA | 5687 | UCUACGUUAAAAGGCAGGA | | [822-840] 3'UTR | [1096-1114] 3'UTR | [813-831] 3'UTR |
| 57 | 5477 | UAGCAAAUGGCAGAACCAA | 5688 | UUGGUUCUGCCAUUUGCUA | Chp | [1102-1120] 3'UTR | [1376-1394] 3'UTR | [1093-1111] 3'UTR |
| 58 | 5478 | CACUGUGUUGGAGUUUUCU | 5689 | AGAAAACUCCAACACAGUG | Chp | [937-955] 3'UTR | [1211-1229] 3'UTR | [928-946] 3'UTR |
| 59 | 5479 | GCACAUUCAUGUGGGCAUU | 5690 | AAUGCCCACAUGAAUGUGC | | [980-998] 3'UTR | [1254-1272] 3'UTR | [971-989] 3'UTR |
| 60 | 5480 | CACUACCGUAAAUGUCCAU | 5691 | AUGGACAUUUACGGUAGUG | | [855-873] 3'UTR | [1129-1147] 3'UTR | [846-864] 3'UTR |
| 61 | 5481 | UAACGUAGAUAUAUGCCUU | 5692 | AAGGCAUAUAUCUACGUUA | Chp | [832-850] 3'UTR | [1106-1124] 3'UTR | [823-841] 3'UTR |
| 62 | 5482 | UGUGAACUAGGGAAGCUCA | 5693 | UGAGCUUCCCUAGUUCACA | Chp | [1050-1068] 3'UTR | [1324-1342] 3'UTR | [1041-1059] 3'UTR |
| 63 | 5483 | AAAAUGCCUGCCUUUUAAC | 5694 | GUUAAAAGGCAGGACAUUU | | [817-835] 3'UTR | [1091-1109] 3'UTR | [808-826] 3'UTR |
| 64 | 5484 | UGACAAGCAUUUUGUGAAC | 5695 | GUUCACAAAAUGCUUGUCA | | [1038-1056] 3'UTR | [1312-1330] 3'UTR | [1029-1047] 3'UTR |
| 65 | 5485 | CUGCGACUUCACACAAG | 5696 | CUUGUCAUGAAGUCGACAG | | [1026-1044] 3'UTR | [1300-1318] 3'UTR | [1017-1035] 3'UTR |
| 66 | 5486 | CCUAAGCGCACAUUCAUGU | 5697 | ACAUGAAUGUGCGCUUAGG | | [973-991] 3'UTR | [1247-1265] 3'UTR | [964-982] 3'UTR |
| 67 | 5487 | ACUGCUAGCAAAUGGCAGA | 5698 | UCUGCCAUUUGCUAGCAGU | Chp | [1097-1115] 3'UTR | [1371-1389] 3'UTR | [1088-1106] 3'UTR |
| 68 | 5488 | GGGUUACUGGCUUCUCUUG | 5699 | CAAGAGAAGCCAGUAACCC | Chp | [1072-1090] 3'UTR | [1346-1364] 3'UTR | [1063-1081] 3'UTR |
| 69 | 5489 | ACCAGAGAGGCUCUGAGAA | 5700 | UUCUCAGAGCCUCUCUGGU | Chp | [688-706] 3'UTR | [962-980] 3'UTR | [679-697] 3'UTR |
| 70 | 5490 | AGCUGUCGACUUCAUGACA | 5701 | UGUCAUGAAGUCGACAGCU | Chp | [1024-1042] 3'UTR | [1298-1316] 3'UTR | [1015-1033] 3'UTR |
| 71 | 5491 | CCGCUUCUGCCUUUUCACU | 5702 | AGUGAAAAGGCAGAAGCGG | Chp | [922-940] 3'UTR | [1196-1214] 3'UTR | [913-931] 3'UTR |
| 72 | 5492 | CUACCGUAAAUGUCCAUUU | 5703 | AAAUGGACAUUUACGGUAG | | [857-875] 3'UTR | [1131-1149] 3'UTR | [848-866] 3'UTR |
| 73 | 5493 | UUAAAAUGCCUGCCUUU | 5704 | AAAGGCAGGACAUUUUUAA | | [813-831] 3'UTR | [1087-1105] 3'UTR | [804-822] 3'UTR |
| 74 | 5494 | GAGCUUUUAAAAAUGCCU | 5705 | AGGACAUUUUUAAAAGCUC | | [807-825] 3'UTR | [1081-1099] 3'UTR | [798-816] 3'UTR |
| 75 | 5495 | GGAAGCUGUCGACUUCAUG | 5706 | CAUGAAGUCGACAGCUUCC | Chp | [1021-1039] 3'UTR | [1295-1313] 3'UTR | [1012-1030] 3'UTR |
| 76 | 5496 | UGUUGGAGUUUUCUGGAGU | 5707 | ACUCCAGAAAACUCCAACA | Chp | [942-960] 3'UTR | [1216-1234] 3'UTR | [933-951] 3'UTR |
| 77 | 5497 | AAAGAAAAACACCGCUUCU | 5708 | AGAAGCGGUGUUUUUCUUU | Chp | [911-929] 3'UTR | [1185-1203] 3'UTR | [902-920] 3'UTR |
| 78 | 5498 | GAUCAUCAGUCACCGAAGG | 5709 | CCUUCGGUGACUGAUGAUC | Chp | [722-740] 3'UTR | [996-1014] 3'UTR | [713-731] 3'UTR |
| 79 | 5499 | UCUCUUGAGUCACACUGCU | 5710 | AGCAGUGUGACUCAAGAGA | Chp | [1084-1102] 3'UTR | [1358-1376] 3'UTR | [1075-1093] 3'UTR |
| 80 | 5500 | CCCGCUUUCGUAGUUUUCA | 5711 | UGAAAACUACGAAAGCGGG | Chp | [777-795] 3'UTR | [1051-1069] 3'UTR | [768-786] 3'UTR |
| 81 | 5501 | CUGCUAGCAAAUGGCAGAA | 5712 | UUCUGCCAUUUGCUAGCAG | Chp | [1098-1116] 3'UTR | [1372-1390] 3'UTR | [1089-1107] 3'UTR |
| 82 | 5502 | GGCUUCUCUUGAGUCACAC | 5713 | GUGUGACUCAAGAGAAGCC | Chp | [1080-1098] 3'UTR | [1354-1372] 3'UTR | [1071-1089] 3'UTR |
| 83 | 5503 | UAGAUCAUCAGUCACCGAA | 5714 | UUCGGUGACUGAUGAUCUA | Chp | [720-738] 3'UTR | [994-1012] 3'UTR | [711-729] 3'UTR |
| 84 | 5504 | AGCACACUGCUAGCAAAU | 5715 | AUUUGCUAGCAGUGUGCU | Chp | [1091-1109] 3'UTR | [1365-1383] 3'UTR | [1082-1100] 3'UTR |
| 85 | 5505 | UCAUGACAAGCAUUUUGUG | 5716 | CACAAAAUGCUUGUCAUGA | | [1035-1053] 3'UTR | [1309-1327] 3'UTR | [1026-1044] 3'UTR |
| 86 | 5506 | AUUCAUGUGGGCAUUUCUU | 5717 | AAGAAAUGCCCACAUGAAU | | [984-1002] 3'UTR | [1258-1276] 3'UTR | [975-993] 3'UTR |
| 87 | 5507 | GUUGGAGUUUUCUGGAGUG | 5718 | CACUCCAGAAAACUCCAAC | Chp | [943-961] 3'UTR | [1217-1235] 3'UTR | [934-952] 3'UTR |
| 88 | 5508 | CUGUGUUGGAGUUUUCUGG | 5719 | CCAGAAAACUCCAACACAG | Chp | [939-957] 3'UTR | [1213-1231] 3'UTR | [930-948] 3'UTR |
| 89 | 5509 | AGUCACCGAAGGUCCUACA | 5720 | UGUAGGACCUUCGGUGACU | Chp | [729-747] 3'UTR | [1003-1021] 3'UTR | [720-738] 3'UTR |
| 90 | 5510 | UCUUGAGUCACACUGCUAG | 5721 | CUAGCAGUGUGACUCAAGA | Chp | [1086-1104] 3'UTR | [1360-1378] 3'UTR | [1077-1095] 3'UTR |
| 91 | 5511 | UUAGAUCAUCAGUCACCGA | 5722 | UCGGUGACUGAUGAUCUAA | Chp | [719-737] 3'UTR | [993-1011] 3'UTR | [710-728] 3'UTR |
| 92 | 5512 | GAAACUUAGAUCAUCAGUC | 5723 | GACUGAUGAUCUAAGUUUC | Chp | [714-732] 3'UTR | [988-1006] 3'UTR | [705-723] 3'UTR |
| 93 | 5513 | GUGUUGGAGUUUUCUGGAG | 5724 | CUCCAGAAAACUCCAACAC | Chp | [941-959] 3'UTR | [1215-1233] 3'UTR | [932-950] 3'UTR |

FIGURE 4 Continued

| | | | | | | | | |
|---|---|---|---|---|---|---|---|---|
| 94 | 5514 | UUUUCACUGUGUUGGAGUU | 5725 | AACUCCAACACAGUGAAAA | Chp | [933-951] 3'UTR | [1207-1225] 3'UTR | [924-942] 3'UTR |
| 95 | 5515 | ACCGUAAAUGUCCAUUUAU | 5726 | AUAAAAUGGACAUUUACGGU | | [859-877] 3'UTR | [1133-1151] 3'UTR | [850-868] 3'UTR |
| 96 | 5516 | GUAACCAUGCCCGCAUAGA | 5727 | UCUAUGCGGGCAUGGUUAC | Chp | [631-649] ORF | [905-923] 3'UTR | [622-640] 3'UTR |
| 97 | 5517 | AAAAAAGAAAAACACCGCU | 5728 | AGCGGUGUUUUUCUUUUUU | Chp | [908-926] 3'UTR | [1182-1200] 3'UTR | [899-917] 3'UTR |
| 98 | 5518 | AGCAUUUUGUGAACUAGGG | 5729 | CCCUAGUUCACAAAAUGCU | | [1043-1061] 3'UTR | [1317-1335] 3'UTR | [1034-1052] 3'UTR |
| 99 | 5519 | UGGAGUUUUCUGGAGUGAG | 5730 | CUCACUCCAGAAAACUCCA | Chp | [945-963] 3'UTR | [1219-1237] 3'UTR | [936-954] 3'UTR |
| 100 | 5520 | UAAAAAUGUCCUGCCUUUU | 5731 | AAAAGGCAGGACAUUUUUA | | [814-832] 3'UTR | [1088-1106] 3'UTR | [805-823] 3'UTR |
| 101 | 5521 | CUGAGAAACCUCGGGAAAC | 5732 | GUUUCCCGAGGUUUCUCAG | | [700-718] 3'UTR | [974-992] 3'UTR | [691-709] 3'UTR |
| 102 | 5522 | GAGAGGCUCUGAGAAACCU | 5733 | AGGUUUCUCAGAGCCUCUC | | [692-710] 3'UTR | [966-984] 3'UTR | [683-701] 3'UTR |
| 103 | 5523 | ACCAGAGGCAGUAACCAUG | 5734 | CAUGGUUACUGCCUCUGGU | Chp | [621-639] ORF | [895-913] 3'UTR | [612-630] 3'UTR |
| 104 | 5524 | ACACUGCUAGCAAAUGGCA | 5735 | UGCCAUUUGCUAGCAGUGU | Chp | [1095-1113] 3'UTR | [1369-1387] 3'UTR | [1086-1104] 3'UTR |
| 105 | 5525 | CUUUUCACUGUGUUGGAGU | 5736 | ACUCCAACACAGUGAAAAG | Chp | [932-950] 3'UTR | [1206-1224] 3'UTR | [923-941] 3'UTR |
| 106 | 5526 | ACCGCUUCUGCCUUUUCAC | 5737 | GUGAAAAGGCAGAAGCGGU | Chp | [921-939] 3'UTR | [1195-1213] 3'UTR | [912-930] 3'UTR |
| 107 | 5527 | CUUGAGUCACACUGCUAGC | 5738 | GCUAGCAGUGUGACUCAAG | Chp | [1087-1105] 3'UTR | [1361-1379] 3'UTR | [1078-1096] 3'UTR |
| 108 | 5528 | GUGAACUAGGGAAGCUCAG | 5739 | CUGAGCUUCCCUAGUUCAC | Chp | [1051-1069] 3'UTR | [1325-1343] 3'UTR | [1042-1060] 3'UTR |
| 109 | 5529 | AUGUGGGCAUUUCUUGCGA | 5740 | UCGCAAGAAAUGCCCACAU | | [988-1006] 3'UTR | [1262-1280] 3'UTR | [979-997] 3'UTR |
| 110 | 5530 | UUGGAGUUUUCUGGAGUGA | 5741 | UCACUCCAGAAAACUCCAA | Chp | [944-962] 3'UTR | [1218-1236] 3'UTR | [935-953] 3'UTR |
| 111 | 5531 | UCACUGUGUUGGAGUUUUC | 5742 | GAAAACUCCAACACAGUGA | Chp | [936-954] 3'UTR | [1210-1228] 3'UTR | [927-945] 3'UTR |
| 112 | 5532 | AAAAAGAAAAACACCGCUU | 5743 | AAGCGGUGUUUUUCUUUUU | Chp | [909-927] 3'UTR | [1183-1201] 3'UTR | [900-918] 3'UTR |
| 113 | 5533 | CGUAGAUAUAUGCCUUCCC | 5744 | GGGAAGGCAUAUAUCUACG | Chp | [835-853] 3'UTR | [1109-1127] 3'UTR | [826-844] 3'UTR |
| 114 | 5534 | AGAACCAGAGAGGCUCUGA | 5745 | UCAGAGCCUCUCUGGUUCU | Chp | [685-703] 3'UTR | [959-977] 3'UTR | [676-694] 3'UTR |
| 115 | 5535 | CACUGCUAGCAAAUGGCAG | 5746 | CUGCCAUUUGCUAGCAGUG | Chp | [1096-1114] 3'UTR | [1370-1388] 3'UTR | [1087-1105] 3'UTR |
| 116 | 5536 | AAGCAUUUUGUGAACUAGG | 5747 | CCUAGUUCACAAAAUGCUU | | [1042-1060] 3'UTR | [1316-1334] 3'UTR | [1033-1051] 3'UTR |
| 117 | 5537 | UUUUAAAAAUGUCCUGCCU | 5748 | AGGCAGGACAUUUUUAAAA | | [811-829] 3'UTR | [1085-1103] 3'UTR | [802-820] 3'UTR |
| 118 | 5538 | CAGAGAGGCUCUGAGAAAC | 5749 | GUUUCUCAGAGCCUCUCUG | Chp | [690-708] 3'UTR | [964-982] 3'UTR | [681-699] 3'UTR |
| 119 | 5539 | AUUUCUUGCGAGCCUCGCA | 5750 | UGCGAGGCUCGCAAGAAAU | | [996-1014] 3'UTR | [1270-1288] 3'UTR | [987-1005] 3'UTR |
| 120 | 5540 | CCUUUUCACUGUGUUGGAG | 5751 | CUCCAACACAGUGAAAAGG | Chp | [931-949] 3'UTR | [1205-1223] 3'UTR | [922-940] 3'UTR |
| 121 | 5541 | GUCCUGCCUUUUAACGUAG | 5752 | CUACGUUAAAAGGCAGGAC | | [821-839] 3'UTR | [1095-1113] 3'UTR | [812-830] 3'UTR |
| 122 | 5542 | AUCAGUCACCGAAGGUCCU | 5753 | AGGACCUUCGGUGACUGAU | Chp | [726-744] 3'UTR | [1000-1018] 3'UTR | [717-735] 3'UTR |
| 123 | 5543 | AACCUCGGGAAACUUUAGAU | 5754 | AUCUAAGUUUCCCGAGGUU | | [706-724] 3'UTR | [980-998] 3'UTR | [697-715] 3'UTR |
| 124 | 5544 | AACCAUGCCCGCAUAGAUG | 5755 | CAUCUAUGCGGGCAUGGUU | Chp | [633-651] ORF | [907-925] 3'UTR | [624-642] 3'UTR |
| 125 | 5545 | AGCUUUUAAAAAUGUCCUG | 5756 | CAGGACAUUUUUAAAAGCU | | [808-826] 3'UTR | [1082-1100] 3'UTR | [799-817] 3'UTR |
| 126 | 5546 | CUGGCUUCUCUUGAGUCAC | 5757 | GUGACUCAAGAGAAGCCAG | Chp | [1078-1096] 3'UTR | [1352-1370] 3'UTR | [1069-1087] 3'UTR |
| 127 | 5547 | AAAACACCGCUUCUGCCUU | 5758 | AAGGCAGAAGCGGUGUUUU | Chp | [916-934] 3'UTR | [1190-1208] 3'UTR | [907-925] 3'UTR |
| 128 | 5548 | CAAAUGGCAGAACCAAAGC | 5759 | GCUUUGGUUCUGCCAUUUG | Chp | [1105-1123] 3'UTR | [1379-1397] 3'UTR | [1096-1114] 3'UTR |
| 129 | 5549 | UCUGCCUUUUCACUGUGUU | 5760 | AACACAGUGAAAAGGCAGA | Chp | [927-945] 3'UTR | [1201-1219] 3'UTR | [918-936] 3'UTR |
| 130 | 5550 | CCCACUACCGUAAAUGUCC | 5761 | GGACAUUUACGGUAGUGGG | | [853-871] 3'UTR | [1127-1145] 3'UTR | [844-862] 3'UTR |
| 131 | 5551 | GCUUUCGUAGUUUUCAUUU | 5762 | AAAUGAAAACUACGAAAGC | Chp | [780-798] 3'UTR | [1054-1072] 3'UTR | [771-789] 3'UTR |
| 132 | 5552 | AAAGAACCAGAGAGGCUCU | 5763 | AGAGCCUCUCUGGUUCUUU | Chp | [683-701] 3'UTR | [957-975] 3'UTR | [674-692] 3'UTR |
| 133 | 5553 | GCUAGCAAAUGGCAGAACC | 5764 | GGUUCUGCCAUUUGCUAGC | Chp | [1100-1118] 3'UTR | [1374-1392] 3'UTR | [1091-1109] 3'UTR |
| 134 | 5554 | CUGCCUUUUCACUGUGUUG | 5765 | CAACACAGUGAAAAGGCAG | Chp | [928-946] 3'UTR | [1202-1220] 3'UTR | [919-937] 3'UTR |
| 135 | 5555 | AAAAGAAAAACACCGCUUC | 5766 | GAAGCGGUGUUUUUCUUUU | Chp | [910-928] 3'UTR | [1184-1202] 3'UTR | [901-919] 3'UTR |
| 136 | 5556 | GACAAGCAUUUUGUGAACU | 5767 | AGUUCACAAAAUGCUUGUC | | [1039-1057] 3'UTR | [1313-1331] 3'UTR | [1030-1048] 3'UTR |
| 137 | 5557 | UUUAAAAAUGUCCUGCCUU | 5768 | AAGGCAGGACAUUUUUAAA | | [812-830] 3'UTR | [1086-1104] 3'UTR | [803-821] 3'UTR |
| 138 | 5558 | UCAGUCACCGAAGGUCCUA | 5769 | UAGGACCUUCGGUGACUGA | Chp | [727-745] 3'UTR | [1001-1019] 3'UTR | [718-736] 3'UTR |
| 139 | 5559 | UGAAAGAACCAGAGAGGCU | 5770 | AGCCUCUCUGGUUCUUUCA | Chp | [681-699] ORF+3'UTR | [955-973] 3'UTR | [672-690] 3'UTR |
| 140 | 5560 | UGUGGGCAUUUCUUGCGAG | 5771 | CUCGCAAGAAAUGCCCACA | | [989-1007] 3'UTR | [1263-1281] 3'UTR | [980-998] 3'UTR |
| 141 | 5561 | AGAGCUUUUAAAAAUGUCC | 5772 | GGACAUUUUAAAAGCUCU | | [806-824] 3'UTR | [1080-1098] 3'UTR | [797-815] 3'UTR |
| 142 | 5562 | GUUUCUGGAGUGAGCACU | 5773 | AGUGCUCACUCCAGAAAAC | | [949-967] 3'UTR | [1223-1241] 3'UTR | [940-958] 3'UTR |
| 143 | 5563 | AACACCGCUUCUGCCUUUU | 5774 | AAAAGGCAGAAGCGGUGUU | | [918-936] 3'UTR | [1192-1210] 3'UTR | [909-927] 3'UTR |
| 144 | 5564 | GAAAAACACCGCUUCUGCC | 5775 | GGCAGAAGCGGUGUUUUUC | Chp | [914-932] 3'UTR | [1188-1206] 3'UTR | [905-923] 3'UTR |
| 145 | 5565 | AUGUCCUGCCUUUUAACGU | 5776 | ACGUUAAAAGGCAGGACAU | | [819-837] 3'UTR | [1093-1111] 3'UTR | [810-828] 3'UTR |
| 146 | 5566 | AUUUUGUGAACUAGGGAAG | 5777 | CUUCCCUAGUUCACAAAAU | Chp | [1046-1064] 3'UTR | [1320-1338] 3'UTR | [1037-1055] 3'UTR |
| 147 | 5567 | GUCGACUUCAUGACAAGCA | 5778 | UGCUUGUCAUGAAGUCGAC | | [1028-1046] 3'UTR | [1302-1320] 3'UTR | [1019-1037] 3'UTR |
| 148 | 5568 | ACUGUGUUGGAGUUUUCUG | 5779 | CAGAAAACUCCAACACAGU | Chp | [938-956] 3'UTR | [1212-1230] 3'UTR | [929-947] 3'UTR |
| 149 | 5569 | UUCACUGUGUUGGAGUUUU | 5780 | AAAACUCCAACACAGUGAA | Chp | [935-953] 3'UTR | [1209-1227] 3'UTR | [926-944] 3'UTR |
| 150 | 5570 | UUGAGUCACACUGCUAGCA | 5781 | UGCUAGCAGUGUGACUCAA | Chp | [1088-1106] 3'UTR | [1362-1380] 3'UTR | [1079-1097] 3'UTR |

FIGURE 4 Continued

| | | | | | | | | |
|---|---|---|---|---|---|---|---|---|
| 151 | 5571 | ACUUCAUGACAAGCAUUUU | 5782 | AAAAUGCUUGUCAUGAAGU | | [1032-1050] 3'UTR | [1306-1324] 3'UTR | [1023-1041] 3'UTR |
| 152 | 5572 | GUAAAAAAGAAAAACACCG | 5783 | CGGUGUUUUUCUUUUUAC | Chp | [906-924] 3'UTR | [1180-1198] 3'UTR | [897-915] 3'UTR |
| 153 | 5573 | GAAAGAACCAGAGAGGCUC | 5784 | GAGCCUCUCUGGUUCUUUC | Chp | [682-700] ORF+3'UTR | [956-974] 3'UTR | [673-691] 3'UTR |
| 154 | 5574 | UUCAUGACAAGCAUUUUGU | 5785 | ACAAAAUGCUUGUCAUGAA | | [1034-1052] 3'UTR | [1308-1326] 3'UTR | [1025-1043] 3'UTR |
| 155 | 5575 | CUUCAUGACAAGCAUUUUG | 5786 | CAAAAUGCUUGUCAUGAAG | | [1033-1051] 3'UTR | [1307-1325] 3'UTR | [1024-1042] 3'UTR |
| 156 | 5576 | UUUCUGGAGUGAGCACUCA | 5787 | UGAGUGCUCACUCCAGAAA | Chp | [951-969] 3'UTR | [1225-1243] 3'UTR | [942-960] 3'UTR |
| 157 | 5577 | CUUCUGCCUUUUCACUGUG | 5788 | CACAGUGAAAAGGCAGAAG | Chp | [925-943] 3'UTR | [1199-1217] 3'UTR | [916-934] 3'UTR |
| 158 | 5578 | ACCUCGGGAAACUUAGAUC | 5789 | GAUCUAAGUUUCCCGAGGU | | [707-725] 3'UTR | [981-999] 3'UTR | [698-716] 3'UTR |
| 159 | 5579 | AGAAAAACACCGCUUCUGC | 5790 | GCAGAAGCGGUGUUUUUCU | Chp | [913-931] 3'UTR | [1187-1205] 3'UTR | [904-922] 3'UTR |
| 160 | 5580 | UUAACGUAGAUAUAUGCCU | 5791 | AGGCAUAUAUCUACGUUAA | Chp | [831-849] 3'UTR | [1105-1123] 3'UTR | [822-840] 3'UTR |
| 161 | 5581 | CUUAGAUCAUCAGUCACCG | 5792 | CGGUGACUGAUGAUCUAAG | Chp | [718-736] 3'UTR | [992-1010] 3'UTR | [709-727] 3'UTR |
| 162 | 5582 | AGAGGCUCUGAGAAACCUC | 5793 | GAGGUUUCUCAGAGCCUCU | Chp | [693-711] 3'UTR | [967-985] 3'UTR | [684-702] 3'UTR |
| 163 | 5583 | CACACUGCUAGCAAAUGGC | 5794 | GCCAUUUGCUAGCAGUGUG | Chp | [1094-1112] 3'UTR | [1368-1386] 3'UTR | [1085-1103] 3'UTR |
| 164 | 5584 | CACAUUCAUGUGGGCAUUU | 5795 | AAAUGCCCACAUGAAUGUG | | [981-999] 3'UTR | [1255-1273] 3'UTR | [972-990] 3'UTR |
| 165 | 5585 | AAGCGCACAUUCAUGUGGG | 5796 | CCCACAUGAAUGUGCGCUU | | [976-994] 3'UTR | [1250-1268] 3'UTR | [967-985] 3'UTR |
| 166 | 5586 | AAAAACACCGCUUCUGCCU | 5797 | AGGCAGAAGCGGUGUUUUU | Chp | [915-933] 3'UTR | [1189-1207] 3'UTR | [906-924] 3'UTR |
| 167 | 5587 | AGUUUCUGGAGUGAGCAC | 5798 | GUGCUCACUCCAGAAACU | Chp | [948-966] 3'UTR | [1222-1240] 3'UTR | [939-957] 3'UTR |
| 168 | 5588 | UUCUGCCUUUUCACUGUGU | 5799 | ACACAGUGAAAAGGCAGAA | Chp | [926-944] 3'UTR | [1200-1218] 3'UTR | [917-935] 3'UTR |
| 169 | 5589 | CUUUUAAAAAUGUCCUGCC | 5800 | GGCAGGACAUUUUUAAAAG | | [810-828] 3'UTR | [1084-1102] 3'UTR | [801-819] 3'UTR |
| 170 | 5590 | AAAUGGCAGAACCAAAGCU | 5801 | AGCUUUGGUUCUGCCAUUU | Chp | [1106-1124] 3'UTR | [1380-1398] 3'UTR | [1097-1115] 3'UTR |
| 171 | 5591 | CGCUUCUGCCUUUUCACUG | 5802 | CAGUGAAAAGGCAGAAGCG | Chp | [923-941] 3'UTR | [1197-1215] 3'UTR | [914-932] 3'UTR |
| 172 | 5592 | AGUAACCAUGCCCGCAUAG | 5803 | CUAUGCGGGCAUGGUUACU | Chp | [630-648] ORF | [904-922] 3'UTR | [621-639] 3'UTR |
| 173 | 5593 | UCAUGUGGGCAUUUCUUGC | 5804 | GCAAGAAAUGCCCACAUGA | | [986-1004] 3'UTR | [1260-1278] 3'UTR | [977-995] 3'UTR |
| 174 | 5594 | ACUACCGUAAAUGUCCAUU | 5805 | AAUGGACAUUUACGGUAGU | | [856-874] 3'UTR | [1130-1148] 3'UTR | [847-865] 3'UTR |
| 175 | 5595 | ACAUUCAUGUGGGCAUUUC | 5806 | GAAAUGCCCACAUGAAUGU | | [982-1000] 3'UTR | [1256-1274] 3'UTR | [973-991] 3'UTR |
| 176 | 5596 | CUUCUCUUGAGUCACACUG | 5807 | CAGUGUGACUCAAGAGAAG | Chp | [1082-1100] 3'UTR | [1356-1374] 3'UTR | [1073-1091] 3'UTR |
| 177 | 5597 | CUAAGCGCACAUUCAUGUG | 5808 | CACAUGAAUGUGCGCUUAG | | [974-992] 3'UTR | [1248-1266] 3'UTR | [965-983] 3'UTR |
| 178 | 5598 | ACACCGCUUCUGCCUUUUC | 5809 | GAAAAGGCAGAAGCGGUGU | Chp | [919-937] 3'UTR | [1193-1211] 3'UTR | [910-928] 3'UTR |
| 179 | 5599 | GCUUUUAAAAAUGUCCUGC | 5810 | GCAGGACAUUUUUAAAAGC | | [809-827] 3'UTR | [1083-1101] 3'UTR | [800-818] 3'UTR |
| 180 | 5600 | UCAUCAGUCACCGAAGGUC | 5811 | GACCUUCGGUGACUGAUGA | Chp | [724-742] 3'UTR | [998-1016] 3'UTR | [715-733] 3'UTR |
| 181 | 5601 | UGAACUAGGGAAGCUCAGG | 5812 | CCUGAGCUUCCCUAGUUCA | Chp | [1052-1070] 3'UTR | [1326-1344] 3'UTR | [1043-1061] 3'UTR |
| 182 | 5602 | UUCAUGUGGGCAUUUCUUG | 5813 | CAAGAAAUGCCCACAUGAA | | [985-1003] 3'UTR | [1259-1277] 3'UTR | [976-994] 3'UTR |
| 183 | 5603 | AACGUAGAUAUAUGCCUUC | 5814 | GAAGGCAUAUAUCUACGUU | Chp | [833-851] 3'UTR | [1107-1125] 3'UTR | [824-842] 3'UTR |
| 184 | 5604 | AGAGAGGCUCUGAGAAACC | 5815 | GGUUUCUCAGAGCCUCUCU | Chp | [691-709] 3'UTR | [965-983] 3'UTR | [682-700] 3'UTR |
| 185 | 5605 | AUCAUCAGUCACCGAAGGU | 5816 | ACCUUCGGUGACUGAUGAU | Chp | [723-741] 3'UTR | [997-1015] 3'UTR | [714-732] 3'UTR |
| 186 | 5606 | UUUGUGAACUAGGGAAGCU | 5817 | AGCUUCCCUAGUUCACAAA | Chp | [1048-1066] 3'UTR | [1322-1340] 3'UTR | [1039-1057] 3'UTR |
| 187 | 5607 | UUCUGGAGUGAGCACUCAC | 5818 | GUGAGUGCUCACUCCAGAA | Chp | [952-970] 3'UTR | [1226-1244] 3'UTR | [943-961] 3'UTR |
| 188 | 5608 | AACUUAGAUCAUCAGUCAC | 5819 | GUGACUGAUGAUCUAAGUU | Chp | [716-734] 3'UTR | [990-1008] 3'UTR | [707-725] 3'UTR |
| 189 | 5609 | UUCUCUUGAGUCACACUGC | 5820 | GCAGUGUGACUCAAGAGAA | Chp | [1083-1101] 3'UTR | [1357-1375] 3'UTR | [1074-1092] 3'UTR |
| 190 | 5610 | UUUUGUGAACUAGGGAAGC | 5821 | GCUUCCCUAGUUCACAAAA | Chp | [1047-1065] 3'UTR | [1321-1339] 3'UTR | [1038-1056] 3'UTR |
| 191 | 5611 | AUUGAAAGAACCAGAGAGG | 5822 | CCUCUCUGGUUCUUUCAAU | Chp | [679-697] ORF+3'UTR | [953-971] 3'UTR | [670-688] 3'UTR |
| 192 | 5612 | AAGCUGUCGACUUCAUGAC | 5823 | GUCAUGAAGUCGACAGCUU | Chp | [1023-1041] 3'UTR | [1297-1315] 3'UTR | [1014-1032] 3'UTR |
| 193 | 5613 | UAAAAAAGAAAAACACCGC | 5824 | GCGGUGUUUUUCUUUUUUA | Chp | [907-925] 3'UTR | [1181-1199] 3'UTR | [898-916] 3'UTR |
| 194 | 5614 | UACUGGCUUCUCUUGAGUC | 5825 | GACUCAAGAGAAGCCAGUA | Chp | [1076-1094] 3'UTR | [1350-1368] 3'UTR | [1067-1085] 3'UTR |
| 195 | 5615 | ACGUAGAUAUAUGCCUUCC | 5826 | GGAAGGCAUAUAUCUACGU | Chp | [834-852] 3'UTR | [1108-1126] 3'UTR | [825-843] 3'UTR |
| 196 | 5616 | UUUCACUGUGUUGGAGUUU | 5827 | AAACUCCAACACAGUGAAA | Chp | [934-952] 3'UTR | [1208-1226] 3'UTR | [925-943] 3'UTR |
| 197 | 5617 | AAUGUCCUGCCUUUUAACG | 5828 | CGUUAAAAGGCAGGACAUU | | [818-836] 3'UTR | [1092-1110] 3'UTR | [809-827] 3'UTR |
| 198 | 5618 | UUUUCUGGAGUGAGCACUC | 5829 | GAGUGCUCACUCCAGAAAA | Chp | [950-968] 3'UTR | [1224-1242] 3'UTR | [941-959] 3'UTR |
| 199 | 5619 | UGUCGACUUCAUGACAAGC | 5830 | GCUUGUCAUGAAGUCGACA | | [1027-1045] 3'UTR | [1301-1319] 3'UTR | [1018-1036] 3'UTR |
| 200 | 5620 | CAUGUGGGCAUUUCUUGCG | 5831 | CGCAAGAAAUGCCCACAUG | | [987-1005] 3'UTR | [1261-1279] 3'UTR | [978-996] 3'UTR |
| 201 | 5621 | AAGAAAAACACCGCUUCUG | 5832 | CAGAAGCGGUGUUUUUCUU | Chp | [912-930] 3'UTR | [1186-1204] 3'UTR | [903-921] 3'UTR |
| 202 | 5622 | UUUGUGAACUAGGGAAGCUC | 5833 | GAGCUUCCCUAGUUCACAA | Chp | [1049-1067] 3'UTR | [1323-1341] 3'UTR | [1040-1058] 3'UTR |
| 203 | 5623 | UGCUAGCAAAUGGCAGAAC | 5834 | GUUCUGCCAUUUGCUAGCA | Chp | [1099-1117] 3'UTR | [1373-1391] 3'UTR | [1090-1108] 3'UTR |
| 204 | 5624 | ACUUAGAUCAUCAGUCACC | 5835 | GGUGACUGAUGAUCUAAGU | Chp | [717-735] 3'UTR | [991-1009] 3'UTR | [708-726] 3'UTR |
| 205 | 5625 | GUCACACUGCUAGCAAAUG | 5836 | CAUUUGCUAGCAGUGUGAC | Chp | [1092-1110] 3'UTR | [1366-1384] 3'UTR | [1083-1101] 3'UTR |
| 206 | 5626 | AAUGGCAGAACCAAAGCUC | 5837 | GAGCUUUGGUUCUGCCAUU | Chp | [1107-1125] 3'UTR | [1381-1399] 3'UTR | [1098-1116] 3'UTR |
| 207 | 5627 | AAGAACCAGAGAGGCUCUG | 5838 | CAGAGCCUCUCUGGUUCUU | Chp | [684-702] 3'UTR | [958-976] 3'UTR | [675-693] 3'UTR |

FIGURE 4 Continued

| | | | | | | | | |
|---|---|---|---|---|---|---|---|---|
| 208 | 5628 | UUGAAAGAACCAGAGAGGC | 5839 | GCCUCUCUGGUUCUUUCAA | Chp | [680-698] ORF+3'UTR | [954-972] 3'UTR | [671-689] 3'UTR |
| 209 | 5629 | UGCCUUUUCACUGUGUUGG | 5840 | CCAACACAGUGAAAAGGCA | Chp | [929-947] 3'UTR | [1203-1221] 3'UTR | [920-938] 3'UTR |
| 210 | 5630 | UAAGCGCACAUUCAUGUGG | 5841 | CCACAUGAAUGUGCGCUUA | | [975-993] 3'UTR | [1249-1267] 3'UTR | [966-984] 3'UTR |
| 211 | 5631 | UUUAACGUAGAUAUAUGCC | 5842 | GGCAUAUAUCUACGUUAAA | Chp | [830-848] 3'UTR | [1104-1122] 3'UTR | [821-839] 3'UTR |

COMPOSITIONS AND METHODS FOR TREATMENT OF EAR DISORDERS

This application is a divisional of U.S. Ser. No. 12,994,725, filed Feb. 25, 2011, §371 national stage of PCT International Application No. PCT/IL2009/000570, filed Jun. 7, 2009, which claims the benefit of U.S. Provisional Application No. 61/131,162, filed Jun. 6, 2008, the contents of each of which are hereby incorporated by reference into this application.

This application incorporates-by-reference nucleotide and/or amino acid sequences which are present in the file named "130422_2094_79459 AZ_PCT_US_SubstituteSequenceListing_LC.txt" which is 1.14 megabytes in size, and which was created Apr. 17, 2013, and which is contained in the text file filed Apr. 22, 2013.

FIELD OF THE INVENTION

The present invention relates to otic compositions and methods for delivery of an oligonucleotide compound, including siRNA, to the middle and inner ear useful in the treatment of an ear disorder, including hearing loss resulting from chemical-induced ototoxicity, acoustic trauma and presbycusis; tumors and microbial infections.

BACKGROUND OF THE INVENTION

The Human Ear

The ear is comprised of three major structural components: the outer, middle, and inner ears, which function together to convert sound waves into nerve impulses that travel to the brain, where they are perceived as sound. The inner ear also helps to maintain balance.

The anatomy of the middle and the inner ear is well known to those of ordinary skill in the art (see, e.g., *Atlas of Sensory Organs: Functional and Clinical Analysis*, Andrs Csillag, Humana Press (2005), pages 1-82, incorporated herein by reference). In brief, the middle ear consists of the eardrum and a small air-filled chamber containing a sequence of three tiny bones known as the ossicles, which link the eardrum to the inner ear.

The inner ear (labyrinth) is a complex structure consisting of the cochlea, which is the organ of hearing and the vestibular system, the organ of balance. The vestibular system consists of the saccule and the utricle, which determine position sense, and the semicircular canals, which help maintain balance.

The cochlea houses the organ of Corti, which consists, in part, of about 20,000 specialized sensory cells, called "inner ear hair cells" or "hair cells". These cells have small hairline projections (cilia) that extend into the cochlear fluid. Sound vibrations transmitted from the ossicles in the middle ear to the oval window in the inner ear cause the fluid and cilia to vibrate. Hair cells in different parts of the cochlea vibrate in response to different sound frequencies and convert the vibrations into nerve impulses which are sent to the brain for processing and interpretation. The inner ear hair cells are surrounded by inner ear support cells. Supporting cells underlie, at least partially surround, and physically support sensory hair cells within the inner ear. Representative examples of support cells include inner rod (pillar cells), outer rod (pillar cells), inner phalangeal cells, outer phalangeal cells (of Deiters), cells of Held, cells of Hensen, cells of Claudius, cells of Boettcher, interdental cells and auditory teeth (of Huschke).

The spiral ganglion is the group of nerve cells that send a representation of sound from the cochlea to the brain. The cell bodies of the spiral ganglion neurons are found in the spiral structure of the cochlea and are part of the central nervous system. Their dendrites make synaptic contact with the base of hair cells, and their axons are bundled together to form the auditory portion of the eighth cranial nerve (vestibulocochlear nerve).

Hearing Loss

Despite the protective effect of the acoustic reflex, loud noise can damage and destroy hair cells. Irreversible hair cell death is elicited by metabolic or biochemical changes in the hair cells that involve reactive oxygen species (ROS). Exposure to certain drugs and continued exposure to loud noise, inter alia, cause progressive damage, eventually resulting in ringing in the ears (tinnitus) and or hearing loss.

Acquired hearing loss can be caused by several factors including exposure to harmful noise levels, exposure to ototoxic drugs such as cisplatin and aminoglycoside antibiotics and aging.

International Patent Publication No. WO 2008/050329 to the assignee of the present invention relates to siRNA compounds, compositions comprising same and to methods of use thereof for treating diseases and disorders related to expression of proapoptotic genes. U.S. Ser. No. 11/655,610 to the assignee of the present invention relates to methods of treating hearing impairment by inhibiting a pro-apoptotic gene in general and p53 in particular. International Patent Publication No. WO 2005/119251 relates to methods of treating deafness. International Patent Publication No. WO/2005/055921 relates to foam compositions for treatment of ear disorders. U.S. Pat. No. 7,087,581 relates to methods of treating diseases and disorders of the inner ear.

There remains a genuine need for easy to use, high compliance pharmaceutical therapies, which effect, inter alia, otoprotection, chemoprotection and hearing regeneration.

SUMMARY OF THE INVENTION

The present invention provides pharmaceutical compositions and methods useful in treating an ear disorder, including middle ear and inner ear disorders. The present invention overcomes certain of the limitations in the prior art by providing a non-invasive method of treating an ear disorder comprising topically administering an oligonucleotide to a target gene, wherein the inhibitory oligonucleotide is formulated for topical, non-invasive application. This method is surprising in view of the size of an oligonucleotide and in view of the use of transtympanic injection for delivery of oligonucleotides heretofore. This method also overcomes the limitations associated with use of oral therapeutics, which are often associated with adverse systemic side effects.

According to one aspect, the present invention provides a method of treating a subject suffering from or at risk of an ear disorder which comprises topically administering to the canal of the subject's ear a pharmaceutical composition comprising an oligonucleotide inhibitor, a permeability enhancer and a pharmaceutically acceptable excipient or mixtures thereof, thereby reducing expression of a gene associated with the disorder in the ear of the subject in an amount effective to treat the subject.

In various embodiments the permeability enhancer is a polyol. In some embodiments the oligonucleotide is in admixture with a polyol. In some embodiments the polyol is selected from glycerol, propylene glycol, polyethylene glycol, sorbitol, xylitol, or maltitol. According to one embodiment the polyol is glycerol. In various embodiments glycerol is present at a final concentration of about 0.1% to about 35%;

about 1% to about 30%; about 5% to about 25%, preferably about 10% to about 20%. In some embodiments the final concentration of glycerol in the pharmaceutical composition is about 2.5%, 5%, 10%, 12.5%, 15%, 17.5%, 20%, 22.5%, 25%, 27.5 A or about 30%. In one preferred embodiment, the final concentration of glycerol in the pharmaceutical composition is about 10%. In some embodiments the pharmaceutical composition is brought to the subject's body temperature, which is about 35° C.-38° C., prior to application to the ear.

In some embodiments, the pharmaceutical composition is applied to the ear canal when the subject's head is tilted to one side and the treated ear is facing upward. In some embodiments, the pharmaceutical composition is applied to the ear using a receptacle for eardrops, for example using a dropper of for example, 10-100 microliter per drop, or a wick.

In some embodiments an ear disorder relates to chemical-induced hearing loss; for example hearing loss induced by inter alia cisplatin and its analogs; aminoglycoside antibiotics, quinine and its analogs; salicylate and its analogs; phosphodiesterase type 5 (PDE5) inhibitors or loop-diuretics. In some embodiments the ear disorder refers to noise-induced hearing loss. In other embodiments the ear disorder is age related hearing loss.

In various embodiments the pharmaceutical composition is formulated as eardrops, ear cream, ear ointment, ear foam or mousse. In certain preferred embodiments the pharmaceutical composition is formulated as eardrops. In some embodiments the method comprising unilateral administration of an oligonucleotide to a subject's ear.

In some embodiments the oligonucleotide is an inhibitory nucleic acid compound selected from the group consisting of an antisense, a siRNA, a shRNA, an aptamer, a ribozyme, a dsRNA or DNA compound. In various preferred embodiment the oligonucleotide is siRNA.

In another embodiment the oligonucleotide comprises a sufficient number of consecutive nucleotides having a sequence of sufficient homology to a nucleic acid sequence present within a target gene to reduce or inhibit expression of the gene in the subject. In certain embodiments the siRNA is chemically synthesized and chemically modified. The modifications comprise base modifications, sugar modifications, internucleotide linkage modifications or combinations thereof.

In one embodiment the method and composition for the present invention utilize a siRNA compound having the following structure:

5' $(N)_x$-Z 3' (antisense strand)
3' Z'-$(N')_y$-z" 5' (sense strand)

wherein each of N and N' is a ribonucleotide which may be unmodified or modified, or an unconventional moiety;
wherein each of $(N)_x$ and $(N')_y$ is an oligonucleotide in which each consecutive N or N' is joined to the next N or N' by a covalent bond;
wherein Z and Z' may be present or absent, but if present is independently 1-5 consecutive nucleotides covalently attached at the 3' terminus of the strand in which it is present;
wherein z" may be present or absent, but if present is a capping moiety covalently attached at the 5' terminus of (N') y;
wherein each of x and y is independently an integer between 18 and 40;
wherein the sequence of $(N')_y$ is substantially complementary to the sequence of $(N)_x$; and wherein $(N)_x$ comprises an antisense sequence $(N)_x$ comprises an antisense sequence substantially complementary to from about 18 to about 40 consecutive ribonucleotides in an mRNA of a target gene associated with an ear disorder.

In various embodiments $(N)_x$ comprises 2'-O-methyl (2'OMe) modified and unmodified ribonucleotides, wherein N at the 3' terminus of $(N)_x$ is a 2'OMe modified ribonucleotide, $(N)_x$ comprises at least five alternating 2'OMe modified ribonucleotides beginning at the 3' end and at least nine 2'OMe modified ribonucleotides in total and each remaining N is an unmodified ribonucleotide and $(N')_y$ comprises at least one mirror nucleotide, or a nucleotide joined to an adjacent nucleotide by a 2'-5' internucleotide phosphate bond.

In additional embodiments $(N)_x$ comprises modified ribonucleotides in alternating positions wherein each N at the 5' and 3' termini are modified in their sugar residues and the middle ribonucleotide is not modified, e.g. ribonucleotide in position 10 in a 19-mer strand. In various embodiments in $(N)_x$ and $(N')_y$ the nucleotides alternate between 2'OMe sugar modified ribonucleotides and unmodified ribonucleotides. In some embodiments the ribonucleotide located at the middle position of $(N)_x$ is unmodified and the ribonucleotide located at the middle position of $(N')_y$ is 2' OMe sugar modified.

For all the structures, in some embodiments the covalent bond joining each consecutive N or N' is a phosphodiester bond. In various embodiments all the covalent bonds are phosphodiester bonds.

In various embodiments x=y and each of x and y is 19, 20, 21, 22 or 23. In some embodiments x=y=21. In other embodiments x=y=19.

In one embodiment of the above structure, $(N')_y$ comprises at least one mirror nucleotide at one terminus or both termini or in a penultimate position. In various embodiments $(N')_y$ comprises one mirror nucleotide at the 3' penultimate position. In one preferred embodiment x=y=19 and $(N')_y$ comprises an L-deoxyribonucleotide at position 18. In one embodiment, a siRNA compound of the invention inhibits the expression of a target gene selected from a viral gene, a bacterial gene and a mammalian gene associated with a disorder in the inner ear of a subject. In some embodiments the target gene is a mammalian gene wherein the gi number of the mRNA of the target gene is set forth in Table 1.

In certain embodiments the target gene is selected from one or more of the group consisting of: TP53BP2 (ASPP2), BNIP3, CASP2, NOX3, HRK, RAC1, DDIT4 (REDD1), DDIT4L (REDD2), NOX4, HTRA2, CAPNS1 (Calpain), ID3, HES1, HES5, and CDKN1B (p27KIP).

For convenience and without wishing to be bound to theory the target genes are classified into two groups: Group I target genes relate to otoprotection and include TP53BP2 (ASPP2), BNIP3, CASP2, NOX3, HRK, RAC1, DDIT4 (REDD1), DDIT4L (REDD2), NOX4, HTRA2, CAPNS1 (Calpain), ID3 and Group II target genes relate to cellular regeneration and proliferation and include ID3, HES1, HES5, and CDKN1B (p27KIP).

According to various embodiments, the method of the present invention provides for inhibiting more than one target gene associated with the ear disorder using one or more oligonucleotides of the invention.

Accordingly, in one embodiment, the method of the invention is directed treating a subject suffering from an ear disorder by inhibiting two or more target genes designated herein as Group I target genes. In a non-limiting example a siRNA compound to each of the following target genes is administered to a subject: at least one of TP53BP2 (ASPP2), CASP2 and HTRA2, optionally in combination with CAPNS1 (Calpain), optionally in combination with at least one of NOX3, NOX4 and RAC1, optionally in combination with at least one of DDIT4, DDIT4L and ID3, and optionally in combination with at least one of HRK and BNIP3. Without being bound by theory, inhibition of at least one these target genes is associated with the protection against ototoxin-induced hearing loss.

In another embodiment, the method of the invention is directed to treating a subject suffering from an ear disorder by inhibiting two or more target genes designated herein as Group II: at least one of CDKN1B and ID3, optionally in combination with at least one of HES1 and HES5. Without being bound by theory, the inhibition of at least one of these target genes is associated with the promotion of proliferation of supporting cells or outer or inner hair cells in the cochlea.

In a preferred embodiment, the method comprises administering the oligonucleotides directed against at least one of CDKN1B and ID3 prior to administering the oligonucleotides directed against at least one of HES1 and HES5. In another embodiment, all oligonucleotides are administered together.

In a further embodiment, an oligonucleotide directed against a target gene in one group is administered sequentially to an oligonucleotide directed against a target gene in the other group. For example, a siRNA that targets a group I gene is administered to a subject before administration of a siRNA that targets a group II gene. In another embodiment, a siRNA directed against a group I gene is administered to a subject together with a siRNA directed against a group II gene. In various embodiments the target gene is a mammalian gene. In certain embodiments the mammalian gene is a human gene wherein the gi number for the mRNA of the human gene is set forth in Table 1.

In a second aspect the present invention provides an otic pharmaceutical composition comprising: (a) a therapeutically effective amount of at least one an oligonucleotide molecule compound which inhibits the expression of a human target gene associated with an ear disorder in the inner ear or middle ear (b) a permeability enhancer; and (c) at least one pharmaceutically acceptable excipient or carrier, or mixtures thereof. In some embodiments the permeability enhancer is a polyol selected from the group consisting of glycerol, propylene glycol, sorbitol, xylitol and maltitol.

In preferred embodiments the polyol is glycerol. In various embodiments glycerol is present at a final concentration of about 0.1% to about 35%; about 1% to about 30%; about 5% to about 25%, about 7% to about 15%, preferably about 10% to about 20%. In some embodiments the final concentration of glycerol in the pharmaceutical composition is about 2.5%, 5%, 10%, 12.5%, 15%, 17.5%, 20%, 22.5%, 25%, 27.5% or about 30%. In one preferred embodiment, the final concentration of glycerol in the pharmaceutical composition is about 10%.

In some embodiments the composition is formulated for non-invasive application to the human ear, preferably to the ear canal. In various embodiments the composition is formulated as a cream, a foam, a mousse, a paste, an ointment, an emulsion, a solution, a gel, a spray, a suspension, a microemulsion, microspheres, microcapsules, nanospheres, nanoparticles, lipid vesicles, liposomes, polymeric vesicles, patches, a biological insert.

In various embodiments the pharmaceutical composition is formulated as liquid eardrops, ear cream, ear ointment, ear foam or mousse. In preferred embodiments the pharmaceutical composition is formulated as liquid eardrops.

In some embodiments the oligonucleotide is an inhibitory nucleic acid compound selected from the group consisting of an antisense, an unmodified siRNA, a chemically modified siRNA, an shRNA, an aptamer, a ribozyme, a dsRNA or DNA compound. In various preferred embodiment the oligonucleotide is siRNA.

In various embodiments the siRNA is chemically modified to increase stability, increase activity, reduce off target effects, and or to reduce innate immune stimulation. The concentration of siRNA in the composition is between 0.1 mg/ml to 100 mg/ml, preferably between 1 mg/ml to 100 mg/ml, and more preferably between 5 mg/ml to 20 mg/ml.

In a preferred embodiment, the target gene is selected from one or more of: TP53BP2 (ASPP2), BNIP3, CASP2, NOX3, HRK, RAC1, DDIT4, DDIT4L, NOX4, HTRA2, CAPNS1 (Calpain), ID3, HES1, HES5, CDKN1B and ID3.

In some embodiments the oligonucleotide reduces or inhibits expression of a gene associated with a middle ear disorder or an inner ear disorder.

In some embodiments the pharmaceutical composition according to the present invention comprises a chemically modified siRNA compound comprising one of Structures (A)-(P) disclosed herein.

BRIEF DESCRIPTION OF THE FIGURES

FIG. 4. provides Tables A1-A7 which set forth antisense and sense sequences useful in the preparation of siRNA compounds to certain target genes useful in practicing the present invention. In Table A1: HES1—hairy and enhancer of split 1, the sense strands of siRNA numbered 1-412 have SEQ ID NOS: 37-448, respectively, and the antisense strands of siRNAs numbered 1-412 have SEQ ID NOS: 449-860, respectively. In Table A1(a), the sense strands of siRNA numbered 262-644 have SEQ ID NOS: 861-1,243, respectively, and the antisense strands of siRNAs numbered 262-644 have SEQ ID NOS: 1,244-1,626, respectively. In Table A2 HES5—hairy and enhancer split 5, the sense strands of siRNA numbered 1-257 have SEQ ID NOS: 1,627-1,883, respectively, and the antisense strands of siRNAs numbered 1-257 have SEQ ID NOS: 1,884-2,140, respectively. In Table A3 ID1—inhibitor of DNA binding 1, the sense strands of siRNA numbered 1-283 have SEQ ID NOS: 2,141-2,423, respectively, and the antisense strands of siRNAs numbered 1-283 have SEQ ID NOS: 2,424-2,706, respectively. In Table A4 ID2—inhibitor of DNA binding 2, the sense strands of siRNA numbered 1-500 have SEQ ID NOS: 2,707-3,206, respectively, and the antisense strands of siRNAs numbered 1-500 have SEQ ID NOS: 3,207-3,706, respectively. In Table A5 ID3—inhibitor of DNA binding 3, the sense strands of siRNA numbered 1-357 have SEQ ID NOS: 3,707-4,063, respectively, and the antisense strands of siRNAs numbered 1-357 have SEQ ID NOS: 4,064-4,420, respectively. In Table A6 CDKN1B—cyclin-dependent kinase inhibitor 1B (p27, Kip1), the sense strands of siRNA numbered 1-500 have SEQ ID NOS: 4,421-4,920, respectively, and the antisense strands of siRNAs numbered 1-500 have SEQ ID NOS: 4,921-5,420, respectively. In Table A7 CDKN2A—cyclin-dependent kinase inhibitor 2A (melanoma, p16, inhibits CDK4), the sense strands of siRNA numbered 1-211 have SEQ ID NOS: 5,421-5,631, respectively, and the antisense strands of siRNAs numbered 1-211 have SEQ ID NOS: 5,632-5,842, respectively.

DETAILED DESCRIPTION OF THE PRESENT INVENTION

Figure 1:
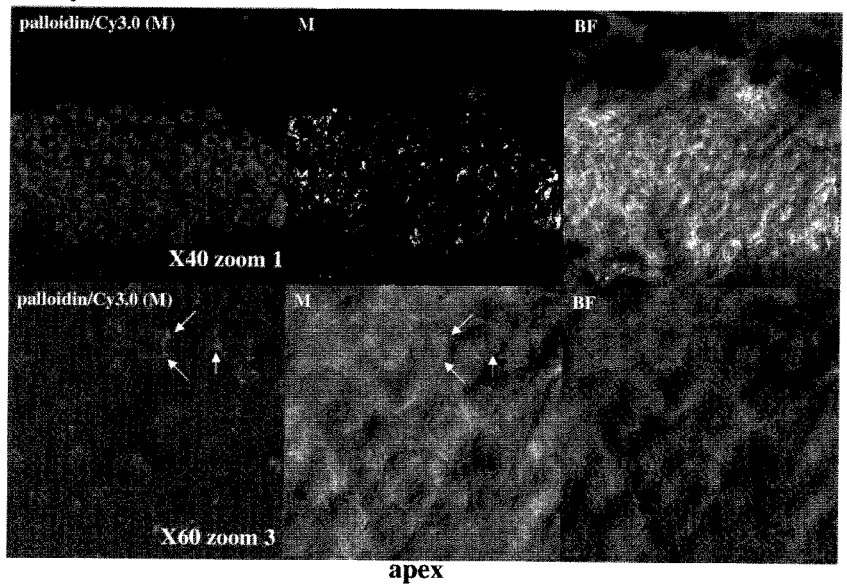
FIG. 1. Cy3 labelled DDIT4 siRNA in spiral ganglion (ganglion of Corti) in the apical turn of the organ of Corti, 3 days after application of eardrops.

The present invention relates in general to compositions and to methods useful in the treatment if middle and inner ear disorders.

Methods, molecules and compositions, which inhibit the genes of the invention, are discussed herein at length, and any of said molecules and/or compositions may be beneficially employed in the treatment of a subject suffering from any of said conditions.

The inhibitory nucleic acids of the present invention are preferably siRNA compounds that possess modifications which may increase activity, increase stability, and/or minimize toxicity when compared to the unmodified compound. These compounds, when admixed with a pharmaceutical vehicle that effects delivery of the nucleic acid to the middle and inner ear, provide effective, safe and patient compliant therapeutic compounds useful in treating a variety of ear disorders. The compounds are designed to prevent or attenuate target gene expression associated with the ear disorder. In certain embodiment the target gene is transcribed into any one of the mRNA polynucleotides set forth in Table 1. In a preferred embodiment, the target gene is selected from one or more of: TP53BP2 (ASPP2), BNIP3, CASP2, NOX3, HRK, RAC1, DDIT4, DDIT4L, NOX4, HTRA2, CAPNS1 (Calpain), ID3, HES1, HES5, CDKN1B.

Without wishing to be bound to theory the target genes are classified in two groups, group I directed to genes associated with otoprotection and include TP53BP2 (ASPP2), BNIP3, CASP2, NOX3, HRK, RAC1, DDIT4, DDIT4L, NOX4, HTRA2, CAPNS1 (Calpain), ID3, and group II associated with regeneration in cells of the inner ear and include ID3, HES1, HES5, CDKN1B. For some of the genes there is no clear group delineation and the grouping is provided for convenience only.

Details of several target genes are presented in Table 1, hereinbelow. This list is intended to be representative and non-limiting.

TABLE 1

Non-limiting example of human target genes for treating hearing loss

| No. | Gene | Full name and Human Gene ID |
|---|---|---|
| 1 | TP53BP2 | tumor protein p53 binding protein, 2<br>gi\|112799848\|ref\|NM_001031685.2 (SEQ ID NO: 1)<br>gi\|112799845\|ref\|NM_005426.2 (SEQ ID NO: 2) |
| 2 | LRDD | leucine-rich repeats and death domain containing<br>gi\|61742781\|ref\|NM_018494.3 (SEQ ID NO: 3)<br>gi\|61742783\|ref\|NM_145886.2 (SEQ ID NO: 4)<br>gi\|61742785\|ref\|NM_145887.2 (SEQ ID NO: 5) |
| 3 | CYBA | cytochrome b-245, alpha polypeptide<br>gi\|68509913\|ref\|NM_000101.2\|(SEQ ID NO: 6) |
| 4 | p53 | tumor protein p53<br>gi8400737, NM_000546.2 (SEQ ID NO: 7) |
| 5 | CASP2 | caspase 2, apoptosis-related cysteine peptidase<br>gi\|39995058\|ref\|NM_032982.2 (SEQ ID NO: 8)<br>gi\|39995060\|ref\|NM_032983.2 (SEQ ID NO: 9) |
| 6 | NOX3 | NADPH oxidase 3<br>gi\|11136625\|ref\|NM_015718.1 (SEQ ID NO: 10) |
| 7 | HRK | harakiri<br>gi\|4504492\|ref\|NM_003806.1 (SEQ ID NO: 11) |
| 8 | CAPNS1 | Calpain small subunit 1<br>gi\|51599152\|ref\|NM_001749.2\|(SEQ ID NO: 12)<br>gi\|51599150\|ref\|NM_001003962.1\|(SEQ ID NO: 13) |
| 9 | RTP801 | Redd1; DNA-damage-inducible transcript 4<br>gi\|56676369\|ref\|NM_019058.2\|(SEQ ID NO: 14) |
| 10 | RTP801L | Redd2; DNA-damage-inducible transcript 4-like<br>gi\|34222182\|ref\|NM_145244.2\|(SEQ ID NO: 15) |
| 11 | Notch1 | Notch homolog 1, translocation-associated (*Drosophila*)<br>gi\|148833507\|ref\|NM_017617.3\|(SEQ ID NO: 16) |
| 12 | Rac1 | ras-related C3 botulinum toxin substrate 1 (rho family, small GTP binding protein)<br>gi\|38505164\|ref\|NM_198829.1 (SEQ ID NO: 17)<br>gi\|156071511\|ref\|NM_018890.3 (SEQ ID NO: 18)<br>gi\|156071503\|ref\|NM_006908.4 (SEQ ID NO: 19) |
| 13 | HES1 | hairy and enhancer of split 1, (*Drosophila*)<br>gi\|8400709\|ref\|NM_005524.2\|(SEQ ID NO: 20) |
| 14 | HES5 | hairy and enhancer of split 5 (*Drosophila*)<br>gi\|145301612\|ref\|NM_001010926.2\|(SEQ ID NO: 21) |
| 15 | ID1 | inhibitor of DNA binding 1, dominant negative helix-loop-helix protein<br>gi\|31317298\|ref\|NM_002165.2\|transcript variant 1 (SEQ ID NO: 22)<br>gi\|31317296\|ref\|NM_181353.1\|transcript variant 2 (SEQ ID NO: 23) |
| 16 | ID2 | inhibitor of DNA binding 2, dominant negative helix-loop-helix protein gi\|33946335\|ref\|NM_002166.4\|(SEQ ID NO: 24) |
| 17 | ID3 | inhibitor of DNA binding 3, dominant negative helix-loop-helix protein gi\|156119620\|ref\|NM_002167.3\|(SEQ ID NO: 25) |
| 18 | CDKN1B | cyclin-dependent kinase inhibitor 1B (p27, Kip1)<br>gi\|17978497\|ref\|NM_004064.2\|(SEQ ID NO: 26) |

TABLE 1-continued

Non-limiting example of human target genes for treating hearing loss

| No. | Gene | Full name and Human Gene ID |
|---|---|---|
| 19 | CDKN2A | cyclin-dependent kinase inhibitor 2A (melanoma, p16, inhibits CDK4)<br>gi|47132605|ref|NM_058195.2|transcript variant 4 (SEQ ID NO: 27)<br>gi|98985803|ref|NM_058197.3|transcript variant 3 (SEQ ID NO: 28)<br>gi|47132606|ref|NM_000077.3|transcript variant 1 (SEQ ID NO: 29) |
| 20 | HTRA2 | Htra serine peptidase 2<br>var 1 gi: 73747817|ref|NM_013247 (SEQ ID NO: 30)<br>var 2 gi: 73747818|ref|NM_145074 (SEQ ID NO: 31) |
| 21 | KEAP1 | Kelch-like ECH-associated protein 1<br>var 1 gi: 45269144|ref|NM_203500 (SEQ ID NO: 32)<br>var 2 gi: 45269143|ref|NM_012289 (SEQ ID NO: 33) |
| 22 | SHC1 | Src homology 2 domain containing) transforming prot. 1<br>var 1 gi: 52693920|ref|NM_183001 (SEQ ID NO: 34)<br>var 2 gi: 34147725|ref|NM_003029 (SEQ ID NO: 35) |
| 23 | ZNHIT1 | Zn finger HIT type 1<br>gi: 37594439|ref|NM_006349 (SEQ ID NO: 36) |

Table 1 provides the gi (GeneInfo identifier) and accession numbers for polynucleotide sequences of the mRNA for certain target genes set forth above.

Ear Disorders

The present invention is directed to compositions and methods useful in treating a patient suffering from or at risk of various ear disorders. Ear disorders include hearing loss induced for example by ototoxins, excessive noise or ageing. Middle and inner ear disorders produce many of the same symptoms, and a disorder of the middle ear may affect the inner ear and vice versa.

In addition to hearing loss, ear disorders include Myringitis, an eardrum infection caused by a variety of viruses and bacteria; Temporal bone fracture for example due to a blow to the head; Auditory nerve tumors (acoustic neuroma, acoustic neurinoma, vestibular schwannoma, eighth nerve tumor).

In various embodiments, the methods and compositions of the invention are useful in treating various conditions of hearing loss. Without being bound by theory, the hearing loss may be due to apoptotic inner ear hair cell damage or loss (Zhang et al., Neuroscience 2003. 120:191-205; Wang et al., J. Neuroscience 23((24):8596-8607), wherein the damage or loss is caused by infection, mechanical injury, loud sound (noise), aging (presbycusis), or chemical-induced ototoxicity.

By "ototoxin" in the context of the present invention is meant a substance that through its chemical action injures, impairs or inhibits the activity of the sound receptors component of the nervous system related to hearing, which in turn impairs hearing (and/or balance). In the context of the present invention, ototoxicity includes a deleterious effect on the inner ear hair cells. Ototoxins include therapeutic drugs including antineoplastic agents, salicylates, loop-diuretics, quinines, and aminoglycoside antibiotics, contaminants in foods or medicinals, and environmental or industrial pollutants. Typically, treatment is performed to prevent or reduce ototoxicity, especially resulting from or expected to result from administration of therapeutic drugs. Preferably a composition comprising therapeutically effective amount of a chemically modified siRNA compound of the invention is given immediately after the exposure to prevent or reduce the ototoxic effect. More preferably, treatment is provided prophylactically, either by administration of the pharmaceutical composition of the invention prior to or concomitantly with the ototoxic pharmaceutical or the exposure to the ototoxin.

Incorporated herein by reference are chapters 196, 197, 198 and 199 of The Merck Manual of Diagnosis and Therapy, 14th Edition, (1982), Merck Sharp & Dome Research Laboratories, N.J. and corresponding chapters in the most recent 16th edition, including Chapters 207 and 210) relating to description and diagnosis of hearing and balance impairments.

Accordingly, in one aspect the present invention provides a method and pharmaceutical compositions for treating a mammal, preferably human, to prevent, reduce, or treat a hearing impairment, disorder or imbalance, preferably an ototoxin-induced hearing condition, by administering to a mammal in need of such treatment a chemically modified siRNA compound of the invention. One embodiment of the invention is a method for treating a hearing disorder or impairment wherein the ototoxicity results from administration of a therapeutically effective amount of an ototoxic pharmaceutical drug. Typical ototoxic drugs are chemotherapeutic agents, e.g. antineoplastic agents, and antibiotics. Other possible candidates include loop-diuretics, quinines or a quinine-like compound, PDE-5 inhibitors and salicylate or salicylate-like compounds.

Ototoxicity is a dose-limiting side effect of antibiotic administration. From 4 to 15% of patients receiving 1 gram per day for greater than 1 week develop measurable hearing loss, which slowly becomes worse and can lead to complete permanent deafness if treatment continues. Ototoxic aminoglycoside antibiotics include but are not limited to neomycin, paromomycin, ribostamycin, lividomycin, kanamycin, amikacin, tobramycin, viomycin, gentamicin, sisomicin, netilmicin, streptomycin, dibekacin, fortimicin, and dihydrostreptomycin, or combinations thereof. Particular antibiotics include neomycin B, kanamycin A, kanamycin B, gentamicin C1, gentamicin C1a, and gentamicin C2, and the like that are known to have serious toxicity, particularly ototoxicity and nephrotoxicity, which reduce the usefulness of such antimicrobial agents (see Goodman and Gilman's The Pharmacological Basis of Therapeutics, 6th ed., A. Goodman Gilman et al., eds; Macmillan Publishing Co., Inc., New York, pp. 1169-71 (1980)).

Ototoxicity is also a serious dose-limiting side-effect for anti-cancer agents. Ototoxic neoplastic agents include but are not limited to vincristine, vinblastine, cisplatin and cisplatin-like compounds and taxol and taxol-like compounds. Cisplatin-like compounds include carboplatin (Paraplatin®), tetraplatin, oxaliplatin, aroplatin and transplatin inter alia and are platinum based chemotherapeutics.

Diuretics with known ototoxic side-effect, particularly "loop" diuretics include, without being limited to, furosemide, ethacrylic acid, and mercurials.

Ototoxic quinines include but are not limited to synthetic substitutes of quinine that are typically used in the treatment of malaria. In some embodiments the hearing disorder is side-effect of inhibitors of type 5 phosphodiesterase (PDE-5), including sildenafil (Viagra®), vardenafil (Levitra®) and tadalafil (Cialis).

Salicylates, such as aspirin, are the most commonly used therapeutic drugs for their anti-inflammatory, analgesic, antipyretic and anti-thrombotic effects. Unfortunately, they too have ototoxic side effects. They often lead to tinnitus ("ringing in the ears") and temporary hearing loss. Moreover, if the drug is used at high doses for a prolonged time, the hearing impairment can become persistent and irreversible.

In some embodiments a method is provided for treatment of infection of a mammal by administration of an aminoglycoside antibiotic, the improvement comprising administering a therapeutically effective amount of one or more chemically modified siRNAs compounds which down-regulate expression a target gene, to the subject in need of such treatment to reduce or prevent ototoxin-induced hearing impairment associated with the antibiotic.

The methods and pharmaceutical and compositions of the present invention are also effective in the treatment of acoustic trauma or mechanical trauma, preferably acoustic or mechanical trauma that leads to inner ear hair cell loss. With more severe exposure, injury can proceed from a loss of adjacent supporting cells to complete disruption of the organ of Corti. Death of the sensory cell can lead to progressive Wallerian degeneration and loss of primary auditory nerve fibers. The methods of the invention are useful in treating acoustic trauma caused by a single exposure to an extremely loud sound, or following long-term exposure to everyday loud sounds above 85 decibels, for treating mechanical inner ear trauma, for example, resulting from the insertion of an electronic device into the inner ear or for preventing or minimizing the damage to inner ear hair cells associated with the operation.

Another type of hearing loss is presbycusis, which is hearing loss that gradually occurs in most individuals as they age. About 30-35 percent of adults between the ages of 65 and 75 years and 40-50 percent of people 75 and older experience hearing loss. The methods of the invention are useful in preventing, reducing or treating the incidence and/or severity of inner ear disorders and hearing impairments associated with presbycusis.

Definitions

For convenience certain terms employed in the specification, examples and claims are described herein.

It is to be noted that, as used herein, the singular forms "a", "an" and "the" include plural forms unless the content clearly dictates otherwise.

Where aspects or embodiments of the invention are described in terms of Markush groups or other grouping of alternatives, those skilled in the art will recognize that the invention is also thereby described in terms of any individual member or subgroup of members of the group.

A "polypeptide" refers to an amino acid sequence encoded by any of the above listed genes, including splice variants, isoforms, orthologs, or paralogs and the like.

An "inhibitor" is a compound which is capable of reducing the expression of a gene or the activity of the product of such gene to an extent sufficient to achieve a desired biological or physiological effect. The term "inhibitor" as used herein refers to one or more of an oligonucleotide or nucleic acid including antisense, siRNA, shRNA, miRNA and ribozyme. Inhibition may also be referred to as down-regulation or, for RNAi, silencing.

The term "inhibit" as used herein refers to reducing the expression of a gene or the activity of the product of such gene to an extent sufficient to achieve a desired biological or physiological effect. Inhibition may be complete or partial.

As used herein, the terms "polynucleotide" and "nucleic acid" may be used interchangeably and refer to nucleotide sequences comprising deoxyribonucleic acid (DNA), and ribonucleic acid (RNA). The terms should also be understood to include, as equivalents, analogs of either RNA or DNA made from nucleotide analogs. Throughout this application mRNA sequences are set forth as representing the corresponding genes. The terms "mRNA polynucleotide sequence" and mRNA are used interchangeably.

"Oligonucleotide" or "oligomer" refers to a single stranded or double stranded deoxyribonucleotide or ribonucleotide sequence or chimera thereof, from about 2 to about 100 nucleotides, preferably about 15 to about 60, or 18 to about 23. Each DNA or RNA nucleotide that makes up the oligonucleotide may be independently natural or synthetic, and or modified or unmodified. Modifications include changes to the sugar moiety, the base moiety and or the linkages between nucleotides in the oligonucleotide. The oligonucleotides or oligonucleotide compounds of the present invention are single or double stranded compounds comprising deoxyribonucleotides, ribonucleotides, modified deoxyribonucleotides, modified ribonucleotides and combinations thereof.

"Nucleotide" or "nucleotide monomer" is meant to encompass a deoxyribonucleotide and a ribonucleotide, which may be natural or synthetic, and or modified or unmodified. Modifications include changes and substitutions to the sugar moiety, the base moiety and/or the internucleotide linkages.

Analogs of, or modifications to, a nucleotide/oligonucleotide are preferably employed with the present invention, provided that said analog or modification does not substantially adversely affect the function of the nucleotide/oligonucleotide. In some embodiments a chemical modification results in an increase in activity or stability or a reduction in of-target effects or induction of innate immune responses. Acceptable modifications include modifications of the sugar moiety, modifications of the base moiety, modifications in the internucleotide linkages and combinations thereof.

The nucleotides can be selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine.

In addition, compounds comprising nucleotide analogs prepared wherein the structure of one or more nucleotide is fundamentally altered and better suited as therapeutic or experimental reagents. An example of a nucleotide analog is a peptide nucleic acid (PNA) wherein the deoxyribose (or ribose) phosphate backbone in DNA (or RNA is replaced with a polyamide backbone which is similar to that found in peptides. PNA analogs have been shown to be resistant to enzymatic degradation and to have extended lives in vivo and in vitro.

Possible modifications to the sugar residue are manifold and include 2'-O alkyl, locked nucleic acid (LNA), glycol nucleic acid (GNA), threose nucleic acid (TNA), arabinoside, altritol (ANA) and other, 6-membered sugars including morpholinos, and cyclohexinyls.

LNA compounds are disclosed in International Patent Publication Nos. WO 00/47599, WO 99/14226, and WO 98/39352. Examples of siRNA compounds comprising LNA nucleotides are disclosed in Elmen et al., (NAR 2005. 33(1): 439-447) and in International Patent Publication No. WO 2004/083430.

Backbone modifications, such as ethyl (resulting in a phospho-ethyl triester); propyl (resulting in a phospho-propyl triester); and butyl (resulting in a phospho-butyl triester) are also possible. Other backbone modifications include polymer backbones, cyclic backbones, acyclic backbones, thiophosphate-D-ribose backbones, amidates, phosphonoacetate derivatives. Certain structures include siRNA compounds having one or a plurality of 2'-5' internucleotide linkages (bridges or backbone).

Additional modifications which may be present in the molecules of the present invention include nucleoside modifications such as artificial nucleic acids, peptide nucleic acid (PNA), morpholino and locked nucleic acid (LNA), glycol nucleic acid (GNA), threose nucleic acid (TNA), arabinoside, and mirror nucleoside (for example, beta-L-deoxynucleoside instead of beta-D-deoxynucleoside Further, said molecules may additionally contain modifications on the sugar, such as 2'-alkyl, 2'-fluoro(2'-deoxy-2'-fluoro), 2'O-allyl, 2' amine and 2' alkoxy. Additional sugar modifications are discussed herein.

Further, the inhibitory nucleic acid molecules of the present invention may comprise one or more gaps and/or one or more nicks and/or one ore more mismatches. Without wishing to be bound by theory, gaps, nicks and mismatches have the advantage of partially destabilizing the nucleic acid/siRNA, so that it may be more easily processed by endogenous cellular machinery such as DICER, DROSHA or RISC into its inhibitory components.

In the context of the present invention, a gap in a nucleic acid refers to the absence of one or more internal nucleotides in one strand, while a nick in a nucleic acid refers to the absence of an internucleotide linkage between two adjacent nucleotides in one strand. Any of the molecules of the present invention may contain one or more gaps and/or one or more nicks.

siRNAs and RNA Interference

RNA interference (RNAi) is a phenomenon involving double-stranded (ds) RNA-dependent gene specific posttranscriptional silencing. Originally, attempts to study this phenomenon and to manipulate mammalian cells experimentally were frustrated by an active, non-specific antiviral defense mechanism which was activated in response to long dsRNA molecules (Gil et al. Apoptosis, 2000. 5:107-114). Later it was discovered that synthetic duplexes of 21 nucleotide RNAs could mediate gene specific RNAi in mammalian cells, without the stimulation of the generic antiviral defense mechanisms (see Elbashir et al. Nature 2001, 411:494-498 and Caplen et al. PNAS USA 2001, 98:9742-9747). As a result, small interfering RNAs (siRNAs), which are short double-stranded RNAs, have become powerful tools in attempting to understand gene function. Thus RNA interference (RNAi) refers to the process of sequence-specific post-transcriptional gene silencing in mammals mediated by small interfering RNAs (siRNAs) (Fire et al, Nature 1998. 391, 806) or microRNAs (miRNA; Ambros, Nature 2004 431: 7006, 350-55; and Bartel, Cell. 2004. 116(2):281-97). The corresponding process in plants is commonly referred to as specific post transcriptional gene silencing or RNA silencing and is referred to as quelling in fungi.

A siRNA is a double-stranded RNA molecule which inhibits, either partially or fully, the expression of a gene/mRNA of its endogenous or cellular counterpart, or of an exogenous gene such as a viral nucleic acid. The mechanism of RNA interference is detailed infra.

Several studies have revealed that siRNA therapeutics are effective in vivo in both mammals and in humans. Bitko et al., have shown that specific siRNA molecules directed against the respiratory syncytial virus (RSV) nucleocapsid N gene are effective in treating mice when administered intranasally (Bitko et al., Nat. Med. 2005, 11(1):50-55). siRNA has recently been successfully used for inhibition in primates (Tolentino et al., Retina 2004. 24(1):132-138). For a review of the use of siRNA as therapeutics, see for example Barik (J. Mol. Med. 2005. 83: 764-773) or Dykxhoorn et al (2006. Gene Ther. 13:541-552).

siRNA Structures

The selection and synthesis of siRNA corresponding to known genes has been widely reported; (see for example Ui-Tei et al., J Biomed Biotech. 2006; 2006: 65052; Chalk et al., BBRC. 2004, 319(1): 264-74; Sioud & Leirdal, Met. Mol. Biol.; 2004, 252:457-69; Levenkova et al., Bioinform. 2004, 20(3):430-2; Ui-Tei et al., NAR. 2004, 32(3):936-48).

For examples of the use of, and production of, modified siRNA see, for example, Braasch et al., Biochem. 2003, 42(26):7967-75; Chiu et al., RNA, 2003, 9(9):1034-48; PCT publications WO 2004/015107 (atugen AG) and WO 02/44321 (Tuschl et al). U.S. Pat. Nos. 5,898,031 and 6,107,094, teach chemically modified oligomers. US Patent Publication Nos. 2005/0080246 and 2005/0042647 relate to oligomeric compounds having an alternating motif and dsRNA compounds having chemically modified internucleoside linkages, respectively.

Other modifications have been disclosed. The inclusion of a 5'-phosphate moiety was shown to enhance activity of siRNAs in *Drosophila* embryos (Boutla, et al., Curr. Biol. 2001, 11:1776-1780) and is required for siRNA function in human HeLa cells (Schwarz et al., Mol. Cell, 2002, 10:537-48). Amarzguioui et al., (NAR, 2003, 31(2):589-95) showed that siRNA activity depended on the positioning of the 2'-O-methyl modifications. Holen et al (NAR. 2003, 31(9):2401-07) report that an siRNA having small numbers of 2'-O-methyl modified nucleosides gave good activity compared to wild type but that the activity decreased as the numbers of 2'-O-methyl modified nucleosides was increased. Chiu and Rana (RNA. 2003, 9:1034-48) teach that incorporation of 2'-O-methyl modified nucleosides in the sense or antisense strand (fully modified strands) severely reduced siRNA activity relative to unmodified siRNA. The placement of a 2'-O-methyl group at the 5'-terminus on the antisense strand was reported to severely limit activity whereas placement at the 3'-terminus of the antisense and at both termini of the sense strand was tolerated (Czauderna et al., NAR. 2003, 31(11):2705-16; WO 2004/015107). The molecules of the present invention offer an advantage in that they are non-toxic and may be formulated as pharmaceutical compositions for treatment of various diseases.

International Patent Publication No. WO 2008/050329 to the assignee of the present invention and hereby incorporated in its entirely relates to siRNA compounds, compositions comprising same and to methods of use thereof for treating diseases and disorders related to expression of proapoptotic genes. U.S. Ser. No. 11/655,610 relates to methods of treating hearing impairment by inhibiting a pro-apoptotic gene in general and p53 in particular. International Patent Publication No. WO 2005/119251 relates to methods of treating deafness. International Patent Publication No. WO/2005/055921 relates to foam compositions for treatment of ear disorders. U.S. Pat. No. 7,087,581 relates to methods of treating diseases and disorders of the inner ear.

According to one aspect the present invention provides a method for the treatment of ear disorders comprising the step of administering a pharmaceutical composition comprising administering a composition comprising a chemically modified inhibitory oligonucleotide compound; a permeability enhancer and pharmaceutically acceptable carrier. The compound comprises at least one modified nucleotide selected from the group consisting of a sugar modification, a base modification and an internucleotide linkage modification.

The present invention also relates to compounds which down-regulate expression of various genes, particularly to novel small interfering RNAs (siRNAs), and to the use of these novel siRNAs in the treatment of hearing loss, in the regeneration of inner ear cells and in preventing chemical-induced hearing loss.

A non-limiting list of human target genes useful in the present invention is provided in Table 1, set forth in SEQ ID NOS 1-36. In a preferred embodiment, the target gene is selected from one or more of: TP53BP2 (ASPP2), BNIP3, CASP2, NOX3, HRK, RAC1, DDIT4, DDIT4L, NOX4, HTRA2, CAPNS1 (Calpain), ID3, HES1, HES5, CDKN1B and ID3. The reference to mRNA associated with those genes is set forth therein. For each gene 19-mer, 21-mer and 23-mer sequences is generated, which are prioritized based on their score in the proprietary algorithm as the best sequences for targeting the human gene expression. The 21- or 23-mer siRNA sequences can also be generated by 5' and/or 3' extension of the 19-mer sequences disclosed herein. Such extension is preferably complementary to the corresponding mRNA sequence. Certain 23-mer oligomers were devised by this method where the order of the prioritization is the order of the corresponding 19-mer. The siRNA oligomers useful in practicing the invention are disclosed in Tables B of U.S. Ser. No. 11/978,089, assigned to the assignee of the present invention and which is hereby incorporated by reference in their entirety and are set forth as SEQ ID NOS:97-68654 in that application. Certain siRNA oligomers useful in the compositions and methods of the present invention are disclosed in U.S. Ser. Nos. 11/207,119, 11/811,112, 11/655,636, and International Patent Application Nos. PCT/IL2008/000797, PCT/IL2008/000874, PCT/IL2009/000053, PCT/IL2009/000302, assigned to the assignee of the present invention and which are hereby incorporated by reference in their entirety. Certain 19-mer antisense and sense oligonucleotides sequences useful in the preparation of siRNA compounds of various lengths are shown in FIG. 4. The abbreviations for cross species sequences are as follows: Chp: chimpanzee, Ms: Mouse, Chn: chinchilla; GP: guinea-pig.

In some embodiments the present invention provides a composition and method comprising a long oligonucleotide, typically about 41-500 nucleotides in length) comprising none or one or more stem and loop structures, which is processed intracellularly by endogenous cellular complexes (e.g. by DROSHA and DICER as described above) to produce one or more smaller double stranded oligonucleotides (siRNAs). In some embodiments the long oligonucleotide is a single stranded oligonucleotide comprising one or more stem and loop structures, wherein each stem region comprises a sense and corresponding antisense siRNA sequence. Any molecules, such as, for example, antisense DNA molecules which comprise the inhibitory sequences disclosed herein (with the appropriate nucleic acid modifications) are particularly desirable and may be used in the same capacity as their corresponding RNAs/siRNAs for all uses and methods disclosed herein.

Oligonucleotides

The present invention provides double-stranded oligonucleotides (e.g. siRNAs), which down-regulate the expression of a desired gene. An siRNA of the invention is a duplex oligoribonucleotide in which the sense strand is derived from the mRNA sequence of the desired gene, and the antisense strand is complementary to the sense strand. In general, some deviation from the target mRNA sequence is tolerated without compromising the siRNA activity (see e.g. Czauderna et al., NAR. 2003, 31(11):2705-2716). An siRNA of the invention inhibits gene expression on a post-transcriptional level with or without destroying the mRNA. Without being bound by theory, siRNA may target the mRNA for specific cleavage and degradation and/or may inhibit translation from the targeted message.

In various embodiments the siRNA comprises an RNA duplex comprising a first strand and a second strand, whereby the first strand comprises a ribonucleotide sequence at least partially complementary to about 18 to about 40 consecutive nucleotides of a target nucleic acid which is mRNA transcribed from a target gene, and the second strand comprises a ribonucleotide sequence at least partially complementary to the first strand and wherein said first strand and or said second strand comprises a one or more chemically modified ribonucleotides and or unconventional moieties.

In one embodiment the siRNA compound comprises at least one ribonucleotide comprising a 2' modification on the sugar moiety ("2' sugar modification"). In certain embodiments the compound comprises 2'O-alkyl or 2'-fluoro or 2'O-allyl or any other 2' modification, optionally on alternate positions. Other stabilizing modifications are also possible (e.g. terminal modifications). In some embodiments a preferred 2'O-alkyl is 2'O-methyl (methoxy, 2'OMe) sugar modification.

In some embodiments the backbone of the oligonucleotides is modified and comprises phosphate-D-ribose entities but may also contain thiophosphate-D-ribose entities, triester, thioate, 2'-5' bridged backbone (also may be referred to as 5'-2'), PACE and the like.

As used herein, the terms "non-pairing nucleotide analog" means a nucleotide analog which comprises a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide. In other embodiments it is a deoxyribonucleotide. In addition, analogues of polynucleotides may be prepared wherein the structure of one or more nucleotide is fundamentally altered and better suited as therapeutic or experimental reagents. An example of a nucleotide analogue is a peptide nucleic acid (PNA) wherein the deoxyribose (or ribose) phosphate backbone in DNA (or RNA is replaced with a polyamide backbone which is similar to that found in peptides. PNA analogues have been shown to be resistant to enzymatic degradation and to enhance stability in vivo and in vitro. Other useful modifications include polymer backbones, cyclic backbones, acyclic backbones, thiophosphate-D-ribose backbones, triester backbones, thioate backbones, 2'-5' bridged backbone, artificial nucleic acids, morpholino nucleic acids, glycol nucleic acid (GNA), threose nucleic acid (TNA), arabinoside, and mirror nucleoside (for example, beta-L-deoxyribonucleoside instead of beta-D-deoxyribonucleoside). The compounds of the present invention can be synthesized using one or more inverted nucleotides, for example inverted thymidine or inverted adenine (see, for example, Takei, et al., 2002, JBC 277(26):23800-06).

Additional modifications include terminal modifications on the 5' and/or 3' part of the oligonucleotides and are also known as capping moieties. Such terminal modifications are selected from a nucleotide, a modified nucleotide, a lipid, a peptide, a sugar and inverted abasic moiety.

What is sometimes referred to in the present invention as an "abasic nucleotide" or "abasic nucleotide analog" is more properly referred to as a pseudo-nucleotide or an unconventional moiety. A nucleotide is a monomeric unit of nucleic acid, consisting of a ribose or deoxyribose sugar, a phosphate, and a base (adenine, guanine, thymine, or cytosine in DNA; adenine, guanine, uracil, or cytosine in RNA). A modified nucleotide comprises a modification in one or more of the sugar, phosphate and or base. The abasic pseudo-nucleotide lacks a base, and thus is not strictly a nucleotide.

The term "unconventional moiety" as used herein refers to abasic ribose moiety, an abasic deoxyribose moiety, a deoxyribonucleotide, a modified deoxyribonucleotide, a mirror nucleotide, a non-base pairing nucleotide analog and a nucleotide joined to an adjacent nucleotide by a 2'-5' internucleotide phosphate bond; bridged nucleic acids including LNA and ethylene bridged nucleic acids. In some embodiments of the present invention a preferred unconventional moiety is an abasic ribose moiety, an abasic deoxyribose moiety, a deoxyribonucleotide, a mirror nucleotide, and a nucleotide joined to an adjacent nucleotide by a 2'-5' internucleotide phosphate bond.

Abasic deoxyribose moiety includes for example abasic deoxyribose-3'-phosphate; 1,2-dideoxy-D-ribofuranose-3-phosphate; 1,4-anhydro-2-deoxy-D-ribitol-3-phosphate. Inverted abasic deoxyribose moiety includes inverted deoxyriboabasic; 3',5' inverted deoxyabasic 5'-phosphate.

A "mirror" nucleotide is a nucleotide with reversed chirality to the naturally occurring or commonly employed nucleotide, i.e., a mirror image (L-nucleotide) of the naturally occurring (D-nucleotide), also referred to as L-RNA in the case of a mirror ribonucleotide, and "spiegelmer". The nucleotide can be a ribonucleotide or a deoxyribonucleotide and my further comprise at least one sugar, base and or backbone modification. See U.S. Pat. No. 6,586,238. Also, U.S. Pat. No. 6,602,858 discloses nucleic acid catalysts comprising at least one L-nucleotide substitution. Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror image dT)) and L-RNA (L-riboadenosine-3'-phosphate (mirror rA); L-ribocytidine-3'-phosphate (mirror rC); L-riboguanosine-3'-phosphate (mirror rG); L-ribouracil-3'-phosphate (mirror dU).

The term "capping moiety" as used herein includes abasic ribose moiety, abasic deoxyribose moiety, modifications abasic ribose and abasic deoxyribose moieties including 2' O alkyl modifications; inverted abasic ribose and abasic deoxyribose moieties and modifications thereof; C6-imino-Pi; a mirror nucleotide including L-DNA and L-RNA; 5'O-Me nucleotide; and nucleotide analogs including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

Certain preferred capping moieties are abasic ribose or abasic deoxyribose moieties; inverted abasic ribose or abasic deoxyribose moieties; C6-amino-Pi; a mirror nucleotide including L-DNA and L-RNA.

A further end modification is a biotin group. Such biotin group may preferably be attached to either the most 5' or the most 3' nucleotide of the first and/or second strand or to both ends. In a more preferred embodiment the biotin group is coupled to a polypeptide or a protein. It is also within the scope of the present invention that the polypeptide or protein is attached through any of the other aforementioned end modifications.

The various end modifications as disclosed herein are preferably located at the ribose moiety of a nucleotide of the nucleic acid according to the present invention. More particularly, the end modification may be attached to or replace any of the OH-groups of the ribose moiety, including but not limited to the 2'OH, 3'OH and 5'OH position, provided that the nucleotide thus modified is a terminal nucleotide. Inverted abasic or abasic are nucleotides, either deoxyribonucleotides or ribonucleotides which do not have a nucleobase moiety (for example see Sternberger, et al., (2002). Antisense Nucleic Acid Drug Dev, 12, 131-43).

Modified deoxyribonucleotide includes, for example 5'OMe DNA (5-methyl-deoxyriboguanosine-3'-phosphate) which may be useful as a nucleotide in the 5' terminal position (position number 1); PACE (deoxyriboadenine 3' phosphonoacetate, deoxyribocytidine 3' phosphonoacetate, deoxyriboguanosine 3' phosphonoacetate, deoxyribothymidine 3' phosphonoacetate.

Bridged nucleic acids include LNA (2'-O, 4'-C-methylene bridged Nucleic Acid adenosine 3' monophosphate, 2'-O,4'-C-methylene bridged Nucleic Acid 5-methyl-cytidine 3' monophosphate, 2'-O,4'-C-methylene bridged Nucleic Acid guanosine 3' monophosphate, 5-methyl-uridine (or thymidine) 3' monophosphate); and ENA (2'-O,4'-C-ethylene bridged nucleic acid adenosine 3' monophosphate, 2'-O,4'-C-ethylene bridged nucleic acid 5-methyl-cytidine 3' monophosphate, 2'-O,4'-C-ethylene bridged nucleic acid guanosine 3' monophosphate, 5-methyl-uridine (or thymidine) 3' monophosphate).

In certain embodiments the complementarity between said first strand and the target nucleic acid is perfect. In some embodiments, the strands are substantially complementary, i.e. having one, two or up to three mismatches between said first strand and the target nucleic acid. Substantially complementary refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

In some embodiments the first strand and the second strand of the compound are linked by a loop structure, which is comprised of a non-nucleic acid polymer such as, inter alia, polyethylene glycol. Alternatively, the loop structure is comprised of a nucleic acid, including modified and non-modified ribonucleotides and modified and non-modified deoxyribonucleotides.

In further embodiments, the 5'-terminus of the first strand of the siRNA is linked to the 3'-terminus of the second strand, or the 3'-terminus of the first strand is linked to the 5'-terminus of the second strand, said linkage being via a nucleic acid linker typically having a length between 2-100 nucleobases, preferably about 2 to about 30 nucleobases.

In preferred embodiments of the compounds of the invention having alternating ribonucleotides modified in at least one of the antisense and the sense strands of the compound, for 19 mer and 23 mer oligomers the ribonucleotides at the 5' and 3' termini of the antisense strand are modified in their sugar residues, and the ribonucleotides at the 5' and 3' termini of the sense strand are unmodified in their sugar residues. For 21 mer oligomers the ribonucleotides at the 5' and 3' termini of the sense strand are modified in their sugar residues, and the ribonucleotides at the 5' and 3' termini of the antisense strand are unmodified in their sugar residues, or may have an optional additional modification at the 3' terminus. As mentioned above, it is preferred that the middle nucleotide of the antisense strand is unmodified.

According to one preferred embodiment of the invention, the antisense and the sense strands of the oligonucleotide/siRNA are phosphorylated at the 3'-terminus and not at the 5'-terminus. According to another preferred embodiment of the invention, the antisense and the sense strands are non-phosphorylated. According to yet another preferred embodiment of the invention, the 5' most ribonucleotide in the sense strand is modified to abolish any possibility of in vivo 5'-phosphorylation.

Any siRNA sequence can be prepared having any of the modifications/structures disclosed herein. The compound comprising a combination of sequence plus structure is useful in the treatment of the conditions disclosed herein.

Structural Motifs

According to the present invention the siRNA compounds are chemically and or structurally modified according to one of the following modifications set forth in Structures (A)-(P) or as tandem siRNA or RNAstar.

In one aspect the present invention provides a compound set forth as Structure (A):

(A) 5' $(N)_x$-Z 3' (antisense strand)
    3' Z'-$(N')_y$ 5' (sense strand)

wherein each of N and N' is a nucleotide selected from an unmodified ribonucleotide, a modified ribonucleotide, an unmodified deoxyribonucleotide and a modified deoxyribonucleotide;
wherein each of $(N)_x$ and $(N')_y$ is an oligonucleotide in which each consecutive N or N' is joined to the next N or N' by a covalent bond;
wherein each of x and y is an integer between 18 and 40;
wherein each of Z and Z' may be present or absent, but if present is 1-5 consecutive nucleotides covalently attached at the 3' terminus of the strand in which it is present;
wherein the sequence of $(N')_y$ is a sequence substantially complementary to $(N)x$; and
wherein the sequence of $(N)_x$ comprises an antisense sequence substantially complementary to from about 18 to about 40 consecutive ribonucleotides in an mRNA of a target gene associated with an ear disorder.

In certain embodiments the present invention provides a compound having structure (B)

(B) 5' $(N)_x$-Z 3' (antisense strand)
    3' Z'-$(N')_y$ 5' (sense strand)

wherein each of $(N)_x$ and $(N')_y$ is an oligomer in which each consecutive N or N' is an unmodified ribonucleotide or a modified ribonucleotide joined to the next N or N' by a covalent bond;
wherein each of Z and Z' may be present or absent, but if present is 1-5 consecutive nucleotides covalently attached at the 3' terminus of the strand in which it is present;
wherein each of x and y=19, 21 or 23 and $(N)_x$ and $(N')_y$ are fully complementary
wherein alternating ribonucleotides in each of $(N)_x$ and $(N')_y$ are modified to result in a 2'-O-methyl modification in the sugar residue of the ribonucleotides;
wherein the sequence of $(N')_y$ is a sequence substantially complementary to $(N)x$; and
wherein the sequence of $(N)_x$ comprises an antisense sequence substantially complementary to the substantially complementary to from about 18 to about 40 consecutive ribonucleotides in an mRNA of a target gene associated with an ear disorder.

In some embodiments each of (N), and $(N')_y$ is independently phosphorylated or non-phosphorylated at the 3' and 5' termini.

In certain embodiments wherein each of x and y=19 or 23, each N at the 5' and 3' termini of $(N)_x$ is modified; and each N' at the 5' and 3' termini of $(N')_y$ is unmodified.

In certain embodiments wherein each of x and y=21, each N at the 5' and 3' termini of $(N)_x$ is unmodified; and each N' at the 5' and 3' termini of $(N')_y$ is modified.

In particular embodiments, when x and y=19, the siRNA is modified such that a 2'-O-methyl (2'-OMe) group is present on the first, third, fifth, seventh, ninth, eleventh, thirteenth, fifteenth, seventeenth and nineteenth nucleotide of the antisense strand (N)x, and whereby the very same modification, i.e. a 2'-OMe group, is present at the second, fourth, sixth, eighth, tenth, twelfth, fourteenth, sixteenth and eighteenth nucleotide of the sense strand (N')y. In various embodiments these particular siRNA compounds are blunt ended at both termini.

In some embodiments, the present invention provides a compound having Structure (C):

(C) 5' $(N)_x$-Z 3' antisense strand
    3' Z'-$(N')_y$ 5' sense strand wherein each of N and N' is a nucleotide independently selected from an unmodified ribonucleotide, a modified ribonucleotide, an unmodified deoxyribonucleotide and a modified deoxyribonucleotide;
wherein each of (N)x and (N')y is an oligomer in which each consecutive nucleotide is joined to the next nucleotide by a covalent bond and each of x and y is an integer between 18 and 40;
wherein in (N)x the nucleotides are unmodified or (N)x comprises alternating modified ribonucleotides and unmodified ribonucleotides; each modified ribonucleotide being modified so as to have a 2'-O-methyl on its sugar and the ribonucleotide located at the middle position of (N)x being modified or unmodified preferably unmodified;
wherein (N')y comprises unmodified ribonucleotides further comprising one modified nucleotide at a terminal or penultimate position, wherein the modified nucleotide is selected from the group consisting of a mirror nucleotide, a bicyclic nucleotide, a 2'-sugar modified nucleotide, an altritol nucleotide, or a nucleotide joined to an adjacent nucleotide by an internucleotide linkage selected from a 2'-5' phosphodiester bond, a P-alkoxy linkage or a PACE linkage;
wherein if more than one nucleotide is modified in (N')y, the modified nucleotides may be consecutive;
wherein each of Z and Z' may be present or absent, but if present is 1-5 deoxyribonucleotides covalently attached at the 3' terminus of any oligomer to which it is attached;
wherein the sequence of $(N')_y$ comprises a sequence substantially complementary to (N)x; and wherein $(N)_x$ comprises an antisense sequence substantially complementary to from about 18 to about 40 consecutive ribonucleotides in an mRNA of a target gene associated with an ear disorder.

In particular embodiments, x=y=19 and in (N)x each modified ribonucleotide is modified so as to have a 2'-O-methyl on its sugar and the ribonucleotide located at the middle of (N)x is unmodified. Accordingly, in a compound wherein x=19, (N)x comprises 2'-O-methyl sugar modified ribonucleotides at positions 1, 3, 5, 7, 9, 11, 13, 15, 17 and 19. In other embodiments, (N)x comprises 2'O Me modified ribonucleotides at positions 2, 4, 6, 8, 11, 13, 15, 17 and 19 and may further comprise at least one abasic or inverted abasic unconventional moiety for example in position 5. In other embodiments, (N)x comprises 2'O Me modified ribonucleotides at positions 2, 4, 8, 11, 13, 15, 17 and 19 and may further comprise at least one abasic or inverted abasic unconventional moiety for example in position 6. In other embodiments, (N)x comprises 2'O Me modified ribonucleotides at positions 2, 4, 6, 8, 11, 13, 17 and 19 and may further comprise at least one abasic or inverted abasic unconventional moiety for example in position 15. In other embodiments, (N)x comprises 2'O Me modified ribonucleotides at positions 2, 4, 6, 8, 11, 13, 15, 17 and 19 and may further comprise at least one abasic or inverted abasic unconventional moiety for example in position 14. In other embodiments, (N)x comprises 2'O Me modified ribonucleotides at positions 1, 2, 3, 7, 9, 11, 13, 15, 17 and 19 and may further comprise at least one abasic or inverted abasic unconventional moiety for example in position 5. In other embodiments, (N)x comprises 2'O Me modified ribonucleotides at positions 1, 2, 3, 5, 7, 9, 11, 13, 15, 17 and 19 and may further comprise at least one abasic or inverted abasic unconventional moiety for example in position 6. In other embodiments, (N)x comprises 2'O Me modified ribonucleotides at positions 1, 2, 3, 5, 7, 9, 11, 13, 17 and 19 and may further comprise at least one abasic or inverted abasic unconventional moiety for example in position 15. In other embodiments, (N)x comprises 2'O Me modified ribonucleotides at positions 1, 2, 3, 5, 7, 9, 11, 13, 15, 17 and 19 and may further comprise at least one abasic or inverted abasic unconventional moiety for example in position 14. In other embodiments, (N)x comprises 2'O Me modified ribonucleotides at positions 2, 4, 6, 7, 9, 11, 13, 15, 17 and 19 and may further comprise at least one abasic or inverted abasic unconventional moiety for example in position 5. In other embodiments, (N)x comprises 2'O Me modified ribonucleotides at positions 1, 2, 4, 6, 7, 9, 11, 13, 15, 17 and 19 and may further comprise at least one abasic or inverted abasic unconventional moiety for example in position 5. In other embodiments, (N)x comprises 2'O Me modified ribonucleotides at positions 2, 4, 6, 8, 11, 13, 14, 16, 17 and 19 and may further comprise at least one abasic or inverted abasic unconventional moiety for example in position 15. In other embodiments, (N)x comprises 2'O Me modified ribonucleotides at positions 1, 2, 3, 5, 7, 9, 11, 13, 14, 16, 17 and 19 and may further comprise at least one abasic or inverted abasic unconventional moiety for example in position 15. In other embodiments, (N)x comprises 2'O Me modified ribonucleotides at positions 2, 4, 6, 8, 11, 13, 15, 17 and 19 and may further comprise at least one abasic or inverted abasic unconventional moiety for example in position 7. In other embodiments, (N)x comprises 2'O Me modified ribonucleotides at positions 2, 4, 6, 11, 13, 15, 17 and 19 and may further comprise at least one abasic or inverted abasic unconventional moiety for example in position 8. In other embodiments, (N)x comprises 2'O Me modified ribonucleotides at positions 2, 4, 6, 8, 11, 13, 15, 17 and 19 and may further comprise at least one abasic or inverted abasic unconventional moiety for example in position 9. In other embodiments, (N)x comprises 2'O Me modified ribonucleotides at positions 2, 4, 6, 8, 11, 13, 15, 17 and 19 and may further comprise at least one abasic or inverted abasic unconventional moiety for example in position 10. In other embodiments, (N)x comprises 2'O Me modified ribonucleotides at positions 2, 4, 6, 8, 13, 15, 17 and 19 and may further comprise at least one abasic or inverted abasic unconventional moiety for example in position 11. In other embodiments, (N)x comprises 2' O Me modified ribonucleotides at positions 2, 4, 6, 8, 11, 13, 15, 17 and 19 and may further comprise at least one abasic or inverted abasic unconventional moiety for example in position 12. In other embodiments, (N)x comprises 2'O Me modified ribonucleotides at positions 2, 4, 6, 8, 11, 15, 17 and 19 and may further comprise at least one abasic or inverted abasic unconventional moiety for example in position 13.

In yet other embodiments $(N)_x$ comprises at least one nucleotide mismatch relative to the one of the genes. In certain preferred embodiments, (N)x comprises a single nucleotide mismatch on position 5, 6, or 14. In one embodiment of Structure (C), at least two nucleotides at either or both the 5' and 3' termini of (N')y are joined by a 2'-5' phosphodiester bond. In certain preferred embodiments x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified; and three nucleotides at the 3' terminus of (N')y are joined by two 2'-5' phosphodiester bonds (set forth herein as Structure I). In other preferred embodiments, x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified; and four consecutive nucleotides at the 5' terminus of (N')y are joined by three 2'-5' phosphodiester bonds. In a further embodiment, an additional nucleotide located in the middle position of (N)y may be modified with 2'-O-methyl on its sugar. In another preferred embodiment, in (N)x the nucleotides alternate between 2'-O-methyl modified ribonucleotides and unmodified ribonucleotides, and in (N')y four consecutive nucleotides at the 5' terminus are joined by three 2'-5' phosphodiester bonds and the 5' terminal nucleotide or two or three consecutive nucleotides at the 5' terminus comprise 3'-O-methyl modifications.

In certain preferred embodiments of Structure C, x=y=19 and in (N')y, at least one position comprises an abasic or inverted abasic unconventional moiety, preferably five positions comprises an abasic or inverted abasic unconventional moieties. In various embodiments, the following positions comprise an abasic or inverted abasic: positions 1 and 16-19, positions 15-19, positions 1-2 and 17-19, positions 1-3 and 18-19, positions 1-4 and 19 and positions 1-5. (N')y may further comprise at least one LNA nucleotide.

In certain preferred embodiments of Structure C, x=y=19 and in (N')y the nucleotide in at least one position comprises a mirror nucleotide, a deoxyribonucleotide and a nucleotide joined to an adjacent nucleotide by a 2'-5' internucleotide bond;

In certain preferred embodiments of Structure C, x=y=19 and (N')y comprises a mirror nucleotide. In various embodiments the mirror nucleotide is an L-DNA nucleotide. In certain embodiments the L-DNA is L-deoxyribocytidine. In some embodiments (N')y comprises L-DNA at position 18. In other embodiments (N')y comprises L-DNA at positions 17 and 18. In certain embodiments (N')y comprises L-DNA substitutions at positions 2 and at one or both of positions 17 and 18. In certain embodiments (N')y further comprises a 5' terminal cap nucleotide such as 5'-O-methyl DNA or an abasic or inverted abasic moiety as an overhang.

In yet other embodiments (N')y comprises a DNA at position 15 and L-DNA at one or both of positions 17 and 18. In that structure, position 2 may further comprise an L-DNA or an abasic unconventional moiety.

Other embodiments of Structure C are envisaged wherein x=y=21 or wherein x=y=23; in these embodiments the modifications for (N')y discussed above instead of being on positions 15, 16, 17, 18 are on positions 17, 18, 19, 20 for 21 mer and on positions 19, 20, 21, 22 for 23 mer; similarly the modifications at one or both of positions 17 and 18 are on one or both of positions 19 or 20 for the 21 mer and one or both of positions 21 and 22 for the 23 mer. All modifications in the 19 mer are similarly adjusted for the 21 and 23 mer.

According to various embodiments of Structure (C), in (N')y 2, 3, 4, 5, 6, 7, 8, 9, 10, 11, 12, 13 or 14 consecutive ribonucleotides at the 3' terminus are linked by 2'-5' internucleotide linkages In one preferred embodiment, four consecutive nucleotides at the 3' terminus of (N')y are joined by three 2'-5' phosphodiester bonds, wherein one or more of the 2'-5' nucleotides which form the 2'-5' phosphodiester bonds further comprises a 3'-O-methyl sugar modification. Preferably the 3' terminal nucleotide of (N')y comprises a 2'-O-methyl sugar modification. In certain preferred embodiments of Structure C, x=y=19 and in (N')y two or more consecutive nucleotides at positions 15, 16, 17, 18 and 19 comprise a nucleotide joined to an adjacent nucleotide by a 2'-5' internucleotide bond. In various embodiments the nucleotide forming the 2'-5' internucleotide bond comprises a 3' deoxyribose nucleotide or a 3' methoxy nucleotide. In some embodiments the nucleotides at positions 17 and 18 in (N')y are joined by a 2'-5' internucleotide bond. In other embodiments the nucleotides at positions 16, 17, 18, 16-17, 17-18, or 16-18 in (N')y are joined by a 2'-5' internucleotide bond.

In certain embodiments (N')y comprises an L-DNA at position 2 and 2'-5' internucleotide bonds at positions 16-17, 17-18, or 16-18. In certain embodiments (N')y comprises 2'-5' internucleotide bonds at positions 16-17, 17-18, or 16-18 and a 5' terminal cap nucleotide.

According to various embodiments of Structure (C), in (N')y 2, 3, 4, 5, 6, 7, 8, 9, 10, 11, 12, 13 or 14 consecutive nucleotides at either terminus or 2-8 modified nucleotides at each of the 5' and 3' termini are independently mirror nucleotides. In some embodiments the mirror nucleotide is an L-ribonucleotide. In other embodiments the mirror nucleotide is an L-deoxyribonucleotide. The mirror nucleotide may further be modified at the sugar or base moiety or in an internucleotide linkage.

In one preferred embodiment of Structure (C), the 3' terminal nucleotide or two or three consecutive nucleotides at the 3' terminus of (N')y are L-deoxyribonucleotides.

In other embodiments of Structure (C), in (N')y 2, 3, 4, 5, 6, 7, 8, 9, 10, 11, 12, 13 or 14 consecutive ribonucleotides at either terminus or 2-8 modified nucleotides at each of the 5' and 3' termini are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe). In one series of preferred embodiments, three, four or five consecutive nucleotides at the 5' terminus of (N')y comprise the 2'-OMe modification. In another preferred embodiment, three consecutive nucleotides at the 3' terminus of (N')y comprise the 2'-O-methyl modification.

In some embodiments of Structure (C), in (N')y 2, 3, 4, 5, 6, 7, 8, 9, 10, 11, 12, 13 or 14 consecutive ribonucleotides at either or 2-8 modified nucleotides at each of the 5' and 3' termini are independently bicyclic nucleotide. In various embodiments the bicyclic nucleotide is a locked nucleic acid (LNA). A 2'-O, 4'-C-ethylene-bridged nucleic acid (ENA) is a species of LNA (see below).

In various embodiments (N')y comprises modified nucleotides at the 5' terminus or at both the 3' and 5' termini.

In some embodiments of Structure (C), at least two nucleotides at either or both the 5' and 3' termini of (N')y are joined by P-ethoxy backbone modifications. In certain preferred embodiments x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle position of (N)x being unmodified; and four consecutive nucleotides at the 3' terminus or at the 5' terminus of (N')y are joined by three P-ethoxy backbone modifications. In another preferred embodiment, three consecutive nucleotides at the 3' terminus or at the 5' terminus of (N')y are joined by two P-ethoxy backbone modifications.

In some embodiments of Structure (C), in (N')y 2, 3, 4, 5, 6, 7 or 8, consecutive ribonucleotides at each of the 5' and 3' termini are independently mirror nucleotides, nucleotides joined by 2'-5' phosphodiester bond, 2' sugar modified nucleotides or bicyclic nucleotide. In one embodiment, the modification at the 5' and 3' termini of (N')y is identical. In one preferred embodiment, four consecutive nucleotides at the 5' terminus of (N')y are joined by three 2'-5' phosphodiester bonds and three consecutive nucleotides at the 3' terminus of (N')y are joined by two 2'-5' phosphodiester bonds. In another embodiment, the modification at the 5' terminus of (N')y is different from the modification at the 3' terminus of (N')y. In one specific embodiment, the modified nucleotides at the 5' terminus of (N')y are mirror nucleotides and the modified nucleotides at the 3' terminus of (N')y are joined by 2'-5' phosphodiester bond. In another specific embodiment, three consecutive nucleotides at the 5' terminus of (N')y are LNA nucleotides and three consecutive nucleotides at the 3' terminus of (N')y are joined by two 2'-5' phosphodiester bonds. In (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified, or the ribonucleotides in (N)x being unmodified In another embodiment of Structure (C), the present invention provides a compound wherein x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified; three nucleotides at the 3' terminus of (N')y are joined by two 2'-5' phosphodiester bonds and three nucleotides at the 5' terminus of (N')y are LNA such as ENA.

In another embodiment of Structure (C), five consecutive nucleotides at the 5' terminus of (N')y comprise the 2'-O-methyl sugar modification and two consecutive nucleotides at the 3' terminus of (N')y are L-DNA.

In yet another embodiment, the present invention provides a compound wherein x=y=19 or x=y=23; (N)x consists of unmodified ribonucleotides; three consecutive nucleotides at the 3' terminus of (N')y are joined by two 2'-5' phosphodiester bonds and three consecutive nucleotides at the 5' terminus of (N')y are LNA such as ENA.

According to other embodiments of Structure (C), in (N')y the 5' or 3' terminal nucleotide, or 2, 3, 4, 5 or 6 consecutive nucleotides at either termini or 1-4 modified nucleotides at each of the 5' and 3' termini are independently phosphonocarboxylate or phosphinocarboxylate nucleotides (PACE nucleotides). In some embodiments the PACE nucleotides are deoxyribonucleotides. In some preferred embodiments in (N')y, 1 or 2 consecutive nucleotides at each of the 5' and 3' termini are PACE nucleotides.

In some embodiments, the present invention provides a compound having Structure (D):
(D) 5' (N)x-Z 3' antisense strand
      3' Z'-(N')y 5' sense strand
wherein each of N and N' is a nucleotide selected from an unmodified ribonucleotide, a modified ribonucleotide, an unmodified deoxyribonucleotide or a modified deoxyribonucleotide;
wherein each of (N)x and (N')y is an oligomer in which each consecutive nucleotide is joined to the next nucleotide by a covalent bond and each of x and y is an integer between 18 and 40;
wherein (N)x comprises unmodified ribonucleotides further comprising one modified nucleotide at the 3' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;
wherein (N')y comprises unmodified ribonucleotides further comprising one modified nucleotide at the 5' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;
wherein in each of (N)x and (N')y modified and unmodified nucleotides are not alternating;
wherein each of Z and Z' may be present or absent, but if present is 1-5 deoxyribonucleotides covalently attached at the 3' terminus of any oligomer to which it is attached;
wherein the sequence of (N')y is a sequence substantially complementary to (N)x; and wherein (N)x comprises an antisense sequence substantially complementary to from about 18 to about 40 consecutive ribonucleotides in an mRNA of a target gene associated with an ear disorder.

In one embodiment of Structure (D), x=y=19 or x=y=23; (N)x comprises unmodified ribonucleotides in which two consecutive nucleotides linked by one 2'-5' internucleotide linkage at the 3' terminus; and (N')y comprises unmodified ribonucleotides in which two consecutive nucleotides linked by one 2'-5' internucleotide linkage at the 5' terminus.

In some embodiments, x=y=19 or x=y=23; (N)x comprises unmodified ribonucleotides in which three consecutive nucleotides at the 3' terminus are joined together by two 2'-5' phosphodiester bonds; and (N')y comprises unmodified ribonucleotides in which four consecutive nucleotides at the 5' terminus are joined together by three 2'-5' phosphodiester bonds (set forth herein as Structure II).

According to various embodiments of Structure (D) 2, 3, 4, 5, 6, 7, 8, 9, 10, 11, 12, 13 or 14 consecutive ribonucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are linked by 2'-5' internucleotide linkages.

According to one preferred embodiment of Structure (D), four consecutive nucleotides at the 5' terminus of (N')y are joined by three 2'-5' phosphodiester bonds and three consecutive nucleotides at the 3' terminus of (N')x are joined by two 2'-5' phosphodiester bonds. Three nucleotides at the 5' terminus of (N')y and two nucleotides at the 3' terminus of (N')x may also comprise 3'-O-methyl modifications.

According to various embodiments of Structure (D), 2, 3, 4, 5, 6, 7, 8, 9, 10, 11, 12, 13 or 14 consecutive nucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are independently mirror nucleotides. In some embodiments the mirror is an L-ribonucleotide. In other embodiments the mirror nucleotide is L-deoxyribonucleotide.

In other embodiments of Structure (D), 2, 3, 4, 5, 6, 7, 8, 9, 10, 11, 12, 13 or 14 consecutive ribonucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe).

In one preferred embodiment of Structure (D), five consecutive nucleotides at the 5' terminus of (N')y comprise a 2'OMe sugar modification and five consecutive nucleotides at the 3' terminus of (N')x comprise the 2'OMe sugar modification. In another preferred embodiment of Structure (D), ten consecutive nucleotides at the 5' terminus of (N')y comprise the 2'OMe sugar modification and five consecutive nucleotides at the 3' terminus of (N')x comprise the 2'OMe sugar modification. In another preferred embodiment of Structure (D), thirteen consecutive nucleotides at the 5' terminus of (N')y comprise the 2'OMe sugar modification and five consecutive nucleotides at the 3' terminus of (N')x comprise the 2'-O-methyl modification.

In some embodiments of Structure (D), in (N')y 2, 3, 4, 5, 6, 7, 8, 9, 10, 11, 12, 13 or 14 consecutive ribonucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are independently a bicyclic nucleotide. In various embodiments the bicyclic nucleotide is a locked nucleic acid (LNA) such as a 2'-O, 4'-C-ethylene-bridged nucleic acid (ENA).

In various embodiments of Structure (D), (N')y comprises a modified nucleotide selected from a bicyclic nucleotide, a 2' sugar modified nucleotide, a mirror nucleotide, an altritol nucleotide or a nucleotide joined to an adjacent nucleotide by an internucleotide linkage selected from a 2'-5' phosphodiester bond, a P-alkoxy linkage or a PACE linkage;

In various embodiments of Structure (D), (N)x comprises a modified nucleotide selected from a bicyclic nucleotide, a 2' sugar modified nucleotide, a mirror nucleotide, an altritol nucleotide or a nucleotide joined to an adjacent nucleotide by an internucleotide linkage selected from a 2'-5' phosphodiester bond, a P-alkoxy linkage or a PACE linkage;

In embodiments wherein each of the 3' and 5' termini of the same strand comprises a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In one specific embodiment of Structure (D), five consecutive nucleotides at the 5' terminus of (N')y comprise the 2'OMe sugar modification and two consecutive nucleotides at the 3' terminus of (N')y are L-DNA. In addition, the compound may further comprise five consecutive 2'OMe sugar modified nucleotides at the 3' terminus of (N')x.

In various embodiments of Structure (D), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (E):
(E) 5' (N)x-Z 3' antisense strand
    3' Z'-(N')y 5' sense strand
wherein each of N and N' is a nucleotide selected from an unmodified ribonucleotide, a modified ribonucleotide, an unmodified deoxyribonucleotide or a modified deoxyribonucleotide;
wherein each of (N)x and (N')y is an oligomer in which each consecutive nucleotide is joined to the next nucleotide by a covalent bond and each of x and y is an integer between 18 and 40;
wherein (N)x comprises unmodified ribonucleotides further comprising one modified nucleotide at the 5' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;
wherein (N')y comprises unmodified ribonucleotides further comprising one modified nucleotide at the 3' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;
wherein in each of (N)x and (N')y modified and unmodified nucleotides are not alternating;
wherein each of Z and Z' may be present or absent, but if present is 1-5 deoxyribonucleotides covalently attached at the 3' terminus of any oligomer to which it is attached;
wherein the sequence of (N')$_y$ is a sequence substantially complementary to (N)x; and wherein the sequence of (N)$_x$ comprises an antisense sequence substantially complementary to from about 18 to about 40 consecutive ribonucleotides in an mRNA of a target gene associated with an ear disorder.

In certain preferred embodiments the ultimate nucleotide at the 5' terminus of (N)x is unmodified.

According to various embodiments of Structure (E) 2, 3, 4, 5, 6, 7, 8, 9, 10, 11, 12, 13 or 14 consecutive ribonucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive ribonucleotides starting at the ultimate or penultimate position of the 3' terminus of (N')y are linked by 2'-5' internucleotide linkages.

According to various embodiments of Structure (E), 2, 3, 4, 5, 6, 7, 8, 9, 10, 11, 12, 13 or 14 consecutive nucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive nucleotides starting at the ultimate or penultimate position of the 3' terminus of (N')y are independently mirror nucleotides. In some embodiments the mirror is an L-ribonucleotide. In other embodiments the mirror nucleotide is L-deoxyribonucleotide.

In other embodiments of Structure (E), 2, 3, 4, 5, 6, 7, 8, 9, 10, 11, 12, 13 or 14 consecutive ribonucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive ribonucleotides starting at the ultimate or penultimate position of the 3' terminus of (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe).

In some embodiments of Structure (E), in (N')y 2, 3, 4, 5, 6, 7, 8, 9, 10, 11, 12, 13 or 14 consecutive ribonucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive ribonucleotides starting at the ultimate or penultimate position of the 3' terminus of (N')y are independently a bicyclic nucleotide. In various embodiments the bicyclic nucleotide is a locked nucleic acid (LNA) such as a 2'-O, 4'-C-ethylene-bridged nucleic acid (ENA).

In various embodiments of Structure (E), (N')y comprises modified nucleotides selected from a bicyclic nucleotide, a 2' sugar modified nucleotide, a mirror nucleotide, an altritol nucleotide, a nucleotide joined to an adjacent nucleotide by a P-alkoxy backbone modification or a nucleotide joined to an adjacent nucleotide by an internucleotide linkage selected from a 2'-5' phosphodiester bond, a P-alkoxy linkage or a PACE linkage at the 3' terminus or at each of the 3' and 5' termini.

In various embodiments of Structure (E), (N)x comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 5' terminus or at each of the 3' and 5' termini.

In one embodiment where both 3' and 5' termini of the same strand comprise a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In various embodiments of Structure (E), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (F):

(F) 5' (N)x-Z 3' antisense strand
    3' Z'-(N')y 5' sense strand wherein each of N and N' is a nucleotide selected from an unmodified ribonucleotide, a modified ribonucleotide, an unmodified deoxyribonucleotide or a modified deoxyribonucleotide;

wherein each of (N)x and (N')y is an oligomer in which each consecutive nucleotide is joined to the next nucleotide by a covalent bond and each of x and y is an integer between 18 and 40;

wherein each of (N)x and (N')y comprise unmodified ribonucleotides in which each of (N)x and (N')y independently comprise one modified nucleotide at the 3' terminal or penultimate position wherein the modified nucleotide is selected from the group consisting of a bicyclic nucleotide, a 2' sugar modified nucleotide, a mirror nucleotide, a nucleotide joined to an adjacent nucleotide by a P-alkoxy backbone modification or a nucleotide joined to an adjacent nucleotide by a 2'-5' phosphodiester bond;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of $(N')_y$ is a sequence substantially complementary to (N)x; and wherein the sequence of $(N)_x$ comprises an antisense sequence substantially complementary to from about 18 to about 40 consecutive ribonucleotides in an mRNA of a target gene associated with an ear disorder.

In some embodiments of Structure (F), x=y=19 or x=y=23; (N')y comprises unmodified ribonucleotides in which two consecutive nucleotides at the 3' terminus comprises two consecutive mirror deoxyribonucleotides; and (N)x comprises unmodified ribonucleotides in which one nucleotide at the 3' terminus comprises a mirror deoxyribonucleotide (set forth as Structure III).

According to various embodiments of Structure (F) 2, 3, 4, 5, 6, 7, 8, 9, 10, 11, 12, 13 or 14 consecutive ribonucleotides independently beginning at the ultimate or penultimate position of the 3' termini of (N)x and (N')y are linked by 2'-5' internucleotide linkages.

According to one preferred embodiment of Structure (F), three consecutive nucleotides at the 3' terminus of (N')y are joined by two 2'-5' phosphodiester bonds and three consecutive nucleotides at the 3' terminus of $(N')_x$ are joined by two 2'-5' phosphodiester bonds.

According to various embodiments of Structure (F), 2, 3, 4, 5, 6, 7, 8, 9, 10, 11, 12, 13 or 14 consecutive nucleotides independently beginning at the ultimate or penultimate position of the 3' termini of (N)x and (N')y are independently mirror nucleotides. In some embodiments the mirror nucleotide is an L-ribonucleotide. In other embodiments the mirror nucleotide is an L-deoxyribonucleotide.

In other embodiments of Structure (F), 2, 3, 4, 5, 6, 7, 8, 9, 10, 11, 12, 13 or 14 consecutive ribonucleotides independently beginning at the ultimate or penultimate position of the 3' termini of (N)x and (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe).

In some embodiments of Structure (F), 2, 3, 4, 5, 6, 7, 8, 9, 10, 11, 12, 13 or 14 consecutive ribonucleotides independently beginning at the ultimate or penultimate position of the 3' termini of (N)x and (N')y are independently a bicyclic nucleotide. In various embodiments the bicyclic nucleotide is a locked nucleic acid (LNA) such as a 2'-O, 4'-C-ethylene-bridged nucleic acid (ENA).

In various embodiments of Structure (F), (N')y comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 3' terminus or at both the 3' and 5' termini.

In various embodiments of Structure (F), (N)x comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 3' terminus or at each of the 3' and 5' termini.

In one embodiment where each of 3' and 5' termini of the same strand comprise a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In various embodiments of Structure (F), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in $(N)_x$ are nucleotides linked by 2'-5' internucleotide linkages and the modified nucleotides in (N')y are mirror nucleotides.

In additional embodiments, the present invention provides a compound having Structure (G):

(G) 5' (N)x-Z 3' antisense strand
    3' Z'-(N')y 5' sense strand wherein each of N and N' is a nucleotide selected from an unmodified ribonucleotide, a modified ribonucleotide, an unmodified deoxyribonucleotide or a modified deoxyribonucleotide;

wherein each of (N)x and (N')y is an oligomer in which each consecutive nucleotide is joined to the next nucleotide by a covalent bond and each of x and y is an integer between 18 and 40;

wherein each of (N)x and (N')y comprise unmodified ribonucleotides in which each of (N)x and (N')y independently comprise one modified nucleotide at the 5' terminal or penultimate position wherein the modified nucleotide is selected from the group consisting of a bicyclic nucleotide, a 2' sugar modified nucleotide, a mirror nucleotide, a nucleotide joined to an adjacent nucleotide by a P-alkoxy backbone modification or a nucleotide joined to an adjacent nucleotide by a 2'-5' phosphodiester bond;

wherein for (N)x the modified nucleotide is preferably at penultimate position of the 5' terminal;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of $(N')_y$ is a sequence substantially complementary to (N)x; and wherein the sequence of $(N)_x$ comprises an antisense sequence substantially complementary to from about 18 to about 40 consecutive ribonucleotides in an mRNA of a target gene associated with an ear disorder.

In some embodiments of Structure (G), x=y=19 or x=y=23.

According to various embodiments of Structure (G) 2, 3, 4, 5, 6, 7, 8, 9, 10, 11, 12, 13 or 14 consecutive ribonucleotides independently beginning at the ultimate or penultimate position of the 5' termini of (N)x and (N')y are linked by 2'-5' internucleotide linkages. For (N)x the modified nucleotides preferably starting at the penultimate position of the 5' terminal According to various embodiments of Structure (G), 2, 3, 4, 5, 6, 7, 8, 9, 10, 11, 12, 13 or 14 consecutive nucleotides independently beginning at the ultimate or penultimate position of the 5' termini of (N)x and (N')y are independently mirror nucleotides. In some embodiments the mirror nucleotide is an L-ribonucleotide. In other embodiments the mirror nucleotide is an L-deoxyribonucleotide. For (N)x the modified nucleotides preferably starting at the penultimate position of the 5' terminal In other embodiments of Structure (G), 2, 3, 4, 5, 6, 7, 8, 9, 10, 11, 12, 13 or 14 consecutive ribonucleotides independently beginning at the ultimate or penultimate position of the 5' termini of (N)x and (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe). In some preferred embodiments the consecutive modified nucleotides preferably begin at the penultimate position of the 5' terminus of (N)x.

In one preferred embodiment of Structure (G), five consecutive ribonucleotides at the 5' terminus of (N')y comprise a 2'OMe sugar modification and one ribonucleotide at the 5' penultimate position of (N')x comprises a 2'OMe sugar modification. In another preferred embodiment of Structure (G), five consecutive ribonucleotides at the 5' terminus of (N')y comprise 2'OMe sugar modification and two consecutive ribonucleotides at the 5' terminal position of (N')x comprise a 2'OMe sugar modification.

In some embodiments of Structure (G), 2, 3, 4, 5, 6, 7, 8, 9, 10, 11, 12, 13 or 14 consecutive ribonucleotides independently beginning at the ultimate or penultimate position of the 5' termini of (N)x and (N')y are bicyclic nucleotides. In various embodiments the bicyclic nucleotide is a locked nucleic acid (LNA) such as a 2'-O, 4'-C-ethylene-bridged nucleic acid (ENA). In some preferred embodiments the consecutive modified nucleotides preferably begin at the penultimate position of the 5' terminus of (N)x.

In various embodiments of Structure (G), (N')y comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 5' terminus or at each of the 3' and 5' termini.

In various embodiments of Structure (G), (N)x comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 5' terminus or at each of the 3' and 5' termini.

In one embodiment where each of 3' and 5' termini of the same strand comprise a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond. In various embodiments of Structure (G), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (H):

(H) 5' (N)x-Z 3' antisense strand
   3' Z'-(N')y 5' sense strand wherein each of N and N' is a nucleotide selected from an unmodified ribonucleotide, a modified ribonucleotide, an unmodified deoxyribonucleotide or a modified deoxyribonucleotide;

wherein each of (N)x and (N')y is an oligomer in which each consecutive nucleotide is joined to the next nucleotide by a covalent bond and each of x and y is an integer between 18 and 40;

wherein (N)x comprises unmodified ribonucleotides further comprising one modified nucleotide at the 3' terminal or penultimate position or the 5' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein (N')y comprises unmodified ribonucleotides further comprising one modified nucleotide at an internal position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of $(N')_y$ is a sequence substantially complementary to (N)x; and wherein the sequence of $(N)_x$ comprises an antisense sequence substantially complementary to from about 18 to about 40 consecutive ribonucleotides in an mRNA of a target gene associated with an ear disorder.

In one embodiment of Structure (H), 2, 3, 4, 5, 6, 7, 8, 9, 10, 11, 12, 13 or 14 consecutive ribonucleotides independently beginning at the ultimate or penultimate position of the 3' terminus or the 5' terminus or both termini of (N)x are independently 2' sugar modified nucleotides, bicyclic nucleotides, mirror nucleotides, altritol nucleotides or nucleotides joined to an adjacent nucleotide by a 2'-5' phosphodiester bond and 2, 3, 4, 5, 6, 7, 8, 9, 10, 11, 12, 13 or 14 consecutive internal ribonucleotides in (N')y are independently 2' sugar modified nucleotides, bicyclic nucleotides, mirror nucleotides, altritol nucleotides or nucleotides joined to an adjacent nucleotide by a 2'-5' phosphodiester bond. In some embodiments the 2' sugar modification comprises the presence of an amino, a fluoro, an alkoxy or an alkyl moiety. In certain embodiments the 2' sugar modification comprises a methoxy moiety (2'-OMe).

In another embodiment of Structure (H), 2, 3, 4, 5, 6, 7, 8, 9, 10, 11, 12, 13 or 14 consecutive ribonucleotides independently beginning at the ultimate or penultimate position of the 3' terminus or the 5' terminus or 2-8 consecutive nucleotides at each of 5' and 3' termini of (N')y are independently 2' sugar modified nucleotides, bicyclic nucleotides, mirror nucleotides, altritol nucleotides or nucleotides joined to an adjacent nucleotide by a 2'-5' phosphodiester bond, and 2, 3, 4, 5, 6, 7, 8, 9, 10, 11, 12, 13 or 14 consecutive internal ribonucleotides in (N)x are independently 2' sugar modified nucleotides, bicyclic nucleotides, mirror nucleotides, altritol nucleotides or nucleotides joined to an adjacent nucleotide by a 2'-5' phosphodiester bond.

In one embodiment wherein each of 3' and 5' termini of the same strand comprises a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In various embodiments of Structure (H), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In one preferred embodiment of Structure (H), x=y=19; three consecutive ribonucleotides at the 9-11 nucleotide positions 9-11 of (N')y comprise 2'OMe sugar modification and five consecutive ribonucleotides at the 3' terminal position of (N')$_x$ comprise 2'OMe sugar modification.

For all the above Structures (A)-(H), in various embodiments x=y and each of x and y is 19, 20, 21, 22 or 23. In certain embodiments, x=y=19. In yet other embodiments x=y=23. In additional embodiments the compound comprises modified ribonucleotides in alternating positions wherein each N at the 5' and 3' termini of (N)x are modified in their sugar residues and the middle ribonucleotide is not modified, e.g. ribonucleotide in position 10 in a 19-mer strand, position 11 in a 21 mer and position 12 in a 23-mer strand.

In some embodiments where x=y=21 or x=y=23 the position of modifications in the 19 mer are adjusted for the 21 and 23 mers with the proviso that the middle nucleotide of the antisense strand is preferably not modified.

In some embodiments, neither (N)x nor (N')y are phosphorylated at the 3' and 5' termini. In other embodiments either or both (N)x and (N')y are phosphorylated at the 3' termini. In yet another embodiment, either or both (N)x and (N')y are phosphorylated at the 3' termini using non-cleavable phosphate groups. In yet another embodiment, either or both (N)x and (N')y are phosphorylated at the terminal 2' termini position using cleavable or non-cleavable phosphate groups. These particular siRNA compounds are also blunt ended and are non-phosphorylated at the termini; however, comparative experiments have shown that siRNA compounds phosphorylated at one or both of the 3'-termini have similar activity in vivo compared to the non-phosphorylated compounds.

In certain embodiments for all the above-mentioned Structures, the compound is blunt ended, for example wherein both Z and Z' are absent. In an alternative embodiment, the compound comprises at least one 3' overhang, wherein at least one of Z or Z' is present. Z and Z' independently comprises one or more covalently linked modified or non-modified nucleotides, for example inverted dT or dA; dT, LNA, mirror nucleotide and the like. In some embodiments each of Z and Z' are independently selected from dT and dTdT. siRNA in which Z and/or Z' is present have similar activity and stability as siRNA in which Z and Z' are absent.

In certain embodiments for all the above-mentioned Structures, the compound comprises one or more phosphonocarboxylate and/or phosphinocarboxylate nucleotides (PACE nucleotides). In some embodiments the PACE nucleotides are deoxyribonucleotides and the phosphinocarboxylate nucleotides are phosphinoacetate nucleotides. Examples of PACE nucleotides and analogs are disclosed in U.S. Pat. Nos. 6,693,187 and 7,067,641, both incorporated herein by reference.

In certain embodiments for all the above-mentioned Structures, the compound comprises one or more locked nucleic acids (LNA) also defined as bridged nucleic acids or bicyclic nucleotides. Preferred locked nucleic acids are 2'-O, 4'-C-ethylene nucleosides (ENA) or 2'-O, 4'-C-methylene nucleosides. Other examples of LNA and ENA nucleotides are disclosed in WO 98/39352, WO 00/47599 and WO 99/14226, all incorporated herein by reference.

In certain embodiments for all the above-mentioned Structures, the compound comprises one or more altritol monomers (nucleotides), also defined as 1,5 anhydro-2-deoxy-D-altrito-hexitol (see for example, Allart, et al., 1998. *Nucleosides & Nucleotides* 17: 1523-1526; Herdewijn et al., 1999. *Nucleosides & Nucleotides* 18:1371-1376; Fisher et al., 2007, *NAR* 35(4):1064-1074; all incorporated herein by reference).

The present invention explicitly excludes compounds in which each of N and/or N' is a deoxyribonucleotide (D-A, D-C, D-G, D-T). In certain embodiments (N)x and (N')y may comprise independently 1, 2, 3, 4, 5, 6, 7, 8, 9 or more deoxyribonucleotides. In certain embodiments the present invention provides a compound wherein each of N is an unmodified ribonucleotide and the 3' terminal nucleotide or 2, 3, 4, 5, 6, 7, 8, 9, 10, 11, 12, 13 or 14 consecutive nucleotides at the 3' terminus of (N')y are deoxyribonucleotides. In yet other embodiments each of N is an unmodified ribonucleotide and the 5' terminal nucleotide or 2, 3, 4, 5, 6, 7, 8, 9, 10, 11, 12, 13 or 14 consecutive nucleotides at the 5' terminus of (N')y are deoxyribonucleotides. In further embodiments the 5' terminal nucleotide or 2, 3, 4, 5, 6, 7, 8, or 9 consecutive nucleotides at the 5' terminus and 1, 2, 3, 4, 5, or 6 consecutive nucleotides at the 3' termini of (N)x are deoxyribonucleotides and each of N' is an unmodified ribonucleotide. In yet further embodiments (N)x comprises unmodified ribonucleotides and 1 or 2, 3 or 4 consecutive deoxyribonucleotides independently at each of the 5' and 3' termini and 1 or 2, 3, 4, 5 or 6 consecutive deoxyribonucleotides in internal positions; and each of N' is an unmodified ribonucleotide. In certain embodiments the 3' terminal nucleotide or 2, 3, 4, 5, 6, 7, 8, 9, 10, 11, 12 13 or 14 consecutive nucleotides at the 3' terminus of (N')y and the terminal 5' nucleotide or 2, 3, 4, 5, 6, 7, 8, 9, 10, 11, 12 13 or 14 consecutive nucleotides at the 5' terminus of (N)x are deoxyribonucleotides. The present invention excludes compounds in which each of N and/or N' is a deoxyribonucleotide. In some embodiments the 5' terminal nucleotide of N or 2 or 3 consecutive of N and 1, 2, or 3 of N' is a deoxyribonucleotide. Certain examples of active DNA/RNA siRNA chimeras are disclosed in US patent publication 2005/0004064, and Ui-Tei, 2008 (NAR 36(7):2136-2151) incorporated herein by reference in their entirety.

Unless otherwise indicated, in preferred embodiments of the structures discussed herein the covalent bond between each consecutive N or N' is a phosphodiester bond.

An additional novel molecule provided by the present invention is an oligonucleotide comprising consecutive nucleotides wherein a first segment of such nucleotides encode a first inhibitory RNA molecule, a second segment of such nucleotides encode a second inhibitory RNA molecule, and a third segment of such nucleotides encode a third inhibitory RNA molecule. Each of the first, the second and the third segment may comprise one strand of a double stranded RNA and the first, second and third segments may be joined together by a linker. Further, the oligonucleotide may comprise three double stranded segments joined together by one or more linker.

Thus, one molecule provided by the present invention is an oligonucleotide comprising consecutive nucleotides which encode three inhibitory RNA molecules; said oligonucleotide may possess a triple stranded structure, such that three double stranded arms are linked together by one or more linker, such as any of the linkers presented hereinabove. This molecule forms a "star"-like structure, and may also be referred to herein as RNAstar. Such structures are disclosed in PCT patent publication WO 2007/091269, assigned to the assignee of the present invention and incorporated herein in its entirety by reference.

A covalent bond refers to an internucleotide linkage linking one nucleotide monomer to an adjacent nucleotide monomer. A covalent bond includes for example, a phosphodiester bond, a phosphorothioate bond, a P-alkoxy bond, a P-carboxy bond and the like. The normal internucleoside linkage of RNA and DNA is a 3' to 5' phosphodiester linkage. In certain preferred embodiments a covalent bond is a phosphodiester bond. Covalent bond encompasses non-phosphorous-containing internucleoside linkages, such as those disclosed in WO 2004/041924 inter alia. Unless otherwise indicated, in preferred embodiments of the structures discussed herein the covalent bond between each consecutive N or N' is a phosphodiester bond.

For all of the structures above, in some embodiments the oligonucleotide sequence of (N)x is fully complementary to the oligonucleotide sequence of (N')y. In other embodiments (N)x and (N')y are substantially complementary. In certain embodiments (N)x is fully complementary to a target sequence. In other embodiments (N)x is substantially complementary to a target sequence.

In some embodiments, neither (N)x nor (N')y are phosphorylated at the 3' and 5' termini. In other embodiments either or both (N)x and (N')y are phosphorylated at the 3' termini (3' Pi). In yet another embodiment, either or both (N)x and (N')y are phosphorylated at the 3' termini with non-cleavable phosphate groups. In yet another embodiment, either or both (N)x and (N')y are phosphorylated at the terminal 2' termini position using cleavable or non-cleavable phosphate groups. Further, the inhibitory nucleic acid molecules of the present invention may comprise one or more gaps and/or one or more nicks and/or one or more mismatches. Without wishing to be bound by theory, gaps, nicks and mismatches have the advantage of partially destabilizing the nucleic acid/siRNA, so that it may be more easily processed by endogenous cellular machinery such as DICER, DROSHA or RISC into its inhibitory components.

In the context of the present invention, a gap in a nucleic acid refers to the absence of one or more internal nucleotides in one strand, while a nick in a nucleic acid refers to the absence of an internucleotide linkage between two adjacent nucleotides in one strand. Any of the molecules of the present invention may contain one or more gaps and/or one or more nicks.

In one aspect the present invention provides a compound having Structure (I):

(I) 5' (N)x-Z 3' (antisense strand)
3' Z'-(N')y-z" 5' (sense strand)

wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein Z and Z' may be present or absent, but if present is independently 1-5 consecutive nucleotides covalently attached at the 3' terminus of the strand in which it is present;
wherein z" may be present or absent, but if present is a capping moiety covalently attached at the 5' terminus of (N')y;
wherein x=18 to 27;
wherein y=18 to 27;
wherein (N)x comprises modified and unmodified ribonucleotides, each modified ribonucleotide having a 2'-O-methyl on its sugar, wherein N at the 3' terminus of (N)x is a modified ribonucleotide, (N)x comprises at least five alternating modified ribonucleotides beginning at the 3' end and at least nine modified ribonucleotides in total and each remaining N is an unmodified ribonucleotide;
wherein in (N')y at least one unconventional moiety is present, which unconventional moiety may be an abasic ribose moiety, an abasic deoxyribose moiety, a modified or unmodified deoxyribonucleotide, a mirror nucleotide, and a nucleotide joined to an adjacent nucleotide by a 2'-5' internucleotide phosphate bond; and
wherein the sequence of $(N')_y$ is a sequence substantially complementary to (N)x; and wherein the sequence of $(N)_x$ comprises an antisense sequence substantially complementary to from about 18 to about 40 consecutive ribonucleotides in an mRNA of a target gene associated with an ear disorder.

In some embodiments x=y=19. In other embodiments x=y=23. In some embodiments the at least one unconventional moiety is present at positions 15, 16, 17, or 18 in (N')y. In some embodiments the unconventional moiety is selected from a mirror nucleotide, an abasic ribose moiety and an abasic deoxyribose moiety. In some preferred embodiments the unconventional moiety is a mirror nucleotide, preferably an L-DNA moiety. In some embodiments an L-DNA moiety is present at position 17, position 18 or positions 17 and 18.

In other embodiments the unconventional moiety is an abasic moiety. In various embodiments (N')y comprises at least five abasic ribose moieties or abasic deoxyribose moieties.

In yet other embodiments (N')y comprises at least five abasic ribose moieties or abasic deoxyribose moieties and at least one of N' is an LNA.

In some embodiments (N)x comprises nine alternating modified ribonucleotides. In other embodiments of Structure (I) (N)x comprises nine alternating modified ribonucleotides further comprising a 2'O modified nucleotide at position 2. In some embodiments $(N)_x$ comprises 2'O Me modified ribonucleotides at the odd numbered positions 1, 3, 5, 7, 9, 11, 13, 15, 17, 19. In other embodiments (N)x further comprises a 2'O Me modified ribonucleotide at one or both of positions 2 and 18. In yet other embodiments (N)x comprises 2' O Me modified ribonucleotides at positions 2, 4, 6, 8, 11, 13, 15, 17, 19.

In various embodiments z" is present and is selected from an abasic ribose moiety, a deoxyribose moiety; an inverted abasic ribose moiety, a deoxyribose moiety; C6-amino-Pi; a mirror nucleotide.

In another aspect the present invention provides a compound having Structure (J) set forth below:
(J) 5' (N)x-Z 3' (antisense strand)
  3' Z'-(N')y-z" 5' (sense strand)
wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein Z and Z' may be present or absent, but if present is independently 1-5 consecutive nucleotides covalently attached at the 3' terminus of the strand in which it is present;
wherein z" may be present or absent but if present is a capping moiety covalently attached at the 5' terminus of (N')y;
wherein x=18 to 27;
wherein y=18 to 27;
wherein (N)x comprises modified or unmodified ribonucleotides, and optionally at least one unconventional moiety;
wherein in (N')y at least one unconventional moiety is present, which unconventional moiety may be an abasic ribose moiety, an abasic deoxyribose moiety, a modified or unmodified deoxyribonucleotide, a mirror nucleotide, a non-base pairing nucleotide analog or a nucleotide joined to an adjacent nucleotide by a 2'-5' internucleotide phosphate bond; and
wherein the sequence of $(N')_y$ is a sequence substantially complementary to (N)x; and wherein the sequence of $(N)_x$ comprises an antisense sequence substantially complementary to from about 18 to about 40 consecutive ribonucleotides in an mRNA of a target gene associated with an ear disorder.

In some embodiments x=y=19. In other embodiments x=y=23. In some preferred embodiments (N)x comprises modified and unmodified ribonucleotides, and at least one unconventional moiety.

In some embodiments in (N)x the N at the 3' terminus is a modified ribonucleotide and (N)x comprises at least 8 modified ribonucleotides. In other embodiments at least 5 of the at least 8 modified ribonucleotides are alternating beginning at the 3' end. In some embodiments (N)x comprises an abasic moiety in one of positions 5, 6, 7, 8, 9, 10, 11, 12, 13, 14 or 15.

In some embodiments the at least one unconventional moiety in (N')y is present at positions 15, 16, 17, or 18. In some embodiments the unconventional moiety is selected from a mirror nucleotide, an abasic ribose moiety and an abasic deoxyribose moiety. In some preferred embodiments the unconventional moiety is a mirror nucleotide, preferably an L-DNA moiety. In some embodiments an L-DNA moiety is present at position 17, position 18 or positions 17 and 18. In other embodiments the at least one unconventional moiety in (N')y is an abasic ribose moiety or an abasic deoxyribose moiety.

In yet another aspect the present invention provides a compound having Structure (K) set forth below:
(K) 5' (N)x-Z 3' (antisense strand)
  3' Z'-(N')y-z" 5' (sense strand)
wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein Z and Z' may be present or absent, but if present is independently 1-5 consecutive nucleotides covalently attached at the 3' terminus of the strand in which it is present;
wherein z" may be present or absent but if present is a capping moiety covalently attached at the 5' terminus of $(N')_y$;
wherein x=18 to 27;
wherein y=18 to 27;
wherein (N)x comprises a combination of modified or unmodified ribonucleotides and unconventional moieties, any modified ribonucleotide having a 2'-O-methyl on its sugar;
wherein (N')y comprises modified or unmodified ribonucleotides and optionally an unconventional moiety, any modified ribonucleotide having a 2' OMe on its sugar;
wherein the sequence of $(N')_y$ is a sequence substantially complementary to (N)x; and wherein the sequence of $(N)_x$ comprises an antisense sequence substantially complementary to from about 18 to about 40 consecutive ribonucleotides in an of a target gene associated with an ear disorder.

In some embodiments x=y=19. In other embodiments x=y=23. In some preferred embodiments the at least one preferred one unconventional moiety is present in (N)x and is an abasic ribose moiety or an abasic deoxyribose moiety. In other embodiments the at least one unconventional moiety is present in (N)x and is a non-base pairing nucleotide analog. In various embodiments (N')y comprises unmodified ribonucleotides. In some embodiments (N)x comprises at least five abasic ribose moieties or abasic deoxyribose moieties or a combination thereof. In certain embodiments (N)x and/or (N')y comprise modified ribonucleotides which do not base pair with corresponding modified or unmodified ribonucleotides in (N')y and/or (N)x.

In various embodiments the present invention provides an siRNA set forth in Structure (L):
(L) 5' $(N)_x$-Z 3' (antisense strand)
  3' Z'-$(N')_y$ 5' (sense strand)
wherein each of N and N' is a nucleotide selected from an unmodified ribonucleotide, a modified ribonucleotide, an unmodified deoxyribonucleotide and a modified deoxyribonucleotide;
wherein each of $(N)_x$ and $(N')_y$ is an oligonucleotide in which each consecutive N or N' is joined to the next N or N' by a covalent bond;
wherein Z and Z' are absent;
wherein x=y=19;
wherein in (N')y the nucleotide in at least one of positions 15, 16, 17, 18 and 19 comprises a nucleotide selected from an abasic unconventional moiety, a mirror nucleotide, a deoxyribonucleotide and a nucleotide joined to an adjacent nucleotide by a 2'-5' internucleotide bond;
wherein (N)x comprises alternating 2'OMe sugar modified ribonucleotides and unmodified ribonucleotides so as to have 2'OMe sugar modified ribonucleotide at the middle position of (N)x; and
wherein the sequence of $(N')_y$ is a sequence substantially complementary to (N)x; and wherein the sequence of $(N)_x$ comprises an antisense substantially complementary to from about 18 to about 40 consecutive ribonucleotides in an mRNA of a target gene associated with an ear disorder.

In some embodiments of Structure (L), in (N')y the nucleotide in one or both of positions 17 and 18 comprises a modified nucleotide selected from an abasic unconventional moiety, a mirror nucleotide and a nucleotide joined to an adjacent nucleotide by a 2'-5' internucleotide bond. In some embodiments the mirror nucleotide is selected from L-DNA and L-RNA. In various embodiments the mirror nucleotide is L-DNA.

In various embodiments (N')y comprises a modified nucleotide at position 15 wherein the modified nucleotide is selected from a mirror nucleotide and a deoxyribonucleotide.

In certain embodiments (N')y further comprises a modified nucleotide or pseudo nucleotide at position 2 wherein the pseudo nucleotide may be an abasic unconventional moiety and the modified nucleotide is optionally a mirror nucleotide.

In various embodiments the antisense strand (N)x comprises 2'O-Me modified ribonucleotides at the odd numbered positions (5' to 3'; positions 1, 3, 5, 7, 9, 11, 13, 15, 17, 19). In some embodiments (N)x further comprises 2'O-Me modified ribonucleotides at one or both positions 2 and 18. In other embodiments (N)x comprises 2'O Me modified ribonucleotides at positions 2, 4, 6, 8, 11, 13, 15, 17, 19.

Other embodiments of Structures (L) are envisaged wherein x=y=21 or wherein x=y=23; in these embodiments the modifications for (N')y discussed above instead of being in positions 17 and 18 are in positions 19 and 20 for 21-mer oligonucleotide and 21 and 22 for 23 mer oligonucleotide; similarly the modifications in positions 15, 16, 17, 18 or 19 are in positions 17, 18, 19, 20 or 21 for the 21-mer oligonucleotide and positions 19, 20, 21, 22, or 23 for the 23-mer oligonucleotide. The 2'O Me modifications on the antisense strand are similarly adjusted. In some embodiments (N)x comprises 2'O Me modified ribonucleotides at the odd numbered positions (5' to 3'; positions 1, 3, 5, 7, 9, 12, 14, 16, 18, 20 for the 21 mer oligonucleotide [nucleotide at position 11 unmodified] and 1, 3, 5, 7, 9, 11, 13, 15, 17, 19, 21, 23 for the 23 mer oligonucleotide [nucleotide at position 12 unmodified]. In other embodiments (N)x comprises 2'O Me modified ribonucleotides at positions 2, 4, 6, 8, 10, 12, 14, 16, 18, 20 [nucleotide at position 11 unmodified for the 21 mer oligonucleotide and at positions 2, 4, 6, 8, 10, 13, 15, 17, 19, 21, 23 for the 23 mer oligonucleotide [nucleotide at position 12 unmodified].

In some embodiments (N')y further comprises a 5' terminal cap nucleotide. In various embodiments the terminal cap moiety is selected from an abasic unconventional moiety, an inverted abasic unconventional moiety, an L-DNA nucleotide, and a C6-imine phosphate (C6 amino linker with phosphate at terminus).

In other embodiments the present invention provides a compound having Structure (M) set forth below:
(M) 5' (N)$_x$-Z 3' (antisense strand)
  3' Z'-(N')$_y$ 5' (sense strand)
wherein each of N and N' is selected from a pseudo-nucleotide and a nucleotide;
wherein each nucleotide is selected from an unmodified ribonucleotide, a modified ribonucleotide, an unmodified deoxyribonucleotide and a modified deoxyribonucleotide;
wherein each of (N)x and (N')y is an oligonucleotide in which each consecutive N or N' is joined to the next N or N' by a covalent bond;
wherein Z and Z' are absent;
wherein x=18 to 27;
wherein y=18 to 27;
wherein the sequence of (N')$_y$ is a sequence substantially complementary to (N)x; and wherein the sequence of (N)$_x$ comprises an antisense sequence substantially complementary to from about 18 to about 40 consecutive ribonucleotides in an mRNA of a target gene associated with an ear disorder.

In other embodiments the present invention provides a double stranded compound having Structure (N) set forth below:
(N) 5' (N)$_x$-Z 3' (antisense strand)
  3' Z'-(N')$_y$ 5' (sense strand)
wherein each of N and N' is a nucleotide selected from an unmodified ribonucleotide, a modified ribonucleotide, an unmodified deoxyribonucleotide and a modified deoxyribonucleotide;
wherein each of (N)$_x$ and (N')$_y$ is an oligonucleotide in which each consecutive N or N' is joined to the next N or N' by a covalent bond;
wherein Z and Z' are absent;
wherein each of x and y is an integer between 18 and 40;
wherein the sequence of (N')$_y$ is a sequence substantially complementary to (N)x; and wherein the sequence of (N)$_x$ comprises an antisense sequence substantially complementary to from about 18 to about 40 consecutive ribonucleotides in an antisense sequence to the mRNA of a target gene associated with an ear disorder;
wherein (N)x, (N')y or (N)x and (N')y comprise non base-pairing modified nucleotides such that (N)x and (N')y form less than 15 base pairs in the double stranded compound.

In other embodiments the present invention provides a compound having Structure (O) set forth below:
(O) 5' (N)$_x$-Z 3' (antisense strand)
  3' Z'-(N')$_y$ 5' (sense strand)
wherein each of N is a nucleotide selected from an unmodified ribonucleotide, a modified ribonucleotide, an unmodified deoxyribonucleotide and a modified deoxyribonucleotide;
wherein each of N' is a nucleotide analog selected from a six membered sugar nucleotide, seven membered sugar nucleotide, morpholino moiety, peptide nucleic acid and combinations thereof;
wherein each of (N)$_x$ and (N')$_y$ is an oligonucleotide in which each consecutive N or N' is joined to the next N or N' by a covalent bond;
wherein Z and Z' are absent;
wherein each of x and y is an integer between 18 and 40;
wherein the sequence of (N')$_y$ is a sequence substantially complementary to (N)x; and wherein the sequence of (N)$_x$ comprises an antisense sequence substantially complementary to from about 18 to about 40 consecutive ribonucleotides in an mRNA of a target gene associated with an ear disorder.

In other embodiments the present invention provides a compound having Structure (P) set forth below:
(P) 5' (N)$_x$-Z 3' (antisense strand)
  3' Z'-(N')$_y$ 5' (sense strand)
wherein each of N and N' is a nucleotide selected from an unmodified ribonucleotide, a modified ribonucleotide, an unmodified deoxyribonucleotide and a modified deoxyribonucleotide;
wherein each of (N)$_x$ and (N')$_y$ is an oligonucleotide in which each consecutive N or N' is joined to the next N or N' by a covalent bond;
wherein Z and Z' are absent;
wherein each of x and y is an integer between 18 and 40;
wherein one of N or N' in an internal position of (N)x or (N')y or one or more of N or N' at a terminal position of (N)x or (N')y comprises an abasic moiety or a 2' modified nucleotide;
wherein the sequence of (N')$_y$ is a sequence substantially complementary to (N)x; and wherein the sequence of (N)$_x$ comprises an antisense sequence substantially substantially complementary to from about 18 to about 40 consecutive ribonucleotides in an mRNA of a target gene associated with an ear disorder.

In various embodiments (N')y comprises a modified nucleotide at position 15 wherein the modified nucleotide is selected from a mirror nucleotide and a deoxyribonucleotide.

In certain embodiments (N')y further comprises a modified nucleotide at position 2 wherein the modified nucleotide is selected from a mirror nucleotide and an abasic unconventional moiety.

In various embodiments the antisense strand (N)x comprises 2'O-Me modified ribonucleotides at the odd numbered positions (5' to 3'; positions 1, 3, 5, 7, 9, 11, 13, 15, 17, 19). In some embodiments (N)x further comprises 2'O-Me modified ribonucleotides at one or both positions 2 and 18. In other embodiments (N)x comprises 2'O Me modified ribonucleotides at positions 2, 4, 6, 8, 11, 13, 15, 17, 19.

An additional novel molecule provided by the present invention is an oligonucleotide comprising consecutive nucleotides wherein a first segment of such nucleotides encode a first inhibitory RNA molecule, a second segment of such nucleotides encode a second inhibitory RNA molecule, and a third segment of such nucleotides encode a third inhibitory RNA molecule. Each of the first, the second and the third segment may comprise one strand of a double stranded RNA and the first, second and third segments may be joined together by a linker. Further, the oligonucleotide may comprise three double stranded segments joined together by one or more linker.

Thus, one molecule provided by the present invention is an oligonucleotide comprising consecutive nucleotides which encode three inhibitory RNA molecules; said oligonucleotide may possess a triple stranded structure, such that three double stranded arms are linked together by one or more linker, such as any of the linkers presented hereinabove. This molecule forms a "star"-like structure, and may also be referred to herein as RNAstar.

Said triple-stranded oligonucleotide may be an oligoribonucleotide having the general structure:

| | | |
|---|---|---|
| 5' Oligo1 (sense) | LINKER A | Oligo2 (sense) 3' |
| 3' Oligo1 (antisense) | LINKER B | Oligo3 (sense) 5' |
| 3' Oligo3 (antisense) | LINKER C | Oligo2 (antisense) 5' |
| or | | |
| 5' Oligo1 (sense) | LINKER A | Oligo2 (antisense) 3' |
| 3' Oligo1 (antisense) | LINKER B | Oligo3 (sense) 5' |
| 3' Oligo3 (antisense) | LINKER C | Oligo2 (sense) 5' |
| or | | |
| 5' Oligo1 (sense) | LINKER A | Oligo3 (antisense) 3' |
| 3' Oligo1 (antisense) | LINKER B | Oligo2 (sense) 5' |
| 5' Oligo3 (sense) | LINKER C | Oligo2 (antisense) 3' | wherein one or more of linker A, linker B or linker C is present; any combination of two or more oligonucleotides and one or more of linkers A-C is possible, so long as the polarity of the strands and the general structure of the molecule remains. Further, if two or more of linkers A-C are present, they may be identical or different.

Thus, a triple-armed structure is formed, wherein each arm comprises a sense strand and complementary antisense strand (i.e. Oligo1 antisense base pairs to Oligo1 sense etc.). The triple armed structure may be triple stranded, whereby each arm possesses base pairing.

Further, the above triple stranded structure may have a gap instead of a linker in one or more of the strands. Such a molecule with one gap is technically quadruple stranded and not triple stranded; inserting additional gaps or nicks will lead to the molecule having additional strands. Preliminary results obtained by the inventors of the present invention indicate that said gapped molecules are more active in inhibiting certain target genes than the similar but non-gapped molecules. This may also be the case for nicked molecules.

According to one preferred embodiment of the invention, the antisense and the sense strands of the siRNA are phosphorylated only at the 3'-terminus and not at the 5'-terminus. According to another preferred embodiment of the invention, the antisense and the sense strands are non-phosphorylated. According to yet another preferred embodiment of the invention, the 5' most ribonucleotide in the sense strand is modified to abolish any possibility of in vivo 5'-phosphorylation.

The invention further provides a vector capable of expressing any of the aforementioned oligoribonucleotides in unmodified form in a cell after which appropriate modification may be made. In preferred embodiment the cell is a mammalian cell, preferably a human cell.

Pharmaceutical Compositions

The inventors of the present invention have overcome many of the obstacles in development of a composition for delivery of a therapeutic oligonucleotide to the middle and inner ear. Accordingly the present invention provides a pharmaceutical composition comprising one or more inhibitory oligonucleotide compounds; a permeability enhancer and a pharmaceutically acceptable vehicle or carrier. In some embodiments the composition comprises a mixture of two or more different oligonucleotides/siRNA compound.

A "penetration enhancer" or "permeability enhancer" includes a polyol such as polyethylene glycol (PEG), glycerol (glycerin), maltitol, sorbitol etc.; diethylene glycol monoethyl ether, azone, benzalkonium chloride (ADBAC), cetylperidium chloride, cetylmethylammonium bromide, dextran sulfate, lauric acid, menthol, methoxysalicylate, oleic acid, phosphatidylcholine, polyoxyethylene, polysorbate 80, sodium glycholate, sodium lauryl sulfate, sodium salicylate, sodium taurocholate, sodium taurodeoxycholate, sulfoxides, sodium deoxycholate, sodium glycodeoxycholate, sodium taurocholate and surfactants such as sodium lauryl sulfate, laureth-9, cetylpyridinium chloride and polyoxyethylene monoalkyl ethers, benzoic acids, such as sodium salicylate and methoxy salicylate, fatty acids, such as lauric acid, oleic acid, undecanoic acid and methyl oleate, fatty alcohols, such as octanol and nonanol, laurocapram, cyclodextrins, thymol, limonene, urea, chitosan and other natural and synthetic polymers.

Suitable polyols for inclusion in the solutions of the invention include glycerol and sugar alcohols such as sorbitol, mannitol or xylitol, polyethylene glycol and derivatives thereof. In some embodiments the composition further includes a preservative. Accepted preservatives such as benzalkonium chloride and disodium edetate (EDTA) are included in the compositions of the invention in concentrations sufficient for effective antimicrobial action, about 0.0001 to 0.1%, based on the weight of the composition.

The invention further provides a pharmaceutical composition comprising at least one compound of the invention covalently or non-covalently bound to one or more compounds of the invention in an amount effective to inhibit one or more genes as disclosed above; and a pharmaceutically acceptable carrier. In some embodiments the compound is processed intracellularly by endogenous cellular complexes to produce one or more oligoribonucleotides of the invention.

Additionally, the invention provides a method of inhibiting the expression of a target gene, by at least 50% as compared to a control, comprising contacting an mRNA transcript of the target gene with composition of the invention. In some embodiments an active siRNA compound inhibits gene expression at a level of at least 50%, 60% or 70% as compared to control. In certain preferred embodiments inhibition is at a level of at least 75%, 80% or 90% as compared to control. In some embodiments the target gene is a human gene as disclosed herein.

In one embodiment the oligoribonucleotide inhibits one or more of the genes as disclosed in the present invention, whereby the inhibition is selected from the group comprising inhibition of gene function, inhibition of polypeptide and inhibition of mRNA expression. In certain embodiments, the target gene is a viral, bacterial or mammalian gene. In various embodiments the target gene is a mammalian gene, preferably a human gene. In some embodiments the target gene having an mRNA selected from any one of SEQ ID NO:1-SEQ ID NO:36.

In one embodiment the compound inhibits expression of a polypeptide encoded by a target gene whereby the inhibition is selected from the group comprising inhibition of function (which may be examined by an enzymatic assay or a binding assay with a known interactor of the native gene/polypeptide, inter alia), inhibition of protein (which may be examined by Western blotting, ELISA or immuno-precipitation, inter alia) and inhibition of mRNA expression (which may be examined by Northern blotting, quantitative RT-PCR, in-situ hybridisation or microarray hybridisation, inter alia).

In additional embodiments the invention provides a method of treating a subject suffering from a disease accompanied by an elevated level a gene of the present invention, the method comprising administering to the subject a compound of the invention in a therapeutically effective dose thereby treating the subject.

Delivery

The siRNA molecules of the present invention is delivered to the ear by direct application of pharmaceutical composition to the outer ear. In some embodiments the pharmaceutical composition is applied to the ear canal. Delivery to the ear may also be refereed to as aural or otic delivery comprising siRNA; a penetration enhancer and a pharmaceutically acceptable vehicle.

In some embodiments the siRNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed, (see, for example, Shen et al FEBS Let. 2003, 539:111-114; Xia et al., Nat. Biotech. 2002, 20:1006-1010; Reich et al., Mol. Vision. 2003, 9: 210-216; Sorensen et al., J. Mol. Biol. 2003. 327: 761-766; Lewis et al., Nat. Gen. 2002, 32: 107-108 and Simeoni et al., NAR 2003, 31, 11: 2717-2724). siRNA has recently been successfully used for inhibition of gene expression in primates (see for example, Tolentino et al., Retina 24(4):660.

The "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art.

In general, the active dose of compound for humans is in the range of from 1 ng/kg to about 20-100 mg/kg body weight per day, preferably about 0.01 mg to about 2-10 mg/kg body weight per day, in a regimen of one dose per day or twice or three or more times per day for a period of 1-4 weeks or longer. In various embodiments the siRNA is chemically modified to increase stability, increase activity, reduce off target effects, and or to reduce innate immune stimulation. Dosage to the ear is determined, inter alia, by the activity of the oligonucleotide, the indication and the severity of the disorder and comprises administering a dose of about 0.1 ng to about 10 mg, about 1 ng to about 1 mg, or about 10 ng to about 1 mg, total oligonucleotide in pharmaceutically acceptable agent. The concentration of siRNA in the composition is between 0.1 mg/ml to 100 mg/ml, preferably between 1 mg/ml to 100 mg/ml, and more preferably between 5 mg/ml to 20 mg/ml.

The compounds of the present invention are administered by topical administration. It should be noted that the compound can be administered as the compound or as pharmaceutically acceptable salt and can be administered alone or as an active ingredient in combination with pharmaceutically acceptable carriers, solvents, diluents, excipients, adjuvants and vehicles. The compounds are administered as eardrops, ear cream, ear ointment, foam, mousse or any of the above in combination with a delivery device. Implants of the compounds are also useful. Liquid forms are prepared as drops. The liquid compositions include aqueous solutions, with and without organic co-solvents, aqueous or oil suspensions, emulsions with edible oils, as well as similar pharmaceutical vehicles. In another embodiment the administration comprises non-invasive topical or local administration. Eardrops may also be referred to as otic drops or aural drops. In a preferred embodiment, the ear drops remain in the ear canal for about 30 min in order to prevent leakage of the drops out of the canal. It is thus preferable that the subject receiving the drops keep his head on the side with the treated ear facing upward to prevent leakage of the drop out of the canal.

In preferred embodiments the subject being treated is a warm-blooded animal and, in particular, mammals including human.

Methods of Treatment

In another aspect, the present invention relates to a method for the treatment of a subject in need of treatment for an ear disease or disorder associated with the abnormal expression of a target gene, comprising administering to the subject an amount of an oligonucleotide which reduces or inhibits expression of a target gene associated with the ear disorder in a pharmaceutical composition comprising the oligonucleotide, a permeability enhancer and a pharmaceutically acceptable carrier. In some embodiments the target gene is listed in Table 1. In a preferred embodiment, the target gene is selected from one or more of: TP53BP2 (ASPP2), BNIP3, CASP2, NOX3, HRK, RAC1, DDIT4, DDIT4L, NOX4, HTRA2, CAPNS1 (Calpain), ID3, HES1, HES5, CDKN1B and ID3.

In preferred embodiments the subject being treated is a warm-blooded animal and, in particular, mammals including human.

The methods of the invention comprise administering to the subject a pharmaceutical composition comprising one or more inhibitory compounds which down-regulate expression of a gene associated with an ear disorder; and a pharmaceutically acceptable vehicle, in a therapeutically effective dose so as to thereby treat the subject.

The term "treatment" refers to both therapeutic treatment and prophylactic or preventative measures, wherein the object is to prevent or slow down (lessen) the ear disorder. Those in need of treatment include those already experiencing the disease or condition, those prone to having the disease or condition, and those in which the disease or condition is to be prevented. The compounds of the invention may be administered before, during or subsequent to the onset of the disease or condition or symptoms associated therewith. In cases where treatment is for the purpose of prevention, then the present invention relates to a method for delaying the onset of or averting the development of the disease or disorder. In some embodiments the method comprises administering eardrops which are warmed to 35° C. to about 38° C. to the subject's ear. In some embodiments the method of comprises administering the composition of the present invention unilaterally, e.g. to one of the subject's ear. In various embodiments the composition is allowed to penetrate the subject's ear for about 5 minutes to about 60 minutes.

One aspect of the present invention relates to combination therapy. The active ingredients that comprise a combination therapy may be administered together via a single dosage form or by separate administration of each active agent. In some embodiments the combination therapy comprises administering to a subject in need thereof a composition according to the present invention and an ototoxin. For example, the present invention is directed to an improved method for treatment of hearing loss in a mammal comprising co-administering to the mammal an ototoxin and a therapeutically effective amount of one or more compounds of the present invention. Ototoxic agents include cisplatin and cisplatin-like compounds, aminoglycosides, loop diuretics, and hydroquinone and their analogs.

Co-administration comprises administering two or more agents, each of which is formulated and administered separately, or by administering two or more agents in a single formulation. While the two or more agents can be administered simultaneously, they need not be. For example, administration of a first agent (or combination of agents) can precede administration of a second agent (or combination of agents) by minutes, hours, days, or weeks. Thus, the two or more agents can be administered within minutes of each other or within any number of hours of each other or within any number or days or weeks of each other. In some cases even longer intervals are possible.

Methods, molecules and compositions, which inhibit the genes of the invention, are discussed herein at length, and any of said molecules and/or compositions may be beneficially employed in the treatment of a subject suffering from any of said conditions.

The present invention also provides for a process of preparing a pharmaceutical composition, which comprises:
providing one or more compounds of the invention; and
admixing said compound with a pharmaceutically acceptable carrier.

The present invention also provides for a process of preparing a pharmaceutical composition, which comprises admixing one or more compounds of the present invention with a pharmaceutically acceptable carrier.

In a preferred embodiment, the compound used in the preparation of a pharmaceutical composition is admixed with a carrier in a pharmaceutically effective dose. In a particular embodiment the compound of the present invention is conjugated to a steroid or to a lipid or to another suitable molecule e.g. to cholesterol.

Oligonucleotide Synthesis

The compounds of the present invention can be synthesized by any of the methods that are well-known in the art for synthesis of ribonucleic (or deoxyribonucleic) oligonucleotides. Such synthesis is, among others, described in Beaucage and Iyer, Tetrahedron 1992; 48:2223-2311; Beaucage and Iyer, Tetrahedron 1993; 49: 6123-6194 and Caruthers, et. al., Methods Enzymol. 1987; 154: 287-313; the synthesis of thioates is, among others, described in Eckstein, Annu. Rev. Biochem. 1985; 54: 367-402, the synthesis of RNA molecules is described in Sproat, in Humana Press 2005 edited by Herdewijn P.; Kap. 2: 17-31 and respective downstream processes are, among others, described in Pingoud et. al., in IRL Press 1989 edited by Oliver R. W. A.; Kap. 7: 183-208.

Other synthetic procedures are known in the art e.g. the procedures as described in Usman et al., J. Am. Chem. Soc., 1987, 109:7845; Scaringe et al., NAR, 1990, 18:5433; Wincott et al., NAR 1995, 23:2677-2684; and Wincott et al., Methods Mol. Bio., 1997, 74:59, and these procedures may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

The oligonucleotides of the present invention can be synthesized separately and joined together post-synthetically, for example, by ligation (Moore et al., Science 1992, 256:9923; International Patent Publication No. WO 93/23569; Shabarova et al., NAR 1991, 19:4247; Bellon et al., Nucleosides & Nucleotides, 1997, 16:951; Bellon et al., Bioconjugate Chem 1997, 8:204), or by hybridization following synthesis and/or deprotection.

It is noted that a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the siRNAs or siRNA fragments of the present invention, two or more such sequences can be synthesized and linked together for use in the present invention.

The compounds of the invention can also be synthesized via tandem synthesis methodology, as described for example in US Patent Publication No. 2004/0019001 (McSwiggen), wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker can be a polynucleotide linker or a non-nucleotide linker.

The present invention further provides for a pharmaceutical composition comprising two or more siRNA molecules for the treatment of any of the diseases and conditions mentioned herein, whereby said two molecules may be physically mixed together in the pharmaceutical composition in amounts which generate equal or otherwise beneficial activity, or may be covalently or non-covalently bound, or joined together by a nucleic acid linker of a length ranging from 2-100, preferably 2-50 or 2-30 nucleotides.

Thus, the siRNA molecules may be covalently or non-covalently bound or joined by a linker to form a tandem siRNA compound. Such tandem siRNA compounds comprising two siRNA sequences are typically about 38-150 nucleotides in length, more preferably 38 or 40-60 nucleotides in length, and longer accordingly if more than two siRNA sequences are included in the tandem molecule. A longer tandem compound comprised of two or more longer sequences which encode siRNA produced via internal cellular processing, e.g., long dsRNAs, is also envisaged, as is a tandem molecule encoding two or more shRNAs. Such tandem molecules are also considered to be a part of the present invention. A tandem compound comprising two or more siRNAs sequences of the invention is envisaged.

An siRNA molecule that targets a gene associated with an ear disorder may be the main active component in a pharmaceutical composition, or may be one active component of a pharmaceutical composition containing two or more siRNAs (or molecules which encode or endogenously produce two or more siRNAs, be it a mixture of molecules or one or more tandem molecules which encode two or more siRNAs), said pharmaceutical composition further being comprised of one or more additional siRNA molecule which targets one or more additional gene. Simultaneous inhibition of said additional gene(s) will likely have an additive or synergistic effect for treatment of the diseases disclosed herein.

Additionally, the siRNA disclosed herein or any nucleic acid molecule comprising or encoding such siRNA can be linked or bound (covalently or non-covalently) to antibodies (including aptamer molecules) against cell surface internalizable molecules expressed on the target cells, in order to achieve enhanced targeting for treatment of the diseases disclosed herein. For example, anti-Fas antibody (preferably a neutralizing antibody) may be combined (covalently or non-covalently) with any other siRNA.

The compounds of the present invention can be delivered for example as double stranded compounds, as double stranded hairpin compounds or as tandem compounds. It is also envisaged that a long oligonucleotide (typically 25-500 nucleotides in length) comprising one or more stem and loop structures, where stem regions comprise the sequences of the oligonucleotides of the invention, may be delivered in a carrier, preferably a pharmaceutically acceptable carrier, and may be processed intracellularly by endogenous cellular complexes (e.g. by DROSHA and DICER as described above) to produce one or more smaller double stranded oligonucleotides (siRNAs) which are oligonucleotides of the invention. This oligonucleotide can be termed a tandem shRNA construct. It is envisaged that this long oligonucleotide is a single stranded oligonucleotide comprising one or more stem and loop structures, wherein each stem region comprises a sense and corresponding antisense siRNA sequence of the genes of the invention. In particular, it is envisaged that this oligonucleotide comprises an antisense sequence (N)x relative to the mRNA transcribed from a mammalian gene selected from the group set forth in Table 1. In a preferred embodiment, the target gene is selected from one or more of: TP53BP2 (ASPP2), BNIP3, CASP2, NOX3, HRK, RAC1, DDIT4, DDIT4L, NOX4, HTRA2, CAPNS1 (Calpain), ID3, HES1, HES5, CDKN1B and ID3.

A number of PCT applications have recently been published that relate to the RNAi phenomenon. These include: PCT publication WO 00/44895; PCT publication WO 00/49035; PCT publication WO 00/63364; PCT publication WO 01/36641; PCT publication WO 01/36646; PCT publication WO 99/32619; PCT publication WO 00/44914; PCT publication WO 01/29058; and PCT publication WO 01/75164.

RNA interference (RNAi) is based on the ability of dsRNA species to enter a cytoplasmic protein complex, where it is then targeted to the complementary cellular RNA and specifically degrade it. The RNA interference response features an endonuclease complex containing an siRNA, commonly referred to as an RNA-induced silencing complex (RISC), which mediates cleavage of single-stranded RNA having a sequence complementary to the antisense strand of the siRNA duplex. Cleavage of the target RNA may take place in the middle of the region complementary to the antisense strand of the siRNA duplex (Elbashir et al., Genes Dev., 2001, 15(2): 188-200). In more detail, longer dsRNAs are digested into short (17-29 bp) dsRNA fragments (also referred to as short inhibitory RNAs, "siRNAs") by type III RNAses (DICER, DROSHA, etc.; Bernstein et al., Nature, 2001, 409(6818): 363-6; Lee et al., Nature, 2003, 425(6956):415-9). The RISC protein complex recognizes these fragments and complementary mRNA. The whole process is culminated by endonuclease cleavage of target mRNA (McManus & Sharp, Nature Rev Genet, 2002, 3(10):737-47; Paddison & Hannon, Curr Opin Mol. Ther. 2003, 5(3):217-24). (For additional information on these terms and proposed mechanisms, see for example Bernstein et al., RNA 2001, 7(11):1509-21; Nishikura, Cell 2001, 107(4):415-8 and PCT publication WO 01/36646).

Several groups have described the development of DNA-based vectors capable of generating siRNA within cells. The method generally involves transcription of short hairpin RNAs that are efficiently processed to form siRNAs within cells (Paddison et al. PNAS USA 2002, 99:1443-1448; Paddison et al. Genes & Dev 2002, 16:948-958; Sui et al. PNAS USA 2002, 8:5515-5520; and Brummelkamp et al. Science 2002, 296:550-553). These reports describe methods to of generate generating siRNAs capable of specifically targeting numerous endogenously and exogenously expressed genes.

The invention has been described in an illustrative manner, and it is to be understood that the terminology used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described. Throughout this application, various publications, including United States patents, are referenced by author and year and patents by number. The disclosures of these publications and patents and patent applications in their entireties are hereby incorporated by reference into this application in order to more fully describe the state of the art to which this invention pertains.

The present invention is illustrated in detail below with reference to examples, but is not to be construed as being limited thereto.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Material and Methods: General

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Md. (1988), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In situ (In cell) PCR in combination with Flow Cytometry can be used for detection of cells containing specific DNA and mRNA sequences (Testoni et al., Blood 1996, 87:3822.) Methods of performing RT-PCR are also well known in the art.

Cell Culture:

HeLa cells (American Type Culture Collection) were cultured as described in Czauderna, et al. (NAR, 2003. 31:670-82). Human keratinocytes were cultured at 37° C. in Dulbecco's modified Eagle medium (DMEM) containing 10% FCS. The mouse cell line, B16V (American Type Culture Collection), was cultured at 37° C. in Dulbecco's modified Eagle medium (DMEM) containing 10% FCS. Culture conditions were as described in (Methods Find Exp Clin Pharmacol. 1997 May; 19(4):231-9).:

In each case, the cells were subject to the experiments as described herein at a density of about 50,000 cells per well and the double-stranded nucleic acid according to the present invention was added at 20 nM, whereby the double-stranded nucleic acid was complexed using 1 µg/ml of a proprietary lipid as described below.

Induction of Hypoxia-Like Conditions:

Where required, cells were treated with $CoCl_2$ for inducing a hypoxia-like condition as follows: siRNA transfections were carried out in 10-cm plates (30-50% confluency) as described by Czauderna et al., 2003; Kretschmer et al., 2003. Briefly, siRNA were transfected by adding a preformed 10× concentrated complex of GB and lipid in serum-free medium to cells in complete medium. The total transfection volume was 10 ml. The final lipid concentration was 1.0 µg/ml; the final siRNA concentration was 20 nM unless otherwise stated. Induction of the hypoxic responses was carried out by adding $CoCl_2$ (100 µM) directly to the tissue culture medium 24 h before lysis.

Preparation of Cell Extracts and Immuno Blotting

The preparation of cell extracts and immuno blot analysis were carried out essentially as described (Klippel et al. Mol Cell Biol, 1998. 18:5699-711; Klippel, A., et al., Mol Cell Biol, 1996. 16:4117-27).

Example 1

In Vitro Testing of siRNA Compounds

About $1.5\text{-}2\times10^5$ tested cells (HeLa cells and/or 293T cells for siRNA targeting human genes and NRK52 cells and/or NMUMG cells for siRNA targeting the rat/mouse gene) were seeded per well in a 6 well plate (70-80% confluent).

24 hours later, cells were transfected with siRNA compounds using the Lipofectamine™ 2000 reagent (Invitrogen) at final concentrations of 5 nM or 20 nM. The cells were incubated at 37° C. in a $CO_2$ incubator for 72 hours.

As positive control for transfection PTEN-Cy3 labeled siRNA compounds were used. An additional positive control used was a blunt-ended 19-mer siRNA, i.e. x=y=19 wherein Z and Z' are both absent. This siRNA was non-phosphorylated and had alternating ribonucleotides modified at the 2' position of the sugar residue in both the antisense and the sense strands, wherein the moiety at the 2' position is methoxy (2'OMe) and wherein the ribonucleotides at the 5' and 3' termini of the antisense strand are modified in their sugar residues, and the ribonucleotides at the 5' and 3' termini of the sense strand are unmodified in their sugar residues.

As negative control for siRNA activity GFP siRNA compounds were used.

At 72 hours after transfection the cells were harvested and RNA is extracted from the cells. Transfection efficiency was tested by fluorescent microscopy.

The percent of inhibition of gene expression using specific preferred siRNA structures is determined using qPCR analysis of a target gene in cells expressing the endogenous gene. In general, the siRNAs having specific sequences that were selected for in vitro testing were specific for human and a second species such as rat or rabbit genes. In some examples, similar results are obtained using siRNAs having these RNA sequences and modified as described herein. The siRNA oligomers tested herein are selected from siRNA compounds comprising oligonucleotides in FIG. 4, from Tables B of U.S. Ser. No. 11/978,089, which are hereby incorporated by reference in their entirety and are set forth as SEQ ID NOS:97-68654. The siRNA oligomers tested herein are also disclosed in U.S. Ser. Nos. or PCT application Ser. Nos. 11/207,119, 11/811,112, 11/655,636, PCT/IL2008/000797, PCT/IL2008/000874, PCT/IL2009/000053, PCT/IL2009/000302 which are hereby incorporated by reference in their entirety.

Example 2

Middle/Inner Ear Delivery Routes of Cy3 Labelled DDIT4 1 siRNA

The objectives of the study were as follows: To establish procedures for topical, non-invasive delivery of a therapeutic oligonucleotide to the middle/inner ear.

To estimate the temporal pattern of distribution of siRNA DDIT4-Cy3 into cochlear structures, following instillation of pharmaceutical compositions into right external auditory canal in rats (REAC).

The substance tested was Cy3-labeled siRNA against RTP801 (DDIT4_1-Cy3) (sense strand: GUGCCAAC-CUGAUGCAGCU (SEQ ID NO:5843); antisense strand: AGCUGCAUCAGGUUGGCAC (SEQ ID NO:5844)).

Description of the test material: double-stranded Cy3-labeled 19-mer siRNA, Cy3 is linked to the 3' end of the anti-sense strand via a dT nucleotide. Both sense and anti-sense strands harbor alternating 2'-OMe modifications on every odd nucleotide of the anti-sense strand and on every even nucleotide of the sense strand. Under sterile conditions, 42.43 mg of DDIT4_1-Cy3 powder (BioSpring) were dissolved in 2.1 ml of sterile double distilled water, to achieve clear 20 mg/ml (1.5 mM) solution. The solution was stored at −80° C. until use. Formulated (formulated compound) sterile 10 mg/ml Cy3DDIT4_1 in 20% sterile glycerol solution in pyrogen free water.

Control Article(s) (including positive/negative controls and vehicle)

Vehicle −20% sterile glycerol solution in pyrogen free water.

Test system: Male rats, 10-14 weeks old, weighing 200-220 gr

Experimental design: The study included 5 experimental groups as described in Table 2, below: Experimental groups I-IV (treated with siRNA (DDIT4_1-Cy3) glycerol based eardrop/3 rats/time point) and group V (a; b and c)-3 rats/time point (20% glycerol treated control group). Rats were treated with a single siRNA (DDIT4_1-Cy3) glycerol based or 20% glycerol only eardrop (warmed to 37° C.; only one ear treated: a.d.=aurio dexrta=right ear (right external auditory canal: REAC)/a.s. aurio sinister=left ear was used as non-treated control) as follows:

Groups I-IV: dose regime: 100 μg/10 μl/ear of 20% glycerol/time point, administration route: REAC 3 rats per time point.

Group V (a-c): REAC 10 μl 20% glycerol only treated control.

TABLE 2

Study Design

| Group | SiRNA Type | Dose μg/rat | Volume (μl) | Route | Time point (Days) | Group Size |
|---|---|---|---|---|---|---|
| I | DDIT4_1-Cy3 | 100 μg | 10.00 | REAC | 1 | 3 |
| II | DDIT4_1-Cy3 | 100 μg | 10.00 | REAC | 3 | 3 |
| III | DDIT4_1-Cy3 | 100 μg | 10.00 | REAC | 7 | 3 |
| IV | DDIT4_1-Cy3 | 100 μg | 10.00 | REAC | 14 | 3 |
| V (a, b, c) | Glycerol 20% | none | 10.00 | REAC | 3; 7; 14 | 3 × 3 |

Preparation of test and control articles for administration: One (1) ml of 100% glycerol with 4 ml pyrogen free water, were mixed by inversion for no less than 30 minutes.

Anesthesia: Rats were anesthetized with Equithesine 4 ml/kg body weight.

Right external auditory canal (REAC) delivery: A 10 μl sample volume (warm glycerol based eardrops, 37° C.) was slowly instilled into external REAC, using blunt pipette tip. This volume was delivered into each right ear (groups I-IV according study design). During and after REAC instillations, rats were observed and returned to cage after regaining consciousness.

Scheduled euthanasia: Rats from all groups were euthanized according to the study design (Table 2, Time points termination).

Termination step: was accomplished by cardiac puncture and blood collection; collected serum/plasma was stored (−20° C.) for further siRNA blood detection analysis (back up).

Tissue Collection: Rats were sacrificed. Left and right temporal bones including cochlea were gently harvested from all animals; and bony cochlea were prepared and proceed for cryosections as described below.

Tissue Embedding Protocol for Cryosections

Perforated bony cochlea: the cochlear apical end of the cochlear capsule was placed in fixative: 4% PFA in PBS pH 7.2-7.4 and incubated at room temperature 1.5 h with rotation on a rotator. The samples were washed 3×5 min with PBS with rotation. The bony cochlea was decalcified in 10% EDTA/PBS pH 7.2-7.4 overnight or longer at 4° C. with rotation. Decalcification was determined by gently pressing on the bony cochlea with a forceps/syringe needles. If decalcification required more time, the decalcification solution (fresh 10% EDTA in PBS) was changed.

For the infiltration step: stock solutions of 10% and 30% sucrose in PBS were prepared. The tissue was rinsed 2×5 min in PBS, pH 7.2-7.4, followed by washing 30 min in 10% sucrose, at room with rotation on the tissue rotator. The tissue was washed 30 min in a 2:1 solution of 10:30% sucrose at of the room temperature with rotation, followed by a 30 min wash in a 1:1 solution of 10:30% sucrose at room temperature with rotation, then in a 1:2 solution of 10:30% sucrose at room temperature with rotation for 30 min, and finally at 4° C. in 30% sucrose with rotation, overnight.

The cochleae were transferred into tubes with degassed OCT (30 min in desiccator) and the vials maintained at 4° C. overnight with rotation.

The cochleae were placed in the OCT and oriented by aligning an imaginary plane through the modiolus parallel with the bottom of the embedding mold, followed by placement in cryostat for cryosectioning.

Evaluation:

Delivery of siRNA was evaluated using fluorescent microscopy and digital imaging. A tissue fragments (cochlea) will be considered positive (i.e., a successful Cy3 DDIT4_1 siRNA transfer incorporation occurred) only if histological (microscopic) examination showed clear fluorescence signal within specific cochlear structures. Background DAPI staining was assisted in identification of cochlea tissue (anatomical or topographical) structure. Inner ear delivery was considered positive if histological examination showed consistency within the group (i.e. time points, time course etc).

FIG. 1 shows the delivery of Cy3-labelled DDIT4 siRNA into the spiral ganglion (ganglion of Corti) in the apical turn of the organ of Corti following application of ear drops containing Cy3-labelled siRNA formulated in 20% glycerol. Upper panel is X40 magnification of phalloidin-labelled cells (left panel), bright field (BF, right panel) and the merge thereof (middle panel, M). Bottom panel is X60 magnification of phalloidin-labelled cells (left panel), bright field (BF, right panel) and the merge thereof (middle panel, M). Three days after eardrop application (100 ug in 10 ul of 20% glycerol of Cy3-labeled DDIT4 siRNA) the rats were perfused with 4% PFA. Temporal bones were removed and the bony cochleae were dissected. Whole mount Corti were prepared with Alexa488 labelled phalloidin which binds to actin filaments. Delivery of siRNA was evaluated using confocal microscopy and digital imaging. A tissue fragment was considered positive (i.e., a successful Cy3 DDIT4 siRNA transfer intracellular incorporation occurred) only where histological (microscopic) examination showed clear fluorescence signal within specific cells or structures.

Figure 2:
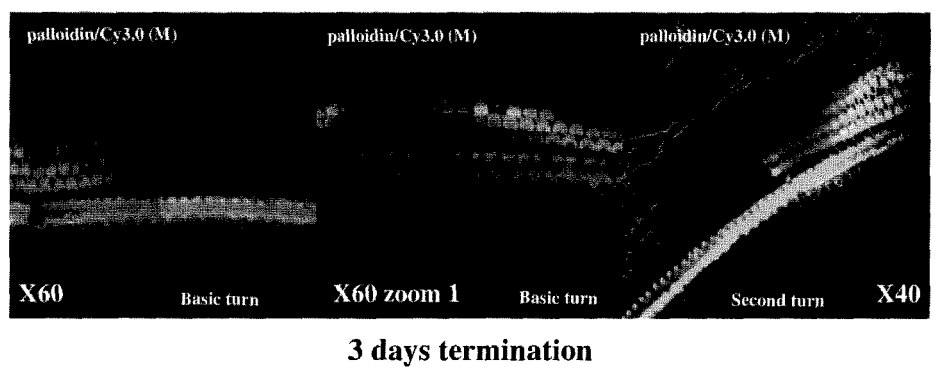
FIG. 2. Shows Cy3 labelled DDIT4 siRNA in three rows of outer hear cells, inner hear cells and supporting cells in all, basic, second and apical turns of organ of Corti.
Figure 2:
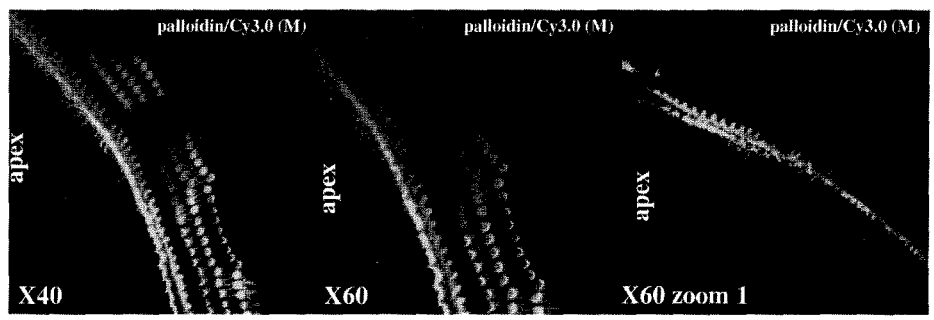

FIG. 2 shows the delivery of Cy3 labelled DDIT4 siRNA in three rows of outer hair cells, inner hair cells and supporting cells in basic, second and apical turns of organ of Corti. The delivery of Cy3 labelled DDIT4 siRNA was determined three days after eardrop application (100 ug in 10 ul of 20% glycerol of Cy3-labeled DDIT4 siRNA).

Figure 3:
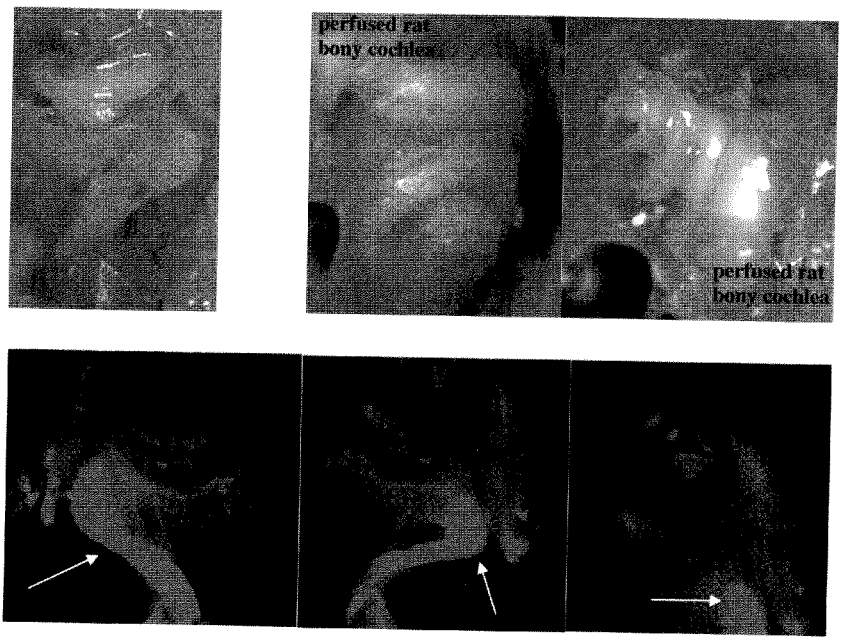
FIG. 3. Shows fluorescence in all parts of the auditory epithelium of dissected rat cochlea 3 days post administration of eardrops (perfused and non perfused).

FIG. 3 shows the delivery of Cy3 labelled DDIT4 siRNA into the rat auditory epithelium. Top panel is dissected rat bony cochlea (perfused with 4% PFA). Bottom panel demonstrates the delivery of Cy3 labelled DDIT4 siRNA into the basic, second and apical turns of the auditory epithelium.

Example 3

Examination of Inner Ear Non-Invasive Delivery of Formulated Cy3-DDIT4 1 siRNA in Rats Description of the test material: double-stranded Cy3-labeled 19-mer DDIT4_1 siRNA, Cy3 is linked to the 3' end of the antisense strand via an extra 'dT' nucleotide. Both sense and anti-sense strands harbor alternating 2'OMe sugar modified ribonucleotides on every odd nucleotide of the antisense strand and on every even nucleotide of the sense strand.

Three different formulations were tested:

Formulation 1: 100 μg of Cy3 DDIT4 siRNA in 10 μl of 30% glycerol.

Formulation 2: 100 μg of Cy3 DDIT4 siRNA in 10 μl of PBS.

Formulation 3: 100 ng of Cy3 DDIT4 siRNA in 10 µl of 20% mineral oil (v/v), 40% Propylene glycol (v/v) and 10% Ethanol (v/v).

Right external auditory canal (REAC) delivery: A 10 µl sample volume (warm formulated eardrops, 37° C.) was

| Group No.: | Treatment QM5 siRNA 100 µg/10 µl of 30% glycerol | Delivery route REAC (10 µl) | Cisplatin I.P. dose regime (2 mg/kg) | Termination time point (hrs) | Group size |
|---|---|---|---|---|---|
| I | Day 1 | ErD | X5 | 72 | 19 |
| II | none | none | none | N/A | 12 (6 × 2) | slowly instilled into external REAC, using blunt pipette tip. This volume was delivered into the right ear. During and after REAC instillations, rats were kept on contralateral side for 40 minutes and returned to its cage following recovery.

Tissue Collection: Rats were decapitated. Both temporal bones were gently harvested from all animals and postfixed for additional 1 hour in 10% neutral buffered formalin. Thereafter the bony cochlea was dissected, followed by Alexa488-phalloidin immunostaining and whole mount organ of Corti preparation and contra stained with DAPI stain.

Delivery of siRNA was evaluated using fluorescence microscopy and digital imaging. Tissue fragments (organ of Corti) were considered positive (i.e., a successful Cy3 DDIT4_1 siRNA delivery occurred) only if histological (microscopic) examination showed clear fluorescent signal within specific cochlea's structures. Background DAPI staining was used for the identification of cochlea tissue structure. Inner ear delivery was considered positive if histological examination had consistency within all turns of organ of Corti (basal, second and apical).

Results:

Positive siRNA delivery into the inner ear cochlear structures was detected following application of 30% glycerol (Formulation 1) or 20% mineral oil (v/v), 40% Propylene glycol (v/v) and 10% Ethanol (v/v) (Formulation 3) using ear drops. All turns of organ of Corti and spiral ganglions were labeled at the amount of 100 ug, however the signal with the mineral oil formulation was weaker than the glycerol formulation.

Example 4

QM5 siRNA Treatment in Ear Drops Induced Knockdown of p53 Protein Expression Levels in the Rat Inner Ear after Cisplatin Administration The objective of this experiment was to evaluate the knockdown of Cisplatin induced p53 protein in the inner ear (Cochlea) of rats that were treated with eardrops contain QM5 siRNA (rat siRNA targeting rat p53).

Experimental group I:was treated once with QM5 siRNA (sense strand: GAAGAAAAUUUCCGCAAAA (SEQ ID NO:5845); antisense strand: UUUUGCGGAAAUUUU-CUUC (SEQ ID NO:5846)); at a dose of 100 µg/30% Glycerol/10 µl, delivered by the eardrops (ErD), route: REAC; QM5 siRNA treatment was performed on day 1, prior to the 1st Cisplatin administration. The contra lateral ear (Left), serves as untreated control. QM5 siRNA is designed as alternating ribonucleotides modified at the 2' position of the sugar residue in both the antisense and the sense strands, wherein the moiety at the 2' position is methoxy (2' OMe sugar modified).

Experimental Group II: untreated normal control rats

Experiment Design:

Measured Variables:

Body weight, Serum Creatinine and P53 protein signal by ELISA. P53 Protein signal The Cisplatin control group (Sample 2) exhibited an increase of 49% in the level of P53 protein signal compared to the Naïve group (Sample 1). Namely, the rats receiving Cisplatin treatment showed increased p53 levels in cochlea with respect naïve rats. The QM5 siRNA treatment caused a reduction of p53 signal to 2.69, which is only 12% higher compared to the Naïve group.

TABLE 3

QM5 siRNA Treatment in eardrop Induced Knockdown of p53 Protein Expression Levels in the Rat Inner Ear After Cisplatin Administration

| Sample | Sample Description | P53 protein level |
|---|---|---|
| 1 | Naïve rat cochlea 346ug/well | 2.40 |
| 2 | Cisplatin only Left ear 346ug/well | 3.58 |
| 3 | Cisplatin plus QM5 siRNA Right ear 346ug/well | 2.69 |

Example 5

Inner Ear Delivery of Fluorescence Labelled siRNA with L-DNA Structure in Rats

Description of the test material: sterile 10 mg/ml Cy3-AS-CASP2_4-Struc-L-DNA (alternating 2-O-methylation in the antisense strand and L-DNA nucleotide in position 18 of the sense strand; Sense: GCCAGAAUGUGGAACUCCU (SEQ ID NO:5847); Antisense: AGGAGUUCCACAUUCUGGC (SEQ ID NO:5848)) or DDIT4_1-Cy3.5 (alternating 2-O-methylation in the sense and antisense strands) in 30% sterile glycerol solution in pyrogen free water. Cy3 is linked to the 3' end of the antisense strand.

General:

The study included 4 experimental groups as described in Table 4: Experimental groups I-IV (treated by siRNA (DDIT4_1-Cy3.5 or Cy3-AS-CASP2_4-Struc-L-DNA) glycerol based eardrop). Rats were treated by Ear Drops (ErD) with a single siRNA dose as follows:

Groups I-IV:

dose regime: 100 µg/10 µl/ear of 30% glycerol administration route: REAC (right external auditory canal))/unilateral (Groups I and III) and REAC/LEAC (right/left external auditory canals)/bilateral (Groups II and IV).

TABLE 4

Study Design

| Group | SiRNA Type | Dose µg/rat | Delivery Vol. (µl) | Route | Termination (Days) | Group Size |
|---|---|---|---|---|---|---|
| I | DDIT4_1-Cy3.5 | 100 µg | 10.00 | REAC/Unilateral | 3 | 1 |
| II | DDIT4_1-Cy3.5 | 100 µg | 10.00 | REAC/LEAC/Bilateral | 3 | 1 |
| III | Cy3-AS-CASP2_4-Struc-L-DNA | 100 µg | 10.00 | REAC/Unilateral | 3 | 1 |
| IV | Cy3-AS-CASP2_4-Struc-L-DNA | 100 µg | 10.00 | REAC/LEAC/Bilateral | 3 | 1 |

Right External Auditory Canal (REAC/Unilateral) Delivery:

A 10 µl sample volume (warm glycerol based eardrops, 37° C.) was slowly instilled into REAC, using blunt pipette tip. This volume was delivered into each right ear (groups I and III according study design). During and after REAC instillations, rats were kept on contra lateral recumbency (left side) for 40 minutes and then returned to its cage after recovery.

Right and Left Bilateral External Auditory Canal (REAC/LEAC/Bilateral) Delivery:

A 10 µl sample volume (warm glycerol based eardrops, 37° C.) was slowly instilled into external REAC, using blunt pipette tip. This volume was delivered into each right ear (groups II and IV according study design). During and after REAC instillations, rats were kept on contra lateral recumbency (left side) for 30 minutes, after that turned to the right side and a 10 µl sample volume (warm glycerol based eardrops, 37° C.) was slowly instilled into LEAC, using blunt pipette tip and were kept for additional 30 minutes and returned to its cage after recovery.

Tissue Collection:

Rats were decapitated. Left and right temporal bones including cochlea were collected and post fixed in 4% PFA, whole mount Corti staining was performed.

Evaluation:

Delivery of siRNA was evaluated using light microscopy and digital imaging. Tissue fragments (cochlea) were considered positive (i.e., a successful siRNA delivery) only if histological (microscopic) examination showed clear fluorescence signal within specific cochlea's structures. Background DAPI staining was used to assist in identifying cochlea tissue structure.

Results:

Positive siRNA delivery into the inner ear cochlear structures following application of the siRNA by ear drops was observed with both siRNA molecules (Cy3.5 labelled DDIT4 with alternating structure, and Cy3 labelled Casp2_4 with L-DNA structure). The siRNA which was delivered by unilateral application (right ear) was detected in all turns of organ of Corti and spiral ganglions at the concentration of 100 ug in 10 ul 30% warm glycerol.

Example 6

The Effect of Glycerol Concentration on siRNA Delivery to Rat Inner Ear Tissues Using Ear Drop Formulation as Determined by siRNA Quantitation 6-A: Rats were subjected to unilateral application of eardrops containing 200 µg siRNA/10 µl of PBS, 5%, 10%, 20% or 30% Glycerol. The concentration of siRNA was 10 mg/ml and the siRNA molecule tested was specific to CASP2 mRNA (CASP2_4 siRNA molecule having alternating 2'OMe sugar modified ribonucleotides in the antisense strand and L-DNA nucleotide in position 18 of the sense strand; Sense sequence: GCCAGAAUGUGGAACUCCU (SEQ ID NO:5847); Antisense sequence: AGGAGUUCCACAUUCUGGC (SEQ ID NO:5848)). The cochlear tissue was dissected four hours following eardrops application and the amount of siRNA in the tissue was determined quantitatively using qPCR. Table 5 below summarizes the quantitative results obtained in this experiment.

These results revealed that the delivery of siRNA into the cochlea by eardrops was effective when the eardrop formulation comprises between 5-20% glycerol as a carrier. The delivery of siRNA into the cochlea by eardrops was most effective when the eardrop formulation comprises 10% glycerol as a carrier.

TABLE 5

| Treatment | No of animals | SiRNA quantity (fmol/1 µg RNA) | Std |
|---|---|---|---|
| 200 µg/10 µl PBS | 3 | 29.09 | 21.20 |
| 200 µg/10 µl 5% Glycerol | 2 | 92.17 | 27.72 |
| 200 µg/10 µl 10% Glycerol | 3 | 161.21 | 16.26 |
| 200 µg/10 µl 20% Glycerol | 2 | 93.78 | 6.52 |
| 200 µg/10 µl 30% Glycerol | 3 | 39.21 | 22.83 |

6-B: The above experiment is carried out in the same format with the exception of treating the animals with cisplatin. 10 experimental groups of (6 rats/group each) as follows: Groups are treated with a single siRNA administration: at a dose of 100 mg/10 ml, PBS, 5%5, 10%, 20% 25% or 30% Glycerol delivered by eardrops (ErD), route: REAC; siRNA treatment is performed on day 1 (study initiation), 24 hours prior to the 1st Cisplatin administration (at Cisplatin dose regime: 4 mg/kg daily; administration route: I.P.; injection volume: 1 ml for 250 g rat BW). Rats are subjected to 3 consecutive i.p. injections of Cisplatin (stock concentration: 50 mg/ml; LD50 I.P. dose 6.4 mg/kg). Termination step is performed 24 hrs after the last Cisplatin administration on Day 5 after study initiation. Control Group is treated with a single Vehicle ErD application 10 µl in the same manner as test groups. One experimental group is untreated intact control. The scheduled euthanasia is performed according to the study design. SiRNA to target genes TP53BP2 (ASPP2), BNIP3, CASP2, NOX3, HRK, RAC1, DDIT4, DDIT4L, NOX4, HTRA2, CAPNS1 (Calpain), ID3, HES1, HES5, CDKN1B and ID3.

Example 7

Chinchilla Models of Hearing Loss (i) Chinchilla Model of Carboplatin-Induced or Cisplatin-Induced Cochlea Hair Cell Death Chinchillas are pre-treated by direct administration of specific siRNA in 5%, 10%, 12.5%, 15%, 20%, 25% or 30% glycerol or other permeability enhancer to the left ear of each animal. Glycerol or other vehicle/agent (same final concentrations) is administered to the right ear of each animal as placebo. Two days following the administration of the specific siRNA compounds of the invention, the animals are treated with carboplatin (75 mg/kg i.p.) or cisplatin (intraperitoneal infusion of 13 mg/kg over 30 minutes). After sacrifice of the chinchillas (two weeks post carboplatin treatment) the % of dead cells of inner hair cells (IHC) and outer hair cells (OHC) is calculated in the left ear (siRNA treated) and in the right ear (saline treated). It is calculated that the percent of dead cells of inner hair cells (IHC) and outer hair cells (OHC) is lower in the left ear (siRNA treated) than in the right ear (vehicle control).

(ii) Chinchilla Model of Acoustic-Induced Cochlea Hair Cell Death

The activity of specific siRNA in an acoustic trauma model is studied in chinchilla. The animals are exposed to an octave band of noise centered at 4 kHz for 2.5 h at 105 dB. The left ear of the noise-exposed chinchillas is pre-treated (48 h before the acoustic trauma) with 30 µg of siRNA in ~10 µL of glycerol; the right ear is pre-treated with vehicle (10% glycerol). The compound action potential (CAP) is a convenient and reliable electrophysiological method for measuring the neural activity transmitted from the cochlea. The CAP is recorded by placing an electrode near the base of the cochlea in order to detect the local field potential that is generated when a sound stimulus, such as click or tone burst, is abruptly turned on. The functional status of each ear is assessed 2.5 weeks after the acoustic trauma. Specifically, the mean threshold of the compound action potential recorded from the round window is determined 2.5 weeks after the acoustic trauma in order to determine if the thresholds in the siRNA-treated ear are lower (better) than the untreated (vehicle control) ear. In addition, the amount of inner and outer hair cell loss is determined in the siRNA-treated and the control ear.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09089591B2). An electronic copy of the "Sequence Listing" will also be available from the USPTO upon request and payment of the fee set forth in 37 CFR 1.19(b)(3).

The invention claimed is:

1. A method of treating a subject suffering from or at risk of an ear disorder, comprising topically administering to the canal of the subject's ear an otic pharmaceutical composition comprising a therapeutically effective amount of at least one oligonucleotide compound, glycerol at a final concentration of about 0.1-30% v/v of the composition, and a pharmaceutically acceptable excipient or carrier, or mixtures thereof, thereby delivering said oligonucleotide compound to the inner ear and/or middle ear of a subject in an amount sufficient for down-regulating expression of a target gene associated with the disorder in the inner ear and/or middle ear of the subject.

2. The method according to claim 1, wherein said ear disorder is hearing loss or balance impairment.

3. The method according to claim 2, wherein the hearing loss or balance impairment results from ototoxin-induced hearing loss, acoustic-induced hearing loss or age-related hearing loss.

4. The method of claim 3, wherein the ototoxin is a chemotherapeutic agent, an antineoplastic agent, an antibiotic, an aminoglycoside antibiotic, a salicylate or a salicylate-like compound, a quinine or a quinine-like compound, a loop-diuretic drug, an environmental pollutant, an industrial pollutant, a food contaminant, or a medicinal contaminant.

5. The method according to claim 1, wherein the target gene is selected from one or more of: TP53BP2 (ASPP2), BNIP3, CASP2, NOX3, HRK, RAC1, DDIT4 (REDD1), DDIT4L (REDD2), NOX4, HTRA2, CAPNS1 (Calpain), HES1, HES5, CDKN1B (p27KIP), CDKN2A (p16), CDKN2D (p19), p53, Notch 1 and ID3.

6. The method according to claim 1, wherein said ear disorder is associated with ear hair cell loss in a subject's inner ear, and wherein the at least one oligonucleotide compound inhibits the expression of a human target gene associated with a hair cell loss in the ear; thereby inducing hair cell regeneration or reducing hair cell death in the subject's inner ear.

7. The method of claim 1, wherein glycerol is present at a final concentration of about 5-20% v/v of the composition.

8. The method of claim 1, wherein glycerol is present at a final concentration of about 7% to about 15% v/v of the composition.

9. The method of claim 1, wherein glycerol is present at a final concentration of about 10% v/v of the composition.

10. The method of claim 1, wherein the composition is designed for topical non-invasive administration.

11. The method of claim 10, wherein the composition is designed for instillation, deposition or spraying into the canal of the subject's ear.

12. The method of claim 11, wherein the composition is formulated as eardrops.

13. A method for delivery of an oligonucleotide compound to the inner ear and/or middle ear of a subject, the method comprising the steps of: providing an otic pharmaceutical composition comprising a therapeutically effective amount of at least one oligonucleotide compound; glycerol at a final concentration of about 0.1-30% v/v of the composition and a pharmaceutically acceptable excipient or carrier, or mixtures thereof and topically administering to the canal of the subject's ear said otic pharmaceutical composition in an amount sufficient to contact the inner ear with a therapeutically effective amount of said oligonucleotide compound.

14. The method of claim 13, wherein glycerol is present at a final concentration of about 5 to 20% v/v of the composition.

15. The method according to claim 4, wherein the ototoxin is an antineoplastic agent selected from the group consisting of vincristine, vinblastine, cisplatin, cisplatin-like compounds, taxol and taxol-like compounds.

* * * * *